US008062906B2

(12) United States Patent
Beltzer et al.

(10) Patent No.: US 8,062,906 B2
(45) Date of Patent: *Nov. 22, 2011

(54) B-LYMPHOCYTE STIMULATOR BINDING POLYPEPTIDES AND METHODS BASED THEREON

(75) Inventors: James P. Beltzer, Carlisle, MA (US); M. Daniel Potter, Acton, MA (US); Tony J. Fleming, Waltham, MA (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/701,301

(22) Filed: Feb. 5, 2010

(65) Prior Publication Data

US 2010/0144058 A1    Jun. 10, 2010

Related U.S. Application Data

(63) Continuation of application No. 11/232,439, filed on Sep. 20, 2005, now abandoned, which is a continuation of application No. 09/932,613, filed on Aug. 17, 2001, now abandoned.

(60) Provisional application No. 60/226,700, filed on Aug. 18, 2000.

(51) Int. Cl.
*G01N 33/566* (2006.01)
*A61K 38/00* (2006.01)

(52) U.S. Cl. .......................................... 436/501; 530/326

(58) Field of Classification Search .................. None
See application file for complete search history.

(56) References Cited

U.S. PATENT DOCUMENTS

| | | | |
|---|---|---|---|
| 4,179,337 A | 12/1979 | Davis et al. |
| 5,223,409 A | 6/1993 | Ladner et al. |
| 5,281,704 A | 1/1994 | Love |
| 5,403,484 A | 4/1995 | Ladner et al. |
| 5,474,981 A | 12/1995 | Leder et al. |
| 5,571,698 A | 11/1996 | Ladner et al. |
| 5,576,195 A | 11/1996 | Robinson et al. |
| 5,595,721 A | 1/1997 | Kasminski et al. |
| 5,605,671 A | 2/1997 | Lyle |
| 5,635,384 A | 6/1997 | Walsh et al. |
| 5,643,575 A | 7/1997 | Martinez et al. |
| 5,795,724 A | 8/1998 | Hillman et al. |
| 5,846,818 A | 12/1998 | Robinson et al. |
| 5,869,331 A | 2/1999 | Dornburg |
| 5,948,619 A | 9/1999 | Bandman et al. |
| 5,962,301 A | 10/1999 | Horvitz et al. |
| 5,969,102 A | 10/1999 | Bram et al. |
| 6,207,160 B1 | 3/2001 | Victoria et al. |
| 6,297,367 B1 | 10/2001 | Tribouley |
| 6,403,770 B1 | 6/2002 | Yu |
| 6,475,987 B1 | 11/2002 | Shu |
| 6,541,224 B2 | 4/2003 | Yu |
| 6,562,579 B1 | 5/2003 | Yu et al. |
| 6,635,482 B1 | 10/2003 | Yu et al. |
| 6,689,579 B1 | 2/2004 | Yu et al. |
| 6,716,576 B1 | 4/2004 | Yu et al. |
| 6,774,106 B2 | 8/2004 | Theill |
| 6,812,327 B1 | 11/2004 | Yu |
| 6,846,476 B2 | 1/2005 | White |
| 6,869,605 B2 | 3/2005 | Browning et al. |
| 6,875,846 B2 | 4/2005 | Rennert et al. |
| 6,881,401 B1 | 4/2005 | Yu |
| 7,083,785 B2 | 8/2006 | Browning et al. |
| 7,118,872 B2 | 10/2006 | Beltzer et al. |
| 7,138,501 B2 | 11/2006 | Ruben et al. |
| 7,220,840 B2 | 5/2007 | Ruben et al. |
| 7,259,137 B2 | 8/2007 | Min et al. |
| 7,317,089 B2 | 1/2008 | Kikly |
| 7,399,593 B1 | 7/2008 | Farrow et al. |
| 7,691,804 B2 | 4/2010 | Jeffrey et al. |
| 2001/0010925 A1 | 8/2001 | Wiley |
| 2002/0037852 A1 | 3/2002 | Browning et al. |
| 2002/0055624 A1 | 5/2002 | Wiley |
| 2002/0115112 A1 | 8/2002 | Yu et al. |
| 2002/0150579 A1 | 10/2002 | Kimberly et al. |
| 2002/0165156 A1 | 11/2002 | Browning et al. |
| 2002/0172674 A1 | 11/2002 | Jeffrey et al. |
| 2003/0012783 A1 | 1/2003 | Kindsvogel |

(Continued)

FOREIGN PATENT DOCUMENTS

EP    0 439 095 A2    7/1991

(Continued)

OTHER PUBLICATIONS

U.S. Appl. No. 08/984,396, Hurle et al. U.S. Appl. No. 09/226,533, Gross et al.
U.S. Appl. No. 09/589,288, Yu et al.
U.S. Appl. No. 09/912,293, Rosen et al.
U.S. Appl. No. 12/170,333, Yu et al.
U.S. Appl. No. 60/033,601, Gorman.
U.S. Appl. No. 60/041,797, Hurle et al.
U.S. Appl. No. 60/048,776, Masiakowsky et al.
U.S. Appl. No. 60/058,786, Tschopp.
U.S. Appl. No. 60/066,386, Masiakowsky et al.
U.S. Appl. No. 60/066,577, Song.

(Continued)

*Primary Examiner* — Patricia A Duffy
(74) *Attorney, Agent, or Firm* — Leydig, Voit & Mayer, Ltd.

(57) ABSTRACT

Binding polypeptides that specifically bind B lymphocyte stimulator protein or B lymphocyte stimulator-like polypeptides can be used in methods of the invention for detecting, diagnosing, or prognosing a disease or disorder associated with aberrant B lymphocyte stimulator or B lymphocyte stimulator receptor expression or inappropriate function of B lymphocyte stimulator or B lymphocyte stimulator receptor, comprising B lymphocyte stimulator binding polypeptides or fragments or variants thereof, that specifically bind to B lymphocyte stimulator. The present invention further relates to methods and compositions for preventing, treating or ameliorating a disease or disorder associated with aberrant B lymphocyte stimulator or B lymphocyte stimulator receptor expression or inappropriate B lymphocyte stimulator function or B lymphocyte stimulator receptor function, comprising administering to an animal, preferably a human, an effective amount of one or more B lymphocyte stimulator binding polypeptides or fragments or variants thereof, that specifically bind to B lymphocyte stimulator.

27 Claims, No Drawings

U.S. PATENT DOCUMENTS

| | | |
|---|---|---|
| 2003/0022233 A1 | 1/2003 | Goodwin |
| 2003/0023038 A1 | 1/2003 | Rennert et al. |
| 2003/0091565 A1 | 5/2003 | Beltzer et al. |
| 2003/0095967 A1 | 5/2003 | MacKay et al. |
| 2003/0148445 A1 | 8/2003 | Shu |
| 2003/0166546 A1 | 9/2003 | Aggarwal |
| 2003/0175208 A1 | 9/2003 | Yu et al. |
| 2003/0194743 A1 | 10/2003 | Beltzer et al. |
| 2003/0223996 A1 | 12/2003 | Ruben et al. |
| 2004/0175801 A1 | 9/2004 | Yu et al. |
| 2004/0175802 A1 | 9/2004 | Yu et al. |
| 2005/0070694 A1 | 3/2005 | Gelfanova et al. |
| 2005/0100548 A1 | 5/2005 | Browning et al. |
| 2005/0169924 A1 | 8/2005 | Browning et al. |
| 2005/0186637 A1 | 8/2005 | Yu et al. |
| 2005/0214543 A1 | 9/2005 | Koumura et al. |
| 2005/0244411 A1 | 11/2005 | MacKay et al. |
| 2005/0255532 A1 | 11/2005 | Ruben et al. |
| 2006/0062789 A1 | 3/2006 | Ruben et al. |
| 2006/0079457 A1 | 4/2006 | Browning et al. |
| 2006/0084608 A1 | 4/2006 | Beltzer et al. |
| 2006/0171919 A1 | 8/2006 | Rosenblum et al. |
| 2006/0193859 A1 | 8/2006 | Yu et al. |
| 2006/0198784 A1 | 9/2006 | Yu et al. |
| 2007/0086979 A1 | 4/2007 | Chevrier et al. |
| 2007/0293434 A9 | 12/2007 | Beltzer et al. |
| 2008/0254030 A1 | 10/2008 | Mackay et al. |
| 2008/0267965 A1 | 10/2008 | Kalled et al. |
| 2009/0081213 A1 | 3/2009 | Chevrier et al. |
| 2009/0098129 A1 | 4/2009 | Farrow et al. |
| 2009/0110676 A1 | 4/2009 | Mackay et al. |
| 2009/0148462 A1 | 6/2009 | Chevrier et al. |
| 2009/0215071 A1 | 8/2009 | Cachero et al. |
| 2010/0040627 A1 | 2/2010 | Jeffrey et al. |
| 2010/0233179 A1 | 9/2010 | Browning et al. |

FOREIGN PATENT DOCUMENTS

| | | |
|---|---|---|
| EP | 0 869 180 A1 | 10/1998 |
| EP | 0 921 194 A1 | 6/1999 |
| EP | 1 157 110 A1 | 11/2001 |
| EP | 1 294 769 A2 | 3/2003 |
| EP | 1 294 949 A2 | 3/2003 |
| EP | 1 309 718 A2 | 5/2003 |
| EP | 1 146 892 B1 | 8/2003 |
| EP | 1 141 274 B1 | 9/2003 |
| EP | 1 354 598 A3 | 10/2003 |
| EP | 1 456 347 A2 | 9/2004 |
| EP | 1 507 793 A1 | 2/2005 |
| EP | 1 577 391 A1 | 9/2005 |
| EP | 1 860 190 A2 | 11/2007 |
| WO | WO 93/21232 A1 | 10/1993 |
| WO | WO 94/20540 A1 | 9/1994 |
| WO | WO 95/07297 A1 | 3/1995 |
| WO | WO 95/20398 A1 | 8/1995 |
| WO | WO 95/24414 A1 | 9/1995 |
| WO | WO 95/24466 A1 | 9/1995 |
| WO | WO 95/31468 A1 | 11/1995 |
| WO | WO 96/14328 A1 | 5/1996 |
| WO | WO 96/34095 A1 | 10/1996 |
| WO | WO 97/33902 A1 | 9/1997 |
| WO | WO 97/34911 A1 | 9/1997 |
| WO | WO 97/46251 A1 | 12/1997 |
| WO | WO 97/49726 A1 | 12/1997 |
| WO | WO 98/07880 A1 | 2/1998 |
| WO | WO 98/18921 A1 | 5/1998 |
| WO | WO 98/27114 A2 | 6/1998 |
| WO | WO 98/39361 A1 | 9/1998 |
| WO | WO 98/50547 A2 | 11/1998 |
| WO | WO 98/55620 A1 | 12/1998 |
| WO | WO 98/55621 A1 | 12/1998 |
| WO | WO 98/55623 A1 | 12/1998 |
| WO | WO 99/10494 A2 | 3/1999 |
| WO | WO 99/11791 A1 | 3/1999 |
| WO | WO 99/12964 A2 | 3/1999 |
| WO | WO 99/33980 A2 | 7/1999 |
| WO | WO 99/35170 A2 | 7/1999 |
| WO | 99/46295 A1 | 9/1999 |
| WO | WO 00/26244 A2 | 5/2000 |
| WO | WO 00/39295 A1 | 7/2000 |
| WO | WO 00/40716 A2 | 7/2000 |
| WO | WO 00/43032 A2 | 7/2000 |
| WO | WO 00/45836 A1 | 8/2000 |
| WO | WO 00/47740 A2 | 8/2000 |
| WO | WO 00/50597 A2 | 8/2000 |
| WO | WO 00/58362 A1 | 10/2000 |
| WO | WO 00/60079 A2 | 10/2000 |
| WO | WO 00/67034 A1 | 11/2000 |
| WO | WO 00/68378 A1 | 11/2000 |
| WO | WO 00/77256 A1 | 12/2000 |
| WO | WO 01/12812 A2 | 2/2001 |
| WO | WO 01/24811 A1 | 4/2001 |
| WO | WO 01/40466 A2 | 6/2001 |
| WO | WO 01/60397 A1 | 8/2001 |
| WO | WO 01/81417 A2 | 11/2001 |
| WO | WO 01/87977 A2 | 11/2001 |
| WO | WO 02/02641 A1 | 1/2002 |
| WO | WO 02/16411 A2 | 2/2002 |
| WO | WO 02/18620 A2 | 3/2002 |
| WO | WO 02/24909 A2 | 3/2002 |
| WO | WO 02/38766 A2 | 5/2002 |
| WO | WO 02/066516 A3 | 8/2002 |
| WO | WO 02/092620 A2 | 11/2002 |
| WO | WO 02/094852 A2 | 11/2002 |
| WO | WO 03/016468 A2 | 2/2003 |
| WO | WO 03/030833 A2 | 4/2003 |
| WO | WO 03/033658 A2 | 4/2003 |
| WO | WO 03/055979 A2 | 7/2003 |
| WO | WO 03/089569 A2 | 10/2003 |
| WO | WO 04/058309 A1 | 7/2004 |
| WO | WO 2004/074511 A1 | 9/2004 |
| WO | WO 2005/005462 A3 | 1/2005 |
| WO | WO 2005/042009 A1 | 5/2005 |

OTHER PUBLICATIONS

U.S. Appl. No. 60/068,959, Tribouley et al.
U.S. Appl. No. 60/096,173, Song.
U.S. Appl. No. 60/106,976, Lenardo et al.
U.S. Appl. No. 60/117,169, McKay et al.
U.S. Appl. No. 60/119,906, Boyle et al.
U.S. Appl. No. 60/132,892, Shu.
U.S. Appl. No. 60/143,228, MacKay et al.
U.S. Appl. No. 60/149,378, MacKay et al.
U.S. Appl. No. 60/157,933, Schneider et al.
U.S. Appl. No. 60/166,271, Boyle et al.
U.S. Appl. No. 60/201,012, Shu.
U.S. Appl. No. 60/204,039, Theill.
U.S. Appl. No. 60/214,591, Theill.
U.S. Appl. No. 60/312,808, Gelfanova.
GB, 9828628.9, Glaxo Group Ltd.
Biogen IDEC's opposition of EP Patent No. 1 141 274 B1. Filed in the European Patent Office on Jun. 10, 2004.
Biogen Inc. and Apoxis SA's Response (including Annexes A and B and the Main Request containing a substitute set of claims) to Human Genome Sciences and Serono's Oppositions of EP Patent No. 1146892. The Response was filed in the European Patent Office on Mar. 14, 2005.
Biogen's Observations in preparation for oral proceedings in defense of the Opposition of EP Patent No. 1146892 lodged by Merck Serono, S.A., and Human Genome Sciences, Inc. The Observations in preparation for oral proceedings was filed in the European Patent Office on Jan. 19, 2007.
Corixa Corporation's opposition of EP Patent No. 1 141 274 B1. Filed in the European Patent Office on Jun. 6, 2004.
Declaration of Dr. Fritz Melchers dated Dec. 1, 2006 in support of Browning et al. in Patent Interference No. 105,485.
Declaration of Dr. Mark S. Schlissel dated Dec. 1, 2006 in support of Browning et al. in Patent Interference No. 105,485.
Second Declaration of Dr. Mark S. Schlissel dated Feb. 8, 2007 in support of Browning et al. in Patent Interference No. 105,485.
Third Declaration of Dr. Mark S. Schlissel dated Apr. 15, 2007.
Declaration of Dr. Randolph J. Noelle dated Feb. 12, 2007 in support of Yu et al. in Patent Interference No. 105,485.

Declaration of Dr. Rodger G. Smith dated and filed on Dec. 14, 2004.
Second Declaration of Dr. Rodger G. Smith dated and filed on Aug. 4, 2005.
Declaration of Dr. Georg Friedrich Melchers dated Jan. 19, 2007 filed in support of EP Patent No. 1146892 in the Opposition to EP Patent No. 1146892 lodged by Merck Serono, S.A., and Human Genome Sciences, Inc.
Declaration of Dr. Carl F. Ware dated and filed on Apr. 16, 2007.
Declaration of Dr. Raif S. Geha dated and filed on Apr. 16, 2007.
Declaration of Patent Interference No. 105,485 between U.S. Appl. No. 09/589,288 and U.S. Patent No. 6,869,605.
Eli Lilly and Company's opposition of EP Patent No. 0 939 804 including supporting documents D1-D16. Filed in the European Patent Office on May 17, 2006.
Eli Lilly and Company's Request for Revocation (Claim # HC06CO2687) against European Patent (UK) No. 0 039 804 including supporting documents. Filed in the High Court of Justice, Chancery Division, Patents Court on Jul. 5, 2006.
European Search Report, European Application No. EP 05 01 2261, mailed Aug. 8, 2005.
Supplementary European Search Report, European Application No. EP 02 78 6413, mailed Dec. 20, 2005.
Supplementary Partial European Search Report, European Application No. EP 00 90 8739, mailed Jun. 30, 2005.
Further experimental evidence concerning anti-TACI antibodies of EP 1 141 274 B1 Patent Example 18 (Zymogenetics' unpublished data).
Genbank Accession No. P01374 (Jul. 1, 1989).
Genbank Accession No. CAA25649 (Jul. 12, 1993).
GenBank Accession No. T87299 (Mar. 17, 1995).
GenBank Accession No. R16882 (Apr. 14, 1995).
GenBank Accession No. R16934 (Apr. 14, 1995).
GenBank Accession No. D79690 (Feb. 9, 1996).
GenBank Accession No. G30081 (Oct. 5, 1996).
GenBank Accession No. AA422749 (Oct. 16, 1997).
GenBank Accession No. AA166695 (Nov. 9, 1997).
GenBank Accession No. AA682496 (Dec. 19, 1997).
GenBank Accession No. AA906714 (Jun. 9, 1998).
GenBank Accession No. AI82472 (Oct. 18, 1998).
GenBank Accession No. AF186114 (Jan. 13, 2000).
GenBank Accession No. AF134715 (Mar. 28, 2000).
Genbank Accession No. Q9Y275 (Oct. 16, 2001).
Genentech's opposition of EP Patent No. 1 141 274 B1. Filed in the European Patent Office on Jun. 10, 2004.
HGS Backgrounder, "B Lymphocyte Stimulator" dated Oct. 30, 2000.
HGS Backgrounder "Systemic Lupus Erythematosus" dated Nov. 1, 2000.
HGS Backgrounder "Immunoglobulin-A-Deficiency" dated Sep. 2001.
HGS Press Release "Human Genome Sciences Announces the Discovery of a Novel immune Stimulant" dated Jul. 8, 1999.
HGS Press Release "Human Genome Sciences Announces Advance in Hodgkins Lymphoma" dated Jul. 14, 1999.
HGS Press Release "New Anti-Angiogenic Proteins Discovered" dated Aug. 5, 1999.
HGS Press Release "Human Genome Sciences Reports 1999 Financial Results" dated Feb. 10, 2000.
HGS Press Release "Human Genome Sciences Reports First Quarter Financial Results" dated Apr. 27, 2000.
HGS Press Release "Human Genome Sciences and Cambridge Antibody Technology Commit to Exclusive Development of Anti-BLyS Antibodies" dated Oct. 30, 2000.
HGS Press Release "High Levels of BlyS Implicated in Lupus and Rheumatoid Arthritis Patients" dated Oct. 30, 2000.
HGS Press Release "Human Genome Sciences and Dow Agree to Develop HGS' Radiolabeled B-Lymphocyte Stimulator" dated Oct. 30, 2000.
HGS Press Release "Human Genome Sciences Reports Financial Results for Fourth Quarter and Full Year 2000" dated Feb. 15, 2001.
HGS Press Release "Human Genome Sciences Completes Construction of Antibody Manufacturing Facility" dated Feb. 21, 2001.
HGS Press Release "Human Genome Sciences Receives Orphan Drug Designation for BlyS Therapeutic Protein for Treatment of Common Variable Immunodeficiency" dated Feb. 27, 2001.
HGS Press Release "Human Genome Sciences Breaks Ground for a Large Scale Manufacturing Plant" dated Oct. 17, 2001.
HGS Press Release "Human Genome Sciences Initiates Trial of a New Drug for Systemic Lupus Erythematosus and Other Autoimmune Diseases" dated Nov. 1, 2001.
HGS Press Release "Human Genome Sciences Data Support Potential of Lymphostat-B as Treatment for Autoimmune Diseases" dated Nov. 14, 2001.
HGS Press Release "Human Genome Sciences Presents Data as American Society of Hematology Meeting" dated Dec. 9, 2001.
HGS Press Release Human Genome Sciences Files Investigational New Drug Application for Lymphorad131, dated Jan. 23, 2002.
HGS Press Release "Human Genome Sciences Reports Financial Results for Full Year and Fourth Quarter 2001" dated Feb. 14, 2002.
HGS Press Release "Human Genome Sciences Provides Update of Company Progress" dated Apr. 30, 2002.
HGS Press Release "Human Genome Sciences Announces Clearance of Investigational New Drug Application for Lymphorad131, A New Anticancer Drug for the Treatment of B-Cell Tumors" dated May 14, 2002.
HGS Press Release "Human Genome Sciences Describes Activity of New cancer Drug at American Society of Clinical Oncology Meeting" dated May 20, 2002.
HGS Press Release "Human Genome Sciences and Cambridge Antibody Technology Commit to Exclusive Development of Antibody to Trial Receptor-2" dated May 20, 2002.
HGS Press Release "Human Genome Sciences Announces Second Quarter 2002 Financial Results" dated Jul. 25, 2002.
HGS Press Release "Human Genome Sciences Reports Progress in Clinical Trials of Five Drugs at JP Morgan H&Q Conference" dated Jan. 6, 2003.
HGS Press Release "Human Genome Sciences Reports Financial Results for Full Year and Fourth Quarter 2002" dated Feb. 14, 2003.
HGS Press Release "Results of Phase 1 Clinical Trial Demonstrate that Lymphostat-B™ is Safe and Biologically Active in Patients with Systemic Lupus Erythematosus" dated Apr. 21, 2003.
HGS Press Release Human Genome Sciences Reports Financial Results for First Quarter of 2003, dated Apr. 24, 2003.
HGS Press Release "Human Genome Sciences Provides Update of Company Progress" dated May 12, 2003.
HGS Press Release "Human Genome Sciences Updates Progress of Clinical Programs at Bio 2003" dated Jun. 25, 2003.
HGS Press Release "Human Genome Sciences Initiates Phase 2 Clinical Trial of Lymphostat-B™ for the Treatment of Systemic Lupus Erythematosus" dated Sep. 25, 2003.
HGS Press Release, "Human Genome Sciences Reports Results of Phase 1 Clinical Trial of Lymphostat-B™ in Patients with Systemic Lupus Erythematosus" dated Oct. 28, 2003.
HGS Press Release "Human Genome Sciences Reports Third Quarter 2003 Financial Results" dated Oct. 28, 2003.
HGS Press Release "Human Genome Sciences Reports Interim Results of Phase 1 Clinical Trials of Lymphorad™ 131 at 45th Annual Meeting of the American Society of Hematology" dated Dec. 9, 2003.
HGS Press Release "Human Genome Sciences Initiates Phase 2 Clinical Trial of Lymphostat-B™ for the Treatment of Rheumatoid Arthritis" dated Jan. 8, 2004.
HGS Press Release "Human Genome Sciences Updates Progress of Six Drugs in Clinical Trials at JPMorgan Conference" dated Jan. 12, 2004.
HGS Press Release "Human Genome Sciences Reports Financial Results for Fourth Quarter and Full Year 2003" dated Feb. 10, 2004.
HGS Press Release "Human Genome Sciences Announces Selection of Lymphostat-B™ for Participation in FDA's Continuous Marketing Application Pilot 2 Program" dated Mar. 4, 2004.
HGS Press Release "Human Genome Sciences Completes Patient Enrollment in a Phase 2 Clinical Trial of Lymphostat-B™ for the Treatment of Rheumatoid Arthritis" dated Jul. 29, 2004.

HGS Press Release "Human Genome Sciences Completes Patient Enrollment in a Phase 2 Clinical Trial of Lymphostat-B™ for the Treatment of Systemic Lupus Erythematosus" dated Jul. 29, 2004.
HGS Press Release "Human Genome Sciences Reports on Progress of Clinical Trials and Announces Goals for 2005 at JPMorgan Healthcare Conference" dated Jan. 10, 2005.
HGS Press Release "Human Genome Sciences Reports Results of a Phase 2 Clinical Trial of Lymphostat-B™ in Patients with Rheumatoid Arthritis" dated Apr. 6, 2005.
HGS Press Release GlaxoSmithKline Exercises Option to Lymphostat-B™, dated Jul. 7, 2005.
HGS Press Release, "Human Genome Sciences to Sponsor Conference Call to Discuss Phase 2 Clinical Results of Lymphostat-B™ in Systemic Lupus Erythematosus" dated Oct. 5, 2005.
HGS Press Release "Human Genome Sciences Reports Results of a Phase 2 Clinical Trial of Lymphostat-B™ in Patients with Systemic Lupus Erythematosus" dated Oct. 5, 2005.
HGS Press Release "Human Genome Sciences Reports on Progress Toward Commercialization and Announces 2006 Goals at JPMorgan Healthcare Conference" dated Jan. 10, 2006.
HGS Press Release "Human Genome Sciences Announces Full Presentation of Results of Phase 2 Clinical Trial of Lymphostat-B™ in Systemic Lupus Erythematosus" dated Jun. 22, 2006.
Human Genome Science's opposition of EP Patent No. 1 141 274 B1. Filed in the European Patent Office on Jun. 7, 2004.
Human Genome Sciences' opposition of EP Patent No. 1 146 892 B1 including Annex A, filed in the European Patent Office on Sep. 19, 2005.
Human Genome Science Inc.'s Reply filed in the European Patent Office on Sep. 19, 2005 in conjunction with its Opposition of EP Patent No. 1 146 892.
Human Genome Sciences, Inc.'s Reply filed in the European Patent Office on Nov. 4, 2005 in conjunction with its Opposition of EP Patent No. 1 141 274.
Preliminary Non-Binding Decision of the Opposition Division and Summons to attend Oral Proceedings issued by the European Patent Office on Oct. 2, 2006 in the matter of Human Genome Sciences' and Serono's Opposition of EP 1 146 892.
Serono International SA's opposition of EP Patent No. 1 146 892 B1 with Annexes I and II, filed in the European Patent Office on Aug. 24, 2005.
Serono International SA's opposition of EP Patent No. 0 939 804 including supporting documents D1-D17, filed in the European Patent of Office on May 17, 2006.
Serono International SA's Reply filed in the European Patent Office on Aug. 24, 2005 in conjunction with its Opposition of EP Patent No. 1 146 892.
Sequence alignment of "Prosite" sequence (D1) and SEQ ID No: 10 of EP 1 141 274.
Table setting out SEQ ID Nos. (provided by Opponent I).
Minutes of the Oral Proceedings before the Opposition Division, issued by the European Patent Office on Apr. 2, 2007 in the matter of Human Genome Sciences' and Serono's Opposition of EP 1 146 892.
Zymogenetics' Observation in Reply (158 pages) to Opposition of EP Patent No. 1441274 lodged by Clorixa Corporation, Human Genome Sciences, Inc., Genentech, Inc., and Biogen Idec., Inc., filed in the European Patent Office on Jun. 7, 2005.
ZymoGenetics' opposition of EP Patent No. 0 939 804 including supporting documents D1-D27. Filed in the European Patent Office on May 17, 2006.
Abbas et al., *Cellular and Molecular Immunology*, W.B. Saunders Company: Philadelphia, pp. 362 and 365 (1991).
Alberts, ed., *Molecular Biology of the Cell*, Second Edition, Garland Publishing, Inc., New York, pp. 117-118 (1989).
Arnett, *Arthritis Rheum.*, "The American Rheumatism Association 1987 revised criteria for the classification of rheumatoid arthritis," 31(3):315-24 (1988).
Ashkenazi, et al., *Nature Immonol.*, "Response," 1:179 (2000).
Baker et al., *Arthritis & Rheumatism*, "Generation and Characterization of LymphoStat-B, a Human Monoclonal Antibody that Antagonizes the Bioactivities of B Lymphocyte Stimulator," 48(11):3253-3285 (2003).

Baker et al. *Autoimmun. Rev.*, "Blys-an essential survival factor for B cells: basic biology, links to pathology and therapeutic target," 3(5):365-375 (2004).
Ballow et al., *JAMA*, "Immunopharmacology: immunomodulation and immunotherapy," 278)22):2008-17 (1997).
Batten et al., *J. Ex. Med.*, "BAFF Mediates Survival of Periperal Immature B Lymphocytes," 192:1453-65 (2000).
Batten et al., "The role of BAFF in Autoimmunity: Is it just a B cell story?" The Midwinter Conference of Immunologists at Asilomar, Pacific Grove, CA (Jan. 22-25, 2005).
Baumgarth, *Nature Immunol.*, "Secreted IgM versus BlyS in germinal center formation," 1:179 (2000).
Bodmer et al., *Trends in Biochemical Sciences*, "The molecular architecture of the TNF superfamily," 27:19-26. (2002).
Bork et al., *Trends in Genetics*, "Go hunting in sequence databases but watch out for the traps," 12:425-7 (1996).
Bork et al., *Genome Res.*, "Powers and pitfalls in sequence analysis: the 70% hurdle," 10(4):398-400 (2000).
Brazelton, *Current Opinion in Immunology*, "Molecular mechanism of action of new xenobiotic immunosuppressive drugs: tacrolimus (FK506), sirolimus (rapamycin), mycophenolate mofetil and lefunomide," 8:710-720 (1996).
Brenner, *Trends Genet.*, "SE, Errors in genome annotation," 15(4):132-3 (1999).
Caliceti et al., *Bioconjug. Chem.*, "Biopharmaceutical Properties of Uricase Conjugated to Neutral and Amphiphilic Polymers," 10:638-646 (1999).
Cerrutti et al, *Immunology and Cell Biology*, "Plasmacytoid dendritic cells and the regulation of immunoglobulin heavy chain class switching," 83: 554-562 (2005).
Chang, *Blood*, "A role for BLyS in this activation of innate immune cells," 108(8):2687-94 (2006).
Cheema et al., *Arthritis and Rheumatism*, "Elevated Serum B. Lymphocyte Stimulator Levels in Patients with Systemic Immune-Based Rheumatic Diseases," 44:1313-1319 (2001).
Chen et al., *Gene*, "Expression vectors for affinity purification and radiolabeling of proteins using *Eschericha coli* as host," 139:73-75 (1994).
Ciruelo et al., *Arthritis and Rheumatism*, "Cumulative rate of relapse of lupus nephritis after successful treatment with cyclophosphamide," 39:2028-2034 (1996).
Cohen (Fundamental Immunology, Paul, ed., Lippincott-Raven, Philadelphia, PA, 1999, chapter 33, pp. 1067-1088.
Couzin, *Science*, "Magnificent Obsession," 307:1712-1715 (2005).
Cragg et al., *B Cell Trophic Factors and B Cell Antagonism in Autoimmune Disease* "The Biology of CD20 and Its Potential as a Target for mAb Therapy," pp. 140-174 (2005).
Cull, *Protocols in Molecular Biology*, Appendix 2.A.2.5, Supp. 35, John Wiley & Sons (1989).
Cull et al., *Proc. Natl. Acad. Sci. USA*, "Screening for receptor ligands using large libraries of peptides limited to the C terminus of the las represser," 89:1865-1869 (1992).
Cwirla et al., *Proc. Natl. Acad. Sci. USA*, "Peptides on phage: A vast library of peptides for identifying ligands," 87:6378-6382 (1990).
Cyster, *Nature Immunol.*, "B cells on the Front Line," 1:9-10 (2000).
Davidson and Diamond, *New England Journal of Medicine*, "Autoimmune Diseases," 345:340-350 (2001).
Davies, *Nature Genetics*, "The EST express gathers speed," 364:554 (1993).
Delves and Roitt, *Encyclopedia of Immunology* 2nd ed. Academic Press Inc., pp. 1554-1559 (1998).
Denardo et al., *Clinical Cancer Res.*, "Comparison of 1,4,7,10-Tetraazacyclododecane-N,N',n",N'''-tetraacetic acid (DOTA)-Peptide-ChL6, a Novel Immunoconjugate with Catabolizable Linker, to 2 iminothioland-2'-p-(Bromoacetamido)benzyl-DOTA-ChL6 in Breast Cancer Xenografts," 4(10):2483-2490 (1998).
Devlin, *Science*, "Random Peptide Libraries: A Source of Specific Protein Binding Molecules," 249:404-406 (1990).
Do et al., *J. Exp. Med.*, "Attenuation of Apoptosis Underlies B Lymphocyte Stimulator Enhancement of Humoral Immune Response," 192:953-964 (2000).
Doerks et al., *Trends Genet.*, "Protein annotation: detective work for function prediction," 14(6):248-50 (1998).

Dorner et al., *Arthritis Res.*, "B cells, BAFF/zTNF4, TACI, and systemic lupus erythematosus," 3:197-99 (2001).
Egner, *J. Clin. Pathol.* "The use of laboratory tests in the diagnosis of SLE," 53(6):424-32 (2000).
Elgert, *Immunology: Understanding the Immune System*, Wiley-Liss: New York, pp. 24, 305 and 324-326 (1996).
Felici, *J. Mol. Biol.*, "Selection of Antibody Ligands from a Large Library of Oligopeptides Expressed on a Multivalent Exposition Vector," 222: 301-310 (1991).
Fell et al., *J. Immunol.*, " Genetic Construction and Characterization of a Fusion Protein Consisting of a Chimeric F(ab') With Specificity for Carcinomas and Human IL-2," 146:2446-2452 (1991).
Ferguson et al., *Human Molecular Genetics*, "Cloning of Tabby, the murine homolog of the human EDA gene: evidence for a membrane-associated protein with a short collagenous domain," 6(9):1589-94 (1997).
Fishman et al., *Nature*, "A new grammar for drug discovery," 437:491-493 (2005).
Fodor, *Nature*, "Multiplexed biochemical assays with biological chips," 364:555-556 (1993).
Furie et al., 67th Annual American College of Rheumatology Scientific Meeting, "Safety, Pharmacokinetic and Pharmacodynamic Results of a Phase 1 Single and Double Dose-Escalation Study of LymphoStat-B (Human Monocional Antibody to BLyS) in SIE Patients," Oct. 23-28, 2003, Orlando, FL.
Gillies et al., *Proc. Natl. Acad. Sci. USA*, "Antibody-targeted interleukin 2 stimulates T-cell killing of autologous tumor cells," 89:1428-1432 (1992).
Goldblum, *Clinical and Experimental Rheumatology*, "Therapy of rheumatoid arthritis with mycophenolate mofetil," Supp. 8:S117-119 (1993).
Golub and Green, eds., *Immunology A Synthesis*, Sinaver Assoc., Inc., p. 134 (1991).
Gras et al., *International Immunology*, "BCMAp: an integral membrane protein in the Golgi apparatus of human mature B lymphocytes," 7:1093-1106. (1995).
Groom et al. *J. Clin. Invest.*, "Association of BAFF/FLyS overexpression and altered B cells differentiation with Sjogren's Syndrome," 109:59-68 (2002).
Gross et al., *Nature*, "TACI and BCMA are receptors for a TNF homologue implicated in B-cell autoimmune disease," 404:995-999 (2000).
Gross et al., *Immunity*, "TACI-Ig neutralizes molecules critical for B cell development and autoimmune disease: Impaired B cell maturation in mice lacking BLyS," 15:289-302 (2001).
Gruss, *Blood*, "Tumor necrosis factor ligand superfamily; Involvement in the pathology of malignant lymphomas," 85(12):3378-404 (1995).
Gruss, *Int. Jour. Clin. Lab. Res.*, "Regulation of murine B cell growth and differentiation by CD30 ligand," 26:143-159 (1996).
Haberman, *Genetic Engineering News*, "Strategies to Move Beyond Target Validation," 25(21): pp. 36 (2005).
Hahne et al., *J. Exp. Med.*, "APRIL, a New Ligand of the Tumor Necrosis Factor Family, Stimulates Tumor Cell Growth," 188(6): 1185-90 (1998).
Hammarstrom et al., *Clin. Exp. Immunol.* "Selective IgA deficiency (StgAD) and common variable immunodeficiency (CVID)," 120(2):225-31 (2000).
Harlow and Lane eds., *Antibodies: A Laboratory Manual*, Cold Spring Harbor Press, pp. 15 and 567-569 (1988).
Hatzoglou et al., *J. Immunol.*, "TNF Receptor Family Member CBMA (B Cell Maturation) Associates with TNF Receptor-Associated Factor (TRAF) 1, TRAF2, TRAF3 and Activates NF-$_k$B, Elk-1, c-Jun N-Terminal Kinase, and p38 Mitogen-Activated Protein Kinase," 165:1322-1330 (2000).
He et al., *J. Immunol.*, "Lymphoma B cells evade apoptosis through the TNF family members BAFF/BLyS and APRIL," 172(5):3268-79 (2004).
He et al., *J. Immunol.*, "HIV-1 Envelope Triggers Polyclonal Ig Class Switch Recombination through a CD40-Independent Mechanism Involving BAFF and C-Type Lectin Receptors," 176:3931-3941 (2006).

Heppeler et al., *Curr. Med. Chem.*, "Receptor Targeting for Tumor Localisation and Therapy with Radiopeptides," 9(7):971-994 (2000).
Houghten, *Bio/Techniques*, "The Use of Synthetic Peptide Combinatorial Libraries for the Identification of Bioactive Peptides," 13: 412-421 (1992).
Hu et al., *Genomics*, "Characterization of TNFRSF19, a novel member of the tumor necrosis factor receptor superfamily," 62:103-107 (1999).
Huard et al., *International Immunology*, "BAFF production by antigen-presenting cells provides T cell co-stimulation," 16:467-475 (2004).
Huard et al., *J. Immunology*, "T cell costimulation by the TNF ligand BAFF," 167(11):6225-31 (2001).
Hymowitz et al., *J. Biol. Chem.*, "Structures of APRIL-receptor complexes: like BCMA, TACI employs only a single cysteine-rich domain for high affinity ligand binding," 280:7218-27 (2005), with Tables S1-S4 and Fig. S1 as published in the online version of this article available at http://www.jbc.org.
Hwang et al., *J. Mol. Cell Cardiol.*, "Single Pass Sequencing of a Unidirectional Human Fetal Heart cDNA Library to Discover Novel Genes of the Cardiovascular System," 26:1329-1333 (1994).
Iglesias et al., *Allergol. Immunopathol. Review*, "Common Variable Immunodeficiency," 29:113-118 (2001).
Janeway and Travers, *Immunobiology: The Immune System in Health and Disease*, Current Biology Ltd./Garland Publishing, London. pp. 12:1-12:19 (1997).
Janeway and Travers. *Immunobiology, The Immune System in Health and Disease*, (Current Biology Ltd./Garland Publishing, London), pp. 1:15, 1:16, 5:28 and 11:19 (1994).
Jiang et al., *Immunogenetics*, "Polymorphism and chromosomal mapping of the mouse gene for B-cell activating factor belonging to the tumor necrosis factor family (Baff) and association with the autoimmune phenotype," 53(9):810-813 (2001).
Kabat et al., *Sequences of Proteins of Immunological Interest*, Fourth Edition, pp. 44, 53-54, 63, 69-70 and 76 (1987).
Kanakaraj et al., *Cytokine*, "BlyS binds to B Cells With High Affinity and Induces Activation of the Transcription Factors NF-$_k$B and Elf-1," 13:25-31 (2001).
Kapas and Krueger, *Amer. J. Physiology*, "Tumor necrosis factor-$\beta$ induces sleep, fever, and anorexia," 263(3):703-707 (1992).
Karpusas et al., *J. Molec. Biol.*, "Crystal Structure of Extracellular Human BAFF, a TNF Family Member that Stimulates B. Lymphocytes," 315(5):1145-1154 (2002).
Kayagaki et al., *Immunity*, "BAFF/BLyS receptor 3 binds the B cell survival factor BAFF ligand through a discrete surface loop and promotes processing of NF-kappaB2," 10:515-24 (2002).
Kehrl et al., *J. Exp. Med.*, "Effect of tumor necrosis factor alpha on mitogen-activated human B cells," 166:786-791 (1987).
Kennell, *Prog. Nucleic Acid. Res. Mol. Biol.*, "Principles and practices of nucleic acid hybridization," 11:259-301 (1971).
Kern, *Blood*, "Involvement of BAFF and APRIL in the resistance to apoptosis of B.CLL through an autocrine pathway," 103(2):679-88 (2004).
Kessel et al., *Clinical and Experimental Immunology*, "Increased susceptibility of cord blood B lymphocytes to undergo spontaneous apoptosis," 145:563-570 (2006).
Khare et al., *PNAS*, "Severe B Cell Hyperplasia and autoimmune disease in TALL-1 transgenic mice," 97:3370-3375 (2000).
Koller and Smithies, *Proc. Natl. Acad. Sci. USA*, "Inactivating the ($\beta_2$-microglobulin locus in mouse embryonic stem cells by homologous recombination," 86: 8932-8935 (1989).
Koo et al., *FEMS Microbiology Letters*, "Cloning of a novel crystal protein gene crylK from *Bacillus thuringiensis* subsp. Morrisoni," 134:159-164 (1995).
Kreitman, *Expert Opn. Biol. Ther.*, "Recombinant Immunotoxins for the Treatment of Hematological Malignancies," 4(7):1115-1128 (2004).
Krumbholz et al., *J. Exp. Med.*, "BAFF is produced by astrocytes and up-regulated in multiple sclerosis lesions and primary central nervous system lymphoma," 201(2):195-200 (2005).
Kwon et al., *J. Biol. Chem.*, "Identification of a Novel Activation-inducible Protein of the Tumor Necrosis Factor Receptor Superfamily and Its Ligand," 274(10): 6056-61 (1999).

Laabi et al., *The EMBO Journal*, "A new gene, BCM, on chromosome 16 is fused to the interleukin 2 gene by a t(4;16)(q26;p13) translocation in a malignant T cell lymphoma," 11:3897-3904 (1992).

Laabi et al., *Nucleic Acids Research*, "The BCMA gene, preferentially expressed during B lymphoid maturation, is bidirectionally transcribed," 22:1147-1154 (1994).

Laabi et al., *Science Magazine*, "Lymphocyte Survival—Ignorane is BlyS," 289:883 (2001).

Lam, *Nature*, "A new type of synthetic peptide library for identifying ligand-binding activity," 354: 82-84 (1991).

Liu et al. *Cell*, "Crystal Structure of sTALL-1 Reveals a Virus-like Assembly of TNF Family Ligands," 108(3):383-394 (2002).

Liu et al., *Nature*, "Ligand Receptor Binding revealed by the TNF family member Tall-1 ," 421 :49-56 (2003).

Looney, *Rheumatology*, "B cells as a therapeutic target in autoimmune diseases other than rheumatoid arthritis," 44 (Suppl. 2): ii13-ii17 (2005).

Lotz et al., *J. Leukoc. Biol.*, "The nerve growth factor/tumor necrosis factor receptor family," 60:1-7 (1996).

Lyu, *Mol. Cancer Ther.* "The rGel/BLyS fusion toxin specifically targets malignant B cells expressing the BlyS receptors Baff-R, TACI, and BCMA," 6(2):460-70 (2007).

MacKay et al., *J. Exp. Med.*, "Mice Transgenic for BAFF Develop Lymphocytic Disorders Along with Autoimmune Manifestations," 190:1697-1710 (1999).

MacKay, *Curr. Dir. Autoimmun.*, "The BAFF/APRIL system: an important player in systemic theumatic diseases," 8:243-65 (2005).

MacKay, *Semin. Immunol.* "The role of the BAFF/APRIL system on T cell function," (5):284-9 (2006).

Madry et al., *International Immunology*, "The characterization of murine BCMA gene defines it as a new member of the tumor necrosis factor receptor superfamily," 10:1693-1702 (1998).

Malvar et al., *Genetics*, "The CCR4 Protein from *Saccharomyces cervisiae* Contains a Leucine-Rich Repeat Region Which Is Required for Its Control of *ADH2* Gene Expression," 132:951-962 (1992).

Marriette et al., 65th Annual American College of Rheumatology Scientific Meeting, "A Role for B Lymphocyte Stimulator (TALL-1, BAFF, Thank, $_z$TNF4) in Sjögren's Syndrome," (Nov. 2001).

Mariette et al., *Annual Rheumatology Discussion*, "The Level of BLyS (BAFF) Correlates With the Titre of Autoantibodies in Human Sjogren's Syndrome," 62:168-171 (2003).

Marsters et al., *Current Biology*, "Interaction of the TNF homologues BlyS and APRIL with the TNF receptor homologues BCMA and TACI," 10:785-788 (2000).

Mauri et al., *Immunity*, "Light, a New member of the TNF Superfamily, and Lymphotoxin a Are Ligands for Herpesvirus Entry Mediator," 8(1): 21-30 (1998).

McGhee, *BMC Pediatr*, "Clinical utility of antinuclear antibody tests in children," 4:13 (2004).

Melchers, *Ann. Rheum. Dis.*, "Actions of BAFF in B cell maturation and its effects on the development of autoimmune disease," 62 Supp. 2:ii25-27 (2003).

Moore, *Clin. Chem.*, "Genetically engineered antibodies," 35(9):1849-53 (1989).

Moore et al., *Science*, "BLyS: Member of the Tumor Necrosis Factor Family and B Lymphocyte Stimulator," 285: 260-263 (1999).

Moreaux, *Blood*, "BAFF and APRIL protect myeloma cells from apoptosis induced by interleukin 6 deprivation and dexamethasone," 103(8):3148-57 (2004).

Morpurgo et al., *Appl. Biochem. Biotechnol.*, "Covalent Modification of Mushroom Tyrosinase with Different Amphiphic Polymers for Pharmaceutical and Biocatalysis Applications," 56:59-72 (1996).

Mukhopadhyay et al., *J. Biol. Chem.*, "Identification and characterization of a novel cytokine, THANK, a TNF Homologue that activates Apoptosis, Nuclear factor-kappaB, and c-Jun NH2-terminal Kinase," 274:15978-15981 (1999).

Nakamura et al., *Immunol. Lett.*, "Mechanisms of cellular cytotoxicity mediated by a recombinant antibody-IL2 fusion protein against human melanoma cells," 39: 91-99 (1994).

Nardelli et al., *Immunobiology*, "Synthesis and release of B-lymphocyte stimulator from myeloid cells," 97:198-204 (2001).

Nardelli et al., *Leukemia and Lymphoma*, "B Lymphocyte Stimulator (BLyS): A Therapeutic Trichotomy for the treatment of B lymphocyte diseases," 43:1367-73 (2002).

Nedwin et al., *J. Immunol.*, "Effect of Interleukin 2. Interferon-y, and Mitogens on the Production of Tumor Necrosis Factors α and β," 135(4): 2492-7 (1985).

Ng et al., *Journal of Immunology*, "B Cell-Activating Factor Belonging to the TNF Family (BAFF)-R is the Principal BAFF Receptor Facilitating BAFF Costimulation of Circulating T and B Cells," 173:807-817 (2004).

Ngo et al., *The Protein Folding Problem and Tertiary Structure Prediction*, "Computational Complexity, Protein Structure Prediction and the Levinthal Paradox," pp. 492-495 (1994).

Nimmanapalli, *Blood*, "The growth factor fusion construct containing B-lymphocyte stimulator (BLyS) and the toxin rGel induces apoptosis specifically in BAFF-R-positive CLL cells," 109(6) 2557-64 (2007).

Novak, *Blood*, "Aberrant expression of B-lymphocyte stimulator by B chronic lymphocytic leukemia cells: a mechanism for survival," 100:2973-9 (2002).

Novak et al., *Blood*, "Expression of BlyS and its receptors in B-cell non-Hodgkin lymphoma: correlation with disease activity and patient outcome," 104(8):2247-53 (2004).

Oren et al., *Nature Struct. Biol.*, "Structural basis of BlyS receptor recognition," 9(4):288-292 (2002).

Otten, *Proc. Natl. Acad. Sci. U.S.A.*, "Nerve growth factor induces growth and differentiation of human B lymphocytes," 86:10059-63 (1989).

Panayi, G.S., *British Journal of Rheumatology*, "The Pathogenesis of Rheumatoid Arthritis: From Molecules to the Whole Patient," 32:533-536 (1993).

Parry et al. *J. Pharmacol. Exp. Therap.*, "Pharmacokinetics and immunological Effects of Exogenously administered Recombinant Human B Lymphocyte Stimulator (BlyS) in Mice," 296:396-404 (2001).

Patel et al., *The Journal of Biological Chemistry*, "Engineering an APRIL-specific B cell maturation antigen," 279:16727-16735 (2003).

Reed et al., *Seminars in Oncology*, "Modulating Apoptosis Pathways in Low Grade B-Cell Malignancies Using Biological Response Modifiers," 29:10-24. (2002).

Roth, *Cell Death Differ.*, "APRIL, a new member of the tumor necrosis family, modulates death ligand-induced apoptosis," 8:403-410 (2001).

Saxon et al., *Immunology*, "Long-term administration of 13-cis retinoic acid in common variable immunodeficiency; circulating interleukin-6 levels, B-cell surface molecule display, and in vitro and in vivo B-cell antibody production," 80(3):477-87 (1993).

Scapini et al., *J. Exp Med.* "G-CSF-stimulated Neutrophils Are a Prominent Source of Functional BLyS," 197(3): 297-302 (2003).

Schaller et al., *Microbiology*, "Characterization of apxIVA, a new RTX determinant of *Actinobacillus pleuropneumoniae*," 145 (pt 8):2105-16 (1999).

Schiemann et al., *Science*, "An essential role for BAFF in the normal development of B cells through a BCMA-independent pathway," 293(5537):2111-2114 (2001).

Scott et al., *Science*, "Searching for Peptide Ligands with an Epitope Library," 249: 386-390(1990).

Schneider et al., *J. Exp. Med.*, "BAFF, a Novel Ligand of the Tumor Necrosis Factor Family, Stimulates B Cell Growth," 189:1747:1756 (1999).

Schwartz et al in "Fundamental Immunology", Paul ed Raven Press, NY. NY., pp. 837 (1989).

Sevach (Fundamental Immunology, Paul ed, Lippincott-Raven Philadelphia, PA, chapter 34, pp. 1089-1125 (1999).

Shanebeck, *Eur. J. Immunol.*, "Regulation of murine B-cell growth and differentiation by CD30 ligand," 25(8):2147-53 (1995).

Shoop et al., *Proceedings of the Twenty-Seventh Annual Hawaii International Conference on System Sciences*, "Automating and Streamlining Inference of Function of Plant ESTs within a Data Analysis System" Extended Abstract (1994).

Shu et al., *J. Leukoc. Bio.*, "TALL-1 is a novel member of the TNF Family that is Down-regulated by Mitogens," 65:680-683 (1999).

Siegel et al., *Nat. Immunol.*, "To B or not to B: TNF family signally in Lymphocytes," 2:577-8 (2001).
Skolnick et al., *Trends Biotechnol.*, "From genes to protein structure and function: novel applications of computational approaches in the genomic era," 18(1):34-9 (2000).
Smith et al., *Principles of Biochemestry: General Aspects*, McGraw-Hill Book Company: New York, pp. 194-195 (1983).
Smith et al. *Nat. Biotechnol.*, "The challenges of genome sequence annotation or 'the devil is in the details,'" 15(12):1222-3 (1997).
Stites and Ten, eds., *Basic and Clinical Immunology*, Chap. 24, pp. 322-334 (1991).
Stohl et al., *Curr. Dir. Autoimmun.*, "Blysfulness does not equal blissfulness in systemic lupus erythematosus: a therapeutic role for BlyS antogonists," 8:289-304 (2005).
Suda et al., *Cell*, "Molecular Cloning and Expression of the Fas Ligand, a Novel Member of the Tumor Necrosis Factor Family," 75(6): 1 169-78 (1993).
Sutherland et al., *Pharmacology and Therapeutics*, "Targeting BAFF: Immunomodulation for autoimmune diseases and lymphomas," 112:774-786 (2006).
Swindell et al. Internet for the Molecular Biologist, Horizon Scientific Press: Portland, pp. 55-149 (1996).
Tai et al., *Cancer Res*, "Role of B-Cell-Activating Factor in the Adhesion and Growth of Human Multiple Myeloma Cells in the Bone Marrow Microenvironment," 66(13): 6675-6682 (2006).
Tesoriero, *Wall Street Journal*, "Drugs in testing show promise for treating lupus," retrieved Dec. 21, 2007 from http://www.post-gazette.com/pf/07023/756127-28.stm.
Thompson et al., *J. Exp. Med.*, "BAFF Binds to the Tumor Necrosis Factor Receptor-like Molecule B Cell Maturation Antigen and Is Important for Maintaining the Peripheral B Cell Population," 192:129-135 (2000).
Thompson et al., *Science*, "BAFF-R, a newly identified TNF receptor that specifically interacts with BAFF," 293(5537):2108-2111 (2001).
Tribouley et al., *Biol. Chem.*, "Characterization of a New member of the TNF Family Expressed on Antigen Presenting Cells," 380:1443-7 (1999).
Tsokos, G.C., *Current Opinion in Rheumatology*, "Lymphocytes, cytokines, inflammation, and immune trafficking," 7:376-383 (1995).
Tuma, *J. Natl. Cancer Inst.*, "Phase I Antibody Risks, Trial Safety Examined," 98(14):956-958 (2006).
Yan et al., *Nature Immunology*, "Identification of a receptor for BlyS demonstrates a crucial role in humoral immunity," 1(1):37-41, (2000).
Vandenberghe et al., *Biochemistry*, "The Primary Structures of the Low-Redox Potential Diheme Cytochromes c from the Phtotrophich Bacteria *Rhodobacter sphaeroides* and *Rhodobacter adriaticus* Reveal a New Structural Family of c-Type Cytochromes," vol. 37: pp. 13075-13081 (1998).
Vaux et al., *J. Clin. Invest.*, "The Buzz about BAFF," 109:17-18 (2002).
Von Bulow and Bram, *Science*, "NF-AT activation induced by a CAML-interacting member of the *tumor* necrosis factor receptor superfamily," 278: 138-141 (1997).
Vorbjev et al., *Nucleosides & Nucleotides*, "Oligonucleotide Conjugated to Linear and Branched High Molecular Weight Polyethylene Glycol as Substrates," 18:2745-2750(1999).
Waldmann, T.A., *Nature Medicine*, "Immunotherapy: Past, Present and Future," 9:269-277 (2003).
Waldschmidt et al., *Science*, "Long live the Mature B Cell—a BAFFling Mystery Resolved," 293:2012-2013 (2001).
Wallach, "TNF Ligands and TNF/NGF Receptor Families" In Cytokine Reference vol. 1: Ligands, eds. Oppenheim and Feldman, Academic Press, pp. 377-411 (2001).
Ware, *J. Exp. Med.*, "April and BAFF connect autoimmunity and cancer," 192:F35-F37 (2000).
Ware, *Cytokine & Growth Factor Reviews*, "The TNF Superfamily," 14:181-184 (2003).
Weinblatt et al., *Arthritis and Rheumatism*, "Methotrexate in rheumatoid arthritis: A five-year prospective multicenter study," 37:1492-1498 (1994).
Wells, *Biochemistry*, "Additivity of mutational effects in proteins," 29(37):8509-17 (1990).
Wiley et al., *Immunity*, "Identification and Characterization of a New Member of the TNF Family that Induces Apoptosis," 3(6): 673-82 (1995).
Williams-Blangero et al., *PNAS*, "Genes on chromosomes 1 and 13 have significant effects on Ascaris infection," 99(8): 5533-5538 (2002).
Winter et al., *Nature*, "Man-made antibodies," 349:293-299 (1991).
Wise et al., *The Journal of Rheumatology*, "Methotrexate in nonrenal lupus and undifferentiated connective tissue disease—a review of 36 patients," 23:1005-1010 (1996).
Wu et al., *J. Biol. Chem.*, "Tumor Necrosis Factor (TNF) Receptor Superfamily Member TACI is a High Affinity Receptor for TNF Family Members APRIL and BlyS," 275:34578-34585 (2000).
Xia et al., *J. Exp. Med.*, "TACI is a TRAF-interacting Receptor for TALL-1, a Tumor Necrosis Factor Family Member involved in B Cell Regulation," 192:137-143 (2000).
Ye et al., *Eur. J. Immunol.*, "BAFF binding to T cell-expressed BAFF-R costimulates T cell proliferation and alloresponses," 34(10):2750-9 (2004).
Yu et al., *Nature Immunol.*, "APRIL and TALL-1 and receptors BCMA and TACI: system for regulating humoral immunity," 1:252-256 (2000).
Zganiacz et al., *J. Clin. Invest.* "TNF-$\alpha$ is a critical negative regulator of type 1 immune activation during intracellular bacterial infection," 113(3):401-413 (2004).
Zhang et al., *J. Immunol.*, "Cutting Edge: A Role for B Lymphocyte Stimulator in Systemic Lupus Erythematosus," 166:6-10 (2001).
Zhou et al., *Blood*, "Therapeutic Potential of Antagonizing BLyS for Chronic Lymphocytic Leukemia," 98(11):808A (2001).
*Arthritis Rheum.*, "The American College of Rheumatology Response Criteria for Systemic Lupus Erythematosus Clinical Trials," 50(11):3418-3426 (2004).
"Guideline on Production and Quality Control of Monoclonal Antibodies and Related Substances", issued by European Medicines Agency on Apr. 5, 2007.
CAT News Release "Cambridge Antibody Technology and Human Genome Sciences Form Alliance in Therapeutic Antibodies" dated Aug. 10, 1999.
CAT News Release "CAT and Human Genome Sciences ("HGSI") Create Major Alliance Dedicated to Developing Human Antibody Therapeutics Against Genomics Targets" dated Mar. 1, 2000.
CAT News Release "Cambridge Antibody Technology Group plc ("CAT") Open Offer & International Offering to Raise £100 Million in a New Share Issue" dated Mar. 7, 2000.
Cat News Release "Cambridge Antibody Technology: Clinical Trials Update" dated Jan. 12, 2004.
CAT News Release "Cambridge Antibody Technology Reports Recent Progress in Licensed Product Candidates" dated Oct. 5, 2005.
HGS Press Release "Cambridge Antibody Technology and Human Genome Sciences Form Alliance in Therapeutic Antibodies" dated Aug. 10, 1999.
HGS Press Release "Human Genome Sciences and Abgenix Enter a Broad Collaboration to Create Fully Human Antibody Therapeutics" dated Dec. 1, 1999.
HGS Press Release "Human Genome Sciences to Initiate Human Clinical Trials of BLyS" dated Jun. 23, 2000.
HGS Press Release "Human Genome Sciences and Medarex Announce Collaboration" dated Jul. 25, 2001.
HGS Press Release "Human Genome Sciences Announces Trial for Treatment of Immunoglobin-A Deficiency" dated Sep. 19, 2001.
International Search Report issued in PCT Application No. PCT/US06/38756, dated Jul. 14, 2008.
International Search Report issued in PCT Application No. PCT/US07/08021, dated Aug. 4, 2008.
Human Genome Sciences Press Release, dated Nov. 1, 2001.
Declaration of Interference 105,485, Paper 1 filed in the United States Patent Office on Aug. 15, 2006.
Order Bd.R 104(c) in Patent Interference 105,485 dated Apr. 19, 2007.
Order Bd.R 104(c) in Patent Interference 105,485 dated Apr. 23, 2007.

Order—Priority times Bd.R. 104(c) in Patent Interference 105,485 dated Apr. 19, 2007.
Decision on Preliminary Motions in Patent Interference 105,485. Filed in the United States Patent Office on Aug. 31, 2007.
Yu Priority Statement in Patent Interference 105,485. Filed in the United States Patent Office on Dec. 1, 2006.
Browning Priority Statement in Patent Interference 105,485. Filed in the United States Patent Office on Dec. 1, 2006.
Browning Amended Priority Statement in Patent Interference 105,485. Filed in the United States Patent Office on Dec. 12, 2006.
Claims involved in Patent Interference 105,485 submitted by Human Genome Sciences . Filed in the United States Patent Office on Aug. 15, 2006.
Browning Notice of Non-filing 135(b) submitted by Biogen, Inc in Patent Interference 105,485. Filed in the United States Patent Office on Nov. 16, 2006.
Browning Observation 1 filed by Biogen, Inc. In Patent Interference 105,485. Filed in the United States Patent Office on Feb. 12, 2007.
Yu reply and Browning Observation on reply in Patent Interference 105,485. Filed in the United States Patent Office on Apr. 16, 2007 and Apr. 30, 2007.
Re-declaration of Interference in Patent Interference 105,485. Filed in the United States Patent Office on Aug. 31, 2007.
Yu Exhibit List submitted by Human Genome Sciences, Inc in Patent Interference 105,485 as of Nov. 28, 2007.
Declaration of Amy Orr dated Nov. 27, 2007 in support of Yu et al. in Patent Interference 105,485.
Declaration of Biegie Lee dated Nov. 27, 2007 in support of Yu et al. in Patent Interference 105,485.
Declaration of David LaFleur dated Nov. 27, 2007 in support of Yu et al. in Patent Interference 105,485.
Declaration of Ding Liu dated Nov. 27, 2007 in support of Yu et al. in Patent Interference 105,485.
Declaration of Ellie Bouffard dated Nov. 27, 2007 in support of Yu et al. in Patent Interference 105,485.
Marked-up Declaration of Dr. Fritz Melchers dated Jan. 16, 2007 in support of Browning et al. in Patent Interference 105,485.
Declaration of Dr. Guo-Liang Yu dated Nov. 27, 2007 in support of Yu et al. in Patent Interference 105,485.
Declaration of Jeffrey Carrell dated Nov. 27, 2007 in support of Yu et al. in Patent Interference 105,485.
Declaration of Krystyna Pieri dated Nov. 27, 2007 in support of Yu et al. in Patent Interference 105,485.
Declaration of Laurie Brewer dated Nov. 28, 2007 in support of Yu et al. in Patent Interference 105,485.
Marked-up Declaration of Dr. Mark S. Schlissel dated Dec. 1, 2006 in support of Browning et al. in Patent Interference 105,485.
Declaration of Meghan Birkholz dated Nov. 27, 2007 in support of Yu et al. in Patent Interference 105,485.
Declaration of Michael Fannon dated Nov. 27, 2007 in support of Yu et al. in Patent Interference 105,485.
Declaration of Dr. Ornella Belvedere dated Nov. 27, 2007 in support of Yu et al. Iin Patent Interference 105,485.
Declaration of Dr. Reinhard Ebner dated Nov. 21, 2007 in support of Yu et al. in Patent Interference 105,485.
Declaration of Scott Conklin dated Nov. 26, 2007 in support of Yu et al. in Patent Interference 105,485.
Declaration of William Derrick dated Nov. 28, 2007 in support of Yu et al. in Patent Interference 105,485.
Second Declaration of Dr. Randolph J. Noelle dated Nov. 28, 2007 in support of Yu et al. in Patent Interference 105,485.
Declaration of Dr. David Hilbert dated Nov. 27, 2007 in support of Yu et al. in Patent Interference 105,485.
Declaration of Dr. Paul Moore dated Nov. 26, 2007 in support of Yu et al. in Patent Interference 105,485.
Transcript of Deposition of Dr. Paul Moore in Patent Interference 105,485 dated Jan. 4, 2008.
Transcript of Deposition of Dr. David Hilbert in Patent Interference 105,485 dated Jan. 5, 2008.
Transcript of Deposition of Jeffrey Carrell in Patent Interference 105,485 dated Feb. 12, 2008.
Transcript of Deposition of Krystyna Pieri in Patent Interference 105,485 dated Feb. 12, 2008.
Transcript of Deposition of Dr. Reinhard Ebner in Patent Interference 105,485 dated Feb. 15, 2008.
Transcript of Deposition of Guo-Liang Yu in Patent Interference 105,485 dated Jan. 4, 2008.
Transcript of Deposition of Amy Orr in Patent Interference 105,485 dated Feb. 22, 2008.
Transcript of Deposition of Dr. Randolph Noelle in Patent Interference 105,485 dated Feb. 26, 2008.
Transcript of Deposition of Eleanor Bouffard in Patent Interference 105,485 dated Feb. 28, 2008.
Application Notice submitted by Human Genome Sciences in support of Human Genome Sciences in UK Revocation suit HC06CO2687 dated Nov. 2, 2006.
International Preliminary Exam Report submitted by Human Genome Sciences in support of Human Genome Sciences in UK Revocation suit HC06CO2687 dated Dec. 20, 1998.
Office communication from European Patent Office submitted by Human Genome Sciences in support of Human Genome Sciences in UK Revocation suit HC06CO2687 dated May 3, 2002.
Human Genome Science's response to Office communication from European Patent Office submitted by Human Genome Sciences in support of Human Genome Sciences in UK Revocation suit HC06CO2687 dated May 30, 2002.
Office communication from European Patent Office submitted by Human Genome Sciences in support of Human Genome Sciences in UK Revocation suit HC06CO2687 dated Jan. 17, 2003.
Human Genome Sciences, Inc response to office communication from European Patent Office submitted by Human Genome Sciences in support of Human Genome Sciences in UK Revocation suit HC06CO2687 dated Jan. 17, 2003.
Office Communication European Patent Office submitted by Human Genome Sciences in support of Human Genome Sciences in UK Revocation suit HC06CO2687 dated Jun. 30, 2004.
Transcript of Examiner Interview dated Oct. 1, 2004 submitted by Human Genome Sciences in support of Human Genome Sciences in UK Revocation suit HC06CO2687.
Human Genome Response to Examiner Interview of Oct. 1, 2004 submitted by Human Genome Sciences in support of Human Genome Sciences in UK Revocation suit HC06CO2687 and dated Oct. 4, 2004.
Office Communication European Patent Office submitted by Human Genome Sciences in support of Human Genome Sciences in UK Revocation suit HC06CO2687 dated Oct. 13, 2004.
Human Genome Sciences, Inc response to office communication from European Patent Office submitted by Human Genome Sciences in support of Human Genome Sciences in UK Revocation suit HC06CO2687 dated Nov. 30, 2004.
Human Genome Sciences amended claims and specification submitted by Human Genome Sciences in support of Human Genome Sciences in UK Revocation suit HC06CO2687 dated Nov. 30, 2004.
Notice of Intent to Grant EP patent No. 0 939 845 submitted by Human Genome Sciences in support of Human Genome Sciences in UK Revocation suit HC06CO2687 dated Jan. 28, 2005.
Human Genome Sciences response to Notice of Intent to Grant submitted by Human Genome Sciences in support of Human Genome Sciences in UK Revocation suit HC06CO2687 dated Jun. 7, 2005.
Transcript of hearing Nov. 8, 2006 in UK Revocation suit HC06CO2687.
Transcript of hearing Nov. 9, 2006 in UK Revocation suit HC06CO2687.
Defendant's civil evidence act notice submitted by Human Genome Sciences in support of Human Genome Sciences in UK Revocation suit HC06CO2687 dated Jun. 1, 2007.
Defendant's civil evidence act notice submitted by Human Genome Sciences in support of Human Genome Sciences in UK Revocation suit HC06CO2687 dated Nov. 29, 2007.
Claimant's civil evidence act notice submitted by Eli Lilly in support of Human Genome Sciences in UK Revocation suit HC06CO2687 dated Jun. 1, 2007.
Defendant's civil evidence act notice submitted by Human Genome Sciences in support of Human Genome Sciences in UK Revocation suit HC06CO2687 dated Dec. 7, 2007.

Claimant's Further Information concerning the statement of opposition submitted by Eli Lilly in UK Revocation suit HC06CO2687 dated May 4, 2007.
Claimant's statement of case relating to SWISS-PROT submitted by Eli Lilly in UK Revocation suit HC06CO2687 dated Nov. 30, 2006.
Claimant's response to defendant's notice of experiments in reply submitted by Eli Lilly in UK Revocation suit HC06CO2687 dated Nov. 30, 2006.
Human Genome Science's response to request to attend oral hearings in UK Revocation suit HC06CO2687 dated Jun. 30, 2004.
Re-reamended grounds of invalidity submitted by Eli Lilly in UK Revocation suit HC06CO2687.
EFPIA website printed Sep. 12, 2007 submitted in UK Revocation suit HC06CO2687.
First Expert Report of Dr. Rolf Apweiler dated May 29, 2007 in support of Eli Lilly in UK Revocation suit HC06CO2687.
Second Expert Report of Dr. Rolf Apweiler dated Jun. 23, 2007 in support of Eli Lilly in UK Revocation suit HC06CO2687.
Fourth Expert Report of Dr. Rolf Apweiler dated Dec. 11, 2007 in support of Eli Lilly in UK Revocation suit HC06CO2687.
Witness Statement of Dr. David E. Cash dated Nov. 14, 2006 in support of Human Genome Sciences in UK Revocation suit HC06CO2687.
Witness Statement of Christa Pennachio dated Apr. 23, 2007 in support of Human Genome Sciences in UK Revocation suit HC06CO2687.
Witness Statement of Christa Pennachio dated May 15, 2007 in support of Eli Lilly in UK Revocation suit HC06CO2687.
Witness Statement of Dr. Stuart Farrow dated Jun. 1, 2007 in support of Human Genome Sciences in UK Revocation suit HC06CO2687.
Witness Statement of Dr. William F. Heath dated Jun. 27, 2007 in support of Eli Lilly in UK Revocation suit HC06CO2687.
First Witness Statement of Mark Hodgson dated Nov. 6, 2007 in support of Eli Lilly in UK Revocation suit HC06CO2687.
Second Witness Statement of Mark Hodgson dated Nov. 7, 2007 in support of Eli Lilly in UK Revocation suit HC06CO2687.
First Expert Report of Dr. Randolph Noelle dated Jun. 1, 2007 in support of Human Genome Sciences in UK Revocation suit HC06CO2687.
Second Expert Report of Dr. Randolph Noelle dated Jun. 22, 2007 in support of Human Genome Sciences in UK Revocation suit HC06CO2687.
First Witness Statement of Dr. Penny X. Gilbert dated Nov. 2, 2006 in support of Human Genome Sciences in UK Revocation suit HC06CO2687.
Second Witness Statement of Dr. Penny X. Gilbert dated Nov. 6, 2006 in support of Human Genome Sciences in UK Revocation suit HC06CO2687.
First Expert Report of Dr. Jeremy Saklatvala dated May 25, 2007 in support of Eli Lilly in UK Revocation suit HC06CO2687.
Second Expert Report of Dr. Jeremy Saklatvala dated Jun. 27, 2007 in support of Eli Lilly in UK Revocation suit HC06CO2687.
Third Expert Report of Dr. Jeremy Saklatvala dated Nov. 23, 2007 in support of Eli Lilly in UK Revocation suit HC06CO2687.
Witness Statement of Simon Mark Wright dated Jun. 6, 2007 in support of Human Genome Sciences in UK Revocation suit HC06CO2687.
Witness Statement of Elisabeth Gasteiger dated Jun. 12, 2007 in support of Human Genome Sciences in UK Revocation suit HC06CO2687.
Declaration of Dr. Thi-Sau Migone dated Jul. 12, 2007 in support of Human Genome Sciences in Opposition of EP Patent No. 1141274.
Second Declaration of Carl F. Ware dated Jan. 28, 2008 in support of Browning et al. in Patent Interference 105,485.
Minutes of Oral Proceedings dated Apr. 2, 2007 in Opposition of Biogen, Inc. Patent EP 1146892.
Biogen Decision dated Nov. 27, 2007 in Opposition of Patent EP 1146892.
Zymogenetics Interlocutory Decision dated Nov. 30, 2007 in Opposition of Patent EP 1141274.
Zymogenetics Preliminary Opinion dated Mar. 15, 2007 in Opposition of Patent EP 1141274.
Extended European Search Report, European Application No. 07 01 2741.0 dated Feb. 8, 2008.
Grounds of Appeal filed by Merck Serono dated Mar. 27, 2008 in Opposition of Patent EP 1 146 892.
Human Genome Sciences Observations on Oppositions to EP 0939804 dated Apr. 2, 2008.
Auxiliary Requests 1-12 submitted by Human Genome Sciences, Inc. in defense of EP Patent No. 0 939 804 dated May 8, 2008.
Eli Lilly's Submission in Opposition of EP Patent No. 0 939 804 including supporting documents D48-D57. Filed in the European Patent Office on Apr. 2, 2008.
Eli Lilly's Submission in Opposition of EP Patent No. 0 939 804 including supporting documents D98-D112. Filed in the European Patent Office on May 30, 2008.
Serono's Opposition of EP Patent No. 0 939 804 including supporting documents D1-D27. Filed in the European Patent Office on May 18, 2006.
Human Genome Science's Observations on the Oppositions against EP Patent No. 0 939 804 including annexes. Filed in the European Patent Office on Apr. 2, 2008.
Declaration of Dr. Andrew Martin and annexes filed in support of Human Genome Science's EP Patent No. 0 939 804 dated Mar. 26, 2008 and filed in the European Patent Office.
Declaration of Dr. David Cash and annexes filed in support of Human Genome Science's Ep Patent No. 0 939 804 dated Mar. 6, 2008 and filed in the European Patent Office.
Declaration of Dr. Randolph Noelle and annexes filed in support of Human Genome Science's EP Patent No. 0 939 804 dated Mar. 23, 2008 and filed in the European Patent Office.
Declaration of Dr. Stuart Farrow and annexes filed in support of Human Genome Science's EP Patent No. 0 939 804 dated Mar. 25, 2008 and filed in the European Patent Office.
Witness statement of Christa Pange Pennacchio and annexes filed in support of Human Genome Science's EP Patent No. 0 939 804 dated Mar. 25, 2008 and filed in the European Patent Office.
List of documents, dated May 29, 2008 in Opposition proceedings against Human Genome Science's EP Patent No. 0 939 804.
Human Genome Science's opposition to Biogen, Inc EP Patent No. 1 146 892 with annexes C15-C25. Filed in the European Patent Office on May 10, 2004.
Serono's opposition to Biogen, Inc EP Patent No. 1 146 892. Filed in the European Patent Office on May 21, 2004.
ZymoGenetics' response to the Oppositions against ZymoGenetics EP Patent No. 1 141 274 filed in the European Patent Office on Jun. 6, 2005.
Human Genome Science's reply to ZymoGenetics' response to the Oppositions against ZymoGenetics EP Patent No. 1 141 274 filed in the European Patent Office on Nov. 4, 2005.
Opposition Division's Preliminary Opinion and annex in the Opposition Proceedings against against ZymoGenetics EP Patent No. 1 141 274 filed in the European Patent Office on Mar. 15, 2007.
Second Declaration of Dr. Andrew Martin filed by Human Genome Sciences in support of HGS EP Patent No. 0 939 804. Filed in the European Patent Office and dated May 7, 2008.
Declaration of Dr. Penny X. Gilbert filed by Human Genome Sciences in support of HGS EP Patent No. 0 939 804. Filed in the European Patent Office and dated May 8, 2008.
Human Genome Sciences Press Release dated Dec. 1, 1999.
Transcript of Deposition of Dr. Randolph Noelle in Patent Interference 105,485 dated Apr. 5, 2007.
Declaration of Henrik Olsen in support of Yu et al. in Patent Interference 105,485 dated Dec. 16, 2007.
Browning opposition and table of content in Patent Interference 105,485. Filed in the United States Patent Office on Feb. 12, 2007.
Yu Exhibit 1200 submitted during the Deposition of Eleanor Bouffard in Patent Interference 105,485 dated Feb. 28, 2008.
Yu Exhibit 1201 submitted during the Deposition of Eleanor Bouffard in Patent Interference 105,485 dated Feb. 28, 2008.
Transcript of a Teleconference in Patent Interference 105,485 dated Feb. 11, 2008.
Claim Form submitted by Eli Lilly and Company requesting revocation of Human Genome Sciences, Inc EP Patent 0 939 804. Filed in the United Kingdom Patent Office on Jul. 5, 2006.

Human Genome Sciences, Inc Defense of EP Patent 0 939 804 filed in the United Kingdom Patent Office on Aug. 3, 2006.
Application to Amend Claims filed by Human Genome Sciences, Inc during UK Revocation suit HC06CO2687 on Feb. 22, 2007.
Approved Judgment by Mr Justice Kitchin in UK Revocation suit HC06CO2687 dated Jul. 31, 2008.
Lexikon der Medizin "Hypertension" filed in Opposition of EP Patent No. 1 146 892 (Filed in the European Patent Office on Sep. 19, 2005).
Sauge-Merle et al., *Eur. J. Biochem.*, "An active ribonucleotide reductase from *Arabidopsis thaliana*: cloning, expression and characterization of the large subunit," 266:62-69 (1999).
Esposito et al., *J. Immunol.*, "Human transaldolase and cross-reactive viral epitopes identified by autoantibodies of multiple sclerosis patients," 163:4027-4032 (1999).
Gruss, *Int. Jour. Clin. Lab. Res.*, "Molecular, structural, and biological characteristics of the tumor necrosis factor ligand superfamily," 26:143-159 (1996).
International Search Report issued in PCT Application No. PCT/US01/25850, dated Apr. 1, 2003.
International Search Report issued in PCT Application No. PCT/US01/25891, dated Apr. 2, 2003.
Alcami et al., *J. Immunol.*, "Blockade of Chemokine Activity by a Soluble Chemokine Binding Protein from Vaccinia Virus," 160:624-633 (1998).
Fleming et al., *J. Mol. Recognit.*, "Discovery of High-Affinity Peptide Binders to BLyS by Phage Display," 18:94-102 (2005).
Sun et al., *Biochem. Biophys. Res. Commun.*, "A Novel BLyS Antagonist Peptide Designed Based on the 3-D Complex Struc ture of BCMA and BLyS," 346:1158-1162 (2006).
Requirement for Restriction/Election issued in U.S. Appl. No. 09/932,613, dated Apr. 8, 2003.
Non-Final Rejection issued in U.S. Appl. No. 09/932,613, dated Jul. 14, 2004.
Final Rejection issued in U.S. Appl. No. 09/932,613, dated Apr. 20, 2005.
Requirement for Restriction/Election issued in U.S. Appl. No. 11/232,439, dated Apr. 24, 2007.
Non-Final Rejection issued in U.S. Appl. No. 11/232,439, dated May 28, 2008.
Final Rejection issued in U.S. Appl. No. 11/232,439, dated May 27, 2009.
Advisory Action issued in U.S. Appl. No. 11/232,439, dated Aug. 14, 2009.
Non-Final Rejection issued in U.S. Appl. No. 11/232,439, dated Nov. 5, 2009.
Requirement for Restriction/Election issued in U.S. Appl. No. 09/932,322, dated Jun. 30, 2004.
Non-Final Rejection issued in U.S. Appl. No. 09/932,322, dated Feb. 9, 2005.
Final Rejection issued in U.S. Appl. No. 09/932,322, dated Aug. 24, 2005.
Notice of Allowance issued in U.S. Appl. No. 09/932,322, dated Feb. 8, 2006.
Han et al., "Characterization of Transformation Function of Cottontail Rabbit Papillomavirus E5 and E8 Genes," *Virology*, 251:253-263 (1998).
Clustal V Alignment of human and mouse TACI filed in Opposition of EP Patent No. 1 141 274 (Filed in the European Patent Office on Jun. 4, 2004).
Browning Demonstrative Exhibits submitted by Biogen, Inc. in Patent Interference 105,485 (Jul. 9, 2007).
Browning motion 2 submitted by Biogen, Inc. in Patent Interference 105,485 (Dec. 1, 2006).
Browning motion 3 submitted by Biogen, Inc. in Patent Interference 105,485 (Dec. 1, 2006).
Browning motion 4 submitted by Biogen, Inc. in Patent Interference 105,485 (Dec. 1, 2006).
Browning motion 5 submitted by Biogen, Inc. in Patent Interference 105,485 (Dec. 1, 2006).
Browning motion 6 submitted by Biogen, Inc. in Patent Interference 105,485 (May 7, 2007).
Browning motion 7 submitted by Biogen, Inc. in Patent Interference 105,485 (Jan. 9, 2008).
Browning motion 8 submitted by Biogen, Inc. in Patent Interference 105,485 (Jan. 28, 2008).
Browning motion 9 submitted by Biogen, Inc. in Patent Interference 105,485 (Jan. 28, 2008).
Browning motion 10 submitted by Biogen, Inc. in Patent Interference 105,485 (Jan. 28, 2008).
Browning reply 2 submitted by Biogen, Inc. in Patent Interference 105,485 (Apr. 16, 2007).
Browning reply 3 submitted by Biogen, Inc. in Patent Interference 105,485 (Apr. 16, 2007).
Browning reply 4 submitted by Biogen, Inc. in Patent Interference 105,485 (Apr. 16, 2007).
Browning reply 5 submitted by Biogen, Inc. in Patent Interference 105,485 (Apr. 16, 2007).
Browning reply 6 submitted by Biogen, Inc. in Patent Interference 105,485 (May 29, 2007).
Yu Demonstrative Exhibits submitted by Human Genome Sciences, Inc. in Patent Interference 105,485 (Jul. 13, 2007).
Yu motion 1 submitted by Human Genome Sciences, Inc. in Patent Interference 105,485 (Nov. 16, 2006).
Yu motion 2 submitted by Human Genome Sciences, Inc. in Patent Interference 105,485 (Dec. 1, 2006).
Yu motion 3 submitted by Human Genome Sciences, Inc. in Patent Interference 105,485 (Apr. 30, 2007).
Yu motion 4 submitted by Human Genome Sciences, Inc. in Patent Interference 105,485 (Nov. 28, 2007).
Yu motion 5 submitted by Human Genome Sciences, Inc. in Patent Interference 105,485 (Nov. 28, 2007).
Yu motion 6 submitted by Human Genome Sciences, Inc. in Patent Interference 105,485 (Jan. 9, 2008).
Yu opposition 2 submitted by Human Genome Sciences, Inc. in Patent Interference 105,485 (Feb. 12, 2007).
Yu opposition 3 submitted by Human Genome Sciences, Inc. in Patent Interference 105,485 (Feb. 12, 2007).
Yu opposition 4 submitted by Human Genome Sciences, Inc. in Patent Interference 105,485 (Feb. 12, 2007).
Yu opposition 5 submitted by Human Genome Sciences, Inc. in Patent Interference 105,485 (Feb. 12, 2007).
Yu opposition 6 submitted by Human Genome Sciences, Inc. in Patent Interference 105,485 (May 21, 2007).
Yu opposition 7 submitted by Human Genome Sciences, Inc. in Patent Interference 105,485 (Jan. 14, 2008).
Defendant's Notice of Experiments in Reply submitted by Human Genome Sciences in support of Human Genome Sciences in UK Revocation suit HC06CO2687 (May 8, 2007).
Work up experiments in relation to Defendant's Notice of Experiments in Reply submitted by Human Genome Sciences in support of Human Genome Sciences in UK Revocation suit HC06CO2687 (May 8, 2007).
Claimant's notice of experiments submitted by Eli Lilly against Human Genome Sciences in UK Revocation suit HC06CO2687 (Feb. 23, 2007).
Defendant's response to claimant's notice of experiments submitted by Human Genome Sciences in support of Human Genome Sciences in UK Revocation suit HC06CO2687 (Mar. 16, 2007).
Alignment of BLyS and Eli Lilly's sequences submitted in UK Revocation suit HC06CO2687 dated Nov. 29, 2007 dated Nov. 29, 2007.
Technician's précis of notice of the notice of experiments submitted in UK Revocation suit HC06CO2687 (Feb. 23, 2007).
Defendant's conditional application to further amend claim 15 submitted by Human Genome Sciences in UK Revocation suit HC06CO2687 (Jan. 2008).
Claimant's grounds for opposition to further amend claim 15 submitted in UK Revocation suit HC06CO2687 (Dec. 14, 2007).
Correspondence between Human Genome Sciences and the United Kingdom Patent Office submitted by Eli Lilly in UK revocation suit HC06CO2687 (feb. 22, 2007).
Defendant's amended response to claimant's request for further information submitted by Human Genome Sciences in UK Revocation suit HC06CO2687 (Apr. 4, 2007).

Defendant's response to claimant's notice to admit submitted in UK Revocation suit HC06CO2687 (Nov. 30, 2006).
Defendant's response to claimant's second request for further information submitted in UK Revocation suit HC06CO2687 (Mar. 30, 2007).
Documents handed up during trial in UK Revocation suit HC06CO2687 (Dec. 2007).
Claims from EP Patent 0 939 804 submitted by Human Genome Sciences in support of Human Genome Sciences in UK Revocation suit HC06CO2687.
Amended claims submitted by Human Genome Sciences in support of Human Genome Sciences in UK Revocation suit HC06CO2687 (Feb. 22, 2007).
Human Genome Science's Opening Arguments in UK Revocation suit HC06CO2687 (Nov. 29, 2007).
Human Genome Science's Closing Arguments in UK Revocation suit HC06CO2687 (Dec. 20, 2007).
Eli Lilly's Opening Arguments in UK Revocation suit HC06CO2687 (Nov. 28, 2007).
Eli Lilly's Closing Arguments in UK Revocation suit HC06CO2687 (Dec. 2007).
Order Confirming Claimant's Undertaking Not to Infringe submitted in UK Revocation suit HC06CO2687 (Nov. 22, 2006).
Order for Directions submitted in UK Revocation suit HC06CO2687 (Sep. 21, 2006).
Order of Mr Justice Pumfrey submitted in UK Revocation suit HC06CO2687 (Apr. 20, 2007).
Order of Mr Justice Warren submitted in UK Revocation suit HC06CO2687 (May 8, 2007).
Particulars of the Claim submitted in UK Revocation suit HC06CO2687 (Jul. 5, 2006).
Statement of Opposition submitted by Eli Lilly in UK Revocation suit HC06CO2687 (Apr. 4, 2007).
Defendant Statement of Reasons to amend the claims of EP Patent No. 0 939 804 submitted by Human Genome Sciences in UK Revocation suit HC06CO2687 (Feb. 22, 2007).
Table of relevant scientific papers submitted in UK Revocation suit HC06CO2687 (Dec. 2007).
Table of selected passages from EP Patent No. 0 939 804 submitted in UK Revocation suit HC06CO2687 (Dec. 2007).
BioTherapeutic Overview submitted in UK Revocation suit HC06CO2687 (Sep. 12, 2007).
Cambridge Antibody Technology website printed Mar. 7, 2007 submitted in UK Revocation suit HC06CO2687.
Eli Lilly website submitted in UK Revocation suit HC06CO2687 (Sep. 12, 2007).
EMEA 2007 Antibody guidelines submitted in UK Revocation suit HC06CO2687 (Apr. 5, 2007).
Wikipedia page submitted by Eli Lilly in UK Revocation suit HC06CO2687 Dec. 2007).
Mobitech website submitted in UK Revocation suit HC06CO2687 (Dec. 2007).
Transcript of trial day 1 of UK Revocation suit HC06CO2687 (Dec. 7, 2007).
Transcript of trial day 2 of UK Revocation suit HC06CO2687 (Dec. 10, 2007).
Transcript of trial day 3 of UK Revocation suit HC06CO2687 (Dec. 11, 2007).
Transcript of trial day 4 of UK Revocation suit HC06CO2687 (Dec. 12, 2007).
Transcript of trial day 5 of UK Revocation suit HC06CO2687 (Dec. 13, 2007).
Transcript of trial day 6 of Uk Revocation suit HC06CO2687 (Dec. 17, 2007).
Transcript of trial day 7 of UK Revocation suit HC06CO2687 (Dec. 18, 2007).
Transcript of trial day 8 of UK Revocation suit HC06CO2687 (Dec. 19, 2007).
Transcript of trial day 9 of UK Revocation suit HC06CO2687 (Dec. 20, 2007).
Transcript of trial day 10 of UK Revocation suit HC06CO2687 (Dec. 21, 2007).
Transcript of trial day 11 of UK Revocation suit HC06CO2687 (Jan. 11, 2008).
Transcript of trial day 12 of UK Revocation suit HC06CO2687 (Jan. 14, 2008).
Transcript of trial day 13 of UK Revocation suit HC06CO2687 (Jan. 15, 2008).
First Expert Report of Dr. Andrew C.R. Martin in support of Human Genome Sciences in UK Revocation suit HC06CO2687 (Jun. 1, 2007).
Second Expert Report of Dr. Andrew C.R. Martin in support of Human Genome Sciences in Uk Revocation suit HC06CO2687 (Jun. 22, 2007).
Human Genome Sciences, Inc Patent in suit as proposed to be amended during UK Revocation suit HC06CO2687 (Dec. 2007).
Agreed Statement of Facts regarding the Image EST submitted in UK Revocation suit HC06CO2687 (Dec. 2007).

```
                        SEQUENCE LISTING

<160> NUMBER OF SEQ ID NOS: 465

<210> SEQ ID NO 1
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Ala, Asn, Lys, or Ser
<220> FEATURE:
<221> NAME/KEY: SITE
<222> LOCATION: (2)..(2)
<223> OTHER INFORMATION: X2 is Ala, Glu, Met, Ser, or Val
<220> FEATURE:
<221> NAME/KEY: SITE
<222> LOCATION: (3)..(3)
<223> OTHER INFORMATION: X3 is Ala, Asn, Lys, or Pro (preferably Lys)
<220> FEATURE:
<221> NAME/KEY: SITE
<222> LOCATION: (5)..(5)
<223> OTHER INFORMATION: X5 is Phe, Trp, or Tyr (preferably Tyr)
<220> FEATURE:
<221> NAME/KEY: SITE
<222> LOCATION: (7)..(7)
<223> OTHER INFORMATION: X7 is Pro or Tyr (preferably Pro)
<220> FEATURE:
<221> NAME/KEY: SITE
<222> LOCATION: (11)..(11)
<223> OTHER INFORMATION: X11 is Ala, Gln, His, Phe, or Val
<220> FEATURE:
<221> NAME/KEY: SITE
<222> LOCATION: (12)..(12)
<223> OTHER INFORMATION: X12 is Asn, Gln, Gly, His, Ser, or Val
<220> FEATURE:
<221> NAME/KEY: SITE
<222> LOCATION: (13)..(13)
<223> OTHER INFORMATION: X13 is Ala, Asn, Gly, Ile, Pro, or Ser,

<400> SEQUENCE: 1

Xaa Xaa Xaa Cys Xaa Phe Xaa Trp Glu Cys Xaa Xaa Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Ala, Asp, Gln, Glu, Gly, His, Ile, Leu,
      Lys, Met, Phe, Pro, Ser, Thr, Trp, Tyr, Val, or is absent
<220> FEATURE:
<221> NAME/KEY: SITE
<222> LOCATION: (2)..(2)
<223> OTHER INFORMATION: X2 is Ala, Asn, Asp, Gln, Gly, His, Ile, Leu,
      Lys, Met, Phe, Pro, Ser, Thr, Trp, Tyr, or Val
<220> FEATURE:
```

```
<221> NAME/KEY: SITE
<222> LOCATION: (3)..(3)
<223> OTHER INFORMATION: X3 is Ala, Arg, Asn, Asp, Gln, Glu, Gly, His,
      Ile, Leu, Lys, Met, Phe, Pro, Ser, Trp, Tyr, or Val (preferably
      Asp)
<220> FEATURE:
<221> NAME/KEY: SITE
<222> LOCATION: (5)..(5)
<223> OTHER INFORMATION: X5 is Asp, Ile, Leu, or Tyr (preferably Asp or
      Leu)
<220> FEATURE:
<221> NAME/KEY: SITE
<222> LOCATION: (6)..(6)
<223> OTHER INFORMATION: X6 is Arg, Asp, Glu, His, Ile, Leu, Lys, Phe,
      Pro, Tyr, or Val (preferably Glu or Leu)
<220> FEATURE:
<221> NAME/KEY: SITE
<222> LOCATION: (7)..(7)
<223> OTHER INFORMATION: X is His, Leu, Lys, or Phe
<220> FEATURE:
<221> NAME/KEY: SITE
<222> LOCATION: (8)..(8)
<223> OTHER INFORMATION: X is Leu, Pro, or Thr
<220> FEATURE:
<221> NAME/KEY: SITE
<222> LOCATION: (9)..(9)
<223> OTHER INFORMATION: X is Arg, Asn, Gly, His, Ile, Lys, Met, or Trp
<220> FEATURE:
<221> NAME/KEY: SITE
<222> LOCATION: (10)..(10)
<223> OTHER INFORMATION: X10 is Ala, Gln, Glu, Gly, His, Ile, Leu, Met,
      Phe, Ser, Trp, Tyr, or Val
<220> FEATURE:
<221> NAME/KEY: SITE
<222> LOCATION: (12)..(12)
<223> OTHER INFORMATION: X12 is Asp, Gln, Glu, Gly, Ile, Leu, Lys, Phe,
      Ser, Trp, Tyr, or Val
<220> FEATURE:
<221> NAME/KEY: SITE
<222> LOCATION: (13)..(13)
<223> OTHER INFORMATION: X13 is Ala, Arg, Asn, Asp, Gln, Glu, Gly, His,
      Leu, Lys, Met, Phe, Pro, Ser, Thr, Trp, Tyr, or Val
<220> FEATURE:
<221> NAME/KEY: SITE
<222> LOCATION: (14)..(14)
<223> OTHER INFORMATION: X14 is Ala, Arg, Asn, Asp, Gln, Glu, Gly, His,
      Ile, Leu, Lys, Phe, Pro, Trp, Tyr, Val, or is absent

<400> SEQUENCE: 2

Xaa Xaa Xaa Cys Xaa Xaa Xaa Xaa Xaa Xaa Cys Xaa Xaa Xaa
1               5                   10

<210> SEQ ID NO 3
<211> LENGTH: 15
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Ala, Arg, Asn, Asp, Leu, Lys, Phe, Pro,
      Ser, or Thr
<220> FEATURE:
<221> NAME/KEY: SITE
<222> LOCATION: (2)..(2)
<223> OTHER INFORMATION: X2 is Asn, Asp, Gln, His, Ile, Lys, Pro, Thr,
      or Trp
<220> FEATURE:
<221> NAME/KEY: SITE
<222> LOCATION: (3)..(3)
<223> OTHER INFORMATION: X3 is Ala, Arg, Asn, Gln, Glu, His, Phe, Pro,
      or Thr (preferably Ala)
<220> FEATURE:
<221> NAME/KEY: SITE
<222> LOCATION: (5)..(5)
<223> OTHER INFORMATION: X5 is Asn, Asp, Pro, Ser, or Thr (preferably
      Asp)
```

```
<220> FEATURE:
<221> NAME/KEY: SITE
<222> LOCATION: (6)..(6)
<223> OTHER INFORMATION: X6 is Arg, Asp, Ile, Leu, Met, Pro, or Val
      (preferably Ile)
<220> FEATURE:
<221> NAME/KEY: SITE
<222> LOCATION: (7)..(7)
<223> OTHER INFORMATION: X7 is Ala, Ile, Leu , Pro, Thr, or Val
      (preferably Val or Leu)
<220> FEATURE:
<221> NAME/KEY: SITE
<222> LOCATION: (8)..(8)
<223> OTHER INFORMATION: X8 is Asn, His, Ile, Leu, Lys, Phe, or Thr
      (preferably Thr)
<220> FEATURE:
<221> NAME/KEY: SITE
<222> LOCATION: (9)..(9)
<223> OTHER INFORMATION: X9 is Asn, Glu, Gly, His, Leu, Lys, Met, Pro,
      or Thr (preferably Leu)
<220> FEATURE:
<221> NAME/KEY: SITE
<222> LOCATION: (10)..(10)
<223> OTHER INFORMATION: X10 is Arg, Asn, Asp, Gln, Glu, Gly, Ile, Lys,
      Met, Pro, Ser, or Trp
<220> FEATURE:
<221> NAME/KEY: SITE
<222> LOCATION: (11)..(11)
<223> OTHER INFORMATION: X11 is Arg, Glu, Gly, Lys, Phe, Ser, Trp, or
      Tyr (preferably Ser)
<220> FEATURE:
<221> NAME/KEY: SITE
<222> LOCATION: (13)..(13)
<223> OTHER INFORMATION: X13 is Gln, Glu, Ile, Leu, Phe, Pro, Ser, Tyr,
      or Val (preferably Val)
<220> FEATURE:
<221> NAME/KEY: SITE
<222> LOCATION: (14)..(14)
<223> OTHER INFORMATION: X14 is Asn, Gly, Ile, Phe, Pro, Thr, Trp, or
      Tyr
<220> FEATURE:
<221> NAME/KEY: SITE
<222> LOCATION: (15)..(15)
<223> OTHER INFORMATION: X15 is Asn, Asp, Glu, Leu, Lys, Met, Pro, or
      Thr (preferably Glu or Pro),

<400> SEQUENCE: 3

Xaa Xaa Xaa Cys Xaa Xaa Xaa Xaa Xaa Xaa Xaa Cys Xaa Xaa Xaa
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Asn, Asp, His, Leu, Phe, Pro, Ser, Tyr,
      or is absent (preferably Ser)
<220> FEATURE:
<221> NAME/KEY: SITE
<222> LOCATION: (2)..(2)
<223> OTHER INFORMATION: X2 is Arg, Asn, Asp, His, Phe, Ser, or Trp
      (preferably Arg)
<220> FEATURE:
<221> NAME/KEY: SITE
<222> LOCATION: (3)..(3)
<223> OTHER INFORMATION: X3 is Asn, Asp, Leu, Pro, Ser, or Val
      (preferably Asn or Asp)
<220> FEATURE:
<221> NAME/KEY: SITE
<222> LOCATION: (5)..(5)
<223> OTHER INFORMATION: X5 is Asp, Gln, His, Ile, Leu, Lys, Met, Phe,
      or Thr
<220> FEATURE:
<221> NAME/KEY: SITE
```

```
<222> LOCATION: (6)..(6)
<223> OTHER INFORMATION: X6 is His, Ile, Leu, Met, Phe, Pro, Trp, or Tyr
<220> FEATURE:
<221> NAME/KEY: SITE
<222> LOCATION: (7)..(7)
<223> OTHER INFORMATION: X7 is Asp, His, Leu, or Ser (preferably Asp)
<220> FEATURE:
<221> NAME/KEY: SITE
<222> LOCATION: (8)..(8)
<223> OTHER INFORMATION: X8 is Ala, Arg, Asp, Glu, Leu, Phe, Pro, or
      Thr (preferably Glu or Pro)
<220> FEATURE:
<221> NAME/KEY: SITE
<222> LOCATION: (9)..(9)
<223> OTHER INFORMATION: X9 is Ala, Arg, Asn, or Leu (preferably Leu)
<220> FEATURE:
<221> NAME/KEY: SITE
<222> LOCATION: (10)..(10)
<223> OTHER INFORMATION: X10 is Ile, Leu, Met, Pro, Ser, or Thr
      (preferably Thr)
<220> FEATURE:
<221> NAME/KEY: SITE
<222> LOCATION: (11)..(11)
<223> OTHER INFORMATION: X11 is Ala, Arg, Asn, Gly, His, Lys, Ser, or
      Tyr
<220> FEATURE:
<221> NAME/KEY: SITE
<222> LOCATION: (12)..(12)
<223> OTHER INFORMATION: X12 is Ala, Arg, Asn, Gln, Leu, Met, Ser, Trp,
      Tyr, or Val
<220> FEATURE:
<221> NAME/KEY: SITE
<222> LOCATION: (14)..(14)
<223> OTHER INFORMATION: X14 is Asp, Gly, Leu, Phe, Tyr, or Val
      (preferably Leu)
<220> FEATURE:
<221> NAME/KEY: SITE
<222> LOCATION: (15)..(15)
<223> OTHER INFORMATION: X15 is Asn, His, Leu, Pro, or Tyr (preferably
      His, Leu or Pro)
<220> FEATURE:
<221> NAME/KEY: SITE
<222> LOCATION: (16)..(16)
<223> OTHER INFORMATION: X16 is Asn, Asp, His, Phe, Ser, or Tyr,
      (preferably Asp or Ser)

<400> SEQUENCE: 4

Xaa Xaa Xaa Cys Xaa Xaa Xaa Xaa Xaa Xaa Xaa Xaa Cys Xaa Xaa Xaa
1               5                   10                  15

<210> SEQ ID NO 5
<211> LENGTH: 18
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Arg, Asp, Gly, His, Leu, Phe, Pro, Ser,
      Trp, Tyr, or is absent (preferably Arg)
<220> FEATURE:
<221> NAME/KEY: SITE
<222> LOCATION: (2)..(2)
<223> OTHER INFORMATION: X2 is Ala, Arg, Asn, Asp, Gly, Pro, Ser, or
      is absent (preferably Asn, Asp, Gly, or Pro)
<220> FEATURE:
<221> NAME/KEY: SITE
<222> LOCATION: (3)..(3)
<223> OTHER INFORMATION: X3 is Arg, Asn, Gln, Glu, Gly, Lys, Met, Pro,
      Trp or Val (preferably Gly or Met)
<220> FEATURE:
<221> NAME/KEY: SITE
<222> LOCATION: (5)..(5)
<223> OTHER INFORMATION: X5 is Arg, Asn, Gln, Glu, His, Leu, Phe, Pro,
      Trp, Tyr, or Val (preferably Trp, Tyr, or Val)
<220> FEATURE:
<221> NAME/KEY: SITE
```

```
<222> LOCATION: (6)..(6)
<223> OTHER INFORMATION: X6 is Arg, Asp, Gln, Gly, Ile, Lys, Phe, Thr,
      Trp, or Tyr (preferably Asp)
<220> FEATURE:
<221> NAME/KEY: SITE
<222> LOCATION: (7)..(7)
<223> OTHER INFORMATION: X7 is Ala, Arg, Asp, Glu, Gly, Leu, Ser, or
      Tyr (preferably Asp)
<220> FEATURE:
<221> NAME/KEY: SITE
<222> LOCATION: (8)..(8)
<223> OTHER INFORMATION: X8 is Asp, Gln, Glu, Leu, Met, Phe, Pro, Ser,
      or Tyr (preferably Leu)
<220> FEATURE:
<221> NAME/KEY: SITE
<222> LOCATION: (9)..(9)
<223> OTHER INFORMATION: X9 is Asp, Leu, Pro, Thr, or Val (preferably
      Leu or Thr)
<220> FEATURE:
<221> NAME/KEY: SITE
<222> LOCATION: (10)..(10)
<223> OTHER INFORMATION: X10 is Arg, Gln, His, Ile, Leu, Lys, Met, Phe,
      Thr, Trp, or Tyr (preferably Lys or Thr)
<220> FEATURE:
<221> NAME/KEY: SITE
<222> LOCATION: (11)..(11)
<223> OTHER INFORMATION: X11 is Ala, Arg, Asn, Gln, Glu, His, Leu, Lys,
      Met, or Thr (preferably Arg or Leu)
<220> FEATURE:
<221> NAME/KEY: SITE
<222> LOCATION: (12)..(12)
<223> OTHER INFORMATION: X12 is Ala, Asn, Gln, Gly, Leu, Lys, Phe, Pro,
      Thr, Trp, or Tyr (preferably Thr or Trp)
<220> FEATURE:
<221> NAME/KEY: SITE
<222> LOCATION: (13)..(13)
<223> OTHER INFORMATION: X13 is Ala, Arg, Gln, His, Lys, Met, Phe, Pro,
      Thr, Trp, or Tyr (preferably Met or Phe)
<220> FEATURE:
<221> NAME/KEY: SITE
<222> LOCATION: (14)..(14)
<223> OTHER INFORMATION: X14 is Arg, Gln, Glu, Gly, His, Leu, Met, Phe,
      Pro, Ser, Thr, Tyr, or Val (preferably Val)
<220> FEATURE:
<221> NAME/KEY: SITE
<222> LOCATION: (16)..(16)
<223> OTHER INFORMATION: X16 is Arg, Asp, Gly, His, Lys, Met, Phe, Pro,
      Ser, or Trp (preferably Met)
<220> FEATURE:
<221> NAME/KEY: SITE
<222> LOCATION: (17)..(17)
<223> OTHER INFORMATION: X17 is Arg, Asn, Asp, Gly, His, Phe, Pro, Ser,
      Trp, or Tyr (preferably Arg, His, or Tyr)
<220> FEATURE:
<221> NAME/KEY: SITE
<222> LOCATION: (18)..(18)
<223> OTHER INFORMATION: X18 is Ala, Arg, Asn, Asp, His, Leu, Phe, or
      Trp (preferably His or Asn),

<400> SEQUENCE: 5

Xaa Xaa Xaa Cys Xaa Xaa Xaa Xaa Xaa Xaa Xaa Xaa Xaa Xaa Cys Xaa
1               5                   10                  15

Xaa Xaa

<210> SEQ ID NO 6
<211> LENGTH: 12
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Ala, Arg, Gly, His, Leu, Lys, Met, Phe,
      Trp, Tyr, or Val (preferably Gly, Tyr, or Val)
<220> FEATURE:
<221> NAME/KEY: SITE
```

```
<222> LOCATION: (2)..(2)
<223> OTHER INFORMATION: X2 is Ala, Arg, Gln, His, Ile, Leu, Phe, Thr,
      Trp, or Tyr (preferably His or Tyr)
<220> FEATURE:
<221> NAME/KEY: SITE
<222> LOCATION: (3)..(3)
<223> OTHER INFORMATION: X3 is Ala, Asp, Lys, Phe, Thr, Trp or Tyr
      (preferably Asp or Tyr)
<220> FEATURE:
<221> NAME/KEY: SITE
<222> LOCATION: (4)..(4)
<223> OTHER INFORMATION: X4 is Arg, Asp, Gln, Lys, Met, Phe, Pro, Ser,
      Tyr, or Val (preferably Asp or Gln)
<220> FEATURE:
<221> NAME/KEY: SITE
<222> LOCATION: (5)..(5)
<223> OTHER INFORMATION: X5 is Asp, Leu, Lys, Phe, Pro, Ser, or Val
      (preferably Leu or Ser)
<220> FEATURE:
<221> NAME/KEY: SITE
<222> LOCATION: (6)..(6)
<223> OTHER INFORMATION: X6 is His, Ile, Leu, Pro, Ser, or Thr
      (preferably Leu or Thr)
<220> FEATURE:
<221> NAME/KEY: SITE
<222> LOCATION: (7)..(7)
<223> OTHER INFORMATION: X7 is Arg, Gly, His, Leu, Lys, Met, or Thr
      (preferably Lys or Thr)
<220> FEATURE:
<221> NAME/KEY: SITE
<222> LOCATION: (8)..(8)
<223> OTHER INFORMATION: X8 is Ala, Arg, Asn, Ile, Leu, Lys, Met, or
      Thr (preferably Leu or Lys)
<220> FEATURE:
<221> NAME/KEY: SITE
<222> LOCATION: (9)..(9)
<223> OTHER INFORMATION: X9 is Ala, Asn, Arg, Asp, Glu, Gly, His, Leu,
      Met, Ser, Trp, Tyr, or Val (preferably Met or Ser)
<220> FEATURE:
<221> NAME/KEY: SITE
<222> LOCATION: (10)..(10)
<223> OTHER INFORMATION: X10 is Ile, Leu, Phe, Ser, Thr, Trp, Tyr, or
      Val (preferably Thr or Leu)
<220> FEATURE:
<221> NAME/KEY: SITE
<222> LOCATION: (11)..(11)
<223> OTHER INFORMATION: X11 is Ala, Arg, Gly, His, Ile, Leu, Lys, Pro,
      Ser, Thr, Trp, Tyr, or Val (preferably Pro or Thr)
<220> FEATURE:
<221> NAME/KEY: SITE
<222> LOCATION: (12)..(12)
<223> OTHER INFORMATION: X12 is Arg, Asp, His, Leu, Lys, Met, Phe, Pro,
      Ser, Trp, Tyr, or Val (preferably Arg or Pro),

<400> SEQUENCE: 6

Xaa Xaa Xaa Xaa Xaa Xaa Xaa Xaa Xaa Xaa Xaa Xaa
1               5                   10

<210> SEQ ID NO 7
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Asp, Gln, Glu, Gly, His, Lys, Met, or
      Trp (preferably Glu, Lys)
<220> FEATURE:
<221> NAME/KEY: SITE
<222> LOCATION: (2)..(2)
<223> OTHER INFORMATION: X2 is Arg, Gln, His, Ile, Leu, or Pro
      (preferably His or Pro)
<220> FEATURE:
<221> NAME/KEY: SITE
<222> LOCATION: (3)..(3)
<223> OTHER INFORMATION: X3 is Asp, Gly, Ile, Lys, Thr, Tyr or Val
```

```
              (preferably Tyr)
<220> FEATURE:
<221> NAME/KEY: SITE
<222> LOCATION: (4)..(4)
<223> OTHER INFORMATION: X4 is Asn, Asp, Gln, Glu, Met, Pro, Ser, or
      Tyr (preferably Asp or Gln)
<220> FEATURE:
<221> NAME/KEY: SITE
<222> LOCATION: (5)..(5)
<223> OTHER INFORMATION: X5 is Asn, Asp, His, Ile, Leu, Met, Pro, Thr
      or Val (preferably Asn or Thr)
<220> FEATURE:
<221> NAME/KEY: SITE
<222> LOCATION: (6)..(6)
<223> OTHER INFORMATION: X6 is Asp, Glu, His, Leu, Lys, Pro, or Val
      (preferably Asp or Pro)
<220> FEATURE:
<221> NAME/KEY: SITE
<222> LOCATION: (7)..(7)
<223> OTHER INFORMATION: X7 is Arg, Asn, Gln, His, Ile, Leu, Met, Pro,
      or Thr (preferably Ile or Pro)
<220> FEATURE:
<221> NAME/KEY: SITE
<222> LOCATION: (8)..(8)
<223> OTHER INFORMATION: X8 is Gln, Gly, His, Leu, Met, Ser, or Thr
      (preferably Leu or Thr)
<220> FEATURE:
<221> NAME/KEY: SITE
<222> LOCATION: (9)..(9)
<223> OTHER INFORMATION: X9 is Asn, Gln, Gly, His, Leu, Lys, Ser, or
      Thr (preferably Lys)
<220> FEATURE:
<221> NAME/KEY: SITE
<222> LOCATION: (10)..(10)
<223> OTHER INFORMATION: X10 is Ala, Gly, Ile, Leu, Lys, Met, or Phe
      (preferably Gly or Met)
<220> FEATURE:
<221> NAME/KEY: SITE
<222> LOCATION: (11)..(11)
<223> OTHER INFORMATION: X11 is Ala, Glu, His, Ile, Leu, Met, Ser, Thr,
      Trp, Tyr, or Val (preferably Ala or Thr)
<220> FEATURE:
<221> NAME/KEY: SITE
<222> LOCATION: (12)..(12)
<223> OTHER INFORMATION: X12 is Arg, Gln, Glu, Gly, His, Ile, Lys, Tyr,
      or Val (preferably Arg or His)
<220> FEATURE:
<221> NAME/KEY: SITE
<222> LOCATION: (13)..(13)
<223> OTHER INFORMATION: X13 is Arg, Asn, Glu, His, Ile, Ser, Thr, Trp,
      or Val (preferably His),

<400> SEQUENCE: 7

Xaa Xaa Xaa Xaa Xaa Xaa Xaa Xaa Xaa Xaa Xaa Xaa Xaa
1               5                   10

<210> SEQ ID NO 8
<211> LENGTH: 7
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (2)..(2)
<223> OTHER INFORMATION: X2 is Phe, Trp, or Tyr (preferably Tyr)
<220> FEATURE:
<221> NAME/KEY: SITE
<222> LOCATION: (4)..(4)
<223> OTHER INFORMATION: X4 is Pro or Tyr (preferably Pro)

<400> SEQUENCE: 8

Cys Xaa Phe Xaa Trp Glu Cys
1               5

<210> SEQ ID NO 9
```

```
<211> LENGTH: 8
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (2)..(2)
<223> OTHER INFORMATION: X2 is Asp, Ile, Leu, or Tyr (preferably Asp or
      Leu)
<220> FEATURE:
<221> NAME/KEY: SITE
<222> LOCATION: (3)..(3)
<223> OTHER INFORMATION: X3 is Arg, Asp, Glu, His, Ile, Leu, Lys, Phe,
      Pro, Tyr, or Val (preferably Glu or Leu)
<220> FEATURE:
<221> NAME/KEY: SITE
<222> LOCATION: (4)..(4)
<223> OTHER INFORMATION: X4 is His, Leu, Lys, or Phe (preferably His or
      Leu)
<220> FEATURE:
<221> NAME/KEY: SITE
<222> LOCATION: (5)..(5)
<223> OTHER INFORMATION: X5 is Leu, Pro, or Thr (preferably Thr or Pro)
<220> FEATURE:
<221> NAME/KEY: SITE
<222> LOCATION: (6)..(6)
<223> OTHER INFORMATION: X6 is Arg, Asn, Gly, His, Ile, Lys, Met, or
      Trp (preferably Lys)
<220> FEATURE:
<221> NAME/KEY: SITE
<222> LOCATION: (7)..(7)
<223> OTHER INFORMATION: X7 is Ala, Asn, Gln, Glu, Gly, His, Ile, Leu,
      Met, Phe, Ser, Trp, Tyr, or Val

<400> SEQUENCE: 9

Cys Xaa Xaa Xaa Xaa Xaa Xaa Cys
1               5

<210> SEQ ID NO 10
<211> LENGTH: 9
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (2)..(2)
<223> OTHER INFORMATION: X2 is Asn, Asp, Pro, Ser, or Thr (preferably
      Asp)
<220> FEATURE:
<221> NAME/KEY: SITE
<222> LOCATION: (3)..(3)
<223> OTHER INFORMATION: X3 is Arg, Asp, Ile, Leu, Met, Pro, or Val
      (preferably Ile)
<220> FEATURE:
<221> NAME/KEY: SITE
<222> LOCATION: (4)..(4)
<223> OTHER INFORMATION: X4 is Ala, Ile, Leu , Pro, Thr, or Val
      (preferably Val or Leu)
<220> FEATURE:
<221> NAME/KEY: SITE
<222> LOCATION: (5)..(5)
<223> OTHER INFORMATION: X5 is Asn, His, Ile, Leu, Lys, Phe, or Thr
      (preferably Thr)
<220> FEATURE:
<221> NAME/KEY: SITE
<222> LOCATION: (6)..(6)
<223> OTHER INFORMATION: X6 is Asn, Glu, Gly, His, Leu, Lys, Met, Pro,
      or Thr (preferably Leu)
<220> FEATURE:
<221> NAME/KEY: SITE
<222> LOCATION: (7)..(7)
<223> OTHER INFORMATION: X7 is Arg, Asn, Asp, Gln, Glu, Gly, Ile, Lys,
      Met, Pro, Ser, or Trp
<220> FEATURE:
<221> NAME/KEY: SITE
<222> LOCATION: (8)..(8)
```

```
<223> OTHER INFORMATION: X8 is Arg, Glu, Gly, Lys, Phe, Ser, Trp, or
      Tyr (preferably Ser)

<400> SEQUENCE: 10

Cys Xaa Xaa Xaa Xaa Xaa Xaa Xaa Cys
1               5

<210> SEQ ID NO 11
<211> LENGTH: 10
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (2)..(2)
<223> OTHER INFORMATION: X2 is Asp, Gln, His, Ile, Leu, Lys, Met, Phe,
      or Thr
<220> FEATURE:
<221> NAME/KEY: SITE
<222> LOCATION: (3)..(3)
<223> OTHER INFORMATION: X3 is His, Ile, Leu, Met, Phe, Pro, Trp, or
      Tyr
<220> FEATURE:
<221> NAME/KEY: SITE
<222> LOCATION: (4)..(4)
<223> OTHER INFORMATION: X4 is Asp, His, Leu, or Ser (preferably Asp)
<220> FEATURE:
<221> NAME/KEY: SITE
<222> LOCATION: (5)..(5)
<223> OTHER INFORMATION: X5 is Ala, Arg, Asp, Glu, Leu, Phe, Pro, or
      Thr (preferably Glu or Pro)
<220> FEATURE:
<221> NAME/KEY: SITE
<222> LOCATION: (6)..(6)
<223> OTHER INFORMATION: X6 is Ala, Arg, Asn, or Leu (preferably Leu)
<220> FEATURE:
<221> NAME/KEY: SITE
<222> LOCATION: (7)..(7)
<223> OTHER INFORMATION: X7 is Ile, Leu, Met, Pro, Ser, or Thr
      (preferably Thr)
<220> FEATURE:
<221> NAME/KEY: SITE
<222> LOCATION: (8)..(8)
<223> OTHER INFORMATION: X8 is Ala, Arg, Asn, Gly, His, Lys, Ser, or
      Tyr
<220> FEATURE:
<221> NAME/KEY: SITE
<222> LOCATION: (9)..(9)
<223> OTHER INFORMATION: X9 is Ala, Arg, Asn, Gln, Leu, Met, Ser, Trp,
      Tyr, or Val

<400> SEQUENCE: 11

Cys Xaa Xaa Xaa Xaa Xaa Xaa Xaa Xaa Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (2)..(2)
<223> OTHER INFORMATION: X2 is Arg, Asn, Gln, Glu, His, Leu, Phe, Pro,
      Trp, Tyr, or Val (preferably Trp, Tyr, or Val)
<220> FEATURE:
<221> NAME/KEY: SITE
<222> LOCATION: (3)..(3)
<223> OTHER INFORMATION: X3 is Arg, Asp, Gln, Gly, Ile, Lys, Phe, Thr,
      Trp or Tyr (preferably Asp)
<220> FEATURE:
<221> NAME/KEY: SITE
<222> LOCATION: (4)..(4)
<223> OTHER INFORMATION: X4 is Ala, Arg, Asp, Glu, Gly, Leu, Ser, or
```

```
             Tyr (preferably Asp)
<220> FEATURE:
<221> NAME/KEY: SITE
<222> LOCATION: (5)..(5)
<223> OTHER INFORMATION: X5 is Asp, Gln, Glu, Leu, Met, Phe, Pro, Ser,
      or Tyr (preferably Leu)
<220> FEATURE:
<221> NAME/KEY: SITE
<222> LOCATION: (6)..(6)
<223> OTHER INFORMATION: X6 is Asp, Leu, Pro, Thr, or Val (preferably
      Leu or Thr)
<220> FEATURE:
<221> NAME/KEY: SITE
<222> LOCATION: (7)..(7)
<223> OTHER INFORMATION: X7 is Arg, Gln, His, Ile, Leu, Lys, Met, Phe,
      Thr, Trp or Tyr (preferably Lys or Thr)
<220> FEATURE:
<221> NAME/KEY: SITE
<222> LOCATION: (8)..(8)
<223> OTHER INFORMATION: X8 is Ala, Arg, Asn, Gln, Glu, His, Leu, Lys,
      Met, or Thr (preferably Arg or Leu)
<220> FEATURE:
<221> NAME/KEY: SITE
<222> LOCATION: (9)..(9)
<223> OTHER INFORMATION: X9 is Ala, Asn, Gln, Gly, Leu, Lys, Phe, Pro,
      Thr, Trp, or Tyr (preferably Thr or Trp)
<220> FEATURE:
<221> NAME/KEY: SITE
<222> LOCATION: (10)..(10)
<223> OTHER INFORMATION: X10 is Ala, Arg, Gln, His, Lys, Met, Phe, Pro,
      Thr, Trp, or Tyr (preferably Met or Phe)
<220> FEATURE:
<221> NAME/KEY: SITE
<222> LOCATION: (11)..(11)
<223> OTHER INFORMATION: X11 is Arg, Gln, Glu, Gly, His, Leu, Met, Phe,
      Pro, Ser, Thr, Tyr, or Val (preferably Val)

<400> SEQUENCE: 12

Cys Xaa Xaa Xaa Xaa Xaa Xaa Xaa Xaa Xaa Cys
1               5                   10

<210> SEQ ID NO 13
<211> LENGTH: 8
<212> TYPE: PRT
<213> ORGANISM: Artificial Sequence
<220> FEATURE:
<223> OTHER INFORMATION: c-terminal linker

<400> SEQUENCE: 13

Pro Gly Pro Glu Gly Gly Gly Lys
1               5

<210> SEQ ID NO 14
<211> LENGTH: 12
<212> TYPE: PRT
<213> ORGANISM: Artificial Sequence
<220> FEATURE:
<223> OTHER INFORMATION: phage display library template
<220> FEATURE:
<221> NAME/KEY: SITE
<222> LOCATION: (1)..(3)
<223> OTHER INFORMATION: X is any amino acid except Cys
<220> FEATURE:
<221> NAME/KEY: SITE
<222> LOCATION: (5)..(8)
<223> OTHER INFORMATION: X is any amino acid except Cys
<220> FEATURE:
<221> NAME/KEY: SITE
<222> LOCATION: (10)..(12)
<223> OTHER INFORMATION: X is any amino acid except Cys

<400> SEQUENCE: 14

Xaa Xaa Xaa Cys Xaa Xaa Xaa Xaa Cys Xaa Xaa Xaa
1               5                   10
```

```
<210> SEQ ID NO 15
<211> LENGTH: 13
<212> TYPE: PRT
<213> ORGANISM: Artificial Sequence
<220> FEATURE:
<223> OTHER INFORMATION: phage display library template
<220> FEATURE:
<221> NAME/KEY: SITE
<222> LOCATION: (1)..(3)
<223> OTHER INFORMATION: X is any amino acid except Cys
<220> FEATURE:
<221> NAME/KEY: SITE
<222> LOCATION: (5)..(9)
<223> OTHER INFORMATION: X is any amino acid except Cys
<220> FEATURE:
<221> NAME/KEY: SITE
<222> LOCATION: (11)..(13)
<223> OTHER INFORMATION: X is any amino acid except Cys

<400> SEQUENCE: 15

Xaa Xaa Xaa Cys Xaa Xaa Xaa Xaa Xaa Cys Xaa Xaa Xaa
 1               5                  10

<210> SEQ ID NO 16
<211> LENGTH: 14
<212> TYPE: PRT
<213> ORGANISM: Artificial Sequence
<220> FEATURE:
<223> OTHER INFORMATION: phage display library template
<220> FEATURE:
<221> NAME/KEY: SITE
<222> LOCATION: (1)..(3)
<223> OTHER INFORMATION: X is any amino acid except Cys
<220> FEATURE:
<221> NAME/KEY: SITE
<222> LOCATION: (5)..(10)
<223> OTHER INFORMATION: X is any amino acid except Cys
<220> FEATURE:
<221> NAME/KEY: SITE
<222> LOCATION: (12)..(14)
<223> OTHER INFORMATION: X is any amino acid except Cys

<400> SEQUENCE: 16

Xaa Xaa Xaa Cys Xaa Xaa Xaa Xaa Xaa Xaa Cys Xaa Xaa Xaa
 1               5                  10

<210> SEQ ID NO 17
<211> LENGTH: 15
<212> TYPE: PRT
<213> ORGANISM: Artificial Sequence
<220> FEATURE:
<223> OTHER INFORMATION: phage display library template
<220> FEATURE:
<221> NAME/KEY: SITE
<222> LOCATION: (1)..(3)
<223> OTHER INFORMATION: X is any amino acid except Cys
<220> FEATURE:
<221> NAME/KEY: SITE
<222> LOCATION: (5)..(11)
<223> OTHER INFORMATION: X is any amino acid except Cys
<220> FEATURE:
<221> NAME/KEY: SITE
<222> LOCATION: (13)..(15)
<223> OTHER INFORMATION: X is any amino acid except Cys

<400> SEQUENCE: 17

Xaa Xaa Xaa Cys Xaa Xaa Xaa Xaa Xaa Xaa Xaa Cys Xaa Xaa Xaa
 1               5                  10                  15

<210> SEQ ID NO 18
<211> LENGTH: 16
<212> TYPE: PRT
<213> ORGANISM: Artificial Sequence
```

```
<220> FEATURE:
<223> OTHER INFORMATION: phage display library template
<220> FEATURE:
<221> NAME/KEY: SITE
<222> LOCATION: (1)..(3)
<223> OTHER INFORMATION: X is any amino acid except Cys
<220> FEATURE:
<221> NAME/KEY: SITE
<222> LOCATION: (5)..(12)
<223> OTHER INFORMATION: X is any amino acid except Cys
<220> FEATURE:
<221> NAME/KEY: SITE
<222> LOCATION: (14)..(16)
<223> OTHER INFORMATION: X is any amino acid except Cys

<400> SEQUENCE: 18

Xaa Xaa Xaa Cys Xaa Xaa Xaa Xaa Xaa Xaa Xaa Xaa Cys Xaa Xaa Xaa
1               5                   10                  15

<210> SEQ ID NO 19
<211> LENGTH: 18
<212> TYPE: PRT
<213> ORGANISM: Artificial Sequence
<220> FEATURE:
<223> OTHER INFORMATION: phage display library template
<220> FEATURE:
<221> NAME/KEY: SITE
<222> LOCATION: (1)..(3)
<223> OTHER INFORMATION: X is any amino acid except Cys
<220> FEATURE:
<221> NAME/KEY: SITE
<222> LOCATION: (5)..(14)
<223> OTHER INFORMATION: X is any amino acid except Cys
<220> FEATURE:
<221> NAME/KEY: SITE
<222> LOCATION: (16)..(18)
<223> OTHER INFORMATION: X is any amino acid except Cys

<400> SEQUENCE: 19

Xaa Xaa Xaa Cys Xaa Xaa Xaa Xaa Xaa Xaa Xaa Xaa Xaa Xaa Cys Xaa
1               5                   10                  15

Xaa Xaa

<210> SEQ ID NO 20
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 20

His Leu Arg Cys Trp Ser Thr Asn Cys Arg Tyr Asp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 21

Val Met Asp Cys Leu Ile Asn Arg Cys Asp Thr Val
1               5                   10

<210> SEQ ID NO 22
<211> LENGTH: 13
<212> TYPE: PRT
<213> ORGANISM: Artificial Sequence
<220> FEATURE:
<223> OTHER INFORMATION: BLyS binding polypeptide
```

```
<400> SEQUENCE: 22

Lys Ser Lys Cys Phe Phe Pro Trp Glu Cys Gln Gln Ala
1               5                   10

<210> SEQ ID NO 23
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 23

Ala Met Lys Cys Tyr Phe Pro Trp Glu Cys Ala Asn Gly
1               5                   10

<210> SEQ ID NO 24
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 24

Glu Asn Val Ala Cys Tyr Phe Pro Trp Glu Cys His His Pro
1               5                   10

<210> SEQ ID NO 25
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 25

Asn Ala Pro Cys Tyr Phe Pro Trp Glu Cys Phe Ser Ile
1               5                   10

<210> SEQ ID NO 26
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 26

Ser Val Asn Cys Trp Phe Pro Trp Glu Cys Val Gly Asn
1               5                   10

<210> SEQ ID NO 27
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 27

Lys Glu Pro Cys Tyr Phe Tyr Trp Glu Cys Ala Val Ser
1               5                   10

<210> SEQ ID NO 28
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 28
```

```
Asp Thr Asn Cys Asp Leu Leu Thr Lys Met Cys Gly Pro Gln
1               5                   10
```

<210> SEQ ID NO 29
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 29

```
Gly Thr Pro Cys Asp Leu Leu Thr Lys Leu Cys Leu Leu Trp
1               5                   10
```

<210> SEQ ID NO 30
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 30

```
Met Ser Glu Cys Asp Leu Leu Thr Lys Ile Cys Leu Met Gly
1               5                   10
```

<210> SEQ ID NO 31
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 31

```
Val Pro Phe Cys Asp Leu Leu Thr Lys His Cys Phe Glu Ala
1               5                   10
```

<210> SEQ ID NO 32
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 32

```
Val Pro Phe Cys Asp Leu Leu Thr Lys His Cys Phe Glu Ala
1               5                   10
```

<210> SEQ ID NO 33
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 33

```
Trp Ser Ala Cys Asp Leu Leu Thr Lys Gln Cys Val Gln Val
1               5                   10
```

<210> SEQ ID NO 34
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 34

```
Asp Gly Cys Asp Glu Leu Thr Lys Ile Cys Gly Met Lys
```

```
<210> SEQ ID NO 35
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 35

Lys Ser Trp Cys Asp Glu Leu Thr Lys Val Cys Phe Asp Pro
1               5                   10

<210> SEQ ID NO 36
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 36

Lys Trp Met Cys Asp Glu Leu Thr Lys Gln Cys Gln Tyr Val
1               5                   10

<210> SEQ ID NO 37
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 37

Met Lys Tyr Cys Asp Glu Leu Thr Lys Ile Cys Val Gly Trp
1               5                   10

<210> SEQ ID NO 38
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 38

Tyr Phe Gln Cys Asp Glu Leu Thr Lys Met Cys Trp Gln Lys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 39

Ala Met His Cys Asp Lys Leu Thr Lys His Cys Lys Phe His
1               5                   10

<210> SEQ ID NO 40
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 40

Val Pro Tyr Cys Asp Lys Leu Thr Lys Ile Cys Gln Trp
1               5                   10
```

<210> SEQ ID NO 41
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 41

Glu Val Phe Cys Asp Val Leu Thr Lys Val Cys Phe His Asp
1               5                   10

<210> SEQ ID NO 42
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 42

Lys Pro Lys Cys Asp Val Leu Thr Lys Met Cys Asp Trp Leu
1               5                   10

<210> SEQ ID NO 43
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 43

Thr Gln His Cys Asp Val Leu Thr Lys Gln Cys Phe Thr Ile
1 5 10

<210> SEQ ID NO 44
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 44

Gly His Phe Cys Asp Arg Leu Thr Lys Tyr Cys Phe Glu Pro
1 5 10

<210> SEQ ID NO 45
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 45

His Ile Gln Cys Asp Arg Leu Thr Lys Ser Cys Leu Ser Val
1 5 10

<210> SEQ ID NO 46
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 46

Ile Lys Ala Cys Asp Ile Leu Thr Lys Val Cys Trp Pro Pro
1 5 10

<210> SEQ ID NO 47

```
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 47

Gln Phe Asp Cys Asp Pro Leu Thr Lys Tyr Cys Gly Glu Phe
1               5                   10

<210> SEQ ID NO 48
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 48

Lys Met Tyr Cys Asp His Leu Thr Gly Tyr Cys Trp Pro Glu
1               5                   10

<210> SEQ ID NO 49
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 49

Met Gln Ser Cys Asp Ile Leu Thr Gly Tyr Cys Phe Lys Arg
1               5                   10

<210> SEQ ID NO 50
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 50

Gly Pro Trp Cys Asp Ile Leu Thr Gly Phe Cys Leu Ala Gln
1               5                   10

<210> SEQ ID NO 51
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 51

Ser Val Arg Cys Asp Leu Leu Thr Gly Trp Cys Pro Val Trp
1               5                   10

<210> SEQ ID NO 52
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 52

Pro Ala Asp Cys Asp Pro Leu Thr Asn Ile Cys Phe Trp Lys
1               5                   10

<210> SEQ ID NO 53
<211> LENGTH: 14
<212> TYPE: PRT
```

<213> ORGANISM: Artificial Sequence
<220> FEATURE:
<223> OTHER INFORMATION: BLyS binding polypeptide

<400> SEQUENCE: 53

Thr Asn Val Cys Asp Pro Leu Thr Asn Val Cys Phe Met Asn
1               5                   10

<210> SEQ ID NO 54
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 54

Glu His Trp Cys Asp Asp Leu Thr His Leu Cys Phe Arg Leu
1               5                   10

<210> SEQ ID NO 55
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 55

Gly Tyr Trp Cys Asp Val Leu Thr Asn Asn Cys Trp Lys Ile
1               5                   10

<210> SEQ ID NO 56
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 56

Leu Tyr Asn Cys Asp Tyr Leu Thr Arg Leu Cys Phe Glu Pro
1               5                   10

<210> SEQ ID NO 57
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 57

His Val Asp Cys Leu Leu His Pro Lys Ala Cys Tyr Lys Tyr
1               5                   10

<210> SEQ ID NO 58
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 58

Val Gln Asp Cys Leu Leu His Pro Lys Ala Cys Gln Met Gln
1               5                   10

<210> SEQ ID NO 59
<211> LENGTH: 14
<212> TYPE: PRT
<213> ORGANISM: Artificial Sequence
<220> FEATURE:

<223> OTHER INFORMATION: BLyS binding polypeptide

<400> SEQUENCE: 59

Lys Phe Asp Cys Leu Leu Lys Pro Met Phe Cys Ser Asn His
1               5                   10

<210> SEQ ID NO 60
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 60

Phe Ala Asp Cys Leu Ile His Pro Lys Ser Cys Lys Pro Leu
1               5                   10

<210> SEQ ID NO 61
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 61

His Gly Asn Cys Tyr Pro Phe Pro Trp Glu Cys Glu Ser Lys
1               5                   10

<210> SEQ ID NO 62
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 62

Met Ile Ile Val Leu Leu Leu Arg Phe Ala Ile Ser Arg
1               5                   10

<210> SEQ ID NO 63
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 63

Ser Leu Leu Val Ile Phe Leu Leu Ile Gly Ala Gly Ser Leu
1               5                   10

<210> SEQ ID NO 64
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 64

Phe His Pro Cys Asp Met Leu Thr Gly Ile Trp Cys Gln Pro Asn
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: BLyS binding polypeptide

```
<400> SEQUENCE: 65

Ser Lys Arg Cys Asp Leu Leu Thr Lys Met Trp Cys Glu Thr Glu
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 66

Thr Lys Phe Cys Asp Arg Leu Thr Met Pro Lys Cys Val Trp Lys
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 67

Asn Thr Phe Cys Pro Asp Pro Leu Thr Gly Arg Cys Val Asn Pro
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 68

Asp Trp Thr Cys Asp Pro Leu Phe His Arg Glu Cys Ile Phe Glu
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 69

Pro Gln Pro Cys Asp Leu Leu Phe Glu Lys Lys Cys Ser Ile Lys
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 70

Arg Trp His Cys Asp Met Leu Ile Asn Pro Ser Cys Leu Pro Asp
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 71
```

-continued

```
Lys Ile Gln Cys Asp Ile Val Asn Leu Ser Ser Cys Val Tyr Pro
1               5                   10                  15
```

<210> SEQ ID NO 72
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 72

```
Leu Asn Ala Cys Asp Ile Val His Pro Asn Tyr Cys Ser Gly Met
1               5                   10                  15
```

<210> SEQ ID NO 73
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 73

```
Ala Lys Ala Cys Ser Ile Val Asn Leu Glu Ser Cys Glu Tyr Leu
1               5                   10                  15
```

<210> SEQ ID NO 74
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 74

```
Arg Gln Ala Cys Ser Ile Ile Thr Pro Trp Gly Cys Pro Ile Pro
1               5                   10                  15
```

<210> SEQ ID NO 75
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 75

```
Ala Asp Asn Cys Thr Val Ala Thr Leu Asp Phe Cys Tyr Trp Thr
1               5                   10                  15
```

<210> SEQ ID NO 76
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 76

```
Lys Pro Glu Cys Asn Ile Thr Lys Pro Gln Phe Cys Phe Gly Glu
1               5                   10                  15
```

<210> SEQ ID NO 77
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 77

```
Asn Asn Cys Gln Trp Asp Glu Leu Thr Ser Met Cys Asp Pro Phe
1               5                   10                  15
```

```
<210> SEQ ID NO 78
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 78

Ser Arg Leu Cys His Met Asp Glu Leu Thr His Val Cys Val His Phe
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 79

Ser Arg Pro Cys Gln Ile Asp Glu Leu Thr Lys Ala Cys Phe Tyr Asn
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 80

Asp Arg Val Cys Lys Leu Asp Phe Leu Thr Tyr Asn Cys Leu Asn His
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 81

His Ser Asn Cys Ile Met Asp Leu Leu Thr Asn Arg Cys Phe Tyr Asp
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 82

Pro Phe Asn Cys Phe His Asp Pro Leu Thr Gly Leu Cys Leu His Ser
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 83

Tyr Asp Ser Cys Thr Tyr Asp Arg Leu Thr Lys Gln Cys Tyr Pro Ser
1               5                   10                  15
```

<210> SEQ ID NO 84
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 84

Phe His Asp Cys Met Tyr Asp Ala Leu Leu Gly Tyr Cys Leu Pro Tyr
1 5 10 15

<210> SEQ ID NO 85
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 85

Asn Arg Ser Cys Asp Pro Leu Thr Arg Pro Lys Ser Cys Gly Leu
1 5 10 15

<210> SEQ ID NO 86
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 86

Leu Ser Asn Cys Asp Trp Asp Asp Leu Ile Arg Gln Cys Leu His Asp
1 5 10 15

<210> SEQ ID NO 87
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 87

Phe Trp Asp Cys Leu Phe His Pro Asn Ser Arg Tyr Cys Val Leu Ser
1 5 10 15

<210> SEQ ID NO 88
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 88

Ser Arg Asp Cys Leu Leu Ser Pro Ala Met Ala Trp Cys Gly Leu Asp
1 5 10 15

<210> SEQ ID NO 89
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 89

Gly Gly Asn Cys Tyr Thr Asp Ser Leu Thr Lys Leu His Phe Cys Met
1 5 10 15

Gly Asp

```
<210> SEQ ID NO 90
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 90

Met Cys Pro Arg Asp Pro Leu Thr Lys Ala Lys Leu Cys Asn Trp His
1               5                   10                  15

<210> SEQ ID NO 91
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 91

Pro Asn Gln Cys Gln Asp Asp Leu Thr Lys Gln Trp Tyr Ser Cys His
1               5                   10                  15

Tyr His

<210> SEQ ID NO 92
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 92

Phe Asp Met Cys Phe Asp Ala Leu Thr Lys Gln Asn Phe Tyr Cys Arg
1               5                   10                  15

Phe His

<210> SEQ ID NO 93
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 93

Arg Asn Met Cys Val Asp Arg Leu Thr Lys Leu Gln His Gly Cys Glu
1               5                   10                  15

Gly Ala

<210> SEQ ID NO 94
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 94

Asp Pro Glu Cys Leu Thr Ser Phe Asp Arg Leu Thr Lys Met Cys Trp
1               5                   10                  15

Pro Trp

<210> SEQ ID NO 95
<211> LENGTH: 18
<212> TYPE: PRT
<213> ORGANISM: Artificial Sequence
<220> FEATURE:
<223> OTHER INFORMATION: BLyS binding polypeptide
```

-continued

```
<400> SEQUENCE: 95

Asp Asp Glu Cys His Tyr Asp Tyr Leu Thr His Tyr Met Arg Cys Asp
1               5                   10                  15

Tyr Arg

<210> SEQ ID NO 96
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 96

Phe Gly Gly Cys Asn Ile Asp Leu Leu Thr Asn Thr Met Met Cys His
1               5                   10                  15

Arg Asn

<210> SEQ ID NO 97
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 97

His Gly Pro Cys Tyr Trp Asp Glu Leu Thr Met Gln Trp His Cys Asn
1               5                   10                  15

His His

<210> SEQ ID NO 98
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 98

Gly Ala Met Cys Val Asp Leu Leu Thr Tyr Thr Phe Arg Pro Cys Met
1               5                   10                  15

Tyr Ala

<210> SEQ ID NO 99
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 99

Ser Asn Lys Cys Trp Asp Glu Leu Thr His Ala Trp Ala Glu Cys Gly
1               5                   10                  15

Arg Phe

<210> SEQ ID NO 100
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 100

Arg Pro Val Cys Tyr Lys Gly Tyr Asp Ile Leu Thr Thr Gln Cys Met
1               5                   10                  15
```

Pro Trp

<210> SEQ ID NO 101
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 101

Pro Ser Arg Cys Trp Phe Asp Leu Leu Phe Asn Lys Phe Val Cys Lys
1               5                   10                  15

Arg Asn

<210> SEQ ID NO 102
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 102

Arg Ser Gly Cys Val Tyr Asp Met Leu Leu Met Thr Met Tyr Cys Pro
1               5                   10                  15

Ser Asn

<210> SEQ ID NO 103
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 103

Ser Asn Arg Cys Glu Gly Asp Gln Leu Met Arg Pro Pro Ser Cys Arg
1               5                   10                  15

His Leu

<210> SEQ ID NO 104
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 104

Tyr Arg Met Cys Trp Trp Asp Asp Leu Leu Arg Gly Phe Val Cys Asp
1 5 10 15

Phe His

<210> SEQ ID NO 105
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 105

His Asp Gly Cys Tyr Asp Glu Leu Leu Tyr Arg Trp Thr Arg Cys Glu
1 5 10 15

His Arg

<210> SEQ ID NO 106
<211> LENGTH: 18

```
<212> TYPE: PRT
<213> ORGANISM: Artificial Sequence
<220> FEATURE:
<223> OTHER INFORMATION: BLyS binding polypeptide

<400> SEQUENCE: 106

Trp Ala Trp Cys Phe Asp Glu Leu Val Gln Arg Tyr Phe Thr Cys Phe
1               5                   10                  15

Asp His

<210> SEQ ID NO 107
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 107

Leu Pro Glu Cys Arg Gln Tyr Phe Pro Trp Glu Lys Gln Val Cys Ser
1               5                   10                  15

Tyr Trp

<210> SEQ ID NO 108
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 108

Val His Tyr Asp Ser Leu Thr Lys Met Trp Thr Arg
1               5                   10

<210> SEQ ID NO 109
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 109

Phe Thr Asp Pro Leu Thr Lys Met Ser Leu His Ser
1               5                   10

<210> SEQ ID NO 110
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 110

Gly Tyr Asp Val Leu Thr Lys Leu Tyr Phe Val Pro
1               5                   10

<210> SEQ ID NO 111
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 111

Tyr Tyr Asp Arg Leu Thr Lys Leu Tyr Ser Ser Met
1               5                   10
```

```
<210> SEQ ID NO 112
<211> LENGTH: 12
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (2)..(2)
<223> OTHER INFORMATION: X is unknown

<400> SEQUENCE: 112

Leu Xaa Lys Asp Pro Leu Thr Lys Leu Tyr Ile Ser
1               5                   10

<210> SEQ ID NO 113
<211> LENGTH: 12
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (9)..(9)
<223> OTHER INFORMATION: X is unknown

<400> SEQUENCE: 113

Gly Tyr Asp Val Leu Thr Lys Leu Xaa Phe Val Pro
1               5                   10

<210> SEQ ID NO 114
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 114

Arg Leu Tyr Asp Pro Leu Thr Lys Leu Val Leu Ser
1               5                   10

<210> SEQ ID NO 115
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 115

Met Phe Asp Pro Leu Thr Lys Ile Ala Phe Pro Ala
1               5                   10

<210> SEQ ID NO 116
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 116

Phe Tyr Asp Ser Leu Thr Lys Thr Asn Leu Arg Asp
1               5                   10

<210> SEQ ID NO 117
<211> LENGTH: 12
<212> TYPE: PRT
<213> ORGANISM: Artificial Sequence
<220> FEATURE:
<223> OTHER INFORMATION: BLyS binding polypeptide
```

```
<400> SEQUENCE: 117

Gly Ile Tyr Asp Lys Leu Thr Arg Ala Trp Leu Pro
1               5                   10

<210> SEQ ID NO 118
<211> LENGTH: 12
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (10)..(10)
<223> OTHER INFORMATION: X is unknown

<400> SEQUENCE: 118

Lys Tyr Asp Pro Leu Thr Arg Ala Arg Xaa Pro Leu
1               5                   10

<210> SEQ ID NO 119
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 119

Tyr Ile Asp Gln Leu Thr Arg Leu Ser Leu Pro Ser
1               5                   10

<210> SEQ ID NO 120
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 120

His Gln Thr Phe Asp Ile Leu Thr Arg Leu His Phe
1               5                   10

<210> SEQ ID NO 121
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 121

Trp Gln Phe Asp Val Leu Thr Arg Ser Trp Thr Pro
1               5                   10

<210> SEQ ID NO 122
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 122

Gly Ala Ala Tyr Asp His Leu Thr Arg Thr Trp Leu
1               5                   10

<210> SEQ ID NO 123
<211> LENGTH: 12
<212> TYPE: PRT
<213> ORGANISM: Artificial Sequence
<220> FEATURE:
```

<223> OTHER INFORMATION: BLyS binding polypeptide

<400> SEQUENCE: 123

Tyr Phe Asp Gln Leu Thr His Leu Ser Ile Lys Lys
1 5 10

<210> SEQ ID NO 124
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 124

Ala Trp Asp Pro Leu Thr Met Leu Val Leu Pro Trp
1 5 10

<210> SEQ ID NO 125
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 125

Ala Leu Trp Met Asp Pro Leu Thr Gly Leu Ala Phe
1 5 10

<210> SEQ ID NO 126
<211> LENGTH: 12
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (8)..(8)
<223> OTHER INFORMATION: X is unknown

<400> SEQUENCE: 126

Trp Gln Phe Asp Val Leu Thr Xaa Ser Trp Thr Pro
1 5 10

<210> SEQ ID NO 127
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 127

Trp Thr Asp Pro Leu Thr His Met Glu Ile Tyr His
1 5 10

<210> SEQ ID NO 128
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 128

Trp Thr Asp Ser Leu Thr Gly Leu Trp Phe Pro Asp
1 5 10

<210> SEQ ID NO 129
<211> LENGTH: 12
<212> TYPE: PRT

```
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (10)..(10)
<223> OTHER INFORMATION: X is unknown

<400> SEQUENCE: 129

Tyr Thr Asp Pro Leu Thr Gly Ile Val Xaa Pro Phe
1               5                   10

<210> SEQ ID NO 130
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 130

Tyr Trp Asp Lys Leu Thr Met Leu His Leu Gly Val
1               5                   10

<210> SEQ ID NO 131
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 131

Tyr Tyr Asp Phe Leu Thr Arg Thr Val Leu Pro Ser
1               5                   10

<210> SEQ ID NO 132
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 132

Arg Leu Asp Pro Leu Ser Lys Asn Asp Phe Pro Arg
1               5                   10

<210> SEQ ID NO 133
<211> LENGTH: 12
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (10)..(10)
<223> OTHER INFORMATION: X is unknown

<400> SEQUENCE: 133

Leu Arg Tyr Asp Pro Leu Leu Lys Ser Xaa Ile Tyr
1               5                   10

<210> SEQ ID NO 134
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 134

Leu Arg Tyr Asp Pro Leu Leu Lys Ser Tyr Ile Tyr
```

<210> SEQ ID NO 135
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 135

Tyr Phe Asp Gln Phe Thr His Leu Ser Ile Lys Lys
1               5                   10

<210> SEQ ID NO 136
<211> LENGTH: 12
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (5)..(5)
<223> OTHER INFORMATION: X is unknown

<400> SEQUENCE: 136

Tyr Phe Asp Gln Xaa Thr His Leu Ser Ile Lys Lys
1               5                   10

<210> SEQ ID NO 137
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 137

Glu His Tyr Tyr Thr Asp Pro Leu Thr Gly Ala Arg Ile
1               5                   10

<210> SEQ ID NO 138
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (4)..(4)
<223> OTHER INFORMATION: X is unknown

<400> SEQUENCE: 138

Glu His Tyr Xaa Thr Asp Pro Leu Thr Gly Ala Arg Ile
1               5                   10

<210> SEQ ID NO 139
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 139

Glu His Tyr Ser Thr Asp Pro Leu Thr Gly Ala Arg Ile
1               5                   10

<210> SEQ ID NO 140
<211> LENGTH: 13
<212> TYPE: PRT
<213> ORGANISM: Artificial Sequence

```
<220> FEATURE:
<223> OTHER INFORMATION: BLyS binding polypeptide
<220> FEATURE:
<221> NAME/KEY: SITE
<222> LOCATION: (9)..(9)
<223> OTHER INFORMATION: X is unknown
<220> FEATURE:
<221> NAME/KEY: SITE
<222> LOCATION: (11)..(11)
<223> OTHER INFORMATION: X is unknown

<400> SEQUENCE: 140

Glu His Tyr Tyr Thr Asp Pro Leu Xaa Gly Xaa Arg Ile
1               5                   10

<210> SEQ ID NO 141
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (9)..(9)
<223> OTHER INFORMATION: X is unknown
<220> FEATURE:
<221> NAME/KEY: SITE
<222> LOCATION: (11)..(11)
<223> OTHER INFORMATION: X is unknown
<220> FEATURE:
<221> NAME/KEY: SITE
<222> LOCATION: (13)..(13)
<223> OTHER INFORMATION: X is unknown

<400> SEQUENCE: 141

Glu His Tyr Tyr Thr Asp Pro Leu Xaa Gly Xaa Arg Xaa
1               5                   10

<210> SEQ ID NO 142
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (9)..(9)
<223> OTHER INFORMATION: X is unknown
<220> FEATURE:
<221> NAME/KEY: SITE
<222> LOCATION: (13)..(13)
<223> OTHER INFORMATION: X is unknown

<400> SEQUENCE: 142

Glu His Tyr Tyr Thr Asp Pro Leu Xaa Gly Ala Arg Xaa
1               5                   10

<210> SEQ ID NO 143
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (3)..(3)
<223> OTHER INFORMATION: X is unknown
<220> FEATURE:
<221> NAME/KEY: SITE
<222> LOCATION: (13)..(13)
<223> OTHER INFORMATION: X is unknown

<400> SEQUENCE: 143
```

```
Glu His Xaa Tyr Thr Asp Pro Leu Asn Gly Ala Arg Xaa
1               5                   10
```

<210> SEQ ID NO 144
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (13)..(13)
<223> OTHER INFORMATION: X is unknown

<400> SEQUENCE: 144

```
Glu His Tyr Tyr Asn Asp Pro Leu Asn Gly Ala Arg Xaa
1               5                   10
```

<210> SEQ ID NO 145
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X is unknown
<220> FEATURE:
<221> NAME/KEY: SITE
<222> LOCATION: (3)..(3)
<223> OTHER INFORMATION: X is unknown
<220> FEATURE:
<221> NAME/KEY: SITE
<222> LOCATION: (13)..(13)
<223> OTHER INFORMATION: X is unknown

<400> SEQUENCE: 145

```
Xaa His Xaa Tyr Asn Asp Pro Leu Asn Gly Ala Arg Xaa
1               5                   10
```

<210> SEQ ID NO 146
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 146

```
Lys Pro Tyr Tyr Asp Pro Ile Thr Lys Met Thr His His
1               5                   10
```

<210> SEQ ID NO 147
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 147

```
Lys Pro Tyr Tyr Asp Pro Ile Thr Lys Met Ser His His
1               5                   10
```

<210> SEQ ID NO 148
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 148

```
Lys Pro Tyr Tyr Asp Pro Ile Ser Lys Met Thr His His
1               5                   10
```

<210> SEQ ID NO 149
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (3)..(4)
<223> OTHER INFORMATION: X is unknown

<400> SEQUENCE: 149

```
Lys Pro Xaa Xaa Asp Pro Ile Ser Lys Met Thr His His
1               5                   10
```

<210> SEQ ID NO 150
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 150

```
Gln Ile Gly Tyr Asp Glu Leu Thr Lys Ala Trp Val Thr
1               5                   10
```

<210> SEQ ID NO 151
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 151

```
Gln Leu Gly Tyr Asp Glu Leu Thr Lys Ala Trp Val Thr
1               5                   10
```

<210> SEQ ID NO 152
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (6)..(6)
<223> OTHER INFORMATION: X is unknown

<400> SEQUENCE: 152

```
Lys Ile Asp Glu Leu Xaa Met Gln Asn Ile Ile Ile Trp
1               5                   10
```

<210> SEQ ID NO 153
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 153

```
Asp His Thr Asp Pro Leu Ile Gln Gly Leu Thr Lys Arg
1               5                   10
```

<210> SEQ ID NO 154
<211> LENGTH: 13

```
<212> TYPE: PRT
<213> ORGANISM: Artificial Sequence
<220> FEATURE:
<223> OTHER INFORMATION: BLyS binding polypeptide

<400> SEQUENCE: 154

Trp His Asp Pro Leu Lys His Met His Phe His His Glu
1               5                   10

<210> SEQ ID NO 155
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 155

Lys His Ile Asp Met Glu Thr Gly Leu Ile Leu Gln Asn
1               5                   10

<210> SEQ ID NO 156
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 156

Met Gln Val Asp Pro Glu Thr Gly Leu Lys Tyr Glu His
1               5                   10

<210> SEQ ID NO 157
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X is unknown
<220> FEATURE:
<221> NAME/KEY: SITE
<222> LOCATION: (8)..(10)
<223> OTHER INFORMATION: X is unknown

<400> SEQUENCE: 157

Xaa Leu Asp Gln His Val Asn Xaa Xaa Xaa Tyr Gln Ser
1               5                   10

<210> SEQ ID NO 158
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (2)..(4)
<223> OTHER INFORMATION: X is unknown
<220> FEATURE:
<221> NAME/KEY: SITE
<222> LOCATION: (6)..(7)
<223> OTHER INFORMATION: X is unknown
<220> FEATURE:
<221> NAME/KEY: SITE
<222> LOCATION: (13)..(13)
<223> OTHER INFORMATION: X is unknown

<400> SEQUENCE: 158

Glu Xaa Xaa Xaa Thr Xaa Xaa Leu Thr Gly Ala Arg Xaa
```

```
<210> SEQ ID NO 159
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (6)..(6)
<223> OTHER INFORMATION: X is unknown
<220> FEATURE:
<221> NAME/KEY: SITE
<222> LOCATION: (9)..(9)
<223> OTHER INFORMATION: X is unknown
<220> FEATURE:
<221> NAME/KEY: SITE
<222> LOCATION: (13)..(13)
<223> OTHER INFORMATION: X is unknown

<400> SEQUENCE: 159

Gly Pro Tyr Asn Ile Xaa Arg Leu Xaa Gly Glu Arg Xaa
1               5                   10

<210> SEQ ID NO 160
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 160

His Ile Lys Met Leu His Gln Gly Ser Phe Val Gly Val
1               5                   10

<210> SEQ ID NO 161
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (6)..(7)
<223> OTHER INFORMATION: X is unknown
<220> FEATURE:
<221> NAME/KEY: SITE
<222> LOCATION: (10)..(10)
<223> OTHER INFORMATION: X is unknown

<400> SEQUENCE: 161

His Pro Thr Asn Thr Xaa Xaa His Gln Xaa Val Tyr Ser
1               5                   10

<210> SEQ ID NO 162
<211> LENGTH: 13
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (6)..(7)
<223> OTHER INFORMATION: X is unknown
<220> FEATURE:
<221> NAME/KEY: SITE
<222> LOCATION: (13)..(13)
<223> OTHER INFORMATION: X is unknown

<400> SEQUENCE: 162

His Arg Gly Gln Val Xaa Xaa Leu Asn Gly Met Val

<210> SEQ ID NO 163
<211> LENGTH: 24
<212> TYPE: PRT
<213> ORGANISM: Artificial Sequence
<220> FEATURE:
<223> OTHER INFORMATION: BLyS binding polypeptide

<400> SEQUENCE: 163

Ala Gly Lys Glu Pro Cys Tyr Phe Tyr Trp Glu Cys Ala Val Ser Gly
1               5                   10                  15

Pro Gly Pro Glu Gly Gly Gly Lys
            20

<210> SEQ ID NO 164
<211> LENGTH: 25
<212> TYPE: PRT
<213> ORGANISM: Artificial Sequence
<220> FEATURE:
<223> OTHER INFORMATION: BLyS binding polypeptide

<400> SEQUENCE: 164

Ala Gly Val Pro Phe Cys Asp Leu Leu Thr Lys His Cys Phe Glu Ala
1               5                   10                  15

Gly Pro Gly Pro Glu Gly Gly Gly Lys
            20                  25

<210> SEQ ID NO 165
<211> LENGTH: 28
<212> TYPE: PRT
<213> ORGANISM: Artificial Sequence
<220> FEATURE:
<223> OTHER INFORMATION: BLyS binding polypeptide

<400> SEQUENCE: 165

Gly Ser Ser Arg Leu Cys His Met Asp Glu Leu Thr His Val Cys Val
1               5                   10                  15

His Phe Ala Pro Pro Gly Pro Glu Gly Gly Gly Lys
            20                  25

<210> SEQ ID NO 166
<211> LENGTH: 29
<212> TYPE: PRT
<213> ORGANISM: Artificial Sequence
<220> FEATURE:
<223> OTHER INFORMATION: BLyS binding polypeptide

<400> SEQUENCE: 166

Gly Asp Gly Gly Asn Cys Tyr Thr Asp Ser Leu Thr Lys Leu His Phe
1               5                   10                  15

Cys Met Gly Asp Glu Pro Gly Pro Glu Gly Gly Gly Lys
            20                  25

<210> SEQ ID NO 167
<211> LENGTH: 22
<212> TYPE: PRT
<213> ORGANISM: Artificial Sequence
<220> FEATURE:
<223> OTHER INFORMATION: BLyS binding polypeptide

<400> SEQUENCE: 167

Gly Tyr Asp Val Leu Thr Lys Leu Tyr Phe Val Pro Gly Gly Pro Gly
1               5                   10                  15

Pro Glu Gly Gly Gly Lys

```
           20

<210> SEQ ID NO 168
<211> LENGTH: 22
<212> TYPE: PRT
<213> ORGANISM: Artificial Sequence
<220> FEATURE:
<223> OTHER INFORMATION: BLyS binding polypeptide

<400> SEQUENCE: 168

Trp Thr Asp Ser Leu Thr Gly Leu Trp Phe Pro Asp Gly Gly Pro Gly
1               5                   10                  15

Pro Glu Gly Gly Gly Lys
            20

<210> SEQ ID NO 169
<211> LENGTH: 24
<212> TYPE: PRT
<213> ORGANISM: Artificial Sequence
<220> FEATURE:
<223> OTHER INFORMATION: modified BLyS binding polypeptide

<400> SEQUENCE: 169

Ala Gly Lys Glu Pro Cys Tyr Phe Tyr Trp Glu Cys Ala Val Ser Gly
1               5                   10                  15

Pro Gly Pro Glu Gly Gly Gly Lys
            20

<210> SEQ ID NO 170
<211> LENGTH: 24
<212> TYPE: PRT
<213> ORGANISM: Artificial Sequence
<220> FEATURE:
<223> OTHER INFORMATION: modified BLyS binding polypeptide

<400> SEQUENCE: 170

Ala Gly Arg Glu Pro Cys Tyr Phe Tyr Trp Glu Cys Ala Val Ser Gly
1               5                   10                  15

Pro Gly Pro Glu Gly Gly Gly Lys
            20

<210> SEQ ID NO 171
<211> LENGTH: 24
<212> TYPE: PRT
<213> ORGANISM: Artificial Sequence
<220> FEATURE:
<223> OTHER INFORMATION: modified BLyS binding polypeptide

<400> SEQUENCE: 171

Ala Gly Gln Glu Pro Cys Tyr Phe Tyr Trp Glu Cys Ala Val Ser Gly
1               5                   10                  15

Pro Gly Pro Glu Gly Gly Gly Lys
            20

<210> SEQ ID NO 172
<211> LENGTH: 25
<212> TYPE: PRT
<213> ORGANISM: Artificial Sequence
<220> FEATURE:
<223> OTHER INFORMATION: modified BLyS binding polypeptide
<220> FEATURE:
<221> NAME/KEY: SITE
<222> LOCATION: (4)..(4)
<223> OTHER INFORMATION: X is norleucine

<400> SEQUENCE: 172
```

```
Ala Gly Asn Xaa Glu Pro Cys Tyr Phe Tyr Trp Glu Cys Ala Val Ser
1               5                  10                  15

Gly Pro Gly Pro Glu Gly Gly Lys
             20              25
```

<210> SEQ ID NO 173
<211> LENGTH: 285
<212> TYPE: PRT
<213> ORGANISM: Homo Sapiens

<400> SEQUENCE: 173

```
Met Asp Asp Ser Thr Glu Arg Glu Gln Ser Arg Leu Thr Ser Cys Leu
1               5                  10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285
```

<210> SEQ ID NO 174
<211> LENGTH: 266
<212> TYPE: PRT
<213> ORGANISM: Homo Sapiens

<400> SEQUENCE: 174

```
Met Asp Asp Ser Thr Glu Arg Glu Gln Ser Arg Leu Thr Ser Cys Leu
1               5                  10                  15

Lys Lys Arg Glu Glu Met Lys Leu Lys Glu Cys Val Ser Ile Leu Pro
```

```
            20                  25                  30
Arg Lys Glu Ser Pro Ser Val Arg Ser Ser Lys Asp Gly Lys Leu Leu
            35                  40                  45

Ala Ala Thr Leu Leu Leu Ala Leu Leu Ser Cys Cys Leu Thr Val Val
        50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Gly Ser Tyr
    130                 135                 140

Thr Phe Val Pro Trp Leu Leu Ser Phe Lys Arg Gly Ser Ala Leu Glu
145                 150                 155                 160

Glu Lys Glu Asn Lys Ile Leu Val Lys Glu Thr Gly Tyr Phe Phe Ile
                165                 170                 175

Tyr Gly Gln Val Leu Tyr Thr Asp Lys Thr Tyr Ala Met Gly His Leu
            180                 185                 190

Ile Gln Arg Lys Lys Val His Val Phe Gly Asp Glu Leu Ser Leu Val
        195                 200                 205

Thr Leu Phe Arg Cys Ile Gln Asn Met Pro Glu Thr Leu Pro Asn Asn
    210                 215                 220

Ser Cys Tyr Ser Ala Gly Ile Ala Lys Leu Glu Glu Gly Asp Glu Leu
225                 230                 235                 240

Gln Leu Ala Ile Pro Arg Glu Asn Ala Gln Ile Ser Leu Asp Gly Asp
                245                 250                 255

Val Thr Phe Phe Gly Ala Leu Lys Leu Leu
            260                 265

<210> SEQ ID NO 175
<211> LENGTH: 309
<212> TYPE: PRT
<213> ORGANISM: mouse

<400> SEQUENCE: 175

Met Asp Glu Ser Ala Lys Thr Leu Pro Pro Pro Cys Leu Cys Phe Cys
1               5                   10                  15

Ser Glu Lys Gly Glu Asp Met Lys Val Gly Tyr Asp Pro Ile Thr Pro
            20                  25                  30

Gln Lys Glu Gly Ala Trp Phe Gly Ile Cys Arg Asp Gly Arg Leu
            35                  40                  45

Leu Ala Ala Thr Leu Leu Leu Ala Leu Leu Ser Ser Ser Phe Thr Ala
        50                  55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
```

```
            130                 135                 140
Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Thr Ile Arg Lys Gly Thr Tyr Thr Phe Val Pro Trp
            180                 185                 190

Leu Leu Ser Phe Lys Arg Gly Asn Ala Leu Glu Glu Lys Glu Asn Lys
        195                 200                 205

Ile Val Val Arg Gln Thr Gly Tyr Phe Phe Ile Tyr Ser Gln Val Leu
210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
                245                 250                 255

Ile Gln Asn Met Pro Lys Thr Leu Pro Asn Asn Ser Cys Tyr Ser Ala
            260                 265                 270

Gly Ile Ala Arg Leu Glu Glu Gly Asp Glu Ile Gln Leu Ala Ile Pro
        275                 280                 285

Arg Glu Asn Ala Gln Ile Ser Arg Asn Gly Asp Asp Thr Phe Phe Gly
    290                 295                 300

Ala Leu Lys Leu Leu
305

<210> SEQ ID NO 176
<211> LENGTH: 290
<212> TYPE: PRT
<213> ORGANISM: mouse

<400> SEQUENCE: 176

Met Asp Glu Ser Ala Lys Thr Leu Pro Pro Pro Cys Leu Cys Phe Cys
1               5                   10                  15

Ser Glu Lys Gly Glu Asp Met Lys Val Gly Tyr Asp Pro Ile Thr Pro
            20                  25                  30

Gln Lys Glu Glu Gly Ala Trp Phe Gly Ile Cys Arg Asp Gly Arg Leu
        35                  40                  45

Leu Ala Ala Thr Leu Leu Leu Ala Leu Leu Ser Ser Ser Phe Thr Ala
50                  55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
    130                 135                 140

Ala Pro Cys Leu Pro Gly Cys Arg His Ser Gln His Asp Asp Asn Gly
145                 150                 155                 160

Met Asn Leu Arg Asn Arg Thr Tyr Thr Phe Val Pro Trp Leu Leu Ser
                165                 170                 175

Phe Lys Arg Gly Asn Ala Leu Glu Glu Lys Glu Asn Lys Ile Val Val
        180                 185                 190

Arg Gln Thr Gly Tyr Phe Phe Ile Tyr Ser Gln Val Leu Tyr Thr Asp
```

```
                195              200              205
Pro Ile Phe Ala Met Gly His Val Ile Gln Arg Lys Lys Val His Val
210                 215                 220

Phe Gly Asp Glu Leu Ser Leu Val Thr Leu Phe Arg Cys Ile Gln Asn
225                 230                 235                 240

Met Pro Lys Thr Leu Pro Asn Asn Ser Cys Tyr Ser Ala Gly Ile Ala
                245                 250                 255

Arg Leu Glu Glu Gly Asp Glu Ile Gln Leu Ala Ile Pro Arg Glu Asn
                260                 265                 270

Ala Gln Ile Ser Arg Asn Gly Asp Asp Thr Phe Phe Gly Ala Leu Lys
                275                 280                 285

Leu Leu
    290

<210> SEQ ID NO 177
<211> LENGTH: 239
<212> TYPE: PRT
<213> ORGANISM: rat

<400> SEQUENCE: 177

Ala Val Gln Ala Asp Leu Met Ser Leu Arg Met Glu Leu Gln Ser Tyr
1               5                   10                  15

Arg Ser Ser Ala Thr Pro Ala Ala Pro Gly Ala Pro Gly Leu Ser Ala
                20                  25                  30

Gly Val Lys Leu Pro Thr Pro Ala Ala Pro Gly Pro His Asn Ser Ser
                35                  40                  45

Arg Gly Gln Arg Asn Arg Arg Ala Phe Gln Gly Pro Glu Glu Thr Glu
        50                  55                  60

Gln Asp Val Asp Leu Ser Ala Thr Pro Ala Pro Ser Leu Pro Gly Asn
65                  70                  75                  80

Cys His Ala Ser His His Asp Glu Asn Gly Leu Asn Leu Arg Thr Ile
                85                  90                  95

Ile Gln Asp Cys Leu Gln Leu Ile Ala Asp Ser Asn Thr Pro Thr Ile
                100                 105                 110

Arg Lys Gly Thr Tyr Thr Phe Val Pro Trp Leu Leu Ser Phe Lys Arg
                115                 120                 125

Gly Asn Ala Leu Glu Glu Lys Glu Asn Lys Ile Val Val Arg Gln Thr
130                 135                 140

Gly Tyr Phe Phe Ile Tyr Ser Gln Val Leu Tyr Thr Asp Pro Ile Phe
145                 150                 155                 160

Ala Met Gly His Val Ile Gln Arg Lys Lys Ile His Val Phe Gly Asp
                165                 170                 175

Glu Leu Ser Leu Val Thr Leu Phe Arg Cys Ile Gln Asn Met Pro Lys
                180                 185                 190

Thr Leu Pro Asn Asn Ser Cys Tyr Ser Ala Gly Ile Ala Lys Leu Glu
                195                 200                 205

Glu Gly Asp Glu Ile Gln Leu Ala Ile Pro Arg Glu Asn Ala Gln Ile
                210                 215                 220

Ser Arg Asn Gly Asp Asp Thr Phe Phe Gly Ala Leu Lys Leu Leu
225                 230                 235

<210> SEQ ID NO 178
<211> LENGTH: 220
<212> TYPE: PRT
<213> ORGANISM: rat

<400> SEQUENCE: 178
```

Ala Val Gln Ala Asp Leu Met Ser Leu Arg Met Glu Leu Gln Ser Tyr
1               5                   10                  15

Arg Ser Ser Ala Thr Pro Ala Ala Pro Gly Ala Pro Gly Leu Ser Ala
                20                  25                  30

Gly Val Lys Leu Pro Thr Pro Ala Ala Pro Gly Pro His Asn Ser Ser
            35                  40                  45

Arg Gly Gln Arg Asn Arg Ala Phe Gln Gly Pro Glu Glu Thr Glu
        50                  55                  60

Gln Asp Val Asp Leu Ser Ala Thr Pro Val Pro Ser Leu Pro Gly Asn
65                  70                  75                  80

Cys His Ala Ser His His Asp Glu Asn Gly Leu Asn Leu Arg Thr Arg
                85                  90                  95

Thr Tyr Thr Phe Val Pro Trp Leu Leu Ser Phe Lys Arg Gly Asn Ala
                100                 105                 110

Leu Glu Glu Lys Glu Asn Lys Ile Val Val Arg Gln Thr Gly Tyr Phe
                115                 120                 125

Phe Ile Tyr Ser Gln Val Leu Tyr Thr Asp Pro Ile Phe Ala Met Gly
        130                 135                 140

His Val Ile Gln Arg Lys Lys Ile His Val Phe Gly Asp Glu Leu Ser
145                 150                 155                 160

Leu Val Thr Leu Phe Arg Cys Ile Gln Asn Met Pro Lys Thr Leu Pro
                165                 170                 175

Asn Asn Ser Cys Tyr Ser Ala Gly Ile Ala Lys Leu Glu Glu Gly Asp
                180                 185                 190

Glu Ile Gln Leu Ala Ile Pro Arg Glu Asn Ala Gln Ile Ser Arg Asn
        195                 200                 205

Gly Asp Asp Thr Phe Phe Gly Ala Leu Lys Leu Leu
210                 215                 220

<210> SEQ ID NO 179
<211> LENGTH: 207
<212> TYPE: PRT
<213> ORGANISM: rat

<400> SEQUENCE: 179

Ala Val Gln Ala Asp Leu Met Ser Leu Arg Met Glu Leu Gln Ser Tyr
1               5                   10                  15

Arg Ser Ser Ala Thr Pro Ala Ala Pro Gly Ala Pro Gly Leu Ser Ala
                20                  25                  30

Gly Val Lys Leu Pro Thr Pro Ala Ala Pro Gly Pro His Asn Ser Ser
            35                  40                  45

Arg Gly Gln Arg Asn Arg Ala Phe Gln Gly Pro Glu Glu Thr Val
        50                  55                  60

Ile Gln Asp Cys Leu Gln Leu Ile Ala Asp Ser Asn Thr Pro Thr Ile
65                  70                  75                  80

Arg Lys Gly Thr Tyr Thr Phe Val Pro Trp Leu Leu Ser Phe Lys Arg
                85                  90                  95

Gly Asn Ala Leu Glu Glu Lys Glu Asn Lys Ile Val Val Arg Gln Thr
                100                 105                 110

Gly Tyr Phe Phe Ile Tyr Ser Gln Val Leu Tyr Thr Asp Pro Ile Phe
            115                 120                 125

Ala Met Gly His Val Ile Gln Arg Lys Lys Ile His Val Phe Gly Asp
        130                 135                 140

Glu Leu Ser Leu Val Thr Leu Phe Arg Cys Ile Gln Asn Met Pro Lys
145                 150                 155                 160

```
Thr Leu Pro Asn Asn Ser Cys Tyr Ser Ala Gly Ile Ala Lys Leu Glu
            165                 170                 175

Glu Gly Asp Glu Val Gln Leu Ala Ile Pro Arg Glu Asn Ala Gln Ile
        180                 185                 190

Ser Arg Asn Gly Asp Asp Thr Phe Phe Gly Ala Leu Lys Leu Leu
    195                 200                 205

<210> SEQ ID NO 180
<211> LENGTH: 188
<212> TYPE: PRT
<213> ORGANISM: rat

<400> SEQUENCE: 180

Ala Val Gln Ala Asp Leu Met Ser Leu Arg Met Glu Leu Gln Ser Tyr
1               5                   10                  15

Arg Ser Ser Ala Thr Pro Ala Ala Pro Gly Ala Pro Gly Leu Ser Ala
            20                  25                  30

Gly Val Lys Leu Pro Thr Pro Ala Ala Pro Gly Pro His Asn Ser Ser
        35                  40                  45

Arg Gly Gln Arg Asn Arg Arg Ala Phe Gln Gly Pro Glu Glu Thr Gly
    50                  55                  60

Thr Tyr Thr Phe Val Pro Trp Leu Leu Ser Phe Lys Arg Gly Asn Ala
65                  70                  75                  80

Leu Glu Glu Lys Glu Asn Lys Ile Val Val Arg Gln Thr Gly Tyr Phe
                85                  90                  95

Phe Ile Tyr Ser Gln Val Leu Tyr Thr Asp Pro Ile Phe Ala Met Gly
            100                 105                 110

His Val Ile Gln Arg Lys Lys Ile His Val Phe Gly Asp Glu Leu Ser
        115                 120                 125

Leu Val Thr Leu Phe Arg Cys Ile Gln Asn Met Pro Lys Thr Leu Pro
    130                 135                 140

Asn Asn Ser Cys Tyr Ser Ala Gly Ile Ala Lys Leu Glu Glu Gly Asp
145                 150                 155                 160

Glu Ile Gln Leu Ala Ile Pro Arg Glu Asn Ala Gln Ile Ser Arg Asn
                165                 170                 175

Gly Asp Asp Thr Phe Phe Gly Ala Leu Lys Leu Leu
            180                 185

<210> SEQ ID NO 181
<211> LENGTH: 243
<212> TYPE: PRT
<213> ORGANISM: monkey

<400> SEQUENCE: 181

Lys Asp Arg Lys Leu Leu Ala Ala Ala Leu Leu Leu Ala Leu Leu Ser
1               5                   10                  15

Cys Cys Leu Met Val Val Ser Phe Tyr Gln Val Ala Ala Leu Gln Gly
            20                  25                  30

Asp Leu Ala Ser Leu Arg Ala Glu Leu Gln Gly His His Ala Glu Lys
        35                  40                  45

Leu Pro Ala Arg Ala Arg Ala Pro Lys Ala Gly Leu Glu Glu Ala Pro
    50                  55                  60

Ala Val Thr Ala Gly Leu Lys Ile Phe Glu Pro Pro Ala Pro Gly Glu
65                  70                  75                  80

Gly Asn Ser Ser Gln Ser Ser Arg Asn Lys Arg Ala Ile Gln Gly Ala
                85                  90                  95
```

```
Glu Glu Thr Val Ile Gln Asp Cys Leu Gln Leu Ile Ala Asp Ser Glu
            100                 105                 110

Thr Pro Thr Ile Gln Lys Gly Ser Tyr Thr Phe Val Pro Trp Leu Leu
        115                 120                 125

Ser Phe Lys Arg Gly Ser Ala Leu Glu Lys Glu Asn Lys Ile Leu
130                 135                 140

Val Lys Glu Thr Gly Tyr Phe Phe Ile Tyr Gly Gln Val Leu Tyr Thr
145                 150                 155                 160

Asp Lys Thr Tyr Ala Met Gly His Leu Ile Gln Arg Lys Lys Val His
                165                 170                 175

Val Phe Gly Asp Glu Leu Ser Leu Val Thr Leu Phe Arg Cys Ile Gln
            180                 185                 190

Asn Met Pro Glu Thr Leu Pro Asn Asn Ser Cys Tyr Ser Ala Gly Ile
        195                 200                 205

Ala Lys Leu Glu Glu Gly Asp Glu Leu Gln Leu Ala Ile Pro Arg Glu
210                 215                 220

Asn Ala Gln Ile Ser Leu Asp Gly Asp Val Thr Phe Phe Gly Ala Leu
225                 230                 235                 240

Lys Leu Leu

<210> SEQ ID NO 182
<211> LENGTH: 219
<212> TYPE: PRT
<213> ORGANISM: monkey

<400> SEQUENCE: 182

Tyr Gln Val Ala Ala Val Gln Gly Asp Leu Ala Ser Leu Arg Ala Glu
1               5                   10                  15

Leu Gln Ser His His Ala Glu Lys Leu Pro Ala Arg Ala Arg Ala Pro
                20                  25                  30

Lys Ala Gly Leu Gly Glu Ala Pro Ala Val Thr Ala Gly Leu Lys Ile
            35                  40                  45

Phe Glu Pro Pro Ala Pro Gly Glu Gly Asn Ser Ser Gln Ser Ser Arg
        50                  55                  60

Asn Lys Arg Ala Ile Gln Gly Ala Glu Glu Thr Val Ile Gln Asp Cys
65                  70                  75                  80

Leu Gln Leu Ile Ala Asp Ser Glu Thr Pro Thr Ile Gln Lys Gly Ser
                85                  90                  95

Tyr Thr Phe Val Pro Trp Leu Leu Ser Phe Lys Arg Gly Ser Ala Leu
            100                 105                 110

Glu Glu Lys Glu Asn Lys Ile Leu Val Lys Glu Thr Gly Tyr Phe Phe
        115                 120                 125

Ile Tyr Gly Gln Val Leu Tyr Thr Asp Lys Thr Tyr Ala Met Gly His
    130                 135                 140

Leu Ile Gln Arg Lys Lys Val His Val Phe Gly Asp Glu Leu Ser Leu
145                 150                 155                 160

Val Thr Leu Phe Arg Cys Ile Gln Asn Met Pro Glu Thr Leu Pro Asn
                165                 170                 175

Asn Ser Cys Tyr Ser Ala Gly Ile Ala Lys Leu Glu Glu Gly Asp Glu
            180                 185                 190

Leu Gln Leu Ala Ile Pro Arg Glu Asn Ala Gln Ile Ser Leu Asp Gly
        195                 200                 205

Asp Val Thr Phe Phe Gly Ala Leu Lys Leu Leu
    210                 215
```

```
<210> SEQ ID NO 183
<211> LENGTH: 8
<212> TYPE: PRT
<213> ORGANISM: Artificial Sequence
<220> FEATURE:
<223> OTHER INFORMATION: epitope tag

<400> SEQUENCE: 183

Asp Tyr Lys Asp Asp Asp Asp Lys
1               5

<210> SEQ ID NO 184
<211> LENGTH: 14
<212> TYPE: PRT
<213> ORGANISM: Artificial Sequence
<220> FEATURE:
<223> OTHER INFORMATION: concensus BLyS binding polypeptide

<400> SEQUENCE: 184

Ala Asn Trp Tyr Asp Ser Leu Thr Lys Leu Trp Leu Pro Asp
1               5                   10

<210> SEQ ID NO 185
<211> LENGTH: 42
<212> TYPE: DNA
<213> ORGANISM: Artificial Sequence
<220> FEATURE:
<223> OTHER INFORMATION: coding sequence for BLyS affinity maturation
      library template
<220> FEATURE:
<221> NAME/KEY: SITE
<222> LOCATION: (4)..(12)
<223> OTHER INFORMATION: N=A or G or C or T
<220> FEATURE:
<221> NAME/KEY: SITE
<222> LOCATION: (16)..(18)
<223> OTHER INFORMATION: N=A or G or C or T
<220> FEATURE:
<221> NAME/KEY: SITE
<222> LOCATION: (25)..(27)
<223> OTHER INFORMATION: N=A or G or C or T
<220> FEATURE:
<221> NAME/KEY: SITE
<222> LOCATION: (31)..(42)
<223> OTHER INFORMATION: N=A or G or C or T

<400> SEQUENCE: 185
gctnnnnnnn nngatnnnct tactnnnctc nnnnnnnnnn nn                          42

<210> SEQ ID NO 186
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 186

Ala Asn Trp Tyr Asp Pro Leu Thr Lys Leu Trp Leu Pro Asp
1               5                   10

<210> SEQ ID NO 187
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 187

Ala Asn Trp Tyr Asp Pro Leu Thr Lys Leu Trp Leu Pro Glu
1               5                   10
```

<210> SEQ ID NO 188
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 188

Ala Asn Trp Tyr Asp Pro Leu Thr Lys Leu Trp Leu Pro Gly
1               5                   10

<210> SEQ ID NO 189
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 189

Ala Asn Trp Tyr Asp Pro Leu Thr Lys Leu Trp Leu Pro Val
1               5                   10

<210> SEQ ID NO 190
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 190

Ala Asn Trp Tyr Asp Pro Leu Thr Lys Leu Trp Leu Ser Asp
1               5                   10

<210> SEQ ID NO 191
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 191

Ala Asn Trp Tyr Asp Pro Leu Thr Lys Leu Trp Leu Asn Asp
1               5                   10

<210> SEQ ID NO 192
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 192

Ala Asn Trp Tyr Asp Pro Leu Thr Lys Leu Trp Leu Pro Thr
1               5                   10

<210> SEQ ID NO 193
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 193

Ala Asn Trp Tyr Asp Pro Leu Thr Lys Leu Trp Leu Pro Ala
1               5                   10

<210> SEQ ID NO 194

```
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 194

Ala Asn Trp Tyr Asp Pro Leu Thr Lys Leu Trp Leu Pro Asn
1               5                   10

<210> SEQ ID NO 195
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 195

Ala Asn Trp Tyr Asp Pro Leu Thr Lys Leu Trp Leu Val Asp
1               5                   10

<210> SEQ ID NO 196
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 196

Ala Asn Trp Tyr Asp Pro Leu Thr Lys Leu Trp Leu His Asp
1               5                   10

<210> SEQ ID NO 197
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 197

Ala Asn Trp Tyr Asp Pro Leu Thr Lys Leu Trp Leu Thr Asp
1               5                   10

<210> SEQ ID NO 198
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 198

Ala Asn Trp Tyr Asp Pro Leu Thr Lys Leu Trp Leu Pro His
1               5                   10

<210> SEQ ID NO 199
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 199

Ala Asn Trp Tyr Asp Pro Leu Thr Lys Leu Trp Leu Thr Val
1               5                   10

<210> SEQ ID NO 200
<211> LENGTH: 14
<212> TYPE: PRT
```

<213> ORGANISM: Artificial Sequence
<220> FEATURE:
<223> OTHER INFORMATION: BLyS binding polypeptide

<400> SEQUENCE: 200

Ala Asn Trp Tyr Asp Pro Leu Thr Lys Leu Trp Leu Leu Asp
1               5                   10

<210> SEQ ID NO 201
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 201

Ala Asn Trp Tyr Asp Pro Leu Thr Lys Leu Trp Leu Leu Glu
1               5                   10

<210> SEQ ID NO 202
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 202

Ala Asn Trp Tyr Asp Pro Leu Thr Lys Leu Trp Leu His Glu
1               5                   10

<210> SEQ ID NO 203
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 203

Ala Asn Trp Tyr Asp Pro Leu Thr Lys Leu Trp Leu Pro Arg
1               5                   10

<210> SEQ ID NO 204
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 204

Ala Asn Trp Tyr Asp Pro Leu Thr Lys Leu Trp Leu Ala Asp
1               5                   10

<210> SEQ ID NO 205
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 205

Ala Asn Trp Tyr Asp Pro Leu Thr Lys Leu Trp Leu Pro Tyr
1               5                   10

<210> SEQ ID NO 206
<211> LENGTH: 14
<212> TYPE: PRT
<213> ORGANISM: Artificial Sequence
<220> FEATURE:

<223> OTHER INFORMATION: BLyS binding polypeptide

<400> SEQUENCE: 206

Ala Asn Trp Tyr Asp Pro Leu Thr Lys Leu Trp Leu Pro Ile
1               5                   10

<210> SEQ ID NO 207
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 207

Ala Asn Trp Tyr Asp Pro Leu Thr Lys Leu Trp Leu Ile Asp
1               5                   10

<210> SEQ ID NO 208
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 208

Ala

```
<400> SEQUENCE: 212

Ala Tyr Trp Tyr Asp Pro Leu Thr Lys Leu Trp Leu Pro Glu
1               5                   10

<210> SEQ ID NO 213
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 213

Ala Tyr Trp Tyr Asp Pro Leu Thr Lys Leu Trp Leu Pro Val
1               5                   10

<210> SEQ ID NO 214
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 214

Ala Tyr Trp Tyr Asp Pro Leu Thr Lys Leu Trp Leu His Gln
1               5                   10

<210> SEQ ID NO 215
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 215

Ala Tyr Trp Tyr Asp Pro Leu Thr Lys Leu Trp Leu Pro Ala
1               5                   10

<210> SEQ ID NO 216
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 216

Ala Tyr Trp Tyr Asp Pro Leu Thr Lys Leu Trp Leu Arg Val
1               5                   10

<210> SEQ ID NO 217
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 217

Ala Tyr Trp Tyr Asp Pro Leu Thr Lys Leu Trp Leu Pro Gly
1               5                   10

<210> SEQ ID NO 218
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 218
```

```
Ala Tyr Trp Tyr Asp Pro Leu Thr Lys Leu Trp Leu Arg Tyr
1               5                   10

<210> SEQ ID NO 219
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 219

Ala Tyr Trp Tyr Asp Pro Leu Thr Lys Leu Trp Leu Pro Tyr
1               5                   10

<210> SEQ ID NO 220
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 220

Ala Tyr Trp Tyr Asp Pro Leu Thr Lys Leu Trp Leu Leu Tyr
1               5                   10

<210> SEQ ID NO 221
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 221

Ala Tyr Trp Tyr Asp Pro Leu Thr Lys Leu Trp Leu Arg Asp
1               5                   10

<210> SEQ ID NO 222
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 222

Ala Tyr Trp Tyr Asp Pro Leu Thr Lys Leu Trp Leu Pro Val
1               5                   10

<210> SEQ ID NO 223
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 223

Ala Tyr Trp Tyr Asp Pro Leu Thr Lys Leu Trp Leu Leu Gly
1               5                   10

<210> SEQ ID NO 224
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 224

Ala Tyr Trp Tyr Asp Pro Leu Thr Lys Leu Trp Leu Thr His
1               5                   10
```

```
<210> SEQ ID NO 225
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 225

Ala Tyr Trp Tyr Asp Pro Leu Thr Lys Leu Trp Leu Pro Thr
1               5                   10

<210> SEQ ID NO 226
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 226

Ala Tyr Trp Tyr Asp Pro Leu Thr Lys Leu Trp Leu Leu Val
1               5                   10

<210> SEQ ID NO 227
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 227

Ala Tyr Trp Tyr Asp Pro Leu Thr Lys Leu Trp Leu Tyr Tyr
1               5                   10

<210> SEQ ID NO 228
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 228

Ala Tyr Trp Tyr Asp Pro Leu Thr Lys Leu Trp Leu Ser Asp
1               5                   10

<210> SEQ ID NO 229
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 229

Ala Ser Trp Tyr Asp Pro Leu Thr Lys Leu Trp Leu Pro Ala
1               5                   10

<210> SEQ ID NO 230
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 230

Ala Ser Trp Tyr Asp Pro Leu Thr Lys Leu Trp Leu His Asp
1               5                   10
```

```
<210> SEQ ID NO 231
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 231

Ala Ser Trp Tyr Asp Pro Leu Thr Lys Leu Trp Leu Pro Gly
1               5                   10

<210> SEQ ID NO 232
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 232

Ala Ser Trp Tyr Asp Pro Leu Thr Lys Leu Trp Leu Pro Gln
1               5                   10

<210> SEQ ID NO 233
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 233

Ala Ser Trp Tyr Asp Pro Leu Thr Lys Leu Trp Leu Pro Tyr
1               5                   10

<210> SEQ ID NO 234
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 234

Ala Ser Trp Tyr Asp Pro Leu Thr Lys Leu Trp Leu Pro His
1               5                   10

<210> SEQ ID NO 235
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 235

Ala Ser Trp Tyr Asp Pro Leu Thr Lys Leu Trp Leu Pro Val
1               5                   10

<210> SEQ ID NO 236
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 236

Ala Ser Trp Tyr Asp Pro Leu Thr Lys Leu Trp Leu Pro Ile
1               5                   10

<210> SEQ ID NO 237
<211> LENGTH: 14
```

```
<212> TYPE: PRT
<213> ORGANISM: Artificial Sequence
<220> FEATURE:
<223> OTHER INFORMATION: BLyS binding polypeptide

<400> SEQUENCE: 237

Ala Ser Trp Tyr Asp Pro Leu Thr Lys Leu Trp Leu Pro Glu
1               5                   10

<210> SEQ ID NO 238
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 238

Ala Phe Trp Tyr Asp Pro Leu Thr Lys Leu Trp Leu Arg Val
1               5                   10

<210> SEQ ID NO 239
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 239

Ala Phe Trp Tyr Asp Pro Leu Thr Lys Leu Trp Leu Pro Glu
1               5                   10

<210> SEQ ID NO 240
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 240

Ala Phe Trp Tyr Asp Pro Leu Thr Lys Leu Trp Leu Leu Glu
1               5                   10

<210> SEQ ID NO 241
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 241

Ala Phe Trp Tyr Asp Pro Leu Thr Lys Leu Trp Leu Pro Val
1               5                   10

<210> SEQ ID NO 242
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 242

Ala Ile Trp Tyr Asp Pro Leu Thr Lys Leu Trp Leu Pro Glu
1               5                   10

<210> SEQ ID NO 243
<211> LENGTH: 14
<212> TYPE: PRT
<213> ORGANISM: Artificial Sequence
```

```
<220> FEATURE:
<223> OTHER INFORMATION: BLyS binding polypeptide

<400> SEQUENCE: 243

Ala Ile Trp Tyr Asp Pro Leu Thr Lys Leu Trp Leu Pro Asp
1               5                   10

<210> SEQ ID NO 244
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 244

Ala Ile Trp Tyr Asp Pro Leu Thr Lys Leu Trp Leu His Asp
1               5                   10

<210> SEQ ID NO 245
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 245

Ala Ile Trp Tyr Asp Pro Leu Thr Lys Leu Trp Leu Thr Asp
1               5                   10

<210> SEQ ID NO 246
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 246

Ala Ile Trp Tyr Asp Pro Leu Thr Lys Leu Trp Leu Pro Phe
1               5                   10

<210> SEQ ID NO 247
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 247

Ala Ile Trp Tyr Asp Pro Leu Thr Lys Leu Trp Leu Leu Asp
1               5                   10

<210> SEQ ID NO 248
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 248

Ala Ile Trp Tyr Asp Pro Leu Thr Lys Leu Trp Leu Pro Arg
1               5                   10

<210> SEQ ID NO 249
<211> LENGTH: 14
<212> TYPE: PRT
<213> ORGANISM: Artificial Sequence
<220> FEATURE:
<223> OTHER INFORMATION: BLyS binding polypeptide
```

```
<400> SEQUENCE: 249

Ala Ile Trp Tyr Asp Pro Leu Thr Lys Leu Trp Leu Pro Ala
1               5                   10

<210> SEQ ID NO 250
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 250

Ala Ile Trp Tyr Asp Pro Leu Thr Lys Leu Trp Leu Thr Ala
1               5                   10

<210> SEQ ID NO 251
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 251

Ala Ile Trp Tyr Asp Pro Leu Thr Lys Leu Trp Leu Ala Val
1               5                   10

<210> SEQ ID NO 252
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 252

Ala Ile Trp Tyr Asp Pro Leu Thr Lys Leu Trp Leu Pro Gly
1               5                   10

<210> SEQ ID NO 253
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 253

Ala Ile Trp Tyr Asp Pro Leu Thr Lys Leu Trp Leu Arg Val
1               5                   10

<210> SEQ ID NO 254
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 254

Ala Ile Trp Tyr Asp Pro Leu Thr Lys Leu Trp Leu Pro His
1               5                   10

<210> SEQ ID NO 255
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 255
```

Ala Ile Trp Tyr Asp Pro Leu Thr Lys Leu Trp Leu Arg Glu
1               5                   10

<210> SEQ ID NO 256
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 256

Ala Ile Trp Tyr Asp Pro Leu Thr Lys Leu Trp Leu Ser Asp
1               5                   10

<210> SEQ ID NO 257
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 257

Ala Thr Trp Tyr Asp Pro Leu Thr Lys Leu Trp Leu Pro Ala
1               5                   10

<210> SEQ ID NO 258
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 258

Ala Thr Trp Tyr Asp Pro Leu Thr Lys Leu Trp Leu Ala Asp
1               5                   10

<210> SEQ ID NO 259
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 259

Ala Thr Trp Tyr Asp Pro Leu Thr Lys Leu Trp Leu Thr Ser
1               5                   10

<210> SEQ ID NO 260
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 260

Ala Thr Trp Tyr Asp Pro Leu Thr Lys Leu Trp Leu Pro Gly
1               5                   10

<210> SEQ ID NO 261
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 261

Ala Thr Trp Tyr Asp Pro Leu Thr Lys Leu Trp Leu Pro Tyr

```
<210> SEQ ID NO 262
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 262

Ala Thr Trp Tyr Asp Pro Leu Thr Lys Leu Trp Leu Ser Gly
1               5                   10

<210> SEQ ID NO 263
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 263

Ala Thr Trp Tyr Asp Pro Leu Thr Lys Leu Trp Leu Pro Val
1               5                   10

<210> SEQ ID NO 264
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 264

Ala Thr Trp Tyr Asp Pro Leu Thr Lys Leu Trp Leu Pro Asp
1               5                   10

<210> SEQ ID NO 265
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 265

Ala Asp Trp Tyr Asp Pro Leu Thr Lys Leu Trp Leu Pro Val
1               5                   10

<210> SEQ ID NO 266
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 266

Ala Asp Trp Tyr Asp Pro Leu Thr Lys Leu Trp Leu Pro Lys
1               5                   10

<210> SEQ ID NO 267
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 267

Ala Asp Trp Tyr Asp Pro Leu Thr Lys Leu Trp Leu Pro Asp
1               5                   10
```

<210> SEQ ID NO 268
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 268

Ala Asp Trp Tyr Asp Pro Leu Thr Lys Leu Trp Leu Pro Glu
1               5                   10

<210> SEQ ID NO 269
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 269

Ala Asp Trp Tyr Asp Pro Leu Thr Lys Leu Trp Leu His Gln
1               5                   10

<210> SEQ ID NO 270
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 270

Ala Glu Trp Tyr Asp Pro Leu Thr Lys Leu Trp Leu Arg Asp
1               5                   10

<210> SEQ ID NO 271
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 271

Ala Glu Trp Tyr Asp Pro Leu Thr Lys Leu Trp Leu Pro Asp
1               5                   10

<210> SEQ ID NO 272
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 272

Ala Glu Trp Tyr Asp Pro Leu Thr Lys Leu Trp Leu Pro Tyr
1               5                   10

<210> SEQ ID NO 273
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 273

Ala Leu Trp Tyr Asp Pro Leu Thr Lys Leu Trp Leu Pro Ala
1               5                   10

<210> SEQ ID NO 274

```
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 274

Ala Leu Trp Tyr Asp Pro Leu Thr Lys Leu Trp Leu Pro Asp
1               5                   10

<210> SEQ ID NO 275
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 275

Ala Leu Trp Tyr Asp Pro Leu Thr Lys Leu Trp Leu Arg Gly
1               5                   10

<210> SEQ ID NO 276
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 276

Ala Leu Trp Tyr Asp Pro Leu Thr Lys Leu Trp Leu Leu Gly
1               5                   10

<210> SEQ ID NO 277
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 277

Ala Met Trp Tyr Asp Pro Leu Thr Lys Leu Trp Leu Pro Ala
1               5                   10

<210> SEQ ID NO 278
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 278

Ala Met Trp Tyr Asp Pro Leu Thr Lys Leu Trp Leu Gln Val
1               5                   10

<210> SEQ ID NO 279
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 279

Ala Met Trp Tyr Asp Pro Leu Thr Lys Leu Trp Leu Leu Gly
1               5                   10

<210> SEQ ID NO 280
<211> LENGTH: 14
<212> TYPE: PRT
```

<213> ORGANISM: Artificial Sequence
<220> FEATURE:
<223> OTHER INFORMATION: BLyS binding polypeptide

<400> SEQUENCE: 280

Ala Ala Trp Tyr Asp Pro Leu Thr Lys Leu Trp Leu Pro Asp
1               5                   10

<210> SEQ ID NO 281
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 281

Ala Ala Trp Tyr Asp Pro Leu Thr Lys Leu Trp Leu Ala Asp
1               5                   10

<210> SEQ ID NO 282
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 282

Ala Ala Trp Tyr Asp Pro Leu Thr Lys Leu Trp Leu Leu Asp
1               5                   10

<210> SEQ ID NO 283
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 283

Ala His Trp Tyr Asp Pro Leu Thr Lys Leu Trp Leu Thr Asp
1               5                   10

<210> SEQ ID NO 284
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 284

Ala His Trp Tyr Asp Pro Leu Thr Lys Leu Trp Leu Pro Val
1               5                   10

<210> SEQ ID NO 285
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 285

Ala His Trp Tyr Asp Pro Leu Thr Lys Leu Trp Leu His Asp
1               5                   10

<210> SEQ ID NO 286
<211> LENGTH: 14
<212> TYPE: PRT
<213> ORGANISM: Artificial Sequence
<220> FEATURE:

<223> OTHER INFORMATION: BLyS binding polypeptide

<400> SEQUENCE: 286

Ala His Trp Tyr Asp Pro Leu Thr Lys Leu Trp Leu Pro Asp
1               5                   10

<210> SEQ ID NO 287
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 287

Ala Pro Trp Tyr Asp Pro Leu Thr Lys Leu Trp Leu His Asp
1               5                   10

<210> SEQ ID NO 288
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 288

Ala Pro Trp Tyr Asp Pro Leu Thr Lys Leu Trp Leu Pro Val
1               5                   10

<210> SEQ ID NO 289
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 289

Ala Gln Trp Tyr Asp Pro Leu Thr Lys Leu Trp Leu Pro Glu
1               5                   10

<210> SEQ ID NO 290
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 290

Ala Gln Trp Tyr Asp Pro Leu Thr Lys Leu Trp Leu Pro Tyr
1               5                   10

<210> SEQ ID NO 291
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 291

Ala Gln Trp Tyr Asp Pro Leu Thr Lys Leu Trp Leu Pro Arg
1               5                   10

<210> SEQ ID NO 292
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 292

Ala Lys Trp Tyr Asp Pro Leu Thr Lys Leu Trp Leu Pro Asp
1 5 10

<210> SEQ ID NO 293
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 293

Ala Lys Trp Tyr Asp Pro Leu Thr Lys Leu Trp Leu Pro Val
1 5 10

<210> SEQ ID NO 294
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 294

Ala Lys Trp Tyr Asp Pro Leu Thr Lys Leu Trp Leu Pro Val
1 5 10

<210> SEQ ID NO 295
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 295

Ala Lys Trp Tyr Asp Pro Leu Thr Lys Leu Trp Leu Asn Gly
1 5 10

<210> SEQ ID NO 296
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 296

Ala Trp Trp Tyr Asp Pro Leu Thr Lys Leu Trp Leu Pro Ala
1 5 10

<210> SEQ ID NO 297
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 297

Ala Val Trp Tyr Asp Pro Leu Thr Lys Leu Trp Leu Thr Asp
1 5 10

<210> SEQ ID NO 298
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 298

```
Ala Tyr Glu Tyr Asp Pro Leu Thr Lys Leu Trp Leu Leu Tyr
1               5                   10
```

<210> SEQ ID NO 299
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 299

```
Ala Thr Lys Tyr Asp Pro Leu Thr Lys Leu Trp Leu Pro Asp
1               5                   10
```

<210> SEQ ID NO 300
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 300

```
Ala Thr Leu Tyr Asp Pro Leu Thr Lys Leu Trp Leu Pro Gly
1               5                   10
```

<210> SEQ ID NO 301
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 301

```
Ala Ile Arg Tyr Asp Pro Leu Thr Lys Leu Trp Leu Pro Tyr
1               5                   10
```

<210> SEQ ID NO 302
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 302

```
Ala Glu Arg Tyr Asp Pro Leu Thr Lys Leu Trp Leu Pro His
1               5                   10
```

<210> SEQ ID NO 303
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 303

```
Ala Asp Arg Tyr Asp Pro Leu Thr Lys Leu Trp Leu Pro Gln
1               5                   10
```

<210> SEQ ID NO 304
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 304

```
Ala Asn Ser Tyr Asp Pro Leu Thr Lys Leu Trp Leu Pro Glu
1               5                   10
```

<210> SEQ ID NO 305
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 305

Ala Ile Leu Tyr Asp Pro Leu Thr Lys Leu Trp Leu Pro Asp
1               5                   10

<210> SEQ ID NO 306
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 306

Ala Asn Trp Phe Asp Pro Leu Thr Lys Leu Trp Leu Pro Gln
1               5                   10

<210> SEQ ID NO 307
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 307

Ala Asn Trp Phe Asp Pro Leu Thr Lys Leu Trp Leu Pro Val
1               5                   10

<210> SEQ ID NO 308
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 308

Ala Asn Trp Phe Asp Pro Leu Thr Lys Leu Trp Leu Thr Asp
1               5                   10

<210> SEQ ID NO 309
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 309

Ala Asn Trp Phe Asp Pro Leu Thr Lys Leu Trp Leu Pro Asp
1               5                   10

<210> SEQ ID NO 310
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 310

Ala Asn Trp Phe Asp Pro Leu Thr Lys Leu Trp Leu Pro Gly
1               5                   10

<210> SEQ ID NO 311
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 311

Ala Asn Trp Phe Asp Pro Leu Thr Lys Leu Trp Leu Pro Glu
1 5 10

<210> SEQ ID NO 312
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 312

Ala Asn Trp Phe Asp Pro Leu Thr Lys Leu Trp Leu Pro Ala
1 5 10

<210> SEQ ID NO 313
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 313

Ala Asn Trp Phe Asp Pro Leu Thr Lys Leu Trp Leu Pro Asn
1 5 10

<210> SEQ ID NO 314
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 314

Ala Asn Trp Phe Asp Pro Leu Thr Lys Leu Trp Leu Ser Glu
1 5 10

<210> SEQ ID NO 315
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 315

Ala Asn Trp Phe Asp Pro Leu Thr Lys Leu Trp Leu His Asp
1 5 10

<210> SEQ ID NO 316
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 316

Ala Asn Trp Phe Asp Pro Leu Thr Lys Leu Trp Leu Val Asp
1 5 10

<210> SEQ ID NO 317
<211> LENGTH: 14

```
<212> TYPE: PRT
<213> ORGANISM: Artificial Sequence
<220> FEATURE:
<223> OTHER INFORMATION: BLyS binding polypeptide

<400> SEQUENCE: 317

Ala Tyr Trp Phe Asp Pro Leu Thr Lys Leu Trp Leu Pro Asp
1               5                   10

<210> SEQ ID NO 318
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 318

Ala Tyr Trp Phe Asp Pro Leu Thr Lys Leu Trp Leu Pro Val
1               5                   10

<210> SEQ ID NO 319
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 319

Ala Tyr Trp Phe Asp Pro Leu Thr Lys Leu Trp Leu Pro Ala
1               5                   10

<210> SEQ ID NO 320
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 320

Ala Gln Trp Phe Asp Pro Leu Thr Lys Leu Trp Leu Pro Asp
1               5                   10

<210> SEQ ID NO 321
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 321

Ala His Trp Phe Asp Pro Leu Thr Lys Leu Trp Leu Pro Asp
1               5                   10

<210> SEQ ID NO 322
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 322

Ala Thr Trp Phe Asp Pro Leu Thr Lys Leu Trp Leu Pro Val
1               5                   10

<210> SEQ ID NO 323
<211> LENGTH: 14
<212> TYPE: PRT
<213> ORGANISM: Artificial Sequence
```

<220> FEATURE:
<223> OTHER INFORMATION: BLyS binding polypeptide

<400> SEQUENCE: 323

Ala Tyr Trp Tyr Asp Ser Leu Thr Lys Leu Trp Leu Pro Val
1               5                   10

<210> SEQ ID NO 324
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 324

Ala Tyr Trp Tyr Asp Ser Leu Thr Lys Leu Trp Leu His Asp
1               5                   10

<210> SEQ ID NO 325
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 325

Ala Asn Trp Tyr Asp Ser Leu Thr Lys Leu Trp Ile Pro Asp
1               5                   10

<210> SEQ ID NO 326
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 326

Ala Asn Trp Tyr Asp Ser Leu Thr Lys Leu Trp Leu Pro Val
1               5                   10

<210> SEQ ID NO 327
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 327

Ala Asn Trp Tyr Asp Ser Leu Thr Lys Leu Trp Leu Pro Asp
1               5                   10

<210> SEQ ID NO 328
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 328

Ala Asn Trp Tyr Asp Ser Leu Thr Lys Leu Trp Leu Ala Asp
1               5                   10

<210> SEQ ID NO 329
<211> LENGTH: 14
<212> TYPE: PRT
<213> ORGANISM: Artificial Sequence
<220> FEATURE:
<223> OTHER INFORMATION: BLyS binding polypeptide

```
<400> SEQUENCE: 329

Ala Asn Trp Tyr Asp Ser Leu Thr Lys Leu Trp Leu Pro Ala
1               5                   10

<210> SEQ ID NO 330
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 330

Ala Asn Trp Tyr Asp Ser Leu Thr Lys Leu Trp Leu Tyr Glu
1               5                   10

<210> SEQ ID NO 331
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 331

Ala Gly Trp Tyr Asp Ser Leu Thr Lys Leu Trp Leu Pro Asp
1               5                   10

<210> SEQ ID NO 332
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 332

Ala Val Trp Tyr Asp Ser Leu Thr Lys Leu Trp Leu Thr Asp
1               5                   10

<210> SEQ ID NO 333
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 333

Ala Asn Trp Tyr Asp Ala Leu Thr Lys Leu Trp Leu Pro Val
1               5                   10

<210> SEQ ID NO 334
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 334

Ala Tyr Trp Tyr Asp Thr Leu Thr Lys Leu Trp Leu Pro Asn
1               5                   10

<210> SEQ ID NO 335
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 335
```

Ala Phe Trp Tyr Asp Pro Leu Thr Asn Leu Trp Leu Leu Glu
1               5                   10

<210> SEQ ID NO 336
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 336

Ala Tyr Trp Tyr Asp Pro Leu Thr Gly Leu Trp Leu Leu Val
1               5                   10

<210> SEQ ID NO 337
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 337

Ala Tyr Trp Tyr Asp Pro Leu Thr Gly Leu Trp Leu Leu Tyr
1               5                   10

<210> SEQ ID NO 338
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 338

Ala Tyr Trp Tyr Asp Pro Leu Thr Gly Leu Trp Leu Arg Val
1               5                   10

<210> SEQ ID NO 339
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 339

Ala Tyr Trp Tyr Asp Pro Leu Thr Glu Leu Trp Leu Arg Leu
1               5                   10

<210> SEQ ID NO 340
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 340

Ala Met Trp Tyr Asp Pro Leu Thr Lys Leu Ser Leu Pro Asp
1               5                   10

<210> SEQ ID NO 341
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 341

Ala Tyr Trp Tyr Asp Pro Leu Thr Lys Leu Ser Leu Leu Val

<210> SEQ ID NO 342
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 342

Ala Ile Trp Tyr Asp Pro Leu Thr Lys Leu Ser Leu Thr Val
1               5                   10

<210> SEQ ID NO 343
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 343

Ala Ile Trp Tyr Asp Pro Leu Thr Lys Leu Ser Leu Leu Val
1               5                   10

<210> SEQ ID NO 344
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 344

Ala Asp Trp Tyr Asp Pro Leu Thr Lys Leu Ser Leu Leu Leu
1               5                   10

<210> SEQ ID NO 345
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 345

Ala Tyr Trp Tyr Asp Pro Leu Thr Lys Leu Arg Leu Leu Glu
1               5                   10

<210> SEQ ID NO 346
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 346

Ala Asp Trp Tyr Asp Pro Leu Thr Lys Leu Arg Leu Leu Val
1 5 10

<210> SEQ ID NO 347
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 347

Ala Asp Trp Tyr Asp Pro Leu Thr Lys Leu Arg Leu Ile Val
1 5 10

<210> SEQ ID NO 348
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 348

Ala Ile Trp Tyr Asp Pro Leu Thr Lys Leu Tyr Leu Pro Asp
1 5 10

<210> SEQ ID NO 349
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 349

Ala Ile Trp Tyr Asp Pro Leu Thr Lys Leu Gly Leu Leu Val
1 5 10

<210> SEQ ID NO 350
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 350

Ala Asn Trp Tyr Asp Pro Leu Thr Lys Leu Thr Leu Leu Val
1 5 10

<210> SEQ ID NO 351
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 351

Ala Asn Trp Tyr Asp Pro Leu Thr Lys Leu Leu Leu Pro Asn
1 5 10

<210> SEQ ID NO 352
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 352

Ala Ser Trp Tyr Asp Pro Leu Thr Lys Leu Trp Phe Pro Asp
1 5 10

<210> SEQ ID NO 353
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 353

Ala Asn Trp Tyr Asp Pro Leu Thr Lys Leu Trp Phe Pro Asp
1 5 10

<210> SEQ ID NO 354

```
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 354

Ala Asn Trp Tyr Asp Pro Leu Thr Lys Leu Trp Phe Ser Asp
1               5                   10

<210> SEQ ID NO 355
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 355

Ala Ser Trp Tyr Asp Pro Leu Thr Lys Leu Trp Phe Pro Val
1               5                   10

<210> SEQ ID NO 356
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 356

Ala Asp Trp Tyr Asp Pro Leu Thr Lys Leu Trp Phe Pro Val
1               5                   10

<210> SEQ ID NO 357
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 357

Ala Ser Trp Tyr Asp Pro Leu Thr Lys Leu Trp Phe Pro Lys
1               5                   10

<210> SEQ ID NO 358
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 358

Ala Lys Trp Tyr Asp Pro Leu Thr Lys Leu Trp Phe Pro Asp
1               5                   10

<210> SEQ ID NO 359
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 359

Ala Ser Trp Tyr Asp Pro Leu Thr Lys Leu Trp Phe Leu Glu
1               5                   10

<210> SEQ ID NO 360
<211> LENGTH: 14
<212> TYPE: PRT
```

<213> ORGANISM: Artificial Sequence
<220> FEATURE:
<223> OTHER INFORMATION: BLyS binding polypeptide

<400> SEQUENCE: 360

Ala Asn Trp Tyr Asp Pro Leu Thr Lys Leu Trp Phe Pro Ala
1               5                   10

<210> SEQ ID NO 361
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 361

Ala Thr Trp Tyr Asp Pro Leu Thr Lys Leu Trp Phe Pro Asp
1               5                   10

<210> SEQ ID NO 362
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 362

Ala Ile Trp Tyr Asp Pro Leu Thr Lys Leu Trp Phe Pro Glu
1               5                   10

<210> SEQ ID NO 363
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 363

Ala Ile Trp Tyr Asp Pro Leu Thr Lys Leu Trp Phe Pro Asp
1               5                   10

<210> SEQ ID NO 364
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 364

Ala Ile Trp Tyr Asp Pro Leu Thr Lys Leu Trp Phe Pro Gly
1               5                   10

<210> SEQ ID NO 365
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 365

Ala Tyr Trp Tyr Asp Pro Leu Thr Lys Leu Trp Phe Pro His
1               5                   10

<210> SEQ ID NO 366
<211> LENGTH: 14
<212> TYPE: PRT
<213> ORGANISM: Artificial Sequence
<220> FEATURE:

<223> OTHER INFORMATION: BLyS binding polypeptide

<400> SEQUENCE: 366

Ala Asn Trp Tyr Asp Pro Leu Thr Lys Leu Trp Phe Pro Val
1               5                   10

<210> SEQ ID NO 367
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 367

Ala Tyr Trp Tyr Asp Pro Leu Thr Lys Leu Trp Phe Pro Asp
1               5                   10

<210> SEQ ID NO 368
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 368

Ala Gly Trp Tyr Asp Pro Leu Thr Lys Leu Trp Phe Pro Asp
1               5                   10

<210> SEQ ID NO 369
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 369

Ala Ile Trp Tyr Asp Pro Leu Thr Lys Leu Trp Phe Pro Thr
1               5                   10

<210> SEQ ID NO 370
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 370

Ala Lys Trp Tyr Asp Pro Leu Thr Lys Leu Trp Phe Pro Ala
1               5                   10

<210> SEQ ID NO 371
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 371

Ala Tyr Trp Tyr Asp Pro Leu Thr Lys Leu Trp Phe Phe Asp
1               5                   10

<210> SEQ ID NO 372
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 372

Ala Asn Trp Tyr Asp Pro Leu Thr Lys Leu Trp Phe Ala Asp
1 5 10

<210> SEQ ID NO 373
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 373

Ala Asn Trp Tyr Asp Pro Leu Thr Lys Leu Trp Phe Pro Tyr
1 5 10

<210> SEQ ID NO 374
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 374

Ala Asp Trp Tyr Asp Pro Leu Thr Lys Leu Trp Phe Arg Asp
1 5 10

<210> SEQ ID NO 375
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 375

Ala Asn Trp Tyr Asp Pro Leu Thr Lys Leu Trp Val Pro Asp
1 5 10

<210> SEQ ID NO 376
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 376

Ala Asp Trp Tyr Asp Pro Leu Thr Lys Leu Trp Val Pro Ala
1 5 10

<210> SEQ ID NO 377
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 377

Ala Asn Trp Tyr Asp Pro Leu Thr Lys Leu Trp Val Pro Asn
1 5 10

<210> SEQ ID NO 378
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 378

Ala Asn Trp Tyr Asp Pro Leu Thr Lys Leu Trp Val Pro Glu
1               5                   10

<210> SEQ ID NO 379
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 379

Ala Asn Trp Tyr Asp Pro Leu Thr Lys Leu Trp Val Pro Gln
1               5                   10

<210> SEQ ID NO 380
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 380

Ala Glu Trp Tyr Asp Pro Leu Thr Lys Leu Trp Val Pro Lys
1               5                   10

<210> SEQ ID NO 381
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 381

Ala Gln Trp Tyr Asp Pro Leu Thr Lys Leu Trp Val Pro Val
1               5                   10

<210> SEQ ID NO 382
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 382

Ala Asn Trp Tyr Asp Pro Leu Thr Lys Leu Trp Val Pro Tyr
1               5                   10

<210> SEQ ID NO 383
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 383

Ala Leu Trp Tyr Asp Pro Leu Thr Lys Leu Trp Val Pro Tyr
1               5                   10

<210> SEQ ID NO 384
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 384

Ala Asn Trp Tyr Asp Pro Leu Thr Lys Leu Trp Val Pro Gly
1               5                   10

<210> SEQ ID NO 385
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 385

Ala Ser Trp Tyr Asp Pro Leu Thr Lys Leu Trp Ile Pro Tyr
1               5                   10

<210> SEQ ID NO 386
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 386

Ala Asp Trp Tyr Asp Pro Leu Thr Lys Leu Trp Ile Pro Gly
1               5                   10

<210> SEQ ID NO 387
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 387

Ala Asn Trp Tyr Asp Pro Leu Thr Lys Leu Trp Ile Pro Tyr
1               5                   10

<210> SEQ ID NO 388
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 388

Ala Lys Trp Tyr Asp Pro Leu Thr Lys Leu Trp Ile Pro Tyr
1               5                   10

<210> SEQ ID NO 389
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 389

Ala Ile Trp Tyr Asp Pro Leu Thr Lys Leu Trp Ile Pro Asn
1 5 10

<210> SEQ ID NO 390
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 390

Ala Thr Trp Tyr Asp Pro Leu Thr Lys Leu Trp Ile Pro Gln
1 5 10

```
<210> SEQ ID NO 391
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 391

Ala Ser Trp Tyr Asp Pro Leu Thr Asn Leu Trp Val Pro Asp
1 5 10

<210> SEQ ID NO 392
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 392

Ala Tyr Glu Tyr Asp Pro Leu Thr Asn Leu Trp Leu Leu Tyr
1 5 10

<210> SEQ ID NO 393
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 393

Ala Tyr Trp Tyr Asp Pro Leu Thr Asn Leu Ser Leu Leu Val
1 5 10

<210> SEQ ID NO 394
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 394

Ala Tyr Trp Tyr Asp Pro Leu Thr Lys Leu Ser Ile Leu Glu
1 5 10

<210> SEQ ID NO 395
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 395

Ala Asn Trp Tyr Asp Ser Leu Thr Lys Leu Trp Ile Pro Tyr
1 5 10

<210> SEQ ID NO 396
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 396

Ala His Trp Phe Asp Pro Leu Thr Gln Leu Lys Ile Arg Val
1 5 10

<210> SEQ ID NO 397
<211> LENGTH: 14

```
<212> TYPE: PRT
<213> ORGANISM: Artificial Sequence
<220> FEATURE:
<223> OTHER INFORMATION: BLyS binding polypeptide

<400> SEQUENCE: 397

Ala Tyr Trp Cys Asp Pro Leu Thr Lys Leu Cys Ile Leu Glu
1               5                   10

<210> SEQ ID NO 398
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 398

Ala Asn Ser Tyr Asp Pro Leu Thr Lys Leu Trp Phe Pro Tyr
1               5                   10

<210> SEQ ID NO 399
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 399

Ala Asn Leu Tyr Asp Pro Leu Thr Lys Leu Trp Val Pro Tyr
1               5                   10

<210> SEQ ID NO 400
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 400

Ala Asn Trp Tyr Asp Ala Leu Thr Lys Leu Trp Leu His Asp
1               5                   10

<210> SEQ ID NO 401
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 401

Ala Asn Trp Tyr Asp Ser Leu Thr Lys Leu Trp Phe Pro Asp
1               5                   10

<210> SEQ ID NO 402
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 402

Ala Thr Ser Tyr Asp Ser Leu Thr Lys Leu Trp Leu Pro Ala
1               5                   10

<210> SEQ ID NO 403
<211> LENGTH: 14
<212> TYPE: PRT
<213> ORGANISM: Artificial Sequence
```

```
<220> FEATURE:
<223> OTHER INFORMATION: BLyS binding polypeptide

<400> SEQUENCE: 403

Ala Cys Trp Tyr Asp Ser Leu Thr Lys Leu Cys His Arg Glu
1               5                   10

<210> SEQ ID NO 404
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 404

Ala Ile Gly Asn Asp Pro Leu Thr Lys Leu Trp Ile Pro Tyr
1               5                   10

<210> SEQ ID NO 405
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 405

Ala Asn Trp Gln Asp Cys Leu Thr Lys Leu Cys Leu Ala Gly
1               5                   10

<210> SEQ ID NO 406
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 406

Ala Tyr Trp Phe Asp Pro Leu Thr Asn Leu Trp Leu Leu Glu
1               5                   10

<210> SEQ ID NO 407
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 407

Ala Tyr Trp Tyr Asp Pro Leu Thr Asn Leu Ser Leu Leu Val
1               5                   10

<210> SEQ ID NO 408
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 408

Ala Asn Cys Phe Asp Ser Leu Thr Arg Leu Trp Leu Cys Asp
1               5                   10

<210> SEQ ID NO 409
<211> LENGTH: 14
<212> TYPE: PRT
<213> ORGANISM: Artificial Sequence
<220> FEATURE:
<223> OTHER INFORMATION: BLyS binding polypeptide
```

```
<400> SEQUENCE: 409

Ala Cys Ala Tyr Asp Ala Leu Thr Lys Leu Cys Leu Pro Ala
1               5                   10

<210> SEQ ID NO 410
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 410

Ala Asn Trp Tyr Asp Pro Leu Thr Asn Leu Ser Leu Leu Leu
1               5                   10

<210> SEQ ID NO 411
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 411

Ala Tyr Trp Tyr Asp Pro Leu Thr Gln Leu Ser Leu Leu Val
1               5                   10

<210> SEQ ID NO 412
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 412

Ala Tyr Arg Tyr Asp Ala Leu Thr Gly Leu Trp Leu Leu Tyr
1               5                   10

<210> SEQ ID NO 413
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 413

Ala Tyr Trp Asn Asp Pro Leu Thr Lys Leu Lys Leu Arg Leu
1               5                   10

<210> SEQ ID NO 414
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 414

Ala Tyr Trp Tyr Asp Pro Leu Thr Gln Leu Ser Leu Leu Val
1               5                   10

<210> SEQ ID NO 415
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 415
```

```
Ala Tyr Arg Tyr Asp Ala Leu Thr Gly Leu Trp Leu Leu Tyr
1               5                   10
```

<210> SEQ ID NO 416
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 416

```
Ala Tyr Arg Tyr Asp Ser Leu Thr Asn Leu Trp Leu Leu Tyr
1               5                   10
```

<210> SEQ ID NO 417
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 417

```
Ala Tyr Trp Tyr Asp Pro Leu Thr Lys Leu Ser Ile Leu Glu
1               5                   10
```

<210> SEQ ID NO 418
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 418

```
Ala Ser Cys Tyr Asp Pro Leu Thr Lys Leu Cys Phe Pro Val
1               5                   10
```

<210> SEQ ID NO 419
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 419

```
Ala Phe Trp Phe Asp Pro Leu Thr Gly Leu Trp Leu Leu Glu
1               5                   10
```

<210> SEQ ID NO 420
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 420

```
Ala His Trp Tyr Asp Pro Leu Thr Lys Leu Ser Ile Arg Val
1               5                   10
```

<210> SEQ ID NO 421
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 421

```
Ala Pro Trp Tyr Asp Ser Leu Thr Lys Leu Trp Phe Pro Ser
```

```
1               5                  10

<210> SEQ ID NO 422
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 422

Ala Asn Cys Tyr Asp Thr Leu Thr Lys Leu Trp Leu Thr Cys
1               5                  10

<210> SEQ ID NO 423
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 423

Ala Asn Trp Tyr Asp Ser Leu Thr Lys Leu Ser Leu Pro Asp
1               5                  10

<210> SEQ ID NO 424
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 424

Ala Tyr Ala Tyr Asp Phe Leu Thr Gln Leu Ser Leu Pro Asp
1               5                  10

<210> SEQ ID NO 425
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 425

Ala Phe Arg Tyr Asp Ser Leu Thr Gly Leu Trp Leu Arg Tyr
1               5                  10

<210> SEQ ID NO 426
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 426

Ala Asn Cys Tyr Asp Ser Leu Thr Lys Leu Trp Leu Pro Cys
1               5                  10

<210> SEQ ID NO 427
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 427

Ala Asn Gly Tyr Asp Leu Leu Thr Asn Leu Ser Val Ser Asp
1               5                  10
```

<210> SEQ ID NO 428
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 428

Ala Asn Trp Tyr Asp Pro Leu Thr Arg Leu Trp Ile Pro Val
1 5 10

<210> SEQ ID NO 429
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 429

Ala Leu Lys Phe Asp Tyr Leu Thr Lys Leu Trp Leu Pro Asp
1 5 10

<210> SEQ ID NO 430
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 430

Ala Tyr Arg Tyr Asp Ser Leu Thr Lys Leu Trp Leu Pro Gly
1 5 10

<210> SEQ ID NO 431
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 431

Ala Tyr Cys Tyr Asp Ser Leu Thr Lys Leu Trp Ile Pro Asp
1 5 10

<210> SEQ ID NO 432
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 432

Ala Ser Trp Glu Asp Ser Leu Thr Lys Leu Trp Leu Ser Lys
1 5 10

<210> SEQ ID NO 433
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 433

Ala Tyr Trp Tyr Asp Ser Leu Thr Gly Leu Ser Leu Leu Val
1 5 10

<210> SEQ ID NO 434

<210> SEQ ID NO 434
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 434

Ala Tyr Trp Tyr Asp Pro Leu Thr Tyr Leu Arg Leu Arg Val
1               5                   10

<210> SEQ ID NO 435
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 435

Ala Lys Cys Tyr Asp Ser Leu Thr Asn Leu Trp Leu Cys Asp
1               5                   10

<210> SEQ ID NO 436
<211> LENGTH: 10
<212> TYPE: PRT
<213> ORGANISM: Artificial Sequence
<220> FEATURE:
<223> OTHER INFORMATION: core peptide of high affinity BLyS binders

<400> SEQUENCE: 436

Trp Tyr Asp Pro Leu Thr Lys Leu Trp Leu
1               5                   10

<210> SEQ ID NO 437
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 437

Ala Asn Trp Tyr Asp Pro Leu Thr Lys Leu Trp Leu Pro Asp Gly Gly
1               5                   10                  15

Lys

<210> SEQ ID NO 438
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 438

Trp Tyr Asp Pro Leu Thr Lys Leu Trp Leu Pro Asp Gly Gly Lys
1               5                   10                  15

<210> SEQ ID NO 439
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 439

Trp Tyr Asp Pro Leu Thr Lys Leu Trp Leu Gly Gly Lys
1               5                   10

<210> SEQ ID NO 440

```
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 440

Ala Asn Trp Tyr Asp Pro Leu Thr Lys Leu Trp Leu Pro Val Gly Gly
1               5                   10                  15

Lys

<210> SEQ ID NO 441
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 441

Ala Asn Trp Phe Asp Pro Leu Thr Lys Leu Trp Leu Pro Asp Gly Gly
1               5                   10                  15

Lys

<210> SEQ ID NO 442
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 442

Ala Asn Trp Tyr Asp Pro Leu Thr Lys Leu Ser Leu Pro Asp Gly Gly
1               5                   10                  15

Lys

<210> SEQ ID NO 443
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 443

Ala Asn Trp Tyr Asp Pro Leu Thr Lys Leu Trp Phe Pro Asp Gly Gly
1               5                   10                  15

Lys

<210> SEQ ID NO 444
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 444

Ala Asn Trp Tyr Asp Ser Leu Thr Lys Leu Trp Leu Pro Asp Gly Gly
1               5                   10                  15

Lys

<210> SEQ ID NO 445
<211> LENGTH: 585
<212> TYPE: PRT
<213> ORGANISM: Homo Sapiens

<400> SEQUENCE: 445
```

-continued

```
Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
            20                  25                  30
Gln Cys Pro Phe Glu Asp His Val Lys Leu Val Asn Glu Val Thr Glu
        35                  40                  45
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
```

```
                        420                 425                 430
Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 446
<211> LENGTH: 4
<212> TYPE: PRT
<213> ORGANISM: Artificial Sequence
<220> FEATURE:
<223> OTHER INFORMATION: recurring structural motif of BLyS binding
      polypeptides
<220> FEATURE:
<221> NAME/KEY: SITE
<222> LOCATION: (2)..(2)
<223> OTHER INFORMATION: X is Pro, Ser, Thr, Phe, Leu, Tyr, Cys, or Ala

<400> SEQUENCE: 446

Asp Xaa Leu Thr
1

<210> SEQ ID NO 447
<211> LENGTH: 14
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (2)..(2)
<223> OTHER INFORMATION: X2 is any amino acid except Arg
<220> FEATURE:
<221> NAME/KEY: SITE
<222> LOCATION: (3)..(3)
<223> OTHER INFORMATION: X3 is Trp, Glu, Lys, Cys, Leu, Ala, Arg, Gly,
      or Ser
<220> FEATURE:
<221> NAME/KEY: SITE
<222> LOCATION: (4)..(4)
<223> OTHER INFORMATION: X4 is Tyr, Phe, Glu, Cys, Asn
<220> FEATURE:
<221> NAME/KEY: SITE
<222> LOCATION: (6)..(6)
<223> OTHER INFORMATION: X6 is Pro, Ser, Thr, Phe, Leu, Tyr, Cys, or
      Ala
<220> FEATURE:
<221> NAME/KEY: SITE
<222> LOCATION: (9)..(9)
<223> OTHER INFORMATION: X9 is Lys, Asn, Gln, Gly, or Arg
<220> FEATURE:
```

```
<221> NAME/KEY: SITE
<222> LOCATION: (11)..(11)
<223> OTHER INFORMATION: X11 is Trp, Ser, Thr, Arg, Cys, Tyr, or Lys
<220> FEATURE:
<221> NAME/KEY: SITE
<222> LOCATION: (12)..(12)
<223> OTHER INFORMATION: X12 is Leu, Phe, Val, Ile, or His
<220> FEATURE:
<221> NAME/KEY: SITE
<222> LOCATION: (13)..(13)
<223> OTHER INFORMATION: X13 is Pro, Leu, His, Ser, Arg, Asn, Gln, Thr,
      Val, Ala, Cys, Ile, Phe, or Tyr
<220> FEATURE:
<221> NAME/KEY: SITE
<222> LOCATION: (14)..(14)
<223> OTHER INFORMATION: X14 is Asp, Glu, Asn, Val, His, Gln, Arg, Gly,
      Ser, Tyr, Ala, Cys, Lys, Ile, Thr or Leu.

<400> SEQUENCE: 447

Ala Xaa Xaa Xaa Asp Xaa Leu Thr Xaa Leu Xaa Xaa Xaa Xaa
1               5                   10

<210> SEQ ID NO 448
<211> LENGTH: 10
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Trp, Glu, Lys, Cys, Leu, Ala, Arg, Gly,
      or Ser
<220> FEATURE:
<221> NAME/KEY: SITE
<222> LOCATION: (2)..(2)
<223> OTHER INFORMATION: X2 is Tyr, Phe, Glu, Cys, Asn
<220> FEATURE:
<221> NAME/KEY: SITE
<222> LOCATION: (4)..(4)
<223> OTHER INFORMATION: X4 is Pro, Ser, Thr, Phe, Leu, Tyr, Cys, or Ala
<220> FEATURE:
<221> NAME/KEY: SITE
<222> LOCATION: (7)..(7)
<223> OTHER INFORMATION: X7 is Lys, Asn, Gln, Gly, or Arg
<220> FEATURE:
<221> NAME/KEY: SITE
<222> LOCATION: (9)..(9)
<223> OTHER INFORMATION: X9 is Trp, Ser, Thr, Arg, Cys, Tyr, or Lys
<220> FEATURE:
<221> NAME/KEY: SITE
<222> LOCATION: (10)..(10)
<223> OTHER INFORMATION: X10 is Leu, Phe, Val, Ile, or His

<400> SEQUENCE: 448

Xaa Xaa Asp Xaa Leu Thr Xaa Leu Xaa Xaa
1               5                   10

<210> SEQ ID NO 449
<211> LENGTH: 733
<212> TYPE: DNA
<213> ORGANISM: Homo Sapiens

<400> SEQUENCE: 449
gggatccgga gcccaaatct tctgacaaaa ctcacacatg cccaccgtgc ccagcacctg      60
aattcgaggg tgcaccgtca gtcttcctct tccccccaaa acccaaggac accctcatga    120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
ggctgaatgg caaggagtac aagtgcaagg tctccaacaa agcccctccca accccatcg    360
```

```
agaaaaccat ctccaaagcc aaagggcagc cccgagaacc acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733

<210> SEQ ID NO 450
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 450

Ala Gly Lys Glu Pro Cys Tyr Phe Tyr Trp Glu Cys Ala Val Ser Gly
1               5                   10                  15

<210> SEQ ID NO 451
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 451

Ala Gly Val Pro Phe Cys Asp Leu Leu Thr Lys His Cys Phe Glu Ala
1               5                   10                  15

Gly

<210> SEQ ID NO 452
<211> LENGTH: 20
<212> TYPE: PRT
<213> ORGANISM: Artificial Sequence
<220> FEATURE:
<223> OTHER INFORMATION: BLyS binding polypeptide

<400> SEQUENCE: 452

Gly Ser Ser Arg Leu Cys His Met Asp Glu Leu Thr His Val Cys Val
1               5                   10                  15

His Phe Ala Pro
            20

<210> SEQ ID NO 453
<211> LENGTH: 21
<212> TYPE: PRT
<213> ORGANISM: Artificial Sequence
<220> FEATURE:
<223> OTHER INFORMATION: BLyS binding polypeptide

<400> SEQUENCE: 453

Gly Asp Gly Gly Asn Cys Tyr Thr Asp Ser Leu Thr Lys Leu His Phe
1               5                   10                  15

Cys Met Gly Asp Glu
            20

<210> SEQ ID NO 454
<211> LENGTH: 14
<212> TYPE: PRT
<213> ORGANISM: Artificial Sequence
```

```
<220> FEATURE:
<223> OTHER INFORMATION: BLyS binding polypeptide

<400> SEQUENCE: 454

Gly Tyr Asp Val Leu Thr Lys Leu Tyr Phe Val Pro Gly Gly
1               5                   10

<210> SEQ ID NO 455
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 455

Trp Thr Asp Ser Leu Thr Gly Leu Trp Phe Pro Asp Gly Gly
1               5                   10

<210> SEQ ID NO 456
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 456

Trp Tyr Asp Pro Leu Thr Lys Leu Trp Leu Pro Asp
1               5                   10

<210> SEQ ID NO 457
<211> LENGTH: 10
<212> TYPE: PRT
<213> ORGANISM: Artificial Sequence
<220> FEATURE:
<223> OTHER INFORMATION: BLyS binding polypeptide

<400> SEQUENCE: 457

Trp Tyr Asp Pro Leu Thr Lys Leu Trp Leu
1               5                   10

<210> SEQ ID NO 458
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 458

Ala Asn Trp Tyr Asp Pro Leu Thr Lys Leu Ser Leu Pro Asp
1               5                   10

<210> SEQ ID NO 459
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 459

Leu Pro Gly Cys Arg Trp Asp Leu Leu Ile Lys Gln Trp Val Cys Asp
1               5                   10                  15

Pro Leu

<210> SEQ ID NO 460
<211> LENGTH: 18
<212> TYPE: PRT
<213> ORGANISM: Artificial Sequence
```

```
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Arg, Asp, Gly, His, Leu, Phe, Pro, Ser,
      Trp, Tyr, or is absent (preferably Arg)
<220> FEATURE:
<221> NAME/KEY: SITE
<222> LOCATION: (2)..(2)
<223> OTHER INFORMATION: X2 is Ala, Arg, Asn, Asp, Gly, Pro, Ser, or
      is absent (preferably Asn, Asp, Gly, or Pro)
<220> FEATURE:
<221> NAME/KEY: SITE
<222> LOCATION: (3)..(3)
<223> OTHER INFORMATION: X3 is Arg, Asn, Gln, Glu, Gly, Lys, Met, Pro,
      Trp or Val (preferably Gly or Met)
<220> FEATURE:
<221> NAME/KEY: SITE
<222> LOCATION: (5)..(5)
<223> OTHER INFORMATION: X5 is Arg, Asn, Gln, Glu, His, Leu, Phe, Pro,
      Trp, Tyr, or Val (preferably Trp, Tyr, or Val)
<220> FEATURE:
<221> NAME/KEY: SITE
<222> LOCATION: (6)..(6)
<223> OTHER INFORMATION: X is  Arg, Asp, Gln, Gly, Ile, Lys, Phe, Thr,
      Trp, or Tyr
<220> FEATURE:
<221> NAME/KEY: SITE
<222> LOCATION: (7)..(7)
<223> OTHER INFORMATION: X7 is Ala, Arg, Asp, Glu, Gly, Leu, Ser, or
      Tyr (preferably Asp)
<220> FEATURE:
<221> NAME/KEY: SITE
<222> LOCATION: (10)..(10)
<223> OTHER INFORMATION: X is Arg, Gln, His, Ile, Leu, Lys, Met, Phe,
      Thr, Trp, or Tyr
<220> FEATURE:
<221> NAME/KEY: SITE
<222> LOCATION: (11)..(11)
<223> OTHER INFORMATION: X11 is Ala, Arg, Asn, Gln, Glu, His, Leu, Lys,
      Met, or Thr (preferably Arg or Leu)
<220> FEATURE:
<221> NAME/KEY: SITE
<222> LOCATION: (12)..(12)
<223> OTHER INFORMATION: X12 is Ala, Asn, Gln, Gly, Leu, Lys, Phe, Pro,
      Thr, Trp, or Tyr (preferably Thr or Trp)
<220> FEATURE:
<221> NAME/KEY: SITE
<222> LOCATION: (13)..(13)
<223> OTHER INFORMATION: X13 is Ala, Arg, Gln, His, Lys, Met, Phe, Pro,
      Thr, Trp, or Tyr (preferably Met or Phe)
<220> FEATURE:
<221> NAME/KEY: SITE
<222> LOCATION: (14)..(14)
<223> OTHER INFORMATION: X14 is Arg, Gln, Glu, Gly, His, Leu, Met, Phe,
      Pro, Ser, Thr, Tyr, or Val (preferably Val)
<220> FEATURE:
<221> NAME/KEY: SITE
<222> LOCATION: (16)..(16)
<223> OTHER INFORMATION: X16 is Arg, Asp, Gly, His, Lys, Met, Phe, Pro,
      Ser, or Trp (preferably Met)
<220> FEATURE:
<221> NAME/KEY: SITE
<222> LOCATION: (17)..(17)
<223> OTHER INFORMATION: X is Arg, Asn, Asp, Gly, His, Phe, Pro, Ser,
      Trp, or Tyr
<220> FEATURE:
<221> NAME/KEY: SITE
<222> LOCATION: (18)..(18)
<223> OTHER INFORMATION: X18 is Ala, Arg, Asn, Asp, His, Leu, Phe, or
      Trp (preferably His or Asn),

<400> SEQUENCE: 460

Xaa Xaa Xaa Cys Xaa Xaa Xaa Leu Leu Xaa Xaa Xaa Xaa Xaa Cys Xaa
1               5                   10                  15

Xaa Xaa
```

```
<210> SEQ ID NO 461
<211> LENGTH: 18
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Arg, Asp, Gly, His, Leu, Phe, Pro, Ser,
      Trp, Tyr, or is absent (preferably Arg)
<220> FEATURE:
<221> NAME/KEY: SITE
<222> LOCATION: (3)..(3)
<223> OTHER INFORMATION: X3 is Arg, Asn, Gln, Glu, Gly, Lys, Met, Pro,
      Trp or Val (preferably Gly or Met)
<220> FEATURE:
<221> NAME/KEY: SITE
<222> LOCATION: (5)..(5)
<223> OTHER INFORMATION: X5 is Arg, Asn, Gln, Glu, His, Leu, Phe, Pro,
      Trp, Tyr, or Val (preferably Trp, Tyr, or Val)
<220> FEATURE:
<221> NAME/KEY: SITE
<222> LOCATION: (6)..(6)
<223> OTHER INFORMATION: X is  Arg, Asp, Gln, Gly, Ile, Lys, Phe, Thr,
      Trp, or Tyr
<220> FEATURE:
<221> NAME/KEY: SITE
<222> LOCATION: (7)..(7)
<223> OTHER INFORMATION: X7 is Ala, Arg, Asp, Glu, Gly, Leu, Ser, or
      Tyr (preferably Asp)
<220> FEATURE:
<221> NAME/KEY: SITE
<222> LOCATION: (8)..(8)
<223> OTHER INFORMATION: X8 is Asp, Gln, Glu, Leu, Met, Phe, Pro, Ser,
      or Tyr (preferably Leu)
<220> FEATURE:
<221> NAME/KEY: SITE
<222> LOCATION: (9)..(9)
<223> OTHER INFORMATION: X9 is Asp, Leu, Pro, Thr, or Val (preferably
      Leu or Thr)
<220> FEATURE:
<221> NAME/KEY: SITE
<222> LOCATION: (10)..(10)
<223> OTHER INFORMATION: X is Arg, Gln, His, Ile, Leu, Lys, Met, Phe,
      Thr, Trp, or Tyr
<220> FEATURE:
<221> NAME/KEY: SITE
<222> LOCATION: (11)..(11)
<223> OTHER INFORMATION: X11 is Ala, Arg, Asn, Gln, Glu, His, Leu, Lys,
      Met, or Thr (preferably Arg or Leu)
<220> FEATURE:
<221> NAME/KEY: SITE
<222> LOCATION: (12)..(12)
<223> OTHER INFORMATION: X12 is Ala, Asn, Gln, Gly, Leu, Lys, Phe, Pro,
      Thr, Trp, or Tyr (preferably Thr or Trp)
<220> FEATURE:
<221> NAME/KEY: SITE
<222> LOCATION: (13)..(13)
<223> OTHER INFORMATION: X13 is Ala, Arg, Gln, His, Lys, Met, Phe, Pro,
      Thr, Trp, or Tyr (preferably Met or Phe)
<220> FEATURE:
<221> NAME/KEY: SITE
<222> LOCATION: (14)..(14)
<223> OTHER INFORMATION: X14 is Arg, Gln, Glu, Gly, His, Leu, Met, Phe,
      Pro, Ser, Thr, Tyr, or Val (preferably Val)
<220> FEATURE:
<221> NAME/KEY: SITE
<222> LOCATION: (16)..(16)
<223> OTHER INFORMATION: X16 is Arg, Asp, Gly, His, Lys, Met, Phe, Pro,
      Ser, or Trp (preferably Met)
<220> FEATURE:
<221> NAME/KEY: SITE
<222> LOCATION: (18)..(18)
<223> OTHER INFORMATION: X18 is Ala, Arg, Asn, Asp, His, Leu, Phe, or
      Trp (preferably His or Asn),

<400> SEQUENCE: 461
```

-continued

```
Xaa Pro Xaa Cys Xaa Xaa Xaa Xaa Xaa Xaa Xaa Xaa Xaa Cys Xaa
1               5                   10                  15

Pro Xaa

<210> SEQ ID NO 462
<211> LENGTH: 18
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Arg, Asp, Gly, His, Leu, Phe, Pro, Ser,
      Trp, Tyr, or is absent (preferably Arg)
<220> FEATURE:
<221> NAME/KEY: SITE
<222> LOCATION: (2)..(2)
<223> OTHER INFORMATION: X2 is Ala, Arg, Asn, Asp, Gly, Pro, Ser, or
      is absent (preferably Asn, Asp, Gly, or Pro)
<220> FEATURE:
<221> NAME/KEY: SITE
<222> LOCATION: (3)..(3)
<223> OTHER INFORMATION: X3 is Arg, Asn, Gln, Glu, Gly, Lys, Met, Pro,
      Trp or Val (preferably Gly or Met)
<220> FEATURE:
<221> NAME/KEY: SITE
<222> LOCATION: (5)..(5)
<223> OTHER INFORMATION: X5 is Arg, Asn, Gln, Glu, His, Leu, Phe, Pro,
      Trp, Tyr, or Val (preferably Trp, Tyr, or Val)
<220> FEATURE:
<221> NAME/KEY: SITE
<222> LOCATION: (7)..(7)
<223> OTHER INFORMATION: X7 is Ala, Arg, Asp, Glu, Gly, Leu, Ser, or
      Tyr (preferably Asp)
<220> FEATURE:
<221> NAME/KEY: SITE
<222> LOCATION: (8)..(8)
<223> OTHER INFORMATION: X8 is Asp, Gln, Glu, Leu, Met, Phe, Pro, Ser,
      or Tyr (preferably Leu)
<220> FEATURE:
<221> NAME/KEY: SITE
<222> LOCATION: (9)..(9)
<223> OTHER INFORMATION: X9 is Asp, Leu, Pro, Thr, or Val (preferably
      Leu or Thr)
<220> FEATURE:
<221> NAME/KEY: SITE
<222> LOCATION: (10)..(10)
<223> OTHER INFORMATION: X is Arg, Gln, His, Ile, Leu, Lys, Met, Phe,
      Thr, Trp, or Tyr
<220> FEATURE:
<221> NAME/KEY: SITE
<222> LOCATION: (11)..(11)
<223> OTHER INFORMATION: X11 is Ala, Arg, Asn, Gln, Glu, His, Leu, Lys,
      Met, or Thr (preferably Arg or Leu)
<220> FEATURE:
<221> NAME/KEY: SITE
<222> LOCATION: (12)..(12)
<223> OTHER INFORMATION: X12 is Ala, Asn, Gln, Gly, Leu, Lys, Phe, Pro,
      Thr, Trp, or Tyr (preferably Thr or Trp)
<220> FEATURE:
<221> NAME/KEY: SITE
<222> LOCATION: (14)..(14)
<223> OTHER INFORMATION: X14 is Arg, Gln, Glu, Gly, His, Leu, Met, Phe,
      Pro, Ser, Thr, Tyr, or Val (preferably Val)
<220> FEATURE:
<221> NAME/KEY: SITE
<222> LOCATION: (16)..(16)
<223> OTHER INFORMATION: X16 is Arg, Asp, Gly, His, Lys, Met, Phe, Pro,
      Ser, or Trp (preferably Met)
<220> FEATURE:
<221> NAME/KEY: SITE
<222> LOCATION: (17)..(17)
<223> OTHER INFORMATION: X is Arg, Asn, Asp, Gly, His, Phe, Pro, Ser,
      Trp, or Tyr
<220> FEATURE:
<221> NAME/KEY: SITE
<222> LOCATION: (18)..(18)
```

```
<223> OTHER INFORMATION: X18 is Ala, Arg, Asn, Asp, His, Leu, Phe, or
      Trp (preferably His or Asn),

<400> SEQUENCE: 462

Xaa Xaa Xaa Cys Xaa Trp Xaa Xaa Xaa Xaa Xaa Xaa Xaa Trp Xaa Cys Xaa
1               5                   10                  15

Xaa Xaa

<210> SEQ ID NO 463
<211> LENGTH: 18
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Arg, Asp, Gly, His, Leu, Phe, Pro, Ser,
      Trp, Tyr, or is absent (preferably Arg)
<220> FEATURE:
<221> NAME/KEY: SITE
<222> LOCATION: (2)..(2)
<223> OTHER INFORMATION: X2 is Ala, Arg, Asn, Asp, Gly, Pro, Ser, or
      is absent (preferably Asn, Asp, Gly, or Pro)
<220> FEATURE:
<221> NAME/KEY: SITE
<222> LOCATION: (3)..(3)
<223> OTHER INFORMATION: X3 is Arg, Asn, Gln, Glu, Gly, Lys, Met, Pro,
      Trp or Val (preferably Gly or Met)
<220> FEATURE:
<221> NAME/KEY: SITE
<222> LOCATION: (5)..(5)
<223> OTHER INFORMATION: X5 is Arg, Asn, Gln, Glu, His, Leu, Phe, Pro,
      Trp, Tyr, or Val (preferably Trp, Tyr, or Val)
<220> FEATURE:
<221> NAME/KEY: SITE
<222> LOCATION: (6)..(6)
<223> OTHER INFORMATION: X is  Arg, Asp, Gln, Gly, Ile, Lys, Phe, Thr,
      Trp, or Tyr
<220> FEATURE:
<221> NAME/KEY: SITE
<222> LOCATION: (8)..(8)
<223> OTHER INFORMATION: X8 is Asp, Gln, Glu, Leu, Met, Phe, Pro, Ser,
      or Tyr (preferably Leu)
<220> FEATURE:
<221> NAME/KEY: SITE
<222> LOCATION: (9)..(9)
<223> OTHER INFORMATION: X9 is Asp, Leu, Pro, Thr, or Val (preferably
      Leu or Thr)
<220> FEATURE:
<221> NAME/KEY: SITE
<222> LOCATION: (10)..(10)
<223> OTHER INFORMATION: X is Arg, Gln, His, Ile, Leu, Lys, Met, Phe,
      Thr, Trp, or Tyr
<220> FEATURE:
<221> NAME/KEY: SITE
<222> LOCATION: (11)..(11)
<223> OTHER INFORMATION: X11 is Ala, Arg, Asn, Gln, Glu, His, Leu, Lys,
      Met, or Thr (preferably Arg or Leu)
<220> FEATURE:
<221> NAME/KEY: SITE
<222> LOCATION: (12)..(12)
<223> OTHER INFORMATION: X12 is Ala, Asn, Gln, Gly, Leu, Lys, Phe, Pro,
      Thr, Trp, or Tyr (preferably Thr or Trp)
<220> FEATURE:
<221> NAME/KEY: SITE
<222> LOCATION: (13)..(13)
<223> OTHER INFORMATION: X13 is Ala, Arg, Gln, His, Lys, Met, Phe, Pro,
      Thr, Trp, or Tyr (preferably Met or Phe)
<220> FEATURE:
<221> NAME/KEY: SITE
<222> LOCATION: (14)..(14)
<223> OTHER INFORMATION: X14 is Arg, Gln, Glu, Gly, His, Leu, Met, Phe,
      Pro, Ser, Thr, Tyr, or Val (preferably Val)
<220> FEATURE:
<221> NAME/KEY: SITE
<222> LOCATION: (17)..(17)
```

-continued

```
<223> OTHER INFORMATION: X is Arg, Asn, Asp, Gly, His, Phe, Pro, Ser,
      Trp, or Tyr
<220> FEATURE:
<221> NAME/KEY: SITE
<222> LOCATION: (18)..(18)
<223> OTHER INFORMATION: X18 is Ala, Arg, Asn, Asp, His, Leu, Phe, or
      Trp (preferably His or Asn),

<400> SEQUENCE: 463

Xaa Xaa Xaa Cys Xaa Xaa Asp Xaa Xaa Xaa Xaa Xaa Xaa Xaa Cys Asp
1               5                   10                  15

Xaa Xaa

<210> SEQ ID NO 464
<211> LENGTH: 18
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Arg, Asp, Gly, His, Leu, Phe, Pro, Ser,
      Trp, Tyr, or is absent (preferably Arg)
<220> FEATURE:
<221> NAME/KEY: SITE
<222> LOCATION: (2)..(2)
<223> OTHER INFORMATION: X2 is Ala, Arg, Asn, Asp, Gly, Pro, Ser, or
      is absent (preferably Asn, Asp, Gly, or Pro)
<220> FEATURE:
<221> NAME/KEY: SITE
<222> LOCATION: (3)..(3)
<223> OTHER INFORMATION: X3 is Arg, Asn, Gln, Glu, Gly, Lys, Met, Pro,
      Trp or Val (preferably Gly or Met)
<220> FEATURE:
<221> NAME/KEY: SITE
<222> LOCATION: (5)..(5)
<223> OTHER INFORMATION: X5 is Arg, Asn, Gln, Glu, His, Leu, Phe, Pro,
      Trp, Tyr, or Val (preferably Trp, Tyr, or Val)
<220> FEATURE:
<221> NAME/KEY: SITE
<222> LOCATION: (8)..(8)
<223> OTHER INFORMATION: X8 is Asp, Gln, Glu, Leu, Met, Phe, Pro, Ser,
      or Tyr (preferably Leu)
<220> FEATURE:
<221> NAME/KEY: SITE
<222> LOCATION: (10)..(10)
<223> OTHER INFORMATION: X10 is Arg, Gln, His, Ile, Leu, Lys, Met, Phe,
      Thr, Trp, or Tyr (preferably Lys or Thr)
<220> FEATURE:
<221> NAME/KEY: SITE
<222> LOCATION: (11)..(11)
<223> OTHER INFORMATION: X11 is Ala, Arg, Asn, Gln, Glu, His, Leu, Lys,
      Met, or Thr (preferably Arg or Leu)
<220> FEATURE:
<221> NAME/KEY: SITE
<222> LOCATION: (14)..(14)
<223> OTHER INFORMATION: X14 is Arg, Gln, Glu, Gly, His, Leu, Met, Phe,
      Pro, Ser, Thr, Tyr, or Val (preferably Val)
<220> FEATURE:
<221> NAME/KEY: SITE
<222> LOCATION: (16)..(16)
<223> OTHER INFORMATION: X16 is Arg, Asp, Gly, His, Lys, Met, Phe, Pro,
      Ser, or Trp (preferably Met)
<220> FEATURE:
<221> NAME/KEY: SITE
<222> LOCATION: (17)..(17)
<223> OTHER INFORMATION: X17 is Arg, Asn, Asp, Gly, His, Phe, Pro, Ser,
      Trp, or Tyr (preferably Arg, His, or Tyr)
<220> FEATURE:
<221> NAME/KEY: SITE
<222> LOCATION: (18)..(18)
<223> OTHER INFORMATION: X18 is Ala, Arg, Asn, Asp, His, Leu, Phe, or
      Trp (preferably His or Asn),

<400> SEQUENCE: 464
```

```
Xaa Xaa Xaa Cys Xaa Trp Asp Xaa Leu Xaa Xaa Gln Trp Xaa Cys Xaa
1               5                   10                  15

Xaa Xaa
```

<210> SEQ ID NO 465
<211> LENGTH: 18
<212> TYPE: PRT
<213> ORGANISM: Artificial Sequence
<220> FEATURE:
<223> OTHER INFORMATION: BLyS binding polypeptide
<220> FEATURE:
<221> NAME/KEY: SITE
<222> LOCATION: (1)..(1)
<223> OTHER INFORMATION: X1 is Arg, Asp, Gly, His, Leu, Phe, Pro, Ser,
      Trp, Tyr, or is absent (preferably Arg)
<220> FEATURE:
<221> NAME/KEY: SITE
<222> LOCATION: (2)..(2)
<223> OTHER INFORMATION: X2 is Ala, Arg, Asn, Asp, Gly, Pro, Ser, or
      is absent (preferably Asn, Asp, Gly, or Pro)
<220> FEATURE:
<221> NAME/KEY: SITE
<222> LOCATION: (3)..(3)
<223> OTHER INFORMATION: X3 is Arg, Asn, Gln, Glu, Gly, Lys, Met, Pro,
      Trp or Val (preferably Gly or Met)
<220> FEATURE:
<221> NAME/KEY: SITE
<222> LOCATION: (5)..(5)
<223> OTHER INFORMATION: X5 is Arg, Asn, Gln, Glu, His, Leu, Phe, Pro,
      Trp, Tyr, or Val (preferably Trp, Tyr, or Val)
<220> FEATURE:
<221> NAME/KEY: SITE
<222> LOCATION: (8)..(8)
<223> OTHER INFORMATION: X8 is Asp, Gln, Glu, Leu, Met, Phe, Pro, Ser,
      or Tyr (preferably Leu)
<220> FEATURE:
<221> NAME/KEY: SITE
<222> LOCATION: (10)..(10)
<223> OTHER INFORMATION: X10 is Arg, Gln, His, Ile, Leu, Lys, Met, Phe,
      Thr, Trp, or Tyr (preferably Lys or Thr)
<220> FEATURE:
<221> NAME/KEY: SITE
<222> LOCATION: (11)..(11)
<223> OTHER INFORMATION: X11 is Ala, Arg, Asn, Gln, Glu, His, Leu, Lys,
      Met, or Thr (preferably Arg or Leu)
<220> FEATURE:
<221> NAME/KEY: SITE
<222> LOCATION: (12)..(12)
<223> OTHER INFORMATION: X12 is Ala, Asn, Gln, Gly, Leu, Lys, Phe, Pro,
      Thr, Trp, or Tyr (preferably Thr or Trp)
<220> FEATURE:
<221> NAME/KEY: SITE
<222> LOCATION: (13)..(13)
<223> OTHER INFORMATION: X13 is Ala, Arg, Gln, His, Lys, Met, Phe, Pro,
      Thr, Trp, or Tyr (preferably Met or Phe)
<220> FEATURE:
<221> NAME/KEY: SITE
<222> LOCATION: (17)..(17)
<223> OTHER INFORMATION: X17 is Arg, Asn, Asp, Gly, His, Phe, Pro, Ser,
      Trp, or Tyr (preferably Arg, His, or Tyr)
<220> FEATURE:
<221> NAME/KEY: SITE
<222> LOCATION: (18)..(18)
<223> OTHER INFORMATION: X18 is Ala, Arg, Asn, Asp, His, Leu, Phe, or
      Trp (preferably His or Asn),

<400> SEQUENCE: 465

```
Xaa Xaa Xaa Cys Xaa Trp Asp Xaa Leu Xaa Xaa Xaa Xaa Val Cys Asp
1               5                   10                  15

Xaa Xaa
```

B-LYMPHOCYTE STIMULATOR BINDING POLYPEPTIDES AND METHODS BASED THEREON

CROSS REFERENCE TO RELATED APPLICATIONS

This application is a continuation of copending U.S. patent application Ser. No. 11/232,439, filed Sep. 20, 2005, which is a continuation of copending U.S. patent application Ser. No. 09/932,613, filed Aug. 17, 2001; now abandoned, which claims the benefit under 35 U.S.C. §119(e) of U.S. Provisional Patent Application No. 60/226,700, filed Aug. 18, 2000. Each of the above-referenced applications is incorporated by reference herein.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 169,071 Byte ASCII (Text) file named "ReplacementSequenceListing3rd.TXT," created on Jul. 22, 2011.

FIELD OF THE INVENTION

The present invention relates to therapeutic and diagnostic uses for molecules that bind to B lymphocyte stimulator protein (BLyS™). In particular, the present invention also relates to methods and compositions for detecting, diagnosing, or prognosing a disease or disorder associated with aberrant B lymphocyte stimulator or B lymphocyte stimulator receptor expression or inappropriate function of B lymphocyte stimulator or B lymphocyte stimulator receptor, comprising B lymphocyte stimulator binding polypeptides or fragments or variants thereof, that specifically bind to B lymphocyte stimulator. The present invention further relates to methods and compositions for preventing, treating or ameliorating a disease or disorder associated with aberrant B lymphocyte stimulator or B lymphocyte stimulator receptor expression or inappropriate B lymphocyte stimulator function or B lymphocyte stimulator receptor function, comprising administering to an animal, preferably a human, an effective amount of one or more B lymphocyte stimulator binding polypeptides or fragments or variants thereof, that specifically bind to B lymphocyte stimulator.

BACKGROUND OF THE INVENTION

B lymphocyte stimulator (BLyS™) is a member of the tumor necrosis factor ("TNF") superfamily that induces both in vivo and in vitro B cell proliferation and differentiation (Moore et al., *Science*, 285: 260-263 (1999)). B lymphocyte stimulator is distinguishable from other B cell growth and differentiation factors such as IL-2, IL-4, IL-5, IL-6, IL-7, IL-13, IL-15, CD40L, or CD27L (CD70) by its monocyte-specific gene and protein expression pattern and its specific receptor distribution and biological activity on B lymphocytes. B lymphocyte stimulator expression is not detected on natural killer ("NK") cells, T cells or B cells, but is restricted to cells of myeloid origin. B lymphocyte stimulator expression on resting monocytes is upregulated by interferon-gamma (IFN-gamma). The gene encoding B lymphocyte stimulator has been mapped to chromosome 13q34.

B lymphocyte stimulator is expressed as a 285 amino acid type II membrane-bound polypeptide and a soluble 152 amino acid polypeptide (Moore et al., 1999, supra). The membrane-bound form of B lymphocyte stimulator has a predicted transmembrane spanning domain between amino acid residues 47 and 73. The $NH_2$-terminus of the soluble form of B lymphocyte stimulator begins at $Ala^{134}$ of the membrane-bound form of B lymphocyte stimulator. Both the soluble and membrane-bound forms of the protein form homotrimers. Soluble recombinant B lymphocyte stimulator has been shown to induce in vitro proliferation of murine splenic B cells and to bind to a cell-surface receptor on these cells (Moore et al., 1999, supra). Soluble B lymphocyte stimulator administration to mice has been shown to result in an increase in the proportion of $CD45R^{dull}$, $Ly6D^{bright}$ (also known as ThB) B cells and an increase in serum IgM and IgA levels (Moore et al., 1999, supra). Thus, B lymphocyte stimulator displays a B cell tropism in both its receptor distribution and biological activity.

Based on its expression pattern and biological activity, B lymphocyte stimulator has been suggested to be involved in the exchange of signals between B cells and monocytes or their differentiated progeny. The restricted expression patterns of B lymphocyte stimulator receptor and ligand suggest that B lymphocyte stimulator may function as a regulator of T cell-independent responses in a manner analogous to that of CD40 and CD40L in T cell-dependent antigen activation.

Accordingly, molecules that specifically bind B lymphocyte stimulator would find a variety of uses in the study of the B lymphocyte stimulator cytokine, in the manufacture and purification of B lymphocyte stimulator in commercial and medically pure quantities, and in the development new therapeutic or diagnostic reagents. B lymphocyte stimulator binding polypeptides may also find medical utility in, for example, the treatment of B cell and/or monocyte disorders associated with autoimmunity, neoplasia, or immunodeficiency syndromes.

SUMMARY OF THE INVENTION

New polypeptides that specifically bind to B lymphocyte stimulator protein (BLyS™) and/or B lymphocyte stimulator-like polypeptides have been discovered, and the therapeutic and diagnostic applications for such polypeptides are disclosed herein. Particular polypeptides useful in the methods of this invention specifically bind to a polypeptide or polypeptide fragment of human B lymphocyte stimulator (SEQ ID NOs:173 and/or 174) or B lymphocyte stimulator expressed on human monocytes; murine B lymphocyte stimulator (SEQ ID NOs:175 and/or 176) or B lymphocyte stimulator expressed on murine monocytes; rat B lymphocyte stimulator (either the soluble forms as given in SEQ ID NOs: 177, 178, 179 and/or 180 or in a membrane associated form, e.g., on the surface of rat monocytes); or monkey B lymphocyte stimulator (e.g., the monkey B lymphocyte stimulator polypeptides of SEQ ID NOS:181 and/or 182, the soluble form of monkey B lymphocyte stimulator, or B lymphocyte stimulator expressed on monkey monocytes), preferably human B lymphocyte stimulator.

In preferred methods of the invention, B lymphocyte stimulator binding polypeptides comprising, or alternatively consisting of, an amino acid sequence selected from the group consisting of SEQ ID NOs:1-12, 20-172, and 186-444, preferably SEQ ID NOs:163-172 and 436-444 as referred to herein and in Tables 1-8, 13, and 14, and fragments and variants thereof, will be used.

In specific preferred embodiments, the B lymphocyte stimulator binding polypeptides bind B lymphocyte stimulator and/or B lymphocyte stimulator-like polypeptides with high affinity. In other embodiments, the B lymphocyte stimulator binding polypeptides reversibly bind B lymphocyte stimulator and/or B lymphocyte stimulator-like polypeptides. In still other embodiments, the B lymphocyte stimulator binding polypeptides irreversibly bind B lymphocyte stimulator and/or B lymphocyte stimulator-like polypeptides.

The cysteine residues in certain polypeptides useful in the methods of the invention are believed to form a disulfide bond, which would cause the polypeptide containing these cysteine residues to form a stable loop structure under non-reducing conditions. Especially preferred B lymphocyte stimulator binding polypeptides useful in the methods of the invention are polypeptide molecules that comprise amino acid sequences that form stable loop structures or other stable structures that bind B lymphocyte stimulator or B lymphocyte stimulator-like polypeptides.

Analysis of the sequences of the B lymphocyte stimulator binding polypeptides described herein shows a strong selection for polypeptides containing the tetrapeptide Asp-Xaa-Leu-Thr (SEQ ID NO:446), and therefore in its broadest aspects, the present invention relates to methods for using polypeptides capable of binding to B lymphocyte stimulator comprising the polypeptide Asp-Xaa-Leu-Thr (SEQ ID NO:446), where Xaa is Pro, Ser, Thr, Phe, Leu, Tyr, Cys, or Ala (preferably Pro or Ser).

In addition, seven consensus sequences (SEQ ID NOs:1-7) are disclosed for peptides useful in the methods of the invention, based on the specific B lymphocyte stimulator binding polypeptides shown in Tables 1-8. In preferred methods according to the invention, B lymphocyte stimulator binding polypeptides comprising one or more of these sequences are used. Such preferred methods utilize B lymphocyte stimulator binding polypeptides including polypeptides with the potential to form a cyclic or loop structure between invariant Cys residues comprising, or alternatively consisting of, an amino acid sequence selected from A-E (SEQ ID NOs:1-5):

(SEQ ID NO: 1)

(A) $X_1$-$X_2$-$X_3$-Cys-$X_5$-Phe-$X_7$-Trp-Glu-Cys-$X_{11}$-$X_{12}$-$X_{13}$, wherein $X_1$ is Ala, Asn, Lys, or Ser;
$X_2$ is Ala, Glu, Met, Ser, or Val;
$X_3$ is Ala, Asn, Lys, or Pro (preferably Lys);
$X_5$ is Phe, Trp, or Tyr (preferably Tyr);
$X_7$ is Pro or Tyr (preferably Pro);
$X_{11}$ is Ala, Gln, His, Phe, or Val;
$X_{12}$ is Asn, Gln, Gly, His, Ser, or Val; and
$X_{13}$ is Ala, Asn, Gly, le, Pro, or Ser,
wherein said polypeptide binds B lymphocyte stimulator and/or B lymphocyte stimulator-like polypeptides; or (SEQ ID NO: 2)

(B)
$X_1$-$X_2$-$X_3$-Cys-$X_5$-$X_6$-$X_7$-$X_8$-$X_9$-$X_{10}$-Cys-$X_{12}$-$X_{13}$-$X_{14}$, wherein $X_1$ is Ala, Asp, Gln, Glu, Gly, His, le, Leu, Lys, Met, Phe, Pro, Ser, Thr, Trp, Tyr, Val, or is absent;
$X_2$ is Ala, Asn, Asp, Gln, Gly, His, Ile, Leu, Lys, Met, Phe, Pro, Ser, Thr, Trp, Tyr, or Val;
$X_3$ is Ala, Arg, Asn, Asp, Gln, Glu, Gly, His, Ile, Leu, Lys, Met, Phe, Pro, Ser, Trp, Tyr, or Val (preferably Asp);
$X_5$ is Asp, Be, Leu, or Tyr (preferably Asp or Leu);
$X_6$ is Arg, Asp, Glu, His, Be, Leu, Lys, Phe, Pro, Tyr, or Val (preferably Glu or Leu);
$X_7$ is His, Leu, Lys, or Phe (preferably His or Leu);
$X_8$ is Leu, Pro, or Thr (preferably Thr or Pro);
$X_9$ is Arg, Asn, Gly, His, Be, Lys, Met, or Trp (preferably Lys);
$X_{10}$ is Ala, Gln, Glu, Gly, His, Ile, Leu, Met, Phe, Ser, Trp, Tyr, or Val;
$X_{12}$ is Asp, Gln, Glu, Gly, Ile, Leu, Lys, Phe, Ser, Trp, Tyr, or Val;
$X_{13}$ is Ala, Arg, Asn, Asp, Gln, Glu, Gly, His, Leu, Lys, Met, Phe, Pro, Ser, Thr, Trp, Tyr, or Val; and
$X_{14}$ is Ala, Arg, Asn, Asp, Gln, Glu, Gly, His, Ile, Leu, Lys, Phe, Pro, Trp, Tyr, Val, or is absent,
wherein said polypeptide binds B lymphocyte stimulator and/or B lymphocyte stimulator-like polypeptides; or (SEQ ID NO: 3)

(C)
$X_1$-$X_2$-$X_3$-Cys-$X_5$-$X_6$-$X_7$-$X_8$-$X_9$-$X_{10}$-$X_{11}$-Cys-$X_{13}$-$X_{14}$-

$X_{15}$, wherein $X_1$ is Ala, Arg, Asn, Asp, Leu, Lys, Phe, Pro, Ser, or Thr;
$X_2$ is Asn, Asp, Gln, His, Be, Lys, Pro, Thr, or Trp;
$X_3$ is Ala, Arg, Asn, Gln, Glu, His, Phe, Pro, or Thr (preferably Ala);
$X_5$ is Asn, Asp, Pro, Ser, or Thr (preferably Asp);
$X_6$ is Arg, Asp, Ile, Leu, Met, Pro, or Val (preferably Ile);
$X_7$ is Ala, Ile, Leu, Pro, Thr, or Val (preferably Val or Leu);
$X_8$ is Asn, His, Be, Leu, Lys, Phe, or Thr (preferably Thr);
$X_9$ is Asn, Glu, Gly, His, Leu, Lys, Met, Pro, or Thr (preferably Leu);
$X_{10}$ is Arg, Asn, Asp, Gln, Glu, Gly, Ile, Lys, Met, Pro, Ser, or Trp;
$X_{11}$ is Arg, Glu, Gly, Lys, Phe, Ser, Trp, or Tyr (preferably Ser);
$X_{13}$ is Gln, Glu, Be, Leu, Phe, Pro, Ser, Tyr, or Val (preferably Val);
$X_{14}$ is Asn, Gly, Ile, Phe, Pro, Thr, Trp, or Tyr; and
$X_{15}$ is Asn, Asp, Glu, Leu, Lys, Met, Pro, or Thr (preferably Glu or Pro),
wherein said polypeptide binds B lymphocyte stimulator and/or B lymphocyte stimulator-like polypeptides; or (SEQ ID NO: 4)

(D)
$X_1$-$X_2$-$X_3$-Cys-$X_5$-$X_6$-$X_7$-$X_8$-$X_9$-$X_{10}$-$X_{11}$-$X_{12}$-Cys-$X_{14}$-

$X_{15}$-$X_{16}$, wherein $X_1$ is Asn, Asp, His, Leu, Phe, Pro, Ser, Tyr, or is absent (preferably Ser);
$X_2$ is Arg, Asn, Asp, His, Phe, Ser, or Trp (preferably Arg);
$X_3$ is Asn, Asp, Leu, Pro, Ser, or Val (preferably Asn or Asp);
$X_5$ is Asp, Gln, His, Ile, Leu, Lys, Met, Phe, or Thr;
$X_6$ is His, Be, Leu, Met, Phe, Pro, Trp, or Tyr;
$X_7$ is Asp, His, Leu, or Ser (preferably Asp);
$X_8$ is Ala, Arg, Asp, Glu, Leu, Phe, Pro, or Thr (preferably Glu or Pro);
$X_9$ is Ala, Arg, Asn, or Leu (preferably Leu);
$X_{10}$ is Be, Leu, Met, Pro, Ser, or Thr (preferably Thr);
$X_{11}$ is Ala, Arg, Asn, Gly, His, Lys, Ser, or Tyr;
$X_{12}$ is Ala, Arg, Asn, Gln, Leu, Met, Ser, Trp, Tyr, or Val;

$X_{14}$ is Asp, Gly, Leu, Phe, Tyr, or Val (preferably Leu);

$X_{15}$ is Asn, His, Leu, Pro, or Tyr (preferably His, Leu or Pro); and $X_{16}$ is Asn, Asp, His, Phe, Ser, or Tyr, (preferably Asp or Ser), wherein said polypeptide binds B lymphocyte stimulator and/or B lymphocyte stimulator-like polypeptides; or (SEQ ID NO: 5)

(E)
$X_1$-$X_2$-$X_3$-Cys-$X_5$-$X_6$-$X_7$-$X_8$-$X_9$-$X_{10}$-$X_{11}$-$X_{12}$-$X_{13}$-$X_{14}$-Cys-$X_{16}$-$X_{17}$-$X_{18}$, wherein $X_1$ is Arg, Asp, Gly, His, Leu, Phe, Pro, Ser, Trp, Tyr, or is absent (preferably Arg);

$X_2$ is Ala, Arg, Asn, Asp, Gly, Pro, Ser, or is absent (preferably Asn, Asp, Gly, or Pro);
$X_3$ is Arg, Asn, Gln, Glu, Gly, Lys, Met, Pro, Trp or Val (preferably Gly or Met);
$X_5$ is Arg, Asn, Gln, Glu, His, Leu, Phe, Pro, Trp, Tyr, or Val (preferably Trp, Tyr, or Val);
$X_6$ is Arg, Asp, Gln, Gly, Ile, Lys, Phe, Thr, Trp or Tyr (preferably Asp);
$X_7$ is Ala, Arg, Asp, Glu, Gly, Leu, Ser, or Tyr (preferably Asp);
$X_8$ is Asp, Gln, Glu, Leu, Met, Phe, Pro, Ser, or Tyr (preferably Leu);
$X_9$ is Asp, Leu, Pro, Thr, or Val (preferably Leu or Thr);

$X_{10}$ is Arg, Gln, His, Be, Leu, Lys, Met, Phe, Thr, Trp or Tyr (preferably Lys or Thr);

$X_{11}$ is Ala, Arg, Asn, Gln, Glu, His, Leu, Lys, Met, or Thr (preferably Arg or Leu);
$X_{12}$ is Ala, Asn, Gln, Gly, Leu, Lys, Phe, Pro, Thr, Trp, or Tyr (preferably Thr or Trp);
$X_{13}$ is Ala, Arg, Gln, His, Lys, Met, Phe, Pro, Thr, Trp, or Tyr (preferably Met or Phe);
$X_{14}$ is Arg, Gln, Glu, Gly, His, Leu, Met, Phe, Pro, Ser, Thr, Tyr, or Val (preferably Val);
$X_{16}$ is Arg, Asp, Gly, His, Lys, Met, Phe, Pro, Ser, or Trp (preferably Met);

$X_{17}$ is Arg, Asn, Asp, Gly, His, Phe, Pro, Ser, Trp or Tyr, (preferably Arg, His, or Tyr); and $X_{18}$ is Ala, Arg, Asn, Asp, His, Leu, Phe, or Trp (preferably His or Asn), wherein said polypeptide binds B lymphocyte stimulator and/or B lymphocyte stimulator-like polypeptides.

Additional preferred embodiments include methods utilizing linear B lymphocyte stimulator binding polypeptides comprising, or alternatively consisting of, an amino acid sequence selected from F and G (SEQ ID NOs:6 and 7):

(SEQ ID NO: 6)

(F) $X_1$-$X_2$-$X_3$-$X_4$-$X_5$-$X_6$-$X_7$-$X_8$-$X_9$-$X_{10}$-$X_{11}$-$X_{12}$, wherein $X_1$ is Ala, Arg, Gly, His, Leu, Lys, Met, Phe, Trp, Tyr, or Val (preferably Gly, Tyr, or Val);

$X_2$ is Ala, Arg, Gln, His, Ile, Leu, Phe, Thr, Trp, or Tyr (preferably His or Tyr);

$X_3$ is Ala, Asp, Lys, Phe, Thr, Trp or Tyr (preferably Asp or Tyr);

$X_4$ is Arg, Asp, Gln, Lys, Met, Phe, Pro, Ser, Tyr, or Val (preferably Asp or Gln);

$X_5$ is Asp, Leu, Lys, Phe, Pro, Ser, or Val (preferably Leu or Ser);

$X_6$ is His, Be, Leu, Pro, Ser, or Thr (preferably Leu or Thr);

$X_7$ is Arg, Gly, His, Leu, Lys, Met, or Thr (preferably Lys or Thr);

$X_8$ is Ala, Arg, Asn, Ile, Leu, Lys, Met, or Thr (preferably Leu or Lys);

$X_9$ is Ala, Asn, Arg, Asp, Glu, Gly, His, Leu, Met, Ser, Trp, Tyr, or Val (preferably Met or Ser);

$X_{10}$ is Be, Leu, Phe, Ser, Thr, Trp, Tyr, or Val (preferably Thr or Leu);

$X_{11}$ is Ala, Arg, Gly, His, Be, Leu, Lys, Pro, Ser, Thr, Trp, Tyr, or Val (preferably Pro or Thr); and $X_{12}$ is Arg, Asp, His, Leu, Lys, Met, Phe, Pro, Ser, Trp, Tyr, or Val (preferably Arg or Pro), wherein said polypeptide binds B lymphocyte stimulator and/or B lymphocyte stimulator-like polypeptides; or (SEQ ID NO: 7)

(G) $X_1$-$X_2$-$X_3$-$X_4$-$X_5$-$X_6$-$X_7$-$X_8$-$X_9$-$X_{10}$-$X_{11}$-$X_{12}$-$X_{13}$, wherein $X_1$ is Asp, Gln, Glu, Gly, His, Lys, Met, or Trp (preferably Glu, Lys);

$X_2$ is Arg, Gln, His, Ile, Leu, or Pro (preferably His or Pro);

$X_3$ is Asp, Gly, Ile, Lys, Thr, Tyr or Val (preferably Tyr);

$X_4$ is Asn, Asp, Gln, Glu, Met, Pro, Ser, or Tyr (preferably Asp or Gln);

$X_5$ is Asn, Asp, His, Be, Leu, Met, Pro, Thr or Val (preferably Asn or Thr);

$X_6$ is Asp, Glu, His, Leu, Lys, Pro, or Val (preferably Asp or Pro);

$X_7$ is Arg, Asn, Gln, His, Be, Leu, Met, Pro, or Thr (preferably Ile or Pro);

$X_8$ is Gln, Gly, His, Leu, Met, Ser, or Thr (preferably Leu or Thr);

$X_9$ is Asn, Gln, Gly, His, Leu, Lys, Ser, or Thr (preferably Lys);

$X_{10}$ is Ala, Gly, Ile, Leu, Lys, Met, or Phe (preferably Gly or Met);

$X_{11}$ is Ala, Glu, His, Ile, Leu, Met, Ser, Thr, Trp, Tyr, or Val (preferably Ala or Thr);

$X_{12}$ is Arg, Gln, Glu, Gly, His, Be, Lys, Tyr, or Val (preferably Arg or His); and $X_{13}$ is Arg, Asn, Glu, His, Ile, Ser, Thr, Trp, or Val (preferably His), wherein said polypeptide binds B lymphocyte stimulator and/or B lymphocyte stimulator-like polypeptides.

Additional polypeptides useful in the methods of the invention include polypeptides comprising, or alternatively consisting of, an amino acid sequence selected from H-L (SEQ ID NOs:8-12):

(H) Cys-$X_2$-Phe-$X_4$-Trp-Glu-Cys, (SEQ ID NO: 8)

wherein $X_2$ is Phe, Trp, or Tyr (preferably Tyr); and $X_4$ is Pro or Tyr (preferably Pro); or (I) Cys-$X_2$-$X_3$-$X_4$-$X_5$-$X_6$-$X_7$-Cys, (SEQ ID NO: 9)

wherein $X_2$ is Asp, Be, Leu, or Tyr (preferably Asp or Leu);

$X_3$ is Arg, Asp, Glu, His, Be, Leu, Lys, Phe, Pro, Tyr, or Val (preferably Glu or Leu);

$X_4$ is His, Leu, Lys, or Phe (preferably His or Leu);

$X_5$ is Leu, Pro, or Thr (preferably Thr or Pro);

$X_6$ is Arg, Asn, Gly, His, Be, Lys, Met, or Trp (preferably Lys); and $X_7$ is Ala, Asn, Gln, Glu, Gly, His, Ile, Leu, Met, Phe, Ser, Trp, Tyr, or Val; or (J)  Cys-$X_2$-$X_3$-$X_4$-$X_5$-$X_6$-$X_7$-$X_8$-Cys,     (SEQ ID NO: 10)

wherein $X_2$ is Asn, Asp, Pro, Ser, or Thr (preferably Asp);

$X_3$ is Arg, Asp, Ile, Leu, Met, Pro, or Val (preferably Ile);

$X_4$ is Ala, Ile, Leu, Pro, Thr, or Val (preferably Val or Leu);

$X_5$ is Asn, His, Ile, Leu, Lys, Phe, or Thr (preferably Thr);

$X_6$ is Asn, Glu, Gly, His, Leu, Lys, Met, Pro, or Thr (preferably Leu);

$X_7$ is Arg, Asn, Asp, Gln, Glu, Gly, Ile, Lys, Met, Pro, Ser, or Trp;

$X_8$ is Arg, Glu, Gly, Lys, Phe, Ser, Trp, or Tyr (preferably Ser); or (K)  Cys-$X_2$-$X_3$-$X_4$-$X_5$-$X_6$-$X_7$-$X_8$-$X_9$-Cys,     (SEQ ID NO: 11)

wherein $X_2$ is Asp, Gln, His, Ile, Leu, Lys, Met, Phe, or Thr;

$X_3$ is His, Ile, Leu, Met, Phe, Pro, Trp, or Tyr;

$X_4$ is Asp, His, Leu, or Ser (preferably Asp);

$X_5$ is Ala, Arg, Asp, Glu, Leu, Phe, Pro, or Thr (preferably Glu or Pro);

$X_6$ is Ala, Arg, Asn, or Leu (preferably Leu);

$X_7$ is Ile, Leu, Met, Pro, Ser, or Thr (preferably Thr);

$X_8$ is Ala, Arg, Asn, Gly, His, Lys, Ser, or Tyr;

$X_9$ is Ala, Arg, Asn, Gln, Leu, Met, Ser, Trp, Tyr, or Val; or (L)  Cys-$X_2$-$X_3$-$X_4$-$X_5$-$X_6$-$X_7$-$X_8$-$X_9$-$X_{10}$-$X_{11}$-Cys,     (SEQ ID NO: 12)

wherein $X_2$ is Arg, Asn, Gln, Glu, His, Leu, Phe, Pro, Trp, Tyr, or Val (preferably Trp, Tyr, or Val);

$X_3$ is Arg, Asp, Gln, Gly, Ile, Lys, Phe, Thr, Trp or Tyr (preferably Asp);

$X_4$ is Ala, Arg, Asp, Glu, Gly, Leu, Ser, or Tyr (preferably Asp);

$X_5$ is Asp, Gln, Glu, Leu, Met, Phe, Pro, Ser, or Tyr (preferably Leu);

$X_6$ is Asp, Leu, Pro, Thr, or Val (preferably Leu or Thr);

$X_7$ is Arg, Gln, His, Ile, Leu, Lys, Met, Phe, Thr, Trp or Tyr (preferably Lys or Thr);

$X_8$ is Ala, Arg, Asn, Gln, Glu, His, Leu, Lys, Met, or Thr (preferably Arg or Leu);

$X_9$ is Ala, Asn, Gln, Gly, Leu, Lys, Phe, Pro, Thr, Trp, or Tyr (preferably Thr or Trp);

$X_{10}$ is Ala, Arg, Gln, His, Lys, Met, Phe, Pro, Thr, Trp, or Tyr (preferably Met or Phe);

$X_{11}$ is Arg, Gln, Glu, Gly, His, Leu, Met, Phe, Pro, Ser, Thr, Tyr, or Val (preferably Val);

wherein said polypeptides bind B lymphocyte stimulator and/or B lymphocyte stimulator-like polypeptides.

In preferred embodiments of the present invention, B lymphocyte stimulator binding polypeptides are used which comprise the following amino acid sequence M (SEQ ID NO:447):

(SEQ ID NO: 447)
(M)  Ala-$X_2$-$X_3$-$X_4$-Asp-$X_6$-Leu-Thr-$X_9$-Leu-$X_{11}$-$X_{12}$-$X_{13}$-$X_{14}$, wherein $X_2$ is Asn, Ser, Tyr, Asp, Phe, Ile, Gln, His, Pro, Lys, Leu, Met, Thr, Val, Glu, Ala, Gly, Cys, or Trp (i.e., any amino acid except Arg; preferably Asn);

$X_3$ is Trp, Glu, Lys, Cys, Leu, Ala, Arg, Gly, or Ser (preferably Trp);

$X_4$ is Tyr, Phe, Glu, Cys, Asn (preferably Tyr);

$X_6$ is Pro, Ser, Thr, Phe, Leu, Tyr, Cys, or Ala (preferably Pro or Ser);

$X_9$ is Lys, Asn, Gln, Gly, or Arg (preferably Lys);

$X_{11}$ is Trp, Ser, Thr, Arg, Cys, Tyr, or Lys (preferably Trp);

$X_{12}$ is Leu, Phe, Val, Ile, or His (preferably Leu);

$X_{13}$ is Pro, Leu, His, Ser, Arg, Asn, Gln, Thr, Val, Ala, Cys, Ile, Phe, or Tyr (i.e., not Asp, Glu, Gly, Lys, Met, or Trp; preferably Pro); and $X_{14}$ is Asp, Glu, Asn, Val, His, Gln, Arg, Gly, Ser, Tyr, Ala, Cys, Lys, Ile, Thr or Leu (i.e., not Phe, Met, Pro, or Trp; preferably Asp, Val or Glu).

Preferred methods will utilize polypeptides comprising a core sequence of the formula N:

(SEQ ID NO: 448)
(N)  $X_1$-$X_2$-Asp-$X_4$-Leu-Thr-$X_7$-Leu-$X_9$-$X_{10}$, wherein $X_1$ is Trp, Glu, Lys, Cys, Leu, Ala, Arg, Gly, or Ser (preferably Trp);

$X_2$ is Tyr, Phe, Glu, Cys, Asn (preferably Tyr);

$X_4$ is Pro, Ser, Thr, Phe, Leu, Tyr, Cys, or Ala (preferably Pro or Ser);

$X_7$ is Lys, Asn, Gln, Gly, or Arg (preferably Lys);

$X_9$ is Trp, Ser, Thr, Arg, Cys, Tyr, or Lys (preferably Trp); and $X_{10}$ is Leu, Phe, Val, Ile, or His (preferably Leu).

Especially preferred methods according to the invention will utilize B lymphocyte stimulator binding polypeptides which comprise the core peptide Trp-Tyr-Asp-Pro-Leu-Thr-Lys-Leu-Trp-Leu (SEQ ID NO:436).

B lymphocyte stimulator binding polypeptides used in the methods of the present invention may also have an amino terminal (N-terminal) capping or functional group, such as an acetyl group, which, for example, blocks the amino terminal amino group from undesirable reactions or is useful in linking the B lymphocyte stimulator binding polypeptide to another molecule, matrix, resin, or solid support. B lymphocyte stimulator binding polypeptides may also have a carboxy terminal (C-terminal) capping or functional group, such as an amide group, which, for example, blocks the C-terminal carboxyl group from undesirable reactions or provides a functional group useful in conjugating the binding polypeptide to other molecules, matrices, resins, or solid supports. Preferably, the N- and/or C-terminal capping groups are polypeptide linker molecules. An especially preferred C-terminal linker molecule that is useful for immobilizing a B lymphocyte stimulator binding polypeptide to a solid support or chromatographic matrix material comprises the amino acid sequence Pro-Gly-Pro-Glu-Gly-Gly-Gly-Lys (SEQ ID NO:13). Another useful C-terminal linker, e.g., for fluoresceinating peptides, is Gly-Gly-Lys (see Table 14).

In the methods of the present invention, it may be advantageous to use B lymphocyte stimulator binding polypeptides that have been modified, for example, to increase or decrease the stability of the molecule, while retaining the ability to bind B lymphocyte stimulator and/or B lymphocyte stimulator-like polypeptides. An example of a modified B lymphocyte stimulator binding polypeptide is a polypeptide in which one of two cysteine residues is substituted with a non-naturally occurring amino acid that is capable of condensing with the remaining cysteine side chain to form a stable thioether bridge, thereby generating a cyclic B lymphocyte stimulator binding polypeptide. Such cyclic thioether molecules of synthetic peptides may be routinely generated using techniques known in the art, e.g., as described in PCT publication WO 97/46251, incorporated herein by reference.

Some of the methods provided herein utilize B lymphocyte stimulator binding polypeptides that have been attached, coupled, linked or adhered to a matrix or resin or solid support. Techniques for attaching, linking or adhering polypeptides to matrices, resins and solid supports are well known in the art. Suitable matrices, resins or solid supports for these materials may be any composition known in the art to which a B lymphocyte stimulator binding polypeptide could be attached, coupled, linked, or adhered, including but not limited to, a chromatographic resin or matrix, such as SEPHAROSE-4 FF agarose beads, the wall or floor of a well in a plastic microtiter dish, such as used in an enzyme-liked immunosorbent assay (ELISA), or a silica based biochip. Materials useful as solid supports on which to immobilize binding polypeptides for use in the methods include, but are not limited to, polyacrylamide, agarose, silica, nitrocellulose, paper, plastic, nylon, metal, and combinations thereof. A B lymphocyte stimulator binding polypeptide may be immobilized on a matrix, resin or solid support material by a non-covalent association or by covalent bonding, using techniques known in the art.

In certain embodiments of the present invention, it is preferred to utilize B lymphocyte stimulator binding polypeptides or phage displaying such binding polypeptides that irreversibly bind the B lymphocyte stimulator protein in its native, soluble trimeric form.

In certain embodiments of the present, it is preferred to utilize B lymphocyte stimulator binding polypeptides of the present invention or phage displaying such binding polypeptides that reversibly bind the B lymphocyte stimulator protein in its native, soluble trimeric form.

In further embodiments of the present invention, a method may call for the use of a composition of matter comprising isolated nucleic acids, preferably DNA, encoding a B lymphocyte stimulator binding polypeptide. In specific embodiments, nucleic acid molecules encode a B lymphocyte stimulator binding polypeptide comprising the amino acid sequence of SEQ ID NOs:1-12, 20-172, or 186-444. In additional embodiments, the nucleic acid molecules encode a polypeptide variant or fragment of a polypeptide comprising an amino acid sequence of SEQ ID NOs:1-12, 20-172, or 186-444. In a further additional embodiment, such nucleic acid molecules encode a B lymphocyte stimulator binding polypeptide, the complementary strand of which nucleic acid hybridizes to a polynucleotide sequence encoding a polypeptide described in Tables 1-8 and 13 and in Examples 2, 5 and 6 (SEQ ID NOs:1-12, 20-172 and 186-444), under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In further embodiments of the invention, recombinant bacteriophage are utilized which display B lymphocyte stimulator binding polypeptides on their surfaces. Such phage may be routinely generated using techniques known in the art and are useful, for example, as screening reagents and reagents for detecting B lymphocyte stimulator.

In other methods according to the invention, a B lymphocyte stimulator binding polypeptide is used to detect or isolate B lymphocyte stimulator or B lymphocyte stimulator-like polypeptides in a solution. Such solutions include, but are not limited to, B lymphocyte stimulator or B lymphocyte stimulator-like polypeptides suspended or dissolved in water or a buffer solution as well as any fluid and/or cell obtained from an individual, biological fluid, body tissue, body cell, cell line, tissue culture, or other source which may contain B lymphocyte stimulator or B lymphocyte stimulator-like polypeptides, such as, cell culture medium, cell extracts, and tissue homogenates. Biological fluids include, but are not limited to, sera, plasma, lymph, blood, blood fractions, urine, synovial fluid, spinal fluid, saliva, and mucous.

Methods according to the present invention may advantageously utilize panels of B lymphocyte stimulator binding polypeptides (including molecules comprising, or alternatively consisting of, B lymphocyte stimulator binding polypeptide fragments or variants) wherein the panel members correspond to one, two, three, four, five, ten, fifteen, twenty, or more different B lymphocyte stimulator binding polypeptides. Methods according to the present invention may alternatively use mixtures of B lymphocyte stimulator binding polypeptides, wherein the mixture corresponds to one, two, three, four, five, ten, fifteen, twenty, or more different B lymphocyte stimulator binding polypeptides. The present invention also provides methods of using compositions comprising, or alternatively consisting of, one, two, three, four, five, ten, fifteen, twenty, or more B lymphocyte stimulator binding polypeptides (including molecules comprising, or alternatively consisting of, B lymphocyte stimulator binding polypeptide fragments or variants thereof). Alternatively, a method according to the invention may utilize a composition comprising, or alternatively consisting of, nucleic acid molecules encoding one or more B lymphocyte stimulator binding polypeptides.

The methods of the present invention also provides for the use of fusion proteins comprising a B lymphocyte stimulator binding polypeptide (including molecules comprising, or alternatively consisting of, B lymphocyte stimulator binding polypeptide fragments or variants thereof), and a heterologous polypeptide. A composition useful in methods of the present invention may comprise, or alternatively consist of, one, two, three, four, five, ten, fifteen, twenty or more fusion proteins capable of binding to B lymphocyte stimulator. Alternatively, a composition useful in methods of the invention may comprise, or alternatively consist of, nucleic acid molecules encoding one, two, three, four, five, ten, fifteen, twenty or more such fusion proteins.

The present invention encompasses methods and compositions for detecting, diagnosing, prognosing, and/or monitoring diseases or disorders associated with aberrant B lymphocyte stimulator or B lymphocyte stimulator receptor expression or inappropriate B lymphocyte stimulator or B lymphocyte stimulator receptor function in an animal, preferably a mammal, and most preferably a human, comprising, or alternatively consisting of, use of B lymphocyte stimulator binding polypeptides (including molecules which comprise, or alternatively consist of, B lymphocyte stimulator binding polypeptide fragments or variants thereof) that specifically bind to B lymphocyte stimulator. Diseases and disorders which can be detected, diagnosed, prognosed and/or monitored with the B lymphocyte stimulator binding polypeptides include, but are not limited to, immune system diseases or disorders (e.g., autoimmune diseases or disorders, immunodeficiencies, lupus, glomerular nephritis, rheumatoid arthritis, multiple sclerosis, graft vs. host disease, myasthenia gravis, Hashimoto's disease, and immunodeficiency syndrome), proliferative diseases or disorders (e.g., cancer, premalignant conditions, benign tumors, hyperproliferative disorders, benign proliferative disorders, leukemia, lymphoma, chronic lymphocytic leukemia, multiple myeloma, Hodgkin's lymphoma, Hodgkin's disease, T cell proliferative diseases and disorders, B cell proliferative diseases and disorders, monocytic proliferative diseases or disorders, acute myelogenous leukemia, macrophage proliferative diseases and disorders, and carcinoma), infectious diseases (e.g., AIDS), and inflammatory disorders (e.g., asthma, allergic disorders, and rheumatoid arthritis).

In specific embodiments, the present invention encompasses methods and compositions for detecting, diagnosing, prognosing and/or monitoring diseases or disorders associated with hypergammaglobulinemia (e.g., AIDS, autoimmune diseases, and some immunodeficiencies). In other specific embodiments, the present invention encompasses methods and compositions for detecting, diagnosing, prognosing and/or monitoring diseases or disorders associated with hypogammaglobulinemia (e.g., an immunodeficiency).

The present invention further encompasses methods and compositions for preventing, treating and/or ameliorating diseases or disorders associated with aberrant B lymphocyte stimulator or B lymphocyte stimulator receptor expression or inappropriate B lymphocyte stimulator or B lymphocyte stimulator receptor function in an animal, preferably a mammal, and most preferably a human, comprising, or alternatively consisting of, administering to an animal in which such treatment, prevention or amelioration is desired one or more B lymphocyte stimulator binding polypeptides (including molecules which comprise, or alternatively consist of, B lymphocyte stimulator binding polypeptide fragments or variants thereof) in an amount effective to treat, prevent or ameliorate the disease or disorder. Diseases and disorders which can be prevented, treated, and/or ameliorated with the B lymphocyte stimulator binding polypeptides include, but are not limited to, immune system diseases or disorders (e.g., autoimmune diseases or disorders, immunodeficiencies, lupus, glomerular nephritis, rheumatoid arthritis, multiple sclerosis, graft vs. host disease, myasthenia gravis, Hashimoto's disease, immunodeficiency syndrome, hypogammaglobulinemia, and hypergammaglobulinemia), proliferative diseases or disorders (e.g., cancer, premalignant conditions, benign tumors, hyperproliferative disorders, benign proliferative disorders, leukemia, lymphoma, chronic lymphocytic leukemia, multiple myeloma, Hodgkin's lymphoma, Hodgkin's disease, T cell proliferative diseases and disorders, B cell proliferative diseases and disorders, monocytic proliferative diseases or disorders, acute myelogenous leukemia, macrophage proliferative diseases and disorders, and carcinoma), infectious diseases (e.g., AIDS), and inflammatory disorders (e.g., asthma, allergic disorders, and rheumatoid arthritis).

In specific embodiments, the present invention encompasses methods and compositions (e.g., B lymphocyte stimulator binding polypeptides that antagonize B lymphocyte stimulator activity) for preventing, treating and/or ameliorating diseases or disorders associated with hypergammaglobulinemia (e.g., AIDS, autoimmune diseases, and some immunodeficiency syndromes). In other specific embodiments, the present invention encompasses methods and compositions (e.g., B lymphocyte stimulator binding polypeptides that enhance B lymphocyte stimulator activity) for preventing, treating or ameliorating diseases or disorders associated with hypogammaglobulinemia (e.g., an immunodeficiency syndrome).

In specific embodiments, the present invention encompasses methods and compositions (e.g., B lymphocyte stimulator binding polypeptides that antagonize B lymphocyte stimulator activity) for preventing, treating and/or ameliorating immune system diseases or disorders, comprising, or alternatively consisting of, administering to an animal in which such treatment, prevention, and/or amelioration is desired, a B lymphocyte stimulator binding polypeptide in an amount effective to treat, prevent and/or ameliorate the disease or disorder.

In specific embodiments, the present invention encompasses methods and compositions (e.g., B lymphocyte stimulator binding polypeptides that antagonize B lymphocyte stimulator activity) for preventing, treating and/or ameliorating diseases or disorders of cells of hematopoietic origin, comprising, or alternatively consisting of, administering to an animal in which such treatment, prevention, and/or amelioration is desired, a B lymphocyte stimulator binding polypeptide in an amount effective to treat, prevent and/or ameliorate the disease or disorder.

Autoimmune disorders, diseases, or conditions that may be detected, diagnosed, prognosed, monitored, treated, prevented, and/or ameliorated using the B lymphocyte stimulator binding polypeptides include, but are not limited to, autoimmune hemolytic anemia, autoimmune neonatal thrombocytopenia, idiopathic thrombocytopenia purpura, autoimmune neutropenia, autoimmunocytopenia, hemolytic anemia, antiphospholipid syndrome, dermatitis, gluten-sensitive enteropathy, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, insulin dependent diabetes mellitis, and autoimmune inflammatory eye, autoimmune thyroiditis, hypothyroidism (i.e., Hashimoto's thyroiditis), systemic lupus erythematosus, discoid lupus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes mellitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulomatous, degenerative, and atrophic disorders).

Immunodeficiencies that may be detected, diagnosed, prognosed, monitored, treated, prevented, and/or ameliorated using the B lymphocyte stimulator binding polypeptides include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

The present invention further encompasses methods and compositions for inhibiting or reducing immunoglobulin production, comprising, or alternatively consisting of, contacting an effective amount of B lymphocyte stimulator binding polypeptide with B lymphocyte stimulator, wherein the effective amount of B lymphocyte stimulator binding polypeptide inhibits or reduces B lymphocyte stimulator mediated immunoglobulin production.

The present invention further encompasses methods and compositions for inhibiting or reducing immunoglobulin production, comprising, or alternatively consisting of, administering to an animal in which such inhibition or reduction is desired, a B lymphocyte stimulator binding polypeptide in an amount effective to inhibit or reduce immunoglobulin production.

The present invention further encompasses methods and compositions for inhibiting or reducing B cell proliferation, comprising, or alternatively consisting of, contacting an effective amount of B lymphocyte stimulator binding polypeptide with B lymphocyte stimulator, wherein the effective amount of B lymphocyte stimulator binding polypeptide inhibits or reduces B lymphocyte stimulator mediated B cell proliferation.

The present invention further encompasses methods and compositions for inhibiting or reducing B cell proliferation comprising, or alternatively consisting of, administering to an animal in which such inhibition or reduction is desired, a B lymphocyte stimulator binding polypeptide in an amount effective to inhibit or reduce B cell proliferation.

The present invention further encompasses methods and compositions for inhibiting or reducing activation of B cells, comprising, or alternatively consisting of, contacting an effective amount of B lymphocyte stimulator binding polypeptide with B lymphocyte stimulator, wherein the effective amount of B lymphocyte stimulator binding polypeptide inhibits or reduces B lymphocyte stimulator mediated B cell activation.

The present invention further encompasses methods and compositions for inhibiting or reducing activation of B cells, comprising, or alternatively consisting of, administering to an animal in which such inhibition or reduction is desired, a B lymphocyte stimulator binding polypeptide in an amount effective to inhibit or reduce B cell activation.

The present invention further encompasses methods and compositions for decreasing lifespan of B cells, comprising, or alternatively consisting of, contacting an effective amount of B lymphocyte stimulator binding polypeptide with B lymphocyte stimulator, wherein the effective amount of B lymphocyte stimulator binding polypeptide inhibits or reduces B lymphocyte stimulator regulated lifespan of B cells.

The present invention further encompasses methods and compositions for decreasing lifespan of B cells, comprising, or alternatively consisting of, administering to an animal in which such decrease is desired, a B lymphocyte stimulator binding polypeptide in an amount effective to decrease B cell lifespan.

The present invention further encompasses methods and compositions for inhibiting or reducing graft rejection, comprising, or alternatively consisting of, administering to an animal in which such inhibition or reduction is desired, a B lymphocyte stimulator binding polypeptide in an amount effective to inhibit or reduce graft rejection.

The present invention further encompasses methods and compositions for killing cells of hematopoietic origin, comprising, or alternatively consisting of, contacting B lymphocyte stimulator binding polypeptides with B lymphocyte stimulator to form a complex; and contacting the complex with cells of hematopoietic origin.

The present invention further encompasses methods and compositions for killing cells of hematopoietic origin, comprising, or alternatively consisting of, administering to an animal in which such killing is desired, a B lymphocyte stimulator binding polypeptide in an amount effective to kill cells of hematopoietic origin.

The present invention further encompasses methods and compositions for stimulating immunoglobulin production, comprising, or alternatively consisting of, contacting an effective amount of B lymphocyte stimulator binding polypeptide with B lymphocyte stimulator, wherein the effective amount of the B lymphocyte stimulator binding polypeptide stimulates B lymphocyte stimulator mediated immunoglobulin production.

The present invention further encompasses methods and compositions for stimulating immunoglobulin production comprising, or alternatively consisting of, administering to an animal in which such stimulation is desired, a B lymphocyte stimulator binding polypeptide in an amount effective to stimulate immunoglobulin production.

The present invention further encompasses methods and compositions for stimulating B cell proliferation, comprising, or alternatively consisting of, contacting an effective amount of B lymphocyte stimulator binding polypeptide with B lymphocyte stimulator, wherein the effective amount of B lymphocyte stimulator binding polypeptide stimulates B lymphocyte stimulator mediated B cell proliferation.

The present invention further encompasses methods and compositions for stimulating B cell proliferation, comprising, or alternatively consisting of, administering to an animal in which such stimulation is desired, a B lymphocyte stimulator binding polypeptide in an amount effective to stimulate B cell proliferation.

The present invention further encompasses methods and compositions for increasing activation of B cells, comprising, or alternatively consisting of, contacting an effective amount of B lymphocyte stimulator binding polypeptide with B lymphocyte stimulator, wherein the effective amount of B lymphocyte stimulator binding polypeptide increases B lymphocyte stimulator mediated activation of B cells.

The present invention further encompasses methods and compositions for increasing activation of B cells, comprising, or alternatively consisting of, administering to an animal in which such increase is desired, a B lymphocyte stimulator binding polypeptide in an amount effective to increase B cell activation.

The present invention further encompasses methods and compositions for increasing lifespan of B cells, comprising, or alternatively consisting of, contacting an effective amount of B lymphocyte stimulator binding polypeptide with B lymphocyte stimulator, wherein the effective amount of B lymphocyte stimulator binding polypeptide increases B lymphocyte stimulator regulated lifespan of B cells.

The present invention further encompasses methods and compositions for increasing lifespan of B cells, comprising, or alternatively consisting of, administering to an animal in which such increase is desired, a B lymphocyte stimulator binding polypeptide in an amount effective to increase lifespan of B cells.

DEFINITIONS

In order that the invention may be clearly understood, the following terms are defined:

The term "recombinant" is used to describe non-naturally altered or manipulated nucleic acids, host cells transfected with exogenous nucleic acids, or polypeptide molecules that are expressed non-naturally, through manipulation of isolated nucleic acid (typically, DNA) and transformation or transfection of host cells. "Recombinant" is a term that specifically encompasses nucleic acid molecules that have been constructed in vitro using genetic engineering techniques, and use of the term "recombinant" as an adjective to describe a molecule, construct, vector, cell, polypeptide or polynucleotide specifically excludes naturally occurring such molecules, constructs, vectors, cells, polypeptides or polynucleotides.

The term "bacteriophage" is defined as a bacterial virus containing a nucleic acid core and a protective shell built up by the aggregation of a number of different protein molecules. The terms "bacteriophage" and "phage" are synonymous and are used herein interchangeably.

The term "affinity ligand" is sometimes used herein and is synonymous with B lymphocyte stimulator binding polypeptides.

The term "B lymphocyte stimulator protein" as used herein encompasses both the membrane (e.g., SEQ ID NOs:173 and 174) and soluble forms (e.g., amino acids 134-285 of SEQ ID NO:173) of B lymphocyte stimulator. B lymphocyte stimulator protein may be monomeric, dimeric, or trimeric or multivalent. Preferably, B lymphocyte stimulator proteins are homotrimeric.

The term "B lymphocyte stimulator-like polypeptide" as used herein encompasses natural B lymphocyte stimulator or full-length recombinant B lymphocyte stimulator as well as fragments and variants thereof, such as, a modified or truncated form of natural B lymphocyte stimulator or full-length recombinant B lymphocyte stimulator, which B lymphocyte stimulator and B lymphocyte stimulator-like polypeptide retain a B lymphocyte stimulator functional activity. B lymphocyte stimulator or B lymphocyte stimulator fragments that may be specifically bound by the compositions useful according to the invention include, but are not limited to, human B lymphocyte stimulator (SEQ ID NOs:173 and/or 174) or B lymphocyte stimulator expressed on human monocytes; murine B lymphocyte stimulator (SEQ ID NOs:175 and/or 176) or B lymphocyte stimulator expressed on murine monocytes; rat B lymphocyte stimulator (either the soluble forms as given in SEQ ID NOs:177, 178, 179 and/or 180 or in a membrane associated form, e.g., on the surface of rat monocytes); or monkey B lymphocyte stimulator (e.g., the monkey B lymphocyte stimulator polypeptides of SEQ ID NOS:181 and/or 182, the soluble form of monkey B lymphocyte stimulator, or B lymphocyte stimulator expressed on monkey monocytes) or fragments thereof. Preferably compositions useful according to the invention bind human B lymphocyte stimulator (SEQ ID NOs:173 and/or 174) or fragments thereof. B lymphocyte stimulator and B lymphocyte stimulator-like polypeptides retain at least one functional activity of the natural or full-length B lymphocyte stimulator, including but not limited to the following activities: binding to B lymphocyte stimulator receptor (e.g., TACI (GenBank accession number AAC51790), and BCMA (GenBank accession number NP_001183)), stimulating B cell proliferation, stimulating immunoglobulin secretion by B cells, stimulating the B lymphocyte stimulator receptor signaling cascade and/or being bound by an anti-B lymphocyte stimulator antibody or other B lymphocyte stimulator binding polypeptide. Assays that can be used to determine the functional activities of B lymphocyte stimulator or B lymphocyte stimulator like polypeptides can readily be determined by one skilled in the art (e.g., see assays disclosed in Moore et al., 1999, supra) "B lymphocyte stimulator-like polypeptides" also include fusion polypeptides in which all or a portion of B lymphocyte stimulator is fused or conjugated to another polypeptide. B lymphocyte stimulator-like polypeptides that are fusion polypeptides retain at least one functional activity of B lymphocyte stimulator, preferably the ability to stimulate B lymphocytes (see, for example, Moore et al., *Science*, 285: 260-263 (1999)), to bind the B lymphocyte stimulator receptors (e.g., TACI or BCMA), and/or to be bound by an anti-B lymphocyte stimulator antibody or other B lymphocyte stimulator binding polypeptide. B lymphocyte stimulator fusion polypeptides may be made by recombinant DNA techniques in which a gene or other polynucleotide coding sequence for B lymphocyte stimulator or a fragment thereof is ligated in-frame (recombined) with the coding sequence of another protein or polypeptide. The resulting recombinant DNA molecule is then inserted into any of a variety of plasmid or phage expression vectors, which enable expression of the fusion protein molecule in an appropriate eukaryotic or prokaryotic host cell. B lymphocyte stimulator fusion polypeptides may be generated by synthetic or semi-synthetic procedures as well.

The terms "B lymphocyte stimulator target" or "B lymphocyte stimulator target protein" are sometimes used herein and encompass B lymphocyte stimulator and/or B lymphocyte stimulator-like polypeptides. Thus, the B lymphocyte stimulator binding polypeptides used according to the methods of the invention bind "B lymphocyte stimulator target proteins" and can be used to bind, detect, remove, and/or purify "B lymphocyte stimulator target proteins."

The term "binding polypeptide" is used herein to refer to any polypeptide capable of forming a binding complex with another molecule, polypeptide, peptidomimetic or transformant.

A "B lymphocyte stimulator binding polypeptide" is a molecule that can bind B lymphocyte stimulator target protein. Non-limiting examples of B lymphocyte stimulator binding polypeptides useful in the methods of the invention are the polypeptide molecules having an amino acid sequence described herein (see SEQ ID NOs:1-12, 20-172, and 186-444). The term B lymphocyte stimulator binding polypeptide also encompasses B lymphocyte stimulator binding fragments and variants (including derivatives) of polypeptides having the specific amino acid sequences described herein (SEQ ID NOs:1-12, 20-172, and 186-444). By "variant" of an amino acid sequence as described herein is meant a polypeptide that binds B lymphocyte stimulator, but does not necessarily comprise an identical or similar amino acid sequence of a B lymphocyte stimulator binding polypeptide specified herein. B lymphocyte stimulator binding polypeptides useful according to the invention which are variants of a B lymphocyte stimulator binding polypeptide specified herein satisfy at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% least 99%, or 100% identical to the amino acid sequence of a B lymphocyte stimulator binding polypeptide sequence disclosed herein (SEQ ID NOs:1-12, 20-172, and 186-444), (b) a polypeptide encoded by a nucleotide sequence, the complementary sequence of which hybridizes under stringent conditions to a nucleotide sequence encoding a B lymphocyte stimulator binding polypeptide disclosed herein (e.g., a nucleic acid sequence encoding the amino acid sequence of SEQ ID NOs:1-12, 20-172, and 186-444), and/or a fragment of a B lymphocyte stimulator binding polypeptide disclosed herein, of at least 5 amino acid residues, at least 10 amino acid residues, at least 15 amino acid residues, or at least 20 amino acid residues. B lymphocyte stimulator binding polypeptides useful according to the invention also encompass polypeptide sequences that have been modified for various applications provided that such modifications do not eliminate the ability to bind a B lymphocyte stimulator target. Specific, non-limiting examples of modifications contemplated include C-terminal or N-terminal amino acid substitutions or peptide chain elongations for the purpose of linking the B lymphocyte stimulator binder to a chromatographic material or other solid support. Other substitutions contemplated herein include substitution of one or both of a pair of cysteine residues that normally form disulfide links, for example with non-naturally occurring amino acid residues having reactive side chains, for the purpose of forming a more stable bond between those amino acid positions than the former disulfide bond. All such modified binding polypeptides are also considered B lymphocyte stimulator binding polypeptides so long as the modified polypeptides retain the ability to bind B lymphocyte stimulator and/or B lymphocyte stimulator-like polypeptides, and therefore, may be used in one or more of the various methods described herein, such as, to detect, purify, or isolate B lymphocyte stimulator or B lymphocyte stimulator-like polypeptides in or from a solution. B lymphocyte stimulator binding polypeptides also include variants of the specific B lymphocyte stimulator binding polypeptide sequences disclosed herein (e.g., SEQ ID NOs:1-12, 20-172, and 186-444) which have an amino acid sequence corresponding to one of these polypeptide sequences, but in which the polypeptide sequence is altered by substitutions, additions or deletions that provide for molecules that bind B lymphocyte stimulator. Thus, the B lymphocyte stimulator binding polypeptides include polypeptides containing, as a primary amino acid sequence, all or part of the particular B lymphocyte stimulator binding polypeptide sequence including altered sequences in which functionally equivalent amino acid residues are substituted for residues within the sequence, resulting in a peptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such B lymphocyte stimulator binding polypeptides can be made either by chemical peptide synthesis or by recombinant production from a nucleic acid encoding the B lymphocyte stimulator binding polypeptide which nucleic acid has been mutated. Any technique for mutagenesis known in the art can be used, including but not limited to, chemical mutagenesis, in vitro site-directed mutagenesis (Hutchinson et al., *J. Biol. Chem.,* 253: 6551 (1978)), use of TAB® linkers (Pharmacia), etc.

As used and understood herein, percent homology or percent identity of two amino acid sequences or of two nucleic acid sequences is determined using the algorithm of Karlin and Atschul (*Proc. Natl. Acad. Sci. USA,* 87: 2264-2268 (1990)), modified as in Karlin and Altschul (*Proc. Natl. Acad. Sci. USA,* 90: 5873-5877 (1993)). Such an algorithm is incorporated into the NBLAST and XBLAST programs of Altschul et al. (*J. Mol. Biol.,* 215: 403-410 (1990)). BLAST nucleotide searches are performed with the NBLAST program to obtain nucleotide sequences homologous to a nucleic acid molecule described herein. BLAST protein searches are performed with the XBLAST program to obtain amino acid sequences homologous to a reference polypeptide. To obtain gapped alignments for comparison purposes, Gapped BLAST is utilized as described in Altschul et al. (*Nucleic Acids Res.,* 25: 3389-3402 (1997)). When utilizing BLAST and Gapped BLAST programs, the default parameters of the respective programs (e.g., XBLAST and NBLAST) are used. See, http://www.ncbi.nlm.nih.gov. Alternatively, the percent identity of two amino acid sequences or of two nucleic acid sequences can be determined once the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The term "polypeptide", as used herein, refers to a linear, branched, or cyclic (e.g., containing a loop structure) polymer of two or more amino acid residues linked with a peptide bond. The term "polypeptide" is not restricted to any particular upper limit of amino acid residues. Thus, the B lymphocyte stimulator affinity ligands that comprise an amino acid sequence described herein are properly referred to as "B lymphocyte stimulator binding polypeptides" because such binding polypeptides contain at least two amino acid residues held together by a peptide bond, even though such molecules may also contain one or more additional moieties or groups that are not amino acids, such as N-terminal and/or C-terminal capping or functional groups, and that may or may not be involved in a peptide bond. The polypeptides may be monovalent, divalent, trivalent, or multivalent and may comprise one or more of the B lymphocyte stimulator binding polypeptides having the amino acid sequence of SEQ ID NOs:1-12, 20-172, and 186-444 and/or fragments or variants thereof. The term "peptide" is used herein to have the same meaning as "polypeptide."

The term "antibody," as used herein, refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. Examples of molecules which are described by the term "antibody" in this application include, but are not limited to: single chain Fvs (scFvs), Fab fragments, Fab' fragments, F(ab')$_2$, disulfide linked Fvs (sdFvs), Fvs, and fragments comprising or alternatively consisting of, either a VL or a VH domain. The term "single chain Fv" or "scFv" as used herein refers to a polypeptide comprising a VL domain of antibody linked to a VH domain of an antibody.

"Feed stream": B lymphocyte stimulator and B lymphocyte stimulator-like polypeptides that are bound by a B lymphocyte stimulator binding polypeptide of this invention may be produced by any method known in the art, including, but not limited to, chemical synthesis; production in transformed host cells; secretion into culture medium by naturally occurring cells or recombinantly transformed bacteria, yeasts, fungi, insect cells, plant cells, and mammalian cells; production in genetically engineered organisms (for example, transgenic mammals); and production in non-genetically engineered organisms. The solution, sample, or mixture that contains a B lymphocyte stimulator or B lymphocyte stimulator-like polypeptide as it is produced or is found present in a production solution will sometimes be referred to as the "feed stream".

The term "binding" refers to the determination by standard techniques that a binding polypeptide recognizes and binds to a given target. Such standard techniques include, but are not limited to, affinity chromatography, equilibrium dialysis, gel filtration, enzyme linked immunosorbent assay (ELISA), FACS analysis, and the monitoring of spectroscopic changes that result from binding, e.g., using fluorescence anisotropy, either by direct binding measurements or competition assays with another binder.

The term "specificity" refers to a binding polypeptide useful according to the invention that has a higher binding affinity for one target over another. Thus, the term "B lymphocyte stimulator target protein specificity" refers to a molecule having a higher affinity for B lymphocyte stimulator target protein as compared with another molecule that is not a B lymphocyte stimulator target protein.

The term "epitopes" as used herein refers to portions of B lymphocyte stimulator having antigenic or immunogenic activity in an animal, preferably a mammal. An epitope having immunogenic activity is a portion of B lymphocyte stimulator that elicits an antibody response in an animal. An epitope having antigenic activity is a portion of B lymphocyte stimulator to which an antibody or B lymphocyte stimulator binding polypeptide specifically binds as determined by any method known in the art, for example, by the immunoassays described herein. Antigenic epitopes need not necessarily be immunogenic.

The term "fragment" as used herein refers to a polypeptide comprising an amino acid sequence of at least 5 amino acid residues, at least 6 amino acid residues, at least 7 amino acid residues, at least 8 amino acid residues, at least 9 amino acid residues, at least 10 amino acid residues, at least 11 amino acid residues, at least 12 amino acid residues, at least 13 amino acid residues, at least 14 amino acid residues, at least 15 amino acid residues, at least 16 amino acid residues, at least 17 amino acid residues, at least 18 amino acid residues, at least 19 amino acid residues, at least 20 amino acid residues, at least 21 amino acid residues, at least 22 amino acid residues, at least 23 amino acid residues, at least 24 amino acid residues, or at least 25 amino acid residues of the amino acid sequence of B lymphocyte stimulator, or a B lymphocyte stimulator binding polypeptide (including molecules that comprise, or alternatively consist of, B lymphocyte stimulator binding polypeptide fragments or variants thereof).

The term "fusion protein" as used herein refers to a polypeptide that comprises, or alternatively consists of, an amino acid sequence of a B lymphocyte stimulator binding polypeptide and an amino acid sequence of a heterologous polypeptide (i.e., a polypeptide unrelated to the B lymphocyte stimulator binding polypeptide).

The term "host cell" as used herein refers to the particular subject cell transfected with a nucleic acid molecule and the progeny or potential progeny of such a cell. Progeny may not be identical to the parent cell transfected with the nucleic acid molecule due to mutations or environmental influences that may occur in succeeding generations or integration of the nucleic acid molecule into the host cell genome.

Other terms are defined as necessary in the text below.

DETAILED DESCRIPTION OF THE INVENTION

The present invention provides methods and compositions for detecting, diagnosing, prognosing, and/or monitoring diseases or disorders associated with aberrant B lymphocyte stimulator or B lymphocyte stimulator receptor expression or inappropriate B lymphocyte stimulator or B lymphocyte stimulator receptor function in an animal, preferably a mammal, and most preferably a human, comprising, or alternatively consisting of, use of B lymphocyte stimulator binding polypeptides (including molecules which comprise, or alternatively consist of, B lymphocyte stimulator binding polypeptide fragments or variants thereof) that specifically bind to B lymphocyte stimulator. Diseases and disorders which can be detected, diagnosed, prognosed and/or monitored with the B lymphocyte stimulator binding polypeptides include, but are not limited to, immune system diseases or disorders (e.g., autoimmune diseases or disorders, immunodeficiencies, lupus, glomerular nephritis, rheumatoid arthritis, multiple sclerosis, graft vs. host disease, myasthenia gravis, Hashimoto's disease, and immunodeficiency syndrome), proliferative diseases or disorders (e.g., cancer, premalignant conditions, benign tumors, hyperproliferative disorders, benign proliferative disorders, leukemia, lymphoma, chronic lymphocytic leukemia, multiple myeloma, Hodgkin's lymphoma, Hodgkin's disease, T cell proliferative diseases and disorders, B cell proliferative diseases and disorders, monocytic proliferative diseases or disorders, acute myelogenous leukemia, macrophage proliferative diseases and disorders, and carcinoma), infectious diseases (e.g., AIDS), and inflammatory disorders (e.g., asthma, allergic disorders, and rheumatoid arthritis).

The present invention further encompasses methods and compositions for preventing, treating and/or ameliorating diseases or disorders associated with aberrant B lymphocyte stimulator or B lymphocyte stimulator receptor expression or inappropriate B lymphocyte stimulator or B lymphocyte stimulator receptor function in an animal, preferably a mammal, and most preferably a human, comprising, or alternatively consisting of, administering to an animal in which such treatment, prevention or amelioration is desired one or more B lymphocyte stimulator binding polypeptides (including molecules which comprise, or alternatively consist of, B lymphocyte stimulator binding polypeptide fragments or variants thereof) in an amount effective to treat, prevent or ameliorate the disease or disorder. Diseases and disorders which can be prevented, treated, and/or ameliorated with the B lymphocyte stimulator binding polypeptides include, but are not limited to, immune system diseases or disorders (e.g., autoimmune diseases or disorders, immunodeficiencies, lupus, glomerular nephritis, rheumatoid arthritis, multiple sclerosis, graft vs. host disease, myasthenia gravis, Hashimoto's disease, immunodeficiency syndrome, hypogammaglobulinemia, and hypergammaglobulinemia), proliferative diseases or disorders (e.g., cancer, premalignant conditions, benign tumors, hyperproliferative disorders, benign proliferative disorders, leukemia, lymphoma, chronic lymphocytic leukemia, multiple myeloma, Hodgkin's lymphoma, Hodgkin's disease, T cell proliferative diseases and disorders, B cell proliferative diseases and disorders, monocytic proliferative diseases or disorders, acute myelogenous leukemia, macrophage proliferative diseases and disorders, and carcinoma), infectious diseases (e.g., AIDS), and inflammatory disorders (e.g., asthma, allergic disorders, and rheumatoid arthritis).

B lymphocyte stimulator Binding Polypeptides

The methods of the present invention may be performed utilizing new polypeptides and families of polypeptides that specifically bind to B lymphocyte stimulator protein (BLyS™) and/or B lymphocyte stimulator-like polypeptides. In particular, the invention encompasses diagnostic and therapeutic uses for polypeptides that specifically bind to a polypeptide or polypeptide fragment of human B lymphocyte stimulator (SEQ ID NOs:173 and/or 174) or B lymphocyte stimulator expressed on human monocytes; murine B lymphocyte stimulator (SEQ ID NOs:175 and/or 176) or B lymphocyte stimulator expressed on murine monocytes; rat B lymphocyte stimulator (either the soluble forms as given in SEQ ID NOs:177, 178, 179 and/or 180 or in a membrane associated form, e.g., on the surface of rat monocytes); or monkey B lymphocyte stimulator (e.g., the monkey B lymphocyte stimulator polypeptides of SEQ ID NOS:181 and/or 182, the soluble form of monkey B lymphocyte stimulator, or B lymphocyte stimulator expressed on monkey monocytes); preferably human B lymphocyte stimulator.

In preferred embodiments, the B lymphocyte stimulator binding polypeptides used according to the present invention (including molecules comprising, or alternatively consisting of, B lymphocyte stimulator binding polypeptide fragments or variants thereof), specifically bind to B lymphocyte stimulator and do not cross-react with any other antigens. In more preferred embodiments, the B lymphocyte stimulator binding polypeptides specifically bind to B lymphocyte stimulator and do not cross-react with TRAIL (Hahne et al., *J. Exp. Med.*, 188(6):1185-90 (1998)), APRIL (Wilet et al., *Immunity*, 3(6):673-82 (1995)), Endokine-alpha (Kwon et al., *J. Biol. Chem.*, 274(10):6056-61 (1999)), TNF-alpha, TNF-beta (Nedwin et al., *J. Immunol.*, 135(4):2492-7 (1985)), Fas-L (Suda et al., *Cell*, 75(6):1169-78 (1993)), or LIGHT (Mauri et al., *Immunity*, 8(1):21-30 (1998)).

Many B lymphocyte stimulator binding polypeptides have been discovered which may be used in the methods of the present invention. Specific B lymphocyte stimulator binding polypeptides for use in the present invention comprise, or alternatively consist of, an amino acid sequence selected from the group consisting of SEQ ID NOs: 1-12, 20-172, and 186-444, preferably SEQ ID NOs:163-172 or 436-444 as referred to above and in Tables 1-8, 13 and 14. In its broadest aspects, the methods of the present invention may be carried out using a polypeptide capable of binding to B lymphocyte stimulator and comprising the polypeptide Asp-Xaa-Leu-Thr (SEQ ID NO:446), where Xaa is Pro, Ser, Thr, Phe, Leu, Tyr, Cys, or Ala (preferably Pro or Ser).

Additional polypeptides for use in the methods described herein include polypeptides with the potential to form a cyclic or loop structure between invariant Cys residues comprising, or alternatively consisting of, an amino acid sequence selected from A-E (SEQ ID NOs:1-5):

(SEQ ID NO: 1)
(A) $X_1-X_2-X_3-Cys-X_5-Phe-X_7-Trp-Glu-Cys-X_{11}-X_{12}-X_{13}$, wherein $X_1$ is Ala, Asn, Lys, or Ser;

$X_2$ is Ala, Glu, Met, Ser, or Val;

$X_3$ is Ala, Asn, Lys, or Pro (preferably Lys);

$X_5$ is Phe, Trp, or Tyr (preferably Tyr);

$X_7$ is Pro or Tyr (preferably Pro);

$X_{11}$ is Ala, Gln, His, Phe, or Val;

$X_{12}$ is Asn, Gln, Gly, His, Ser, or Val; and $X_{13}$ is Ala, Asn, Gly, Ile, Pro, or Ser, wherein said polypeptide binds B lymphocyte stimulator and/or B lymphocyte stimulator-like polypeptides; or (SEQ ID NO: 2)
(B) $X_1-X_2-X_3-Cys-X_5-X_6-X_7-X_8-X_9-X_{10}-Cys-X_{12}-X_{13}-X_{14}$, wherein $X_1$ is Ala, Asp, Gln, Glu, Gly, His, Ile, Leu, Lys, Met, Phe, Pro, Ser, Thr, Trp, Tyr, Val, or is absent;

$X_2$ is Ala, Asn, Asp, Gln, Gly, His, Ile, Leu, Lys, Met, Phe, Pro, Ser, Thr, Trp, Tyr, or Val;

$X_3$ is Ala, Arg, Asn, Asp, Gln, Glu, Gly, His, Ile, Leu, Lys, Met, Phe, Pro, Ser, Trp, Tyr, or Val (preferably Asp);

$X_5$ is Asp, Be, Leu, or Tyr (preferably Asp or Leu);

$X_6$ is Arg, Asp, Glu, His, Be, Leu, Lys, Phe, Pro, Tyr, or Val (preferably Glu or Leu);

$X_7$ is His, Leu, Lys, or Phe (preferably His or Leu);

$X_8$ is Leu, Pro, or Thr (preferably Thr or Pro);

$X_9$ is Arg, Asn, Gly, His, Be, Lys, Met, or Trp (preferably Lys);

$X_{10}$ is Ala, Gln, Glu, Gly, His, Ile, Leu, Met, Phe, Ser, Trp, Tyr, or Val;

$X_{12}$ is Asp, Gln, Glu, Gly, Ile, Leu, Lys, Phe, Ser, Trp, Tyr, or Val;

$X_{13}$ is Ala, Arg, Asn, Asp, Gln, Glu, Gly, His, Leu, Lys, Met, Phe, Pro, Ser, Thr, Trp, Tyr, or Val; and $X_{14}$ is Ala, Arg, Asn, Asp, Gln, Glu, Gly, His, Ile, Leu, Lys, Phe, Pro, Trp, Tyr, Val, or is absent, wherein said polypeptide binds B lymphocyte stimulator and/or B lymphocyte stimulator-like polypeptides; or

```
                                        (SEQ ID NO: 3)
(C) X1-X2-X3-Cys-X5-X6-X7-X8-X9-X10-X11-Cys-X13-X14-X15,
``` wherein $X_1$ is Ala, Arg, Asn, Asp, Leu, Lys, Phe, Pro, Ser, or Thr;
$X_2$ is Asn, Asp, Gln, His, Be, Lys, Pro, Thr, or Trp;
$X_3$ is Ala, Arg, Asn, Gln, Glu, His, Phe, Pro, or Thr (preferably Ala);
$X_5$ is Asn, Asp, Pro, Ser, or Thr (preferably Asp);
$X_6$ is Arg, Asp, Ile, Leu, Met, Pro, or Val (preferably Ile);
$X_7$ is Ala, Ile, Leu, Pro, Thr, or Val (preferably Val or Leu);
$X_8$ is Asn, His, Be, Leu, Lys, Phe, or Thr (preferably Thr);
$X_9$ is Asn, Glu, Gly, His, Leu, Lys, Met, Pro, or Thr (preferably Leu);
$X_{10}$ is Arg, Asn, Asp, Gln, Glu, Gly, Ile, Lys, Met, Pro, Ser, or Trp;
$X_{11}$ is Arg, Glu, Gly, Lys, Phe, Ser, Trp, or Tyr (preferably Ser);
$X_{13}$ is Gln, Glu, Be, Leu, Phe, Pro, Ser, Tyr, or Val (preferably Val);
$X_{14}$ is Asn, Gly, Ile, Phe, Pro, Thr, Trp, or Tyr; and
$X_{15}$ is Asn, Asp, Glu, Leu, Lys, Met, Pro, or Thr (preferably Glu or Pro), wherein said polypeptide binds B lymphocyte stimulator and/or B lymphocyte stimulator-like polypeptides; or

```
                                        (SEQ ID NO: 4)
(D) X1-X2-X3-Cys-X5-X6-X7-X8-X9-X10-X11-X12-
Cys-X14-X15-X16,
``` wherein $X_1$ is Asn, Asp, His, Leu, Phe, Pro, Ser, Tyr, or is absent (preferably Ser);
$X_2$ is Arg, Asn, Asp, His, Phe, Ser, or Trp (preferably Arg);
$X_3$ is Asn, Asp, Leu, Pro, Ser, or Val (preferably Asn or Asp);
$X_5$ is Asp, Gln, His, Ile, Leu, Lys, Met, Phe, or Thr;
$X_6$ is His, Be, Leu, Met, Phe, Pro, Trp, or Tyr;
$X_7$ is Asp, His, Leu, or Ser (preferably Asp);
$X_8$ is Ala, Arg, Asp, Glu, Leu, Phe, Pro, or Thr (preferably Glu or Pro);
$X_9$ is Ala, Arg, Asn, or Leu (preferably Leu);
$X_{10}$ is Ile, Leu, Met, Pro, Ser, or Thr (preferably Thr);
$X_{11}$ is Ala, Arg, Asn, Gly, His, Lys, Ser, or Tyr;
$X_{12}$ is Ala, Arg, Asn, Gln, Leu, Met, Ser, Trp, Tyr, or Val;
$X_{14}$ is Asp, Gly, Leu, Phe, Tyr, or Val (preferably Leu);
$X_{15}$ is Asn, His, Leu, Pro, or Tyr (preferably His, Leu or Pro); and
$X_{16}$ is Asn, Asp, His, Phe, Ser, or Tyr, (preferably Asp or Ser), wherein said polypeptide binds B lymphocyte stimulator and/or B lymphocyte stimulator-like polypeptides; or

```
                                        (SEQ ID NO: 5)
(E) X1-X2-X3-Cys-X5-X6-X7-X8-X9-X10-X11-X12-X13-X14-
Cys-X16-X17-X18,
``` wherein $X_1$ is Arg, Asp, Gly, His, Leu, Phe, Pro, Ser, Trp, Tyr, or is absent (preferably Arg);
$X_2$ is Ala, Arg, Asn, Asp, Gly, Pro, Ser, or is absent (preferably Asn, Asp, Gly, or Pro);
$X_3$ is Arg, Asn, Gln, Glu, Gly, Lys, Met, Pro, Trp or Val (preferably Gly or Met);

$X_5$ is Arg, Asn, Gln, Glu, His, Leu, Phe, Pro, Trp, Tyr, or Val (preferably Trp, Tyr, or Val);
$X_6$ is Arg, Asp, Gln, Gly, Ile, Lys, Phe, Thr, Trp or Tyr (preferably Asp);
$X_7$ is Ala, Arg, Asp, Glu, Gly, Leu, Ser, or Tyr (preferably Asp);
$X_8$ is Asp, Gln, Glu, Leu, Met, Phe, Pro, Ser, or Tyr (preferably Leu);
$X_9$ is Asp, Leu, Pro, Thr, or Val (preferably Leu or Thr);
$X_{10}$ is Arg, Gln, His, Be, Leu, Lys, Met, Phe, Thr, Trp or Tyr (preferably Lys or Thr);
$X_{11}$ is Ala, Arg, Asn, Gln, Glu, His, Leu, Lys, Met, or Thr (preferably Arg or Leu);
$X_{12}$ is Ala, Asn, Gln, Gly, Leu, Lys, Phe, Pro, Thr, Trp, or Tyr (preferably Thr or Trp);
$X_{13}$ is Ala, Arg, Gln, His, Lys, Met, Phe, Pro, Thr, Trp, or Tyr (preferably Met or Phe);
$X_{14}$ is Arg, Gln, Glu, Gly, His, Leu, Met, Phe, Pro, Ser, Thr, Tyr, or Val (preferably Val);
$X_{16}$ is Arg, Asp, Gly, His, Lys, Met, Phe, Pro, Ser, or Trp (preferably Met);
$X_{17}$ is Arg, Asn, Asp, Gly, His, Phe, Pro, Ser, Trp or Tyr, (preferably Arg, His, or Tyr); and
$X_{18}$ is Ala, Arg, Asn, Asp, His, Leu, Phe, or Trp (preferably His or Asn), wherein said polypeptide binds B lymphocyte stimulator and/or B lymphocyte stimulator-like polypeptides.

Additional B lymphocyte stimulator binding polypeptides that may be used in the methods of the present invention include linear polypeptides comprising, or alternatively consisting of, an amino acid sequence selected from F and G (SEQ ID NOs:6 and 7):

```
                                        (SEQ ID NO: 6)
(F) X1-X2-X3-X4-X5-X6-X7-X8-X9-X10-X11-X12,
``` wherein $X_1$ is Ala, Arg, Gly, His, Leu, Lys, Met, Phe, Trp, Tyr, or Val (preferably Gly, Tyr, or Val);
$X_2$ is Ala, Arg, Gln, His, Ile, Leu, Phe, Thr, Trp, or Tyr (preferably His or Tyr);
$X_3$ is Ala, Asp, Lys, Phe, Thr, Trp or Tyr (preferably Asp or Tyr);
$X_4$ is Arg, Asp, Gln, Lys, Met, Phe, Pro, Ser, Tyr, or Val (preferably Asp or Gln);
$X_5$ is Asp, Leu, Lys, Phe, Pro, Ser, or Val (preferably Leu or Ser);
$X_6$ is His, Be, Leu, Pro, Ser, or Thr (preferably Leu or Thr);
$X_7$ is Arg, Gly, His, Leu, Lys, Met, or Thr (preferably Lys or Thr);
$X_8$ is Ala, Arg, Asn, Ile, Leu, Lys, Met, or Thr (preferably Leu or Lys);
$X_9$ is Ala, Asn, Arg, Asp, Glu, Gly, His, Leu, Met, Ser, Trp, Tyr, or Val (preferably Met or Ser);
$X_{10}$ is Ile, Leu, Phe, Ser, Thr, Trp, Tyr, or Val (preferably Thr or Leu);
$X_{11}$ is Ala, Arg, Gly, His, Be, Leu, Lys, Pro, Ser, Thr, Trp, Tyr, or Val (preferably Pro or Thr); and
$X_{12}$ is Arg, Asp, His, Leu, Lys, Met, Phe, Pro, Ser, Trp, Tyr, or Val (preferably Arg or Pro), wherein said polypeptide binds B lymphocyte stimulator and/or B lymphocyte stimulator-like polypeptides; or (G) $X_1-X_2-X_3-X_4-X_5-X_6-X_7-X_8-X_9-X_{10}-X_{11}-X_{12}-X_{13}$, (SEQ ID NO: 7)

wherein
$X_1$ is Asp, Gln, Glu, Gly, His, Lys, Met, or Trp (preferably Glu, Lys);
$X_2$ is Arg, Gln, His, Ile, Leu, or Pro (preferably His or Pro);
$X_3$ is Asp, Gly, Ile, Lys, Thr, Tyr or Val (preferably Tyr);
$X_4$ is Asn, Asp, Gln, Glu, Met, Pro, Ser, or Tyr (preferably Asp or Gln);
$X_5$ is Asn, Asp, His, Ile, Leu, Met, Pro, Thr or Val (preferably Asn or Thr);
$X_6$ is Asp, Glu, His, Leu, Lys, Pro, or Val (preferably Asp or Pro);
$X_7$ is Arg, Asn, Gln, His, Ile, Leu, Met, Pro, or Thr (preferably Ile or Pro);
$X_8$ is Gln, Gly, His, Leu, Met, Ser, or Thr (preferably Leu or Thr);
$X_9$ is Asn, Gln, Gly, His, Leu, Lys, Ser, or Thr (preferably Lys);
$X_{10}$ is Ala, Gly, Ile, Leu, Lys, Met, or Phe (preferably Gly or Met);
$X_{11}$ is Ala, Glu, His, Ile, Leu, Met, Ser, Thr, Trp, Tyr, or Val (preferably Ala or Thr);
$X_{12}$ is Arg, Gln, Glu, Gly, His, Ile, Lys, Tyr, or Val (preferably Arg or His); and
$X_{13}$ is Arg, Asn, Glu, His, Ile, Ser, Thr, Trp, or Val (preferably His),
wherein said polypeptide binds B lymphocyte stimulator and/or B lymphocyte stimulator-like polypeptides.

Additional B lymphocyte stimulator binding polypeptides that may be used in the methods of the present invention include B lymphocyte stimulator binding polypeptides comprising, or alternatively consisting of, an amino acid sequence selected from H-L (SEQ ID NOs:8-12):

(H) Cys-$X_2$-Phe-$X_4$-Trp-Glu-Cys, (SEQ ID NO: 8)

wherein
$X_2$ is Phe, Trp, or Tyr (preferably Tyr); and
$X_4$ is Pro or Tyr (preferably Pro); or (I) Cys-$X_2$-$X_3$-$X_4$-$X_5$-$X_6$-$X_7$-Cys, (SEQ ID NO: 9)

wherein
$X_2$ is Asp, Be, Leu, or Tyr (preferably Asp or Leu);
$X_3$ is Arg, Asp, Glu, His, Be, Leu, Lys, Phe, Pro, Tyr, or Val (preferably Glu or Leu);
$X_4$ is His, Leu, Lys, or Phe (preferably His or Leu);
$X_5$ is Leu, Pro, or Thr (preferably Thr or Pro);
$X_6$ is Arg, Asn, Gly, His, Be, Lys, Met, or Trp (preferably Lys); and
$X_7$ is Ala, Asn, Gln, Glu, Gly, His, Ile, Leu, Met, Phe, Ser, Trp, Tyr, or Val; or (J) Cys-$X_2$-$X_3$-$X_4$-$X_5$-$X_6$-$X_7$-$X_8$-Cys, (SEQ ID NO: 10)

wherein
$X_2$ is Asn, Asp, Pro, Ser, or Thr (preferably Asp);
$X_3$ is Arg, Asp, Ile, Leu, Met, Pro, or Val (preferably Ile);
$X_4$ is Ala, Ile, Leu, Pro, Thr, or Val (preferably Val or Leu);
$X_5$ is Asn, His, Be, Leu, Lys, Phe, or Thr (preferably Thr);
$X_6$ is Asn, Glu, Gly, His, Leu, Lys, Met, Pro, or Thr (preferably Leu);
$X_7$ is Arg, Asn, Asp, Gln, Glu, Gly, Ile, Lys, Met, Pro, Ser, or Trp;
$X_8$ is Arg, Glu, Gly, Lys, Phe, Ser, Trp, or Tyr (preferably Ser); or (K) Cys-$X_2$-$X_3$-$X_4$-$X_5$-$X_6$-$X_7$-$X_8$-$X_9$-Cys, (SEQ ID NO: 11)

wherein
$X_2$ is Asp, Gln, His, Ile, Leu, Lys, Met, Phe, or Thr;
$X_3$ is His, Be, Leu, Met, Phe, Pro, Trp, or Tyr;
$X_4$ is Asp, His, Leu, or Ser (preferably Asp);
$X_5$ is Ala, Arg, Asp, Glu, Leu, Phe, Pro, or Thr (preferably Glu or Pro);
$X_6$ is Ala, Arg, Asn, or Leu (preferably Leu);
$X_7$ is Ile, Leu, Met, Pro, Ser, or Thr (preferably Thr);
$X_8$ is Ala, Arg, Asn, Gly, His, Lys, Ser, or Tyr;
$X_9$ is Ala, Arg, Asn, Gln, Leu, Met, Ser, Trp, Tyr, or Va; or (L) Cys-$X_2$-$X_3$-$X_4$-$X_5$-$X_6$-$X_7$-$X_8$-$X_9$-$X_{10}$-$X_{11}$-Cys, (SEQ ID NO: 12)

wherein
$X_2$ is Arg, Asn, Gln, Glu, His, Leu, Phe, Pro, Trp, Tyr, or Val (preferably Trp, Tyr, or Val);
$X_3$ is Arg, Asp, Gln, Gly, Ile, Lys, Phe, Thr, Trp or Tyr (preferably Asp);
$X_4$ is Ala, Arg, Asp, Glu, Gly, Leu, Ser, or Tyr (preferably Asp);
$X_5$ is Asp, Gln, Glu, Leu, Met, Phe, Pro, Ser, or Tyr (preferably Leu);
$X_6$ is Asp, Leu, Pro, Thr, or Val (preferably Leu or Thr);
$X_7$ is Arg, Gln, His, Ile, Leu, Lys, Met, Phe, Thr, Trp or Tyr (preferably Lys or Thr);
$X_8$ is Ala, Arg, Asn, Gln, Glu, His, Leu, Lys, Met, or Thr (preferably Arg or Leu);
$X_9$ is Ala, Asn, Gln, Gly, Leu, Lys, Phe, Pro, Thr, Trp, or Tyr (preferably Thr or Trp);
$X_{10}$ is Ala, Arg, Gln, His, Lys, Met, Phe, Pro, Thr, Trp, or Tyr (preferably Met or Phe);
$X_{11}$ is Arg, Gln, Glu, Gly, His, Leu, Met, Phe, Pro, Ser, Thr, Tyr, or Val (preferably Val);
wherein said polypeptides bind B lymphocyte stimulator and/or B lymphocyte stimulator-like polypeptides.

Additional B lymphocyte stimulator binding polypeptides that may be used in the methods of the present invention include linear polypeptides comprise the following amino acid sequence M (SEQ ID NO:447):

(M) Ala-$X_2$-$X_3$-$X_4$-Asp-$X_6$-Leu-Thr-$X_9$-Leu-$X_{11}$-$X_{12}$-$X_{13}$-$X_{14}$, (SEQ ID NO: 447)

wherein
$X_2$ is Asn, Ser, Tyr, Asp, Phe, Ile, Gln, His, Pro, Lys, Leu, Met, Thr, Val, Glu, Ala, Gly, Cys, or Trp (i.e., any amino acid except Arg; preferably Asn);
$X_3$ is Trp, Glu, Lys, Cys, Leu, Ala, Arg, Gly, or Ser (preferably Trp);
$X_4$ is Tyr, Phe, Glu, Cys, Asn (preferably Tyr);
$X_6$ is Pro, Ser, Thr, Phe, Leu, Tyr, Cys, or Ala (preferably Pro or Ser);
$X_9$ is Lys, Asn, Gln, Gly, or Arg (preferably Lys);
$X_{11}$ is Trp, Ser, Thr, Arg, Cys, Tyr, or Lys (preferably Trp);
$X_{12}$ is Leu, Phe, Val, Ile, or His (preferably Leu);

$X_{13}$ is Pro, Leu, His, Ser, Arg, Asn, Gln, Thr, Val, Ala, Cys, Ile, Phe, or Tyr (i.e., not Asp, Glu, Gly, Lys, Met, or Trp; preferably Pro); and $X_{14}$ is Asp, Glu, Asn, Val, His, Gln, Arg, Gly, Ser, Tyr, Ala, Cys, Lys, Ile, Thr or Leu (i.e., not Phe, Met, Pro, or Trp; preferably Asp, Val or Glu).

Preferred B lymphocyte stimulator binding polypeptides that may be used in the methods of the present invention include linear polypeptides comprising a core sequence of the formula N:

```
                              (SEQ ID NO: 448)
(N) X1-X2-Asp-X4-Leu-Thr-X7-Leu-X9-X10,
``` wherein $X_1$ is Trp, Glu, Lys, Cys, Leu, Ala, Arg, Gly, or Ser (preferably Trp);

$X_2$ is Tyr, Phe, Glu, Cys, Asn (preferably Tyr);

$X_4$ is Pro, Ser, Thr, Phe, Leu, Tyr, Cys, or Ala (preferably Pro or Ser);

$X_7$ is Lys, Asn, Gln, Gly, or Arg (preferably Lys);

$X_9$ is Trp, Ser, Thr, Arg, Cys, Tyr, or Lys (preferably Trp); and $X_{10}$ is Leu, Phe, Val, Ile, or His (preferably Leu).

Especially preferred B lymphocyte stimulator binding polypeptides that may be used in the methods of the present invention include linear polypeptides comprising the core peptide Trp-Tyr-Asp-Pro-Leu-Thr-Lys-Leu-Trp-Leu (SEQ ID NO:436).

In performing certain methods according to the present invention, it is preferred that the B lymphocyte stimulator binding polypeptides, or phage displaying such binding polypeptides, irreversibly bind the B lymphocyte stimulator protein in its native, soluble trimeric form.

In performing certain methods according to the present invention, it is preferred that the B lymphocyte stimulator binding polypeptides of the present invention, or phage displaying such binding polypeptides, reversibly bind the B lymphocyte stimulator protein in its native, soluble trimeric form.

In performing certain methods according to the invention, it may be advantageous for a B lymphocyte stimulator binding polypeptide to bind B lymphocyte stimulator target protein with high affinity. In specific embodiments, B lymphocyte stimulator binding polypeptides used in this invention will bind B lymphocyte stimulator target proteins with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, B lymphocyte stimulator binding polypeptides used in the invention will bind B lymphocyte stimulator target proteins with a dissociation constant or $K_D$ less than or equal to $5\times10^{-6}$ M, $10^{-6}$ M, $5\times10^{-7}$ M, $10^{-7}$M, $5\times10^{-8}$ M, or $10^{-8}$ M. Even more preferably, B lymphocyte stimulator binding polypeptides used in the methods of the invention bind B lymphocyte stimulator target proteins with a dissociation constant or $K_D$ less than or equal to $5\times10^{-9}$ M, $10^{-9}$ M, $5\times10^{-10}$ M, $10^{-10}$ M, $5\times10^{-11}$ M, $10^{-11}$M, $5\times10^{-12}$ M, $10^{-12}$ M, $5\times^{-13}$ M, $10^{-13}$ M, $5\times10^{14}$ M, $10^{14}$ M, $5\times10^{-15}$ M, or $10^{-15}$ M.

In certain preferred embodiments, B lymphocyte stimulator binding polypeptides reversibly bind B lymphocyte stimulator and/or B lymphocyte stimulator-like polypeptides and release bound B lymphocyte stimulator protein in an active form, preferably in the native soluble trimeric form, under specific release conditions. In specific embodiments, B lymphocyte stimulator binding polypeptides bind B lymphocyte stimulator target proteins with off-rates or $k_{off}$ greater than or equal to $10^{-10}$ $s^{-1}$, $5\times10^{-9}$ $s^{-1}$, $10^{-9}$ $s^{-1}$, $5\times10^{-8}$ $s^{-1}$, $10^{-8}$ $s^{-1}$, $5\times10^{-7}$ $s^{-1}$, $10^{-7}$ $s^{-1}$, $5\times10^{-6}$ $s^{-1}$, $10^{-6}$ $s^{-1}$, $5\times10^{-5}$ $s^{-1}$, $10^{-5}$ $s^{-1}$, $5\times10^{-4}$ $s^{-1}$, $10^{-4}$ $s^{-1}$, $5\times10^{-3}$ $s^{-1}10^{-3}$ $s^{-1}$, $5\times10^{-2}$ $s^{-1}$, $10^{-2}$ $s^{-1}$, $5\times10^{-1}$ $s^{-1}$, or $10^{-1}s^{-1}$.

Binding experiments to determine $K_D$ and off-rates can be performed in a number of conditions including, but not limited to, [pH 6.0, 0.01% Tween 20], [pH 6.0, 0.1% gelatin], [pH5.0, 0.01% Tween 20], [pH9.0, 0.1% Tween 20], [pH6.0, 15% ethylene glycol, 0.01% Tween20], [pH5.0, 15% ethylene glycol, 0.01% Tween 20], and [pH9.0, 15% ethylene glycol, 0.01% Tween 20] The buffers in which to make these solutions can readily be determined by one of skill in the art, and depend largely on the desired pH of the final solution. Low pH solutions (<pH 5.5) can be made, for example, in citrate buffer, glycine-HCl buffer, or in succinic acid buffer. High pH solutions can be made, for example, in Tris-HCl, phosphate buffers, or sodium bicarbonate buffers. A number of conditions may be used to determine $K_D$ and off-rates for the purpose of determining, for example, optimal pH and/or salt concentrations.

In certain embodiments, B lymphocyte stimulator binding polypeptides reversibly bind B lymphocyte stimulator and/or B lymphocyte stimulator-like polypeptides, preferably in the native soluble, trimeric form.

In preferred embodiments, B lymphocyte stimulator binding polypeptides reversibly bind only the native soluble, trimeric form of B lymphocyte stimulator.

In certain embodiments, B lymphocyte stimulator binding polypeptides irreversibly bind B lymphocyte stimulator and/or B lymphocyte stimulator-like polypeptides, preferably in the native soluble, trimeric form.

In preferred embodiments, B lymphocyte stimulator binding polypeptides irreversibly bind only the native soluble, trimeric form of B lymphocyte stimulator.

In some screening or assay procedures, it is possible and more convenient to use recombinant bacteriophage that display a particular B lymphocyte stimulator binding polypeptide instead of using isolated B lymphocyte stimulator binding polypeptide. Such procedures include phage-based ELISA protocols and immobilization of phage displaying a binding polypeptide to chromatographic materials. Such screening assays and procedures are routine in the art and may be readily adapted for procedures using recombinant bacteriophage such as disclosed herein.

Specific methods of the present invention contemplate the use of B lymphocyte stimulator binding polypeptides that competitively inhibit the binding of a B lymphocyte stimulator binding molecule. Competitive inhibition can be determined by any suitable method known in the art, for example, using the competitive binding assays described herein. In preferred embodiments, the polypeptide competitively inhibits the binding of a B lymphocyte stimulator binding molecule to B lymphocyte stimulator by at least 95%, at least 90%, at least 85%, at least 80%, at least 75%, at least 70%, at least 60%, or at least 50%. In a more preferred embodiment, the B lymphocyte stimulator binding polypeptide competitively inhibits the binding of a B lymphocyte stimulator binding molecule to the native soluble trimeric form of B lymphocyte stimulator, by at least 95%, at least 90%, at least 85%, at least 80%, at least 75%, at least 70%, at least 60%, or at least 50%.

B lymphocyte stimulator binding polypeptides (including molecules comprising, or alternatively consisting of, B lymphocyte stimulator binding polypeptide fragments or variants thereof) useful in the practice of the methods of the present invention may have one or more of the same biological characteristics as one or more of the B lymphocyte stimulator binding polypeptides specifically described herein. By "biological characteristics" is meant, the in vitro or in vivo activities or properties of the B lymphocyte stimulator binding polypeptides, such as, for example, the ability to bind to B lymphocyte stimulator (e.g., the soluble form of B lymphocyte stimulator, the membrane-bound form of B lymphocyte stimulator, the soluble form and membrane-bound form of B lymphocyte stimulator), and/or an antigenic and/or epitope region of B lymphocyte stimulator), the ability to substantially block B lymphocyte stimulator/B lymphocyte stimulator receptor (e.g., TACI and BCMA) binding, the ability to substantially increase B lymphocyte stimulator/B lymphocyte stimulator receptor (e.g., TACI and BCMA) binding, the ability to block B lymphocyte stimulator mediated biological activity (e.g., stimulation of B cell proliferation and immunoglobulin production), or, the ability to enhance or stimulate B lymphocyte stimulator mediated biological activity (e.g., stimulation of B cell proliferation and immunoglobulin production). Optionally, the B lymphocyte stimulator binding polypeptides useful according to the invention will bind to the same epitope as at least one of the B lymphocyte stimulator binding polypeptides specifically referred to herein. Such epitope binding can be routinely determined using assays known in the art.

B lymphocyte stimulator binding polypeptides (including molecules comprising, or alternatively consisting of, B lymphocyte stimulator binding polypeptide fragments or variants thereof) useful in the practice of the methods of the present invention may be polypeptides that neutralize B lymphocyte stimulator or a fragment thereof. By a B lymphocyte stimulator binding polypeptide that "neutralizes B lymphocyte stimulator or a fragment thereof" is meant a B lymphocyte stimulator binding polypeptide that inhibits (i.e., is effective to reduce or abolish) or abolishes the ability of B lymphocyte stimulator: to bind to its receptor (e.g., TACI and BCMA), to stimulate B cell activation, to stimulate B cell proliferation, to stimulate immunoglobulin secretion by B cells, to increase B cell lifespan, and/or to stimulate the B lymphocyte stimulator receptor signalling cascade.

B lymphocyte stimulator binding polypeptides (including molecules comprising, or alternatively consisting of, B lymphocyte stimulator binding polypeptide fragments or variants thereof) useful in the practice of the methods of the present invention may also be effective to inhibit or abolish B lymphocyte stimulator-mediated B cell proliferation as determined by any method known in the art such as, for example, the assays described in the Examples, infra, said B lymphocyte stimulator binding polypeptides comprising, or alternatively consisting of, a polypeptide having an amino acid sequence of any one of SEQ ID NOs:1-12, 20-172, and 186-444, preferably of SEQ ID NOs:163-172 and 436-444, or a fragment or variant thereof.

B lymphocyte stimulator binding polypeptides (including molecules comprising, or alternatively consisting of, B lymphocyte stimulator binding polypeptide fragments or variants thereof) useful in the practice of the methods of the present invention may also be effective to enhance the activity of B lymphocyte stimulator or a fragment thereof, said B lymphocyte stimulator binding polypeptides comprising, or alternatively consisting of, a polypeptide having an amino acid sequence of any one of SEQ ID NOs:1-12, 20-172, and 186-444, preferably of SEQ ID NOs:163-172 or 436-444, or a fragment or variant thereof. By a B lymphocyte stimulator binding polypeptide that "enhances the activity of B lymphocyte stimulator or a fragment thereof" is meant a B lymphocyte stimulator binding polypeptide that increases the ability of B lymphocyte stimulator: to bind to its receptor (e.g., TACI and BCMA), to stimulate B cell proliferation, to stimulate immunoglobulin secretion by B cells, to activate B cells, to increase B cell lifespan and/or to stimulate a B lymphocyte stimulator receptor signalling cascade (e.g., to activate calcium-modulator and cyclophilin ligand ("CAML"), calcineurin, nuclear factor of activated T cells transcription factor ("NF-AT"), nuclear factor-kappa B ("NF-kappa B"), activator protein-1 (AP-1), SRF, extracellular-signal regulated kinase 1 (ERK-1), polo like kinases (PLK), ELF-1, high mobility group I (HMG-I), and/or high mobility group Y (HMG-Y)). Nucleic acid molecules encoding these B lymphocyte stimulator binding polypeptides are also encompassed by the invention.

B lymphocyte stimulator binding polypeptides (including molecules comprising, or alternatively consisting of, B lymphocyte stimulator binding polypeptide fragments or variants thereof) useful in the practice of the methods of the present invention may also be effective to stimulate B lymphocyte stimulator mediated B cell proliferation as determined by any method known in the art, such as, for example, the assays described in the Examples, infra, said B lymphocyte stimulator binding polypeptides comprising, or alternatively consisting of, a polypeptide having an amino acid sequence of any one of SEQ ID NOs:1-12, 20-172, and 186-444, preferably of SEQ ID NOs:163-172 or 436-444, or a fragment or variant thereof. Nucleic acid molecules encoding these B lymphocyte stimulator binding polypeptides are also encompassed by the invention.

B lymphocyte stimulator binding polypeptides (including molecules comprising, or alternatively consisting of, B lymphocyte stimulator binding polypeptide fragments or variants thereof) useful in the practice of the methods of the present invention may include polypeptides effective to specifically bind to the soluble form of B lymphocyte stimulator, polypeptides that specifically bind to the membrane-bound form of B lymphocyte stimulator, and polypeptides that specifically bind to both the soluble form and membrane-bound form of B lymphocyte stimulator.

The methods of the present invention may also be carried out using mixtures of B lymphocyte stimulator binding polypeptides (including molecules comprising, or alternatively consisting of, B lymphocyte stimulator binding polypeptide fragments or variants thereof) that specifically bind to B lymphocyte stimulator, wherein the mixture contains at least one, two, three, four, five or more different B lymphocyte stimulator binding polypeptides. In particular, the invention provides for the use of mixtures of different B lymphocyte stimulator binding polypeptides that specifically bind to the soluble form of B lymphocyte stimulator, the membrane-bound form of B lymphocyte stimulator, and/or both the membrane-bound form and soluble form of B lymphocyte stimulator. In specific embodiments, the methods of the invention utilize mixtures of at least 2, preferably at least 4, at least 6, at least 8, at least 10, at least 12, at least 15, at least 20, or at least 25 different B lymphocyte stimulator binding polypeptides that specifically bind to B lymphocyte stimulator, wherein at least 1, at least 2, at least 4, at least 6, or at least 10, B lymphocyte stimulator binding polypeptides of the mixture are B lymphocyte stimulator binding polypeptides.

The methods of the present invention may also be carried out using panels of B lymphocyte stimulator binding polypeptides (including molecules comprising, or alternatively consisting of, B lymphocyte stimulator binding polypeptide fragments or variants thereof) that specifically bind to B lymphocyte stimulator, wherein the panel has at least one, two, three, four, five or more different B lymphocyte stimulator binding polypeptides. In particular, the invention provides for the use of panels of different B lymphocyte stimulator binding polypeptides that specifically bind to the soluble form of B lymphocyte stimulator, the membrane-bound form of B lymphocyte stimulator, and/or both the membrane-bound form and soluble form of B lymphocyte stimulator. In specific embodiments, the invention provides for the use of panels of B lymphocyte stimulator binding polypeptides that have different affinities for B lymphocyte stimulator, different specificities for B lymphocyte stimulator, or different dissociation rates. The invention provides for the use of panels of at least 10, preferably at least 25, at least 50, at least 75, or at least 100 B lymphocyte stimulator binding polypeptides. Panels of B lymphocyte stimulator binding polypeptides can be used, for example, in 96 well plates for assays such as ELISAs.

The methods of the present invention may also be carried out using compositions comprising one or more B lymphocyte stimulator binding polypeptides (including molecules comprising, or alternatively consisting of B lymphocyte stimulator binding polypeptide fragments or variants). In one embodiment, a composition used in a method of the present invention comprises, one, two, three, four, five, or more B lymphocyte stimulator binding polypeptides that comprise or alternatively consist of, a polypeptide having an amino acid sequence of any one or more of the B lymphocyte stimulator binding polypeptides contained in SEQ ID NOs:1-12, 20-172, and 186-444 as disclosed in Tables 1-8 and 13, or a variant thereof.

As discussed in more detail below, a composition useful in the methods of the invention may be used either alone or in combination with other compositions. The B lymphocyte stimulator binding polypeptides (including molecules comprising, or alternatively consisting of B lymphocyte stimulator binding polypeptide fragments or variants of the present invention) may further be recombinantly fused to a heterologous polypeptide at the N- or C-terminus or chemically conjugated (including covalently and non-covalently conjugations) to polypeptides or other compositions. For example, B lymphocyte stimulator binding polypeptides of the present invention may be recombinantly fused or conjugated to molecules useful as labels in detection assays and effector molecules such as heterologous polypeptides, polypeptide linkers, drugs, radionuclides, or toxins. See, e.g., PCT publications WO 92/08495; WO 91/14438; WO 89/12624; U.S. Pat. No. 5,314,995; and EP 0 396 387.

Production and Modification of B Lymphocyte Stimulator Binding Polypeptides

B lymphocyte stimulator binding polypeptides useful in practicing the methods of the present invention may be produced by chemical synthesis, semi-synthetic methods, and recombinant DNA methodologies known in the art.

In certain embodiments, B lymphocyte stimulator binding polypeptides of the present invention are produced by chemical or semi-synthetic methodologies known in the art (see, Kelley et al. in *Genetic Engineering Principles and Methods*, Setlow, J. K., ed. (Plenum Press, NY., 1990), vol. 12, pp. 1-19; Stewart et al., *Solid-Phase Peptide Synthesis*, W.H. Freeman Co., San Francisco, 1989). One advantage of these methodologies is that they allow for the incorporation of non-natural amino acid residues into the sequence of the B lymphocyte stimulator binding polypeptide.

In preferred embodiments, B lymphocyte stimulator binding polypeptides are chemically synthesized (see, e.g., Merrifield, *J. Am. Chem. Soc.*, 85: 2149 (1963); Houghten, *Proc. Natl. Acad. Sci. USA*, 82: 5132 (1985)). For example, polypeptides can be synthesized by solid phase techniques, cleaved from the resin, and purified by preparative high performance liquid chromatography (see, e.g., Creighton, *Proteins: Structures and Molecular Properties* (W.H. Freeman and Co., N.Y., 1983), pp. 50-60). B lymphocyte stimulator binding polypeptides can also be synthesized by use of a peptide synthesizer. The composition of the synthetic polypeptides may be confirmed by amino acid analysis or sequencing (e.g., the Edman degradation procedure; see Creighton, *Proteins: Structures and Molecular Properties* (W.H. Freeman and Co., N.Y., 1983), pp. 34-49). Furthermore, if desired, B lymphocyte stimulator binding polypeptides may contain non-classical amino acids or chemical amino acid analogs, which can routinely be introduced during chemical synthesis as a substitution or addition into the B lymphocyte stimulator binding polypeptides. Non-classical amino acids include, but are not-limited to, the D-isomers of the common amino acids, 2,4-diaminobutyric acid, alpha-aminoisobutyric acid, 4-aminobutyric acid (4Abu), 2-aminobutyric acid (Abu), 6-aminohexanoic acid (epsilon-Ahx), 2-aminoisobutyric acid (Aib), 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine (bAla), fluoro-amino acids, designer amino acids such as beta-methyl amino acids, Calpha-methyl amino acids, Nalpha-methyl amino acids, and amino acid analogs in general. Furthermore, the amino acid can be D (dextrorotary) or L (levorotary).

Solid phase peptide synthesis begins at the carboxy (C) terminus of the putative polypeptide by coupling a protected amino acid to a suitable resin, which reacts with the carboxyl group of the C-terminal amino acid to form a bond that is readily cleaved later, for example, a halomethyl resin such as chloromethyl resin, bromomethyl resin, hydroxymethyl resin, aminomethyl resin, benzhydrylamine resin, or t-alkyloxycarbonyl-hydrazide resin. After removal of the α-amino protecting group with, for example, trifluoroacetic acid (TFA) in methylene chloride and neutralization with, for example TEA, the next cycle in the synthesis is ready to proceed. The remaining α-amino and, if necessary, side-chain-protected amino acids are then coupled sequentially in the desired order by condensation to obtain an intermediate compound connected to the resin. Alternatively, some amino acids may be coupled to one another forming an oligopeptide prior to addition to the growing solid phase polypeptide chain.

The condensation between two amino acids, or an amino acid and a peptide, or a peptide and a peptide can be carried out according to condensation methods known in the art, including but not limited to, the azide method, mixed acid anhydride method, DCC (dicyclohexylcarbodiimide) method, active ester method (p-nitrophenyl ester method, BOP [benzotriazole-1-yl-oxy-tris (dimethylamino) phosphonium hexafluorophosphate] method, N-hydroxysuccinic acid imido ester method), and Woodward reagent K method.

Common to chemical synthesis of peptides is the protection or capping (blocking) of the reactive side chain groups of the various amino acid residues with suitable protecting or capping groups at that site until the group is ultimately removed after the polypeptide chain has been completely assembled. Also common is the protection or capping of the α-amino group on an amino acid or a fragment while that entity reacts at the carboxyl group followed by the selective removal of the α-amino-protecting group to allow subsequent reaction to take place at that location. Accordingly, during synthesis, intermediate compounds are produced which includes each of the amino acid residues located in the desired sequence in the peptide chain with various of these residues having side-chain protecting or capping groups. These protecting or capping groups on amino acid side chains are then removed substantially at the same time so as to produce the desired resultant product following purification.

The typical protective, capping, or blocking groups for a- and E-amino side chain groups found in amino acids are exemplified by benzyloxycarbonyl (Z), isonicotinyloxycarbonyl (iNOC), O-chlorobenzyloxycarbonyl [Z(NO$_2$)], p-methoxybenzyloxycarbonyl [Z(OMe)], t-butoxycarbonyl (Boc), t-amyioxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthalyl, formyl, 2-nitrophenylsulphenyl (NPS), diphenylphosphinothioyl (Ppt), dimethylophosphinothioyl (Mpt), and the like.

Protective, capping, or blocking groups for the carboxyl group of amino acids include, for example, benzyl ester (OBzl), cyclohexyl ester (Chx), 4-nitrobenzyl ester (ONb), t-butyl ester (Obut), 4-pyridylmethyl ester (OPic), and the like. It is usually also desirable that side chain groups of specific amino acids such as arginine, cysteine, and serine, are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenysulfonyl (Mts), and the like. The thiol group in cysteine may be protected with p-methoxybenzyl, triphenylmethyl, acetylaminomethyl ethylcarbamoyl, 4-methylbenzyl, 2,4,6-trimethyl-benzyl (Tmb), etc., and the hydroxyl group in the serine can be protected with benzyl, t-butyl, acetyl, tetrahydropyranyl, etc.

After the desired amino acid sequence has been completed, the intermediate polypeptide is removed from the resin support by treatment with a reagent, such as liquid HF and one or more thio-containing scavengers, which cleaves the peptide molecule from the resin and all the remaining side-chain protecting groups. Following HF cleavage, the protein sequence is washed with ether, transferred to a large volume of dilute acetic acid, and stirred at pH adjusted to about 8.0 with ammonium hydroxide. Upon pH adjustment, the polypeptide takes its desired conformational arrangement.

By way of example but not by way of limitation, polypeptides can be chemically synthesized and purified as follows: Peptides can be synthesized by employing the N- alpha-9-fluorenylmethyloxycarbonyl or Fmoc solid phase peptide synthesis chemistry using a Rainin Symphony Multiplex Peptide Synthesizer. The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection to with 20% piperidine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HBTU) in DMF; (5) allowing the solution to mix for 45 minutes; and (6) washing the peptide-resin three times for 30 seconds of DMF. This cycle can be repeated as necessary with the appropriate amino acids in sequence to produce the desired peptide. Exceptions to this cycle program are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. Additionally, in the first coupling step in peptide synthesis, the resin can be allowed to swell for more efficient coupling by increasing the time of mixing in the initial DMF washes to three 15 minute washes rather than three 30 second washes.

After peptide synthesis, the peptide can be cleaved from the resin as follows: (1) washing the peptide-resin three times for 30 seconds with DMF; (2) removing the Fmoc protective group on the amino terminus by washing two times for 15 minutes it 20% piperidine in DMF; (3) washing the peptide-resin three times for 30 seconds with DMF; and (4) mixing a cleavage cocktail consisting of 95% trifluoroacetic acid (TFA), 2.4% water, 2.4% phenol, and 0.2% triisopropysilane with the peptide-resin for two hours, then filtering the peptide in the cleavage cocktail away from the resin, and precipitating the peptide out of solution by addition of two volumes of ethyl ether. Specifically, to isolate the peptide, the ether-peptide solution can be allowed to sit at −20° C. for 20 minutes, then centrifuged at 6,000×G for 5 minutes to pellet the peptide, and the peptide can be washed three times with ethyl ether to remove residual cleavage cocktail ingredients. The final peptide product can be purified by reversed phase high pressure liquid chromatography (RP-HPLC) with the primary solvent consisting of 0.1% TFA and the eluting buffer consisting of 80% acetonitrile and 0.1% TFA. The purified peptide can then be lyophilized to a powder.

In other specific embodiments, branched versions of the B lymphocyte stimulator binding polypeptides described herein are provided, e.g., by substituting one or more amino acids within the B lymphocyte stimulator binding polypeptide sequence with an amino acid or amino acid analog with a free side chain capable of forming a peptide bond with one or more amino acids (and thus capable of forming a "branch").

Branched peptides may be prepared by any method known in the art for covalently linking any naturally occurring or synthetic amino acid to any naturally occurring or synthetic amino acid in a peptide chain which has a side chain group able to react with the amino or carboxyl group on the amino acids so as to become covalently attached to the peptide chain. In particular, amino acids with a free amino side chain group, such as, but not limited to, diaminobutyric acid, lysine, arginine, ornithine, diaminopropionic acid and citrulline, can be incorporated into a peptide so that an amino acid can form a branch therewith, for example, by forming a peptide bond to the free amino side group, from that residue. Alternatively, amino acids with a free carboxyl side chain group, such as, but not limited to, glutamic acid, aspartic acid and homocitrulline, can be incorporated into the peptide so that an amino acid can form a branch therewith, for example, by forming a peptide bond to the free carboxyl side group, from that residue. The amino acid forming the branch can be linked to a side chain group of an amino acid in the peptide chain by any type of covalent bond, including, but not limited to, peptide bonds, ester bonds and disulfide bonds. In a specific embodiment, amino acids, such as those described above, that are capable of forming a branch point, are substituted for B lymphocyte stimulator binding polypeptide residues within a peptide including a B lymphocyte stimulator binding polypeptide sequence.

Branched peptides can be prepared by any method known in the art. For example, but not by way of limitation, branched peptides can be prepared as follows: (1) the amino acid to be branched from the main peptide chain can be purchased as an N-alpha-tert-butyloxycarbonyl (Boc) protected amino acid pentafluorophenyl (Opfp) ester and the residue within the main chain to which this branched amino acid will be attached can be an N-Fmoc-alpha-gamma-diaminobutyric acid; (2) the coupling of the Boc protected amino acid to diaminobutyric acid can be achieved by adding 5 grams of each precursor to a flask containing 150 ml DMF, along with 2.25 ml pyridine and 50 mg dimethylaminopyridine and allowing the solution to mix for 24 hours; (3) the peptide can then be extracted from the 150 ml coupling reaction by mixing the reaction with 400 ml dichlormethane (DCM) and 200 ml 0.12N HCl in a 1 liter separatory funnel, and allowing the phases to separate, saving the bottom aqueous layer and re-extracting the top layer two more times with 200 ml 0.12N HCl; (4) the solution containing the peptide can be dehydrated by adding 2-5 grams magnesium sulfate, filtering out the magnesium sulfate, and evaporating the remaining solution to a volume of about 2-5 ml; (5) the dipeptide can then be precipitated by addition of ethyl acetate and then 2 volumes of hexanes and then collected by filtration and washed two times with cold hexanes; and (6) the resulting filtrate can be lyophilized to achieve a light powder form of the desired dipeptide. Branched peptides prepared by this method will have a substitution of diaminobutyric acid at the amino acid position which is branched. Branched peptides containing an amino acid or amino acid analog substitution other than diaminobutyric acid can be prepared analogously to the procedure described above, using the N-Fmoc coupled form of the amino acid or amino acid analog.

In a preferred embodiment, the B lymphocyte stimulator binding polypeptide is a cyclic peptide. Cyclization can be, for example, but not by way of limitation, via a disulfide bond between two cysteine residues or via an amide linkage. For example, but not by way of limitation, disulfide bridge formation can be achieved by (1) dissolving the purified peptide at a concentration of between 0.1-0.5 mg/ml in 0.01 M ammonium acetate, pH 7.5; (2) adding to the dissolved peptide 0.01 M potassium ferricyanide dropwise until the solution appears pale yellow in color and allowing this solution to mix for 24 hours; (3) concentrating the cyclized peptide to 5-10 ml of solution, repurifying the peptide by reverse phase-high pressure liquid chromatography (RP-HPLC) and finally lyophilizing the peptide. In a specific embodiment, in which the peptide does not contain two appropriately situated cysteine residues, cysteine residues can be introduced at the amino-terminus and/or carboxy-terminus and/or internally such that the peptide to be cyclized contains two cysteine residues spaced such that the residues can form a disulfide bridge. Alternatively, a cyclic peptide can be obtained by generating an amide linkage using, for example but not limited to, the following protocol: An allyl protected amino acid, such as aspartate, glutamate, asparagine or glutamine, can be incorporated into the peptide as the first amino acid, and then the remaining amino acids are coupled on. The allyl protective group can be removed by a two hour mixing of the peptide-resin with a solution of tetrakistriphenylphosphine palladium (0) in a solution of chloroform containing 5% acetic acid and 2.5% N-methylmorpholine. The peptide resin can be washed three times with 0.5% N,N-diisopropylethylamine (DIEA) and 0.5% sodium diethyldithiocabamate in DMF. The amino terminal Fmoc group on the peptide chain can be removed by two incubations for 15 minutes each in 20% piperidine in DMF, and washed three times with DMF for 30 seconds each. The activator mix, N-methylmorpholine and HBTU in DMF, can be brought onto the column and allowed to couple the free amino terminal end to the carboxyl group generated by removal of the allyl group to cyclize the peptide. The peptide can be cleaved from the resin as described in the general description of chemical peptide synthesis above and the peptide purified by reverse phase-high pressure liquid chromatography (RP-HPLC). In a specific embodiment, in which the peptide to be cyclized does not contain an allyl protected amino acid, an allyl protected amino acid can be introduced into the sequence of the peptide, at the amino-terminus, carboxy-terminus or internally, such that the peptide can be cyclized.

In addition, according to certain embodiments, it is preferable that the B lymphocyte stimulator binding polypeptides are produced having or retaining an amino terminal (N-terminal) and/or a carboxy terminal (C-terminal) capping group, which may protect the N-terminal or C-terminal amino acid from undesirable chemical reactions during use or which may permit further conjugations or manipulations of the binding polypeptide, for example, in conjugating the binding polypeptide to a chromatographic support resin or matrix or to another peptide to tether the binding polypeptide to a resin or support. Such N-terminal and C-terminal groups may also be used to label or tag the binding polypeptide to detect bound complexes or to locate the binding polypeptide (whether bound or unbound to a B lymphocyte stimulator target protein) for example, at some point in a separation procedure. Accordingly, a B lymphocyte stimulator binding polypeptide synthesized in its final form for use in a detection or separation procedure may contain an N-terminal and/or a C-terminal capping group. A particularly preferred N-terminal capping group, which may be present or retained in binding polypeptides, is an acetyl group (Ac). A particularly preferred C-terminal capping group, which may be present or retained in binding polypeptides, is an amide group. In a further preferred embodiment, the B lymphocyte stimulator binding polypeptides have an acetyl group as an N-terminal capping group and an amide group as a C-terminal capping group.

The B lymphocyte stimulator binding polypeptides may also be prepared commercially by companies providing polypeptide synthesis as a service (e.g., BACHEM Bioscience, Inc., King of Prussia, Pa.; Quality Controlled Biochemicals, Inc., Hopkinton, Mass.).

The nucleic acid sequence encoding a B lymphocyte stimulator binding polypeptide can be produced and isolated using well-known techniques in the art. In one example, nucleic acids encoding the B lymphocyte stimulator binding polypeptides are chemically synthesized based on knowledge of the amino acid sequence of the B lymphocyte stimulator binding polypeptide (preferably the sequence is codon optimized to the host system in which the polypeptide will be expressed). In another example, nucleic acids encoding a B lymphocyte stimulator binding polypeptide are obtained by screening an expression library (e.g., a phage display library) to identify phage expressing B lymphocyte stimulator binding polypeptides, and isolating B lymphocyte stimulator binding polypeptide encoding nucleic acid sequences from the identified library member (e.g., via polymerase chain reaction methodology using primers flanking the polypeptide encoding sequences).

Thus, B lymphocyte stimulator binding polypeptidess can also be obtained by recombinant expression techniques. (See, e.g., Sambrook et al., 1989, *Molecular Cloning, A Laboratory Manual*, 2d Ed., Glover, D. M. (ed.), (Cold Spring Harbor Laboratory, Cold Spring Harbor, N.Y., 1989); *DNA Cloning: A Practical Approach* (MRL Press, Ltd., Oxford, U.K., 1985), Vols. I, II.

To produce a recombinant B lymphocyte stimulator binding polypeptide, a nucleic acid sequence encoding the B lymphocyte stimulator binding polypeptide is operatively linked to a promoter such that the B lymphocyte stimulator binding polypeptide is produced from said sequence. For example, a vector can be introduced into a cell, within which cell the vector or a portion thereof is expressed, producing the B lymphocyte stimulator binding polypeptides. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or, become chromosomally integrated, as long as it can be transcribed to produce the desired RNA. Such vectors can be constructed by recombinant DNA technology methods standard in the art. Vectors can be bacteriophage, plasmid, viral, retroviral, or others known in the art, used for replication and expression in bacterial, fungal, plant, insect or mammalian cells. Retroviral vectors may be replication competent or replication defective. In the latter case, viral propagation generally will occur only in complementing host cells. Introduction of the vector construct into the host cell can be effected by techniques known in the art which include, but are not limited to, calcium phosphate transfection, DEAE-dextran mediated transfection, cationic lipid-mediated transfection, electroporation, transduction, infection or other methods. Such methods are well known in the art and are described, for example, in many standard laboratory manuals, such as Davis et al., *Basic Methods In Molecular Biology* (1986).

The present invention also contemplates the use of B lymphocyte stimulator binding polypeptides (including molecules comprising, or alternatively consisting of, B lymphocyte stimulator binding polypeptide fragments or variants thereof) that are recombinantly fused or chemically conjugated (including both covalent and non-covalent conjugations) to a heterologous polypeptide (or portion thereof, preferably at least 10, at least 20, at least 30, at least 40, at least 50, at least 60, at least 70, at least 80, at least 90 or at least 100 amino acids of the heterologous polypeptide) to generate fusion proteins. The fusion does not necessarily need to be direct, but may occur through linker sequences. For example, B lymphocyte stimulator binding polypeptides may be used to target heterologous polypeptides to particular cell types (e.g., cells of monocytic lineage and B-cells), either in vitro or in vivo, by fusing or conjugating the heterologous polypeptides to B lymphocyte stimulator binding polypeptides that are specific for particular cell surface antigens (e.g., membrane-bound B lymphocyte stimulator on cells of monocytic lineage) or which bind antigens (i.e., B lymphocyte stimulator) that bind particular cell surface receptors (e.g., TACI and/or BCMA located on B cells). B lymphocyte stimulator binding polypeptides fused or conjugated to heterologous polypeptides may also be used in in vitro immunoassays and purification methods using methods known in the art. See e.g., Harbor et al., supra, and PCT publication WO 93/2 1232; EP 439 095; Naramura et al., *Immunol. Lett.,* 39:91-99 (1994); U.S. Pat. No. 5,474,981; Gillies et al., *Proc. Nat'l Acad. Sci. USA,* 89:1428-1432 (1992); Fell et al., *J. Immunol.,* 146:2446-2452 (1991), which are incorporated by reference in their entireties.

The present invention further contemplates the use of compositions comprising, or alternatively consisting of, heterologous polypeptides fused or conjugated to B lymphocyte stimulator binding polypeptide fragments.

Fusion proteins useful in the methods of the invention may be generated through the techniques of gene-shuffling, motif-shuffling, exon-shuffling, and/or codon-shuffling (collectively referred to as "DNA shuffling"). DNA shuffling may be employed to modulate the activities of B lymphocyte stimulator binding polypeptides (including molecules comprising, or alternatively consisting of, B lymphocyte stimulator binding polypeptide fragments or variants thereof), such methods can be used to generate B lymphocyte stimulator binding polypeptides with altered activity (e.g., B lymphocyte stimulator binding polypeptides with higher affinities and lower dissociation rates). See, generally, U.S. Pat. Nos. 5,605,793; 5,811,238; 5,830,721; 5,834,252; and 5,837,458, and Patten et al., *Curr. Opinion Biotechnol.,* 8:724-33 (1997); Harayama, *Trends Biotechnol.,* 16(2):76-82 (1998); Hansson, et al., *J. Mol. Biol.,* 287:265-76 (1999); and Lorenzo and Blasco, *Biotechniques,* 24(2):308-13 (1998) (each of these patents and publications are hereby incorporated by reference in its entirety). In one embodiment, polynucleotides encoding B lymphocyte stimulator binding polypeptides may be altered by being subjected to random mutagenesis by error-prone PCR, random nucleotide insertion or other methods prior to recombination. In another embodiment, one or more portions of a polynucleotide encoding a B lymphocyte stimulator binding polypeptide which portions specifically bind to B lymphocyte stimulator may be recombined with one or more components, motifs, sections, parts, domains, fragments, etc. of one or more heterologous molecules.

Polypeptides of the present invention include products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides may also include an initial modified methionine residue, in some cases as a result of host-mediated processes.

The B lymphocyte stimulator binding polypeptides that are used in the methods of the present invention may be modified during or after synthesis or translation, e.g., by glycosylation, acetylation, benzylation, phosphorylation, amidation, pegylation, formylation, derivatization by known protecting/blocking groups, proteolytic cleavage, linkage to an antibody molecule, hydroxylation, iodination, methylation, myristoylation, oxidation, pegylation, proteolytic processing, phosphorylation, prenylation, racemization, selenoylation, sulfation, ubiquitination, etc. (See, for instance, Creighton, *Proteins: Structures and Molecular Properties, 2d Ed.* (W.H. Freeman and Co., N.Y., 1992); *Postranslational Covalent Modification of Proteins*, Johnson, ed. (Academic Press, New York, 1983), pp. 1-12; Seifter et al., *Meth. Enzymol.,* 182:626-646 (1990); Rattan et al., *Ann. NY Acad. Sci.,* 663:48-62 (1992).) In specific embodiments, the peptides are acetylated at the N-terminus and/or amidated at the C-terminus.

B lymphocyte stimulator binding polypeptides containing two or more residues that have the potential to interact, such as for example, two cysteine residues in a polypeptide, may be treated under oxidizing conditions or other conditions that promote interaction of these residues (e.g, dislulfide bridge formation).

Further B lymphocyte stimulator binding polypeptide modifications contemplated herein include, for example, any of numerous chemical modifications carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc. Additional post-translational/post-synthesis modifications that may be employed include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression.

Chemically modified derivatives of B lymphocyte stimulator binding polypetides may be used which may provide additional advantages such as increased affinity, decreased off-rate, solubility, stability and in vivo or in vitro circulating time of the polypeptide, or decreased immunogenicity (see, U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any, on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.*, 56:59-72 (1996); Vorobjev et al., *Nucleosides Nucleotides,* 18:2745-2750 (1999); and Caliceti et al., *Bioconjug. Chem.,* 10:638-646 (1999), the disclosures of each of which are incorporated herein by reference.

The polyethylene glycol molecules (or other chemical moieties) should be attached to the B lymphocyte stimulator binding polypeptide with consideration of effects on functional domains of the polypeptide. There are a number of attachment methods available to those skilled in the art, e.g., EP 0 401 384, herein incorporated by reference (coupling PEG to G-CSF), see also Malik et al., *Exp. Hematol.,* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. In a preferred embodiment, the polyethylene glycol molecule is attached at an amino group, such as attachment at the N-terminus or to a lysine side chain amino group.

As suggested above, polyethylene glycol may be attached to polypeptides via linkage to any of a number of amino acid residues. For example, polyethylene glycol can be linked to a polypeptide via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the polypeptide or to more than one type of amino acid residue (e.g., lysine, histidine, aspartic acid, glutamic acid, cysteine and combinations thereof) of the polypeptide.

One may specifically desire proteins chemically modified at the N-terminus. Using polyethylene glycol as an illustration, one may select from a variety of polyethylene glycol molecules (by molecular weight, branching, etc.), the proportion of polyethylene glycol molecules to polypeptide molecules in the reaction mix, the type of pegylation reaction to be performed, and the method of obtaining the selected N-terminally pegylated polypeptide. The method of obtaining the N-terminally pegylated preparation (i.e., separating this moiety from other monopegylated moieties if necessary) may be by purification of the N-terminally pegylated material from a population of pegylated polypeptide molecules. Selective N-terminal modification of proteins may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As indicated above, pegylation of the polypeptides may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.,* 9:249-304 (1992); Francis et al., *Intern. J. of Hematol.,* 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of polypeptides without an intervening linker employs tresylated MPEG, which is produced by the modification of monomethoxy polyethylene glycol (MPEG) using tresylchloride ($ClSO_2CH_2CF_3$). Upon reaction of protein with tresylated MPEG, polyethylene glycol is directly attached to amine groups of the polypeptide. Thus, the invention includes polypeptide-polyethylene glycol conjugates produced by reacting polypeptides with a polyethylene glycol molecule having a 2,2,2-trifluoreothane sulphonyl group.

Polyethylene glycol can also be attached to polypeptides using a number of different intervening linkers. For example, U.S. Pat. No. 5,612,460, the entire disclosure of which is incorporated herein by reference, discloses urethane linkers for connecting polyethylene glycol to polypeptides. Polypeptide-polyethylene glycol conjugates wherein the polyethylene glycol is attached to the polypeptide by a linker can also be produced by reaction of polypeptides with compounds such as MPEG-succinimidylsuccinate, MPEG activated with 1,1'-carbonyldiimidazole, MPEG-2,4,5-trichlorophenylcarbonate, MPEG-p-nitrophenolcarbonate, and various MPEG-succinate derivatives. A number of additional polyethylene glycol derivatives and reaction chemistries for attaching polyethylene glycol to polypeptides are described in WO 98/32466, the entire disclosure of which is incorporated herein by reference. Pegylated B lymphocyte stimulator binding polypeptide products produced using the reaction chemistries set out herein are included within the scope of the invention.

The number of polyethylene glycol moieties attached to each polypeptide (i.e., the degree of substitution) may also vary. For example, the pegylated polypeptides may be linked, on average, to 1, 2, 3, 4, 5, 6, 7, 8, 9, 10, 12, 15, 17, 20, or more polyethylene glycol molecules. Similarly, the average degree of substitution may range within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per polypeptide molecule. Methods for determining the degree of substitution are discussed, for example, in Delgado et al., *Crit. Rev. Thera. Drug Carrier Sys.,* 9:249-304 (1992).

B Lymphocyte Stimulator Binding Polypeptide Multimers, Conjugates and Fusions

The methods of the present invention may also be carried out using multivalent B lymphocyte stimulator binding polypeptides. B lymphocyte stimulator binding polypeptides may be monomeric, dimeric, trimeric, or higher-order multimers. In a preferred embodiment multivalent B lymphocyte stimulator binding polypeptides are homotrimeric. In another preferred embodiment a homotrimeric B lymphocyte stimulator binding polypeptide binds a single homotrimeric B lymphocyte stimulator.

In another preferred embodiment, monomeric or multimeric B lymphocyte stimulator binding polypeptides are conjugated with another polypeptide or other chemical compound. For example, B lymphocyte stimulator binding polypeptide(s) may be conjugated to a radioactive or other toxic compound so as to target and destroy cells expressing B lymphocyte stimulator.

The present invention also encompasses the use of heteromeric multimers comprised of one or more B lymphocyte stimulator binding polypeptides and one or more non-B lymphocyte stimulator binding polypeptides or other chemical moieties. Such heteromeric multimers may be monomeric, dimeric, trimeric, tetrameric, pentameric, or higher-order multimers. Heteromeric B lymphocyte stimulator binding multimers may be used to target, bind, inhibit, and/or activate responses in cells expressing B lymphocyte stimulator and receptors for the heterologous, non-B lymphocyte stimulator binding polypeptide or other chemical moiety. Such activated responses may include, for example, apoptosis or other biologically and chemically mediated forms of cell destruction. Heteromeric B lymphocyte stimulator binding multimers may also be used to target B lymphocyte stimulator expressing cells so as to introduce a desired molecule or compound to the cells. For example, a heteromeric B lymphocyte stimulator binding multimer may be conjugated with a radioactive or otherwise toxic compound so as to kill B lymphocyte stimulator expressing cells. As an alternative example, a heteromeric B lymphocyte stimulator binding and Adenovirus-binding multimer could be used to specifically target and introduce adenovirus-mediated gene therapeutics into B lymphocyte stimulator expressing cells.

B lymphocyte stimulator binding polypeptide multimers may be fused or conjugated as homopolymers and heteropolymers using methods known in the art. In a preferred embodiment B lymphocyte stimulator binding polypeptides are linked as homomultimers wherein the linker or linkers provide sufficient length and flexibility such that each B lymphocyte stimulator binding polypeptide may simultaneously bind an individual B lymphocyte stimulator molecule. In another preferred embodiment B lymphocyte stimulator binding polypeptides are linked as heteromultimers wherein the linker or linkers provide sufficient length and flexibility such that each B lymphocyte stimulator binding polypeptide may simultaneously bind individual B lymphocyte stimulator molecules and the heterologous polypeptide or chemical moiety may simultaneously bind to its target. Numerous examples of suitable linker molecules are known in the art. (See, for example, Todorovska et al., *J. Immunol. Methods,* 248(1-2):47-66 (2001); Mehvar, *J. Control Release,* 69(1):1-25 (2000); Francis et. al., *Int. J. Hematol.,* 68(1):1-18 (1998).) In specific embodiments, the linker is a member selected from the group consisting of: (a) a peptide linker; (b) a glutamate linker; and (c) a polyethylene glycol linker. The length of linkers to be used according to the methods of the invention may routinely be determined using techniques known in the art. In specific embodiments, the linker is 5-60 angstroms in length. In other embodiments, the linker is 10-50, 10-40, 10-30, or 10-20 angstroms in length. In further embodiments, the linker is about 5, 10, 15, 20, 25, 30, 35, 40, 45, 50, 55, 60, 65, 70, 75, 80, 85, 90, 95, or 100 angstroms in length. In this context "about" includes the recited length, and/or lengths that are larger or smaller by several (5, 4, 3, 2, or 1) angstroms. In other embodiments, the linker is at least 5, 10, 15, 20, 25, 30, 35, 40, 45, 50, 55, 60, 65, 70, 75, 80, 85, 90, 95, or 100 angstroms in length.

In a preferred embodiment, B lymphocyte stimulator binding polypeptides may be fused with human serum albumin (HA). See, e.g., U.S. application Ser. No. 09/833,245, filed Apr. 12, 2001, which is hereby incorporated by reference herein. In one embodiment, the albumin fusion protein comprises HA as the N-terminal portion, and a B lymphocyte stimulator binding polypeptide as the C-terminal portion. In another embodiment the albumin fusion protein comprise HA as the C-terminal portion, and a B lymphocyte stimulator binding polypeptide as the N-terminal portion.

In other embodiments, the albumin fusion protein has a B lymphocyte stimulator binding polypeptide fused to both the N-terminus and the C-terminus of albumin. In one preferred embodiment, the B lymphocyte stimulator binding polypeptides fused at the N- and C-termini are the same B lymphocyte stimulator binding polypeptides. In another preferred embodiment, the B lymphocyte stimulator binding polypeptides fused at the N- and C-termini are different B lymphocyte stimulator binding polypeptides. In another preferred embodiment, a B lymphocyte stimulator binding polypeptide is fused at either the N- or C-terminus of HA and a different (non-B lymphocyte stimulator binding) polypeptide is fused at either the C- or N-terminus, respectively.

In addition to albumin fusion proteins in which the B lymphocyte stimulator binding polypeptide(s) is (are) fused to the N-terminus and/or C-terminus of HA, B lymphocyte stimulator binding polypeptide/albumin fusion proteins may also be produced by inserting the B lymphocyte stimulator binding polypeptide into an internal region or regions of HA. For instance, within the protein sequence of the HA molecule a number of loops or turns exist between the end and beginning of α-helices, which are stabilized by disulphide bonds (see FIGS. 9-11 in U.S. application Ser. No. 09/833,245). The loops, as determined from the crystal structure of HA (FIG. 13 of U.S. application Ser. No. 09/833,245) (PDB identifiers 1AO6, 1BJ5, 1BKE, 1BM0, 1E7E to 1E7I and 1UOR) for the most part extend away from the body of the molecule. These loops are useful for the insertion, or internal fusion, of therapeutically active peptides (particularly those requiring a secondary structure to be functional) or therapeutic proteins, to essentially generate an albumin molecule with specific biological activity.

Loops in human albumin structure into which binding polypeptides may be inserted to generate albumin fusion proteins include: Val54-Asn61, Thr76-Asp89, Ala92-Glu100, Gln170-Ala176, His 247-Glu252, Glu 266-Glu277, Glu 280-His288, Ala362-Glu368, Lys439-Pro447, Val462-Lys475, Thr478-Pro486, and Lys560-Thr566. In more preferred embodiments, polypeptides are inserted into the Val54-Asn61, Gln170-Ala176, and/or Lys560-Thr566 loops of mature human serum albumin (SEQ ID NO:445).

In specific embodiments, B lymphocyte stimulator binding polypeptides are attached to macrocyclic chelators useful for conjugating radiometal ions, including but not limited to, $^{111}$In, $^{177}$Lu, $^{90}$Y, $^{166}$Ho, and $^{153}$Sm, to polypeptides. In a preferred embodiment, the radiometal ion associated with the macrocyclic chelators attached to B lymphocyte stimulator binding polypeptides is $^{111}$In. In another preferred embodiment, the radiometal ion associated with the macrocyclic chelator attached to B lymphocyte stimulator binding polypeptides is $^{90}$Y. In specific embodiments, the macrocyclic chelator is 1,4,7,10-tetraazacyclododecane-N,N',N'',N'''-tetraacetic acid (DOTA). In other specific embodiments, the DOTA is attached to the B lymphocyte stimulator binding polypeptides via a linker molecule. Examples of linker molecules useful for conjugating DOTA to a polypeptide are commonly known in the art—see, for example, DeNardo et al., *Clin. Cancer Res.*, 4(10):2483-90 (1998); Peterson et al., *Bioconjug. Chem.*, 10(4):553-7 (1999); and Zimmerman et al, *Nucl. Med. Biol.,* 26(8):943-50 (1999), which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art would be readily able to adapt the method disclosed therein in order to conjugate chelating agents to other polypeptides.

The B lymphocyte stimulator binding polypeptides can be recovered and purified by known methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

The B lymphocyte stimulator binding polypeptides may also be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of B lymphocyte stimulator target. The detectable substance may be coupled or conjugated either directly to the polypeptides or indirectly, through an intermediate (such as, for example, a linker known in the art) using techniques known in the art. Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, $^{213}$Bi, or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115}$ In, $^{113m}$In, $^{112}$In, $^{111}$In), and technetium ($^{99}$Tc, $^{99m}$Tc), thallium ($^{201}$Ti) gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin.

In specific embodiments, B lymphocyte stimulator binding polypeptides are attached macrocyclic chelators useful for conjugating radiometal ions, including but not limited to $^{177}$Lu, $^{90}$Y, $^{166}$Ho, and $^{153}$Sm, to polypeptides. In specific embodiments, the macrocyclic chelator is 1,4,7,10-tetraazacyclododecane-N,N',N",N'"-tetraacetic acid (DOTA). In other specific embodiments, the DOTA is attached to the B lymphocyte stimulator binding polypeptide via a linker molecule. Examples of linker molecules useful for conjugating DOTA to a polypeptide are commonly known in the art—see, for example, DeNardo et al., *Clin. Cancer Res.,* 4(10):2483-90 (1998); Peterson et al., *Bioconjug. Chem.,* 10(4):553-7 (1999); and Zimmerman et al, *Nucl. Med. Biol.,* 26(8):943-50 (1999), which are hereby incorporated by reference in their entirety.

In a specific embodiment, B lymphocyte stimulator binding polypeptides are labeled with biotin.

The present invention further encompasses the use of B lymphocyte stimulator binding polypeptides (including molecules comprising, or alternatively consisting of, B lymphocyte stimulator binding polypeptide fragments or variants thereof), conjugated to a diagnostic or therapeutic agent. The B lymphocyte stimulator binding polypeptides can be used diagnostically to, for example, monitor or prognose the development or progression of a tumor as part of a clinical testing procedure to, e.g., determine the efficacy of a given treatment regimen. Detection can be facilitated by coupling the B lymphocyte stimulator binding polypeptide to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions such as, for example, those described herein. The detectable substance may be coupled or conjugated either directly to the B lymphocyte stimulator binding polypeptide or indirectly, through an intermediate (such as, for example, a linker known in the art) using techniques known in the art. See, for example, U.S. Pat. No. 4,741,900 for metal ions which can be conjugated to B lymphocyte stimulator binding polypeptides for use as diagnostics according to the present invention.

Further, a B lymphocyte stimulator binding polypeptide (including a molecule comprising, or alternatively consisting of, B lymphocyte stimulator binding polypeptide fragments or variants thereof), may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{135}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, and $^{188}$Rhenium. A cytotoxin or cytotoxic agent includes any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and fragments, variants or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques known in the art may be applied to label B lymphocyte stimulator binding polypeptides. Such techniques include, but are not limited to, the use of bifunctional conjugating agents (see, e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

The B lymphocyte stimulator binding polypeptides which are conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, but are not limited to, for example, a toxin such as abrin, ricin A, alpha toxin, pseudomonas exotoxin, or diphtheria toxin, saporin, momordin, gelonin, pokeweed antiviral protein, alpha-sarcin and cholera toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/33899), AIM II (see, International Publication No. WO 97/34911), fas ligand (Takahashi et al., *Int. Immunol.*, 6:1567-1574 (1994)), VEGI (see, International Publication No. WO 99/23105), a thrombotic agent or an anti-angiogenic agent, e.g., angiostatin or endostatin; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

A B lymphocyte stimulator binding polypeptide (including a molecule comprising, or alternatively consisting of, a B lymphocyte stimulator binding polypeptide fragment or variant thereof), with or without a therapeutic moiety conjugated to it, administered alone or in combination with cytotoxic factor(s) and/or cytokine(s) can be used as a therapeutic.

Characterization of B Lymphocyte Stimulator Binding Polypeptides

B lymphocyte stimulator binding polypeptides (including molecules comprising, or alternatively consisting of, B lymphocyte stimulator binding polypeptide fragments or variants thereof) may be characterized in a variety of ways. In particular, B lymphocyte stimulator binding polypeptides and related molecules may be assayed for the ability to specifically bind to B lymphocyte stimulator or a fragment of B lymphocyte stimulator (e.g., to the soluble form or the membrane-bound form of B lymphocyte stimulator) using techniques described herein or routinely modifying techniques known in the art. B lymphocyte stimulator or B lymphocyte stimulator fragments that may be specifically bound by the compositions useful according to the invention include, but are not limited to, human B lymphocyte stimulator (SEQ ID NOs:173 and/or 174) or B lymphocyte stimulator expressed on human monocytes; murine B lymphocyte stimulator (SEQ ID NOs:175 and/or 176) or B lymphocyte stimulator expressed on murine monocytes; rat B lymphocyte stimulator (either the soluble forms as given in SEQ ID NOs:177, 178, 179 and/or 180 or in a membrane associated form, e.g., on the surface of rat monocytes); or monkey B lymphocyte stimulator (e.g., the monkey B lymphocyte stimulator polypeptides of SEQ ID NOS:181 and/or 182, the soluble form of monkey B lymphocyte stimulator, or B lymphocyte stimulator expressed on monkey monocytes) or fragments thereof. Preferably compositions useful according to the invention bind human B lymphocyte stimulator (SEQ ID NOs:173 and/or 174) or fragments thereof. Assays for the ability of the B lymphocyte stimulator binding polypeptides to specifically bind B lymphocyte stimulator or a fragment of B lymphocyte stimulator may be performed in solution (e.g., Houghten, *Bio/Techniques,* 13:412-421 (1992)), on beads (e.g., Lam, *Nature,* 354:82-84 (1991)), on chips (e.g., Fodor, *Nature,* 364:555-556 (1993)), on bacteria (e.g., U.S. Pat. No. 5,223,409), on spores (e.g., U.S. Pat. Nos. 5,571,698; 5,403,484; and 5,223,409), on plasmids (e.g., Cull et al., *Proc. Natl. Acad. Sci. USA,* 89:1865-1869 (1992)) or on phage (e.g., Scott and Smith, *Science,* 249:386-390 (1990); Devlin, *Science,* 249:404-406 (1990); Cwirla et al., *Proc. Natl. Acad. Sci. USA,* 87:6378-6382 (1990); and Felici, *J. Mol. Biol.,* 222:301-310 (1991)) (each of these references is incorporated herein in its entirety by reference). B lymphocyte stimulator binding polypeptides that have been identified to specifically bind to B lymphocyte stimulator or a fragment of B lymphocyte stimulator can then be assayed for their specificity and affinity for B lymphocyte stimulator or a fragment of B lymphocyte stimulator using or routinely modifying techniques described herein or otherwise known in the art.

The B lymphocyte stimulator binding polypeptides may be assayed for specific binding to B lymphocyte stimulator and cross-reactivity with other B lymphocyte stimulator-like polypeptides by any method known in the art. In particular, the ability of a B lymphocyte stimulator binding polypeptide to specifically bind to the soluble form or membrane-bound form of B lymphocyte stimulator and the specificity of the B lymphocyte stimulator binding polypeptide, fragment, or variant for B lymphocyte stimulator polypeptide from a particular species (e.g., murine, monkey or human, preferably human) may be determined using or routinely modifying techniques described herein or otherwise known in art.

Assays which can be used to analyze specific binding and cross-reactivity include, but are not limited to, competitive and non-competitive assay systems using techniques such as western blots, radioimmunoassays, ELISA (enzyme linked immunosorbent assay), "sandwich" assays, "immunoprecipitation" assays, precipitin reactions, gel diffusion precipitin reactions, immunodiffusion assays, agglutination assays, complement-fixation assays, radiometric assays, and fluorescent assays, to name but a few. Such assays are routine and well known in the art (see, e.g., *Current Protocols in Molecular Biology, Vol.* 1, Ausubel et al, eds. (John Wiley & Sons, Inc., New York 1994), which is incorporated by reference herein in its entirety) and could easily be adapted to make use of a B lymphocyte stimulator binding polypeptide (possibly in conjunction with an anti-B lymphocyte stimulator binding polypeptide antibody) in place of an anti-B lymphocyte stimulator antibody. Exemplary immunoassays that could be modified to use a B lymphocyte stimulator binding polypeptide are described briefly below (but are not intended by way of limitation).

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), incubating the membrane with B lymphocyte stimulator binding polypeptide (the B lymphocyte stimulator binding polypeptide of interest) diluted in blocking buffer, washing the membrane in washing buffer, incubating the membrane with a secondary antibody (which recognizes the B lymphocyte stimulator binding polypeptide) conjugated to an enzyme (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. Alternatively, the B lymphocyte stimulator binding polypeptide may be directly conjugated to a detection molecule (e.g., an enzyme or radiolabel), thereby omitting the need for a secondary anti-B lymphocyte stimulator binding polypeptide antibody. One of skill in the art would be knowledgeable as to the parameters that can be modified to increase the signal detected and to reduce the background noise. For further discussion regarding western blot protocols see, e.g., *Current Protocols in Molecular Biology, Vol.* 1, Ausubel et al, eds. (John Wiley & Sons, Inc., New York 1994) at 10.8.1.

ELISAs comprise preparing antigen (e.g., B lymphocyte stimulator target), coating the well of a 96-well microtiter plate with the antigen, washing away antigen that did not bind the wells, adding the B lymphocyte stimulator binding polypeptide of interest conjugated to a detectable compound such as an enzyme (e.g., horseradish peroxidase or alkaline phosphatase) to the wells and incubating for a period of time, washing away unbound B lymphocyte stimulator binding polypeptides or non-specifically bound B lymphocyte stimulator binding polypeptides, and detecting the presence of the B lymphocyte stimulator binding polypeptides specifically bound to the antigen coating the well. In ELISAs the B lymphocyte stimulator binding polypeptide employed in the assay does not have to be conjugated to a detectable compound; instead, an antibody that recognizes the B lymphocyte stimulator binding polypeptide and that is conjugated to a detectable compound may be added to the well. Further, instead of coating the well with the antigen, the B lymphocyte stimulator binding polypeptide may be coated to the well. In this case, the detectable molecule could be the antigen conjugated to a detectable compound such as an enzyme (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., *Current Protocols in Molecular Biology, Vol.* 1, Ausubel et al, eds. (John Wiley & Sons, Inc., New York 1994) at 11.2.1.

Immunoprecipitation protocols generally use antibody molecules to immunopreciptate a protein of interest. A B lymphocyte stimulator precipitation protocol could easily be modified to use a B lymphocyte stimulator binding polypeptide in place of an anti-B lymphocyte stimulator antibody. Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40 degrees C., adding protein A and/or protein G sepharose beads to the cell lysate, incubating for about an hour or more at 40 degrees C., washing the beads in lysis buffer and resuspending the beads in SDS/sample buffer. If one wanted to substitute a B lymphocyte stimulator binding polypeptide for the anti-B lymphocyte stimulator antibody one could readily do so, and then isolate the B lymphocyte stimulator-B lymphocyte stimulator binding polypeptide complexes with an antibody that recognizes the B lymphocyte stimulator binding polypeptide. Then the triple complex of B lymphocyte stimulator, B lymphocyte stimulator binding polypeptide, and anti-B lymphocyte stimulator binding polypeptide antibody could be isolated using protein A and/or Protein G as described above. Such a protocol may be desirable if, for example, the anti-B lymphocyte stimulator binding polypeptide antibody has a higher affinity for the B lymphocyte stimulator binding polypeptide than the anti-B lymphocyte stimulator antibody may have for B lymphocyte stimulator.

The effectiveness of incorporating a B lymphocyte stimulator binding polypeptide in an immunoprecipitation protocol to precipitate B lymphocyte stimulator can be assessed by, e.g., western blot analysis. One of skill in the art would be knowledgeable as to the parameters that can be modified to increase the binding of the B lymphocyte stimulator binding polypeptide to an antigen and decrease the background (e.g., pre-clearing the cell lysate with sepharose beads). For further discussion regarding immunoprecipitation protocols see, e.g., *Current Protocols in Molecular Biology, Vol.* 1, Ausubel et al, eds. (John Wiley & Sons, Inc., New York 1994) at 10.16.1.

The binding affinity of a B lymphocyte stimulator binding polypeptide (including molecules comprising, or alternatively consisting of, B lymphocyte stimulator binding polypeptide fragments or variants thereof) to an antigen and the off-rate of an B lymphocyte stimulator binding polypeptide-antigen interaction can be determined by competitive binding assays. One example of a competitive binding assay is a modified radioimmunoassay comprising the incubation of labeled antigen (e.g., $^{3}H$- or $^{125}I$-labeled B lymphocyte stimulator target) with the B lymphocyte stimulator binding polypeptide of interest in the presence of increasing amounts of unlabeled antigen, followed by detection of the B lymphocyte stimulator binding polypeptide bound to the labeled antigen. The affinity of the B lymphocyte stimulator binding polypeptide of the present invention for B lymphocyte stimulator and the binding off-rates can be determined from the data by Scatchard plot analysis. Competition with an anti-B lymphocyte stimulator antibody or B lymphocyte stimulator binding polypeptide can also be determined using radioimmunoassays. In this case, B lymphocyte stimulator is incubated with a B lymphocyte stimulator binding polypeptide of the present invention conjugated to a labeled compound (e.g., with $^{3}H$ or $^{125}I$) in the presence of increasing amounts of an unlabeled B lymphocyte stimulator binding polypeptide or anti-B lymphocyte stimulator antibody.

In a preferred embodiment, BIAcore kinetic analysis is used to determine the binding on and off rates of B lymphocyte stimulator binding polypeptides (including molecules comprising, or alternatively consisting of, B lymphocyte stimulator binding polypeptide fragments or variants thereof) to B lymphocyte stimulator, or fragments of B lymphocyte stimulator. BIAcore kinetic analysis comprises analyzing the binding and dissociation of B lymphocyte stimulator from chips with immobilized B lymphocyte stimulator binding polypeptides on their surface (see Example 6, infra).

The B lymphocyte stimulator binding polypeptides (including molecules comprising, or alternatively consisting of, B lymphocyte stimulator binding polypeptide fragments or variants thereof) can also be assayed for their ability to inhibit, increase, or not significantly alter, the binding of B lymphocyte stimulator to a B lymphocyte stimulator receptor (e.g., TACI and BCMA) using techniques known to those skilled in the art. For example, cells expressing a receptor for B lymphocyte stimulator (e.g., IM9, REH, ARH-77cells, Namalwa, and RPMI-8226 B cell tumor lines as well as peripheral CD20+ B cells) can be contacted with B lymphocyte stimulator in the presence or absence of a B lymphocyte stimulator binding polypeptide, and the ability of the B lymphocyte stimulator binding polypeptide to inhibit, increase, or not significantly alter, B lymphocyte stimulator binding to the cells can be measured. Alternatively, the B lymphocyte stimulator binding polypeptide may be preincubated with the B lymphocyte stimulator prior to exposure of the B lymphocyte stimulator to cells expressing the B lymphocyte stimulator receptor. B lymphocyte stimulator binding to cells can be measured by, for example, flow cytometry or a scintillation assay. B lymphocyte stimulator or the B lymphocyte stimulator binding polypeptide can be labeled with a detectable compound such as a radioactive label (e.g., $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an interaction between B lymphocyte stimulator and a B lymphocyte stimulator receptor and/or B lymphocyte stimulator and a B lymphocyte stimulator binding polypeptide.

The ability of B lymphocyte stimulator binding polypeptides to inhibit, increase, or not significantly alter, B lymphocyte stimulator binding to a B lymphocyte stimulator receptor can also be determined in cell-free assays. For example, native or recombinant B lymphocyte stimulator (e.g., having the amino acid sequence of amino acids 134-285 of SEQ ID NO:173) or a fragment thereof can be contacted with a B lymphocyte stimulator binding polypeptide and the ability of the B lymphocyte stimulator binding polypeptide to inhibit, increase, or not significantly alter, B lymphocyte stimulator from binding to a B lymphocyte stimulator receptor can be determined. Preferably, the B lymphocyte stimulator binding polypeptide or B lymphocyte stimulator receptor is immobilized on a solid support and B lymphocyte stimulator or a B lymphocyte stimulator fragment is labeled with a detectable compound. Alternatively, B lymphocyte stimulator or a B lymphocyte stimulator fragment is immobilized on a solid support and the B lymphocyte stimulator binding polypeptide is labeled with a detectable compound. B lymphocyte stimulator may be partially or completely purified (e.g., partially or completely free of other polypeptides) or part of a cell lysate. Further, the B lymphocyte stimulator polypeptide may be a fusion protein comprising B lymphocyte stimulator or a biologically active portion thereof and a domain such as an Immunoglobulin Fc or glutathionine-S-transferase. Additionally, the B lymphocyte stimulator binding polypeptide and/or B lymphocyte stimulator receptor may be a fusion protein comprising a B lymphocyte stimulator binding portion of the polypeptide or receptor and a domain such as an Immunoglobulin Fc or glutathionine-S-transferase. For example, amino acid residues 1-154 of TACI (GenBank accession number AAC51790), or 1-48 of BCMA (GenBank accession number NP_001183) may be fused to the Fc region of an IgG molecule and used in a cell free assay to determine the ability of B lymphocyte stimulator binding polypeptides to inhibit, increase, or not significantly alter, B lymphocyte stimulator binding to a B lymphocyte stimulator receptor. Alternatively, B lymphocyte stimulator can be biotinylated using techniques well known to those skilled in the art (e.g., biotinylation kit, Pierce Chemicals; Rockford, Ill.).

The B lymphocyte stimulator binding polypeptides (including molecules comprising, or alternatively consisting of, B lymphocyte stimulator binding polypeptide fragments or variants thereof), can also be assayed for their ability to inhibit, stimulate, or not significantly alter, B lymphocyte stimulator-induced B-cell proliferation using techniques known to those of skill in the art. For example, B-cell proliferation can be assayed by $^3$H-thymidine incorporation assays and trypan blue cell counts (see, e.g., Moore et al., *Science*, 285: 260-263 (1999)). Further, the B lymphocyte stimulator binding polypeptides, or fragments or variants thereof, can be assayed for their ability to inhibit, stimulate, or not significantly alter, B lymphocyte stimulator-induced activation of cellular signaling molecules and transcription factors such as calcium-modulator and cyclophilin ligand (CAML), calcineurin, nuclear factor of activated T cells transcription factor (NF-AT), nuclear factor-kappa B (NF-kappa B), SRF, activator protein-1 (AP-1), extracellular-signal regulated kinase 1 (ERK-1), polo like kinases (PLK), ELF-1, high mobility group I (HMG-I), and/or high mobility group Y (HMG-Y) using techniques known to those of skill in the art (see, e.g., von Bulow and Bram, *Science*, 278:138-141 (1997)). For example, NF-AT activity can be determined by electromobility gel shift assays, by detecting the expression of a protein known to be regulated by NF-AT (e.g., IL-2 expression), by detecting the induction of a reporter gene (e.g., an NF-AT regulatory element operably linked to a nucleic acid encoding a detectable marker such as luciferase, beta-galactosidase or chloramphenicol acetyltransferase (CAT)), or by detecting a cellular response (e.g., cellular differentiation, or cell proliferation).

The B lymphocyte stimulator binding polypeptides, or fragments or variants thereof can also be assayed for their ability to neutralize, enhance, or not significantly alter, B lymphocyte stimulator activity. For example, B lymphocyte stimulator binding polypeptides or fragments or variants thereof, may be routinely tested for their ability to inhibit B lymphocyte stimulator from binding to cells expressing the receptor for B lymphocyte stimulator.

Uses of the Binding Polypeptides and Recombinant Bacteriophage

The B lymphocyte stimulator binding polypeptides described herein are especially useful to detect, isolate, or remove B lymphocyte stimulator target proteins in solutions. Such solutions may be simple dispersions or solutions of B lymphocyte stimulator and/or B lymphocyte stimulator-like polypeptide in water or aqueous buffer or more complex solutions, such as, a blood and other biological fluids, tissue homogenates cell extracts, or biopsy samples, and cell culture media containing B lymphocyte stimulator or B lymphocyte stimulator-like polypeptides. Biological fluids include, but are not limited to sera, plasma, lymph, blood, blood fractions urine, synovial fluid, spinal fluid, saliva, and mucous.

In one embodiment, the present invention provides a method for detecting a B lymphocyte stimulator protein and/or a B lymphocyte stimulator-like polypeptide in a solution comprising contacting the solution with a B lymphocyte stimulator binding polypeptide and detecting binding of B lymphocyte stimulator or B lymphocyte stimulator-like polypeptide to the B lymphocyte stimulator binding polypeptide. The B lymphocyte stimulator binding polypeptide may be either free or immobilized. Preferably, the B lymphocyte stimulator binding polypeptide is a polypeptide immobilized on a solid surface or chromatographic material or the well of a plastic microtiter assay dish.

Another embodiment of the present invention is a method for isolating B lymphocyte stimulator protein and/or B lymphocyte stimulator-like polypeptide from a solution containing it, comprising:
(a) contacting the solution with a B lymphocyte stimulator binding polypeptide under conditions that permit binding of B lymphocyte stimulator and/or B lymphocyte stimulator-like polypeptides to B lymphocyte stimulator binding polypeptide, and
(b) recovering the B lymphocyte stimulator and/or B lymphocyte stimulator-like polypeptides.

A further embodiment of the present invention is a method for isolating B lymphocyte stimulator protein and/or B lymphocyte stimulator-like polypeptide from a solution containing it, comprising:
(a) contacting the solution with a B lymphocyte stimulator binding polypeptide under conditions that permit binding of B lymphocyte stimulator and/or B lymphocyte stimulator-like polypeptides to B lymphocyte stimulator binding polypeptide, and
(b) separating the complex(es) formed by the B lymphocyte stimulator binding polypeptide and B lymphocyte stimulator and/or B lymphocyte stimulator-like polypeptides from other components of the solution.

Preferably such method also includes the further steps of:
(c) dissociating the B lymphocyte stimulator binding polypeptide from the B lymphocyte stimulator and/or B lymphocyte stimulator-like polypeptides, and
(d) recovering the dissociated, B lymphocyte stimulator and/or B lymphocyte stimulator-like polypeptide.

The invention also provides for the use of kits containing a binding polypeptide for use in methods of detecting or isolating B lymphocyte stimulator and/or B lymphocyte stimulator-like polypeptides.

According to the invention, detection or isolation of B lymphocyte stimulator target proteins comprises contacting a solution containing a B lymphocyte stimulator target protein with a B lymphocyte stimulator binding polypeptide. Depending on the particular application, the B lymphocyte stimulator binding polypeptide may be free in solution or immobilized on a solid support or chromatographic material. Sufficient time is allowed to permit binding between the B lymphocyte stimulator target protein and the binding polypeptides, and non-binding components in the solution or mixture are removed or washed away. The formation of a binding complex between the binding polypeptide and the B lymphocyte stimulator target protein can then be detected, for example, by detecting the signal from a label on the binding polypeptide, which is one component of the binding complex. A label may be any label that generates a signal that can be detected by standard methods, such as a fluorescent label, a radioactive compound, or an enzyme that reacts with a substrate to generate a detectable signal. Suitable such labels are discussed above. A phage binding polypeptide according to the invention, that is, a recombinant phage displaying a B lymphocyte stimulator binding polypeptide on its surface, may form a complex with B lymphocyte stimulator and/or B lymphocyte stimulator-like polypeptides that is detectable as a precipitate or sediment in a reaction tube, which can be detected visually after settling or centrifugation. Alternatively, a sandwich-type assay may be used, wherein a B lymphocyte stimulator binding polypeptide is immobilized on a solid support such as a plastic tube or well, or a chromatographic support matrix such as agarose beads, then the solution suspected of containing the B lymphocyte stimulator target is contacted with the immobilized binding polypeptide and non-binding materials or components are removed or washed away.

The binding polypeptides according to this invention are particularly useful for detection and/or isolation of B lymphocyte stimulator and/or B lymphocyte stimulator-like polypeptides by affinity chromatography methods. Any conventional method of chromatography may be employed. Preferably, a B lymphocyte stimulator binding polypeptide will be immobilized on a solid support suitable, for example, for packing a chromatography column. The immobilized B lymphocyte stimulator binding polypeptide affinity ligand can then be loaded or contacted with a feed stream under conditions favorable to formation of binding polypeptide/B lymphocyte stimulator (or B lymphocyte stimulator-like polypeptide) complexes. Non-binding materials can be washed away. Examples of suitable wash conditions can readily be determined by one of skill in the art and include but are not limited to [PBS/0.01% Tween 20, pH7.2] and [1M NaCl/10 mM Tris, pH7.5]. Tris wash buffers may be preferable since phosphates can preciptate in 50% ethylene glycol. In general, non-limiting terms, wash buffers are pH7.0, optionally containing 0.0 to 1.5 M NaCl, more preferably 1M NaCl. Additionally, wash buffers may optionally contain a mild detergent, such as, for example, Tween 20, Tween 80, or NP-80. B lymphocyte stimulator or B lymphocyte stimulator-like polypeptide can be eluted from the B lymphocyte stimulator binding polypeptide by introducing solution conditions that favor dissociation of the binding complex. Suitable elution solutions can readily be determined by one of skill in the art and include but are not limited to [50% ethylrne glycol/ 100 mM NaOAc]. By way of non-limiting example, useful elution buffers, for the purposes of the present invention contain 40-60% ethylene glycol, preferably 50% ethylene glycol; and 50-100 mM NaOAc with a pH in the range of pH 4-pH7, more preferably, pH 4-pH 6 and most preferably pH 4.5-pH 5.5. Preferably, a fast flow affinity chromatographic technique is used to bind the molecules and from which purified B lymphocyte stimulator or B lymphocyte stimulator-like polypeptides are eluted.

Alternatively, batch chromatography can be carried out by mixing a solution containing the B lymphocyte stimulator target and the B lymphocyte stimulator binding polypeptide, then isolating complexes of the B lymphocyte stimulator target and the binding polypeptides. For this type of separation, many methods are known. For example, the binding polypeptide may be immobilized on a solid support such as beads, then separated from the feed stream along with the B lymphocyte stimulator target by filtration. In another example, the B lymphocyte stimulator binding polypeptide may be modified with its own affinity tag, such as a polyHis tail or streptavidin binding region, which can be used to isolate the binding polypeptide after complexes have formed using an immobilized metal affinity chromatographic resin or steptavidin-coated substrate. Once separated, the B lymphocyte stimulator target can be released from the binding polypeptide under elution conditions and recovered in a purified form.

Methods of producing B lymphocyte stimulator or a B lymphocyte stimulator-like polypeptides usually yield B lymphocyte stimulator or B lymphocyte stimulator-like polypeptides in a feed stream that additionally contains impurities (with respect to the B lymphocyte stimulator target). One purpose of the present invention is to produce B lymphocyte stimulator binding polypeptides and preparations (such as affinity chromatography media or surfaces) comprising B lymphocyte stimulator binding polypeptides that allow rapid and highly specific purification of B lymphocyte stimulator target proteins from a feed stream. B lymphocyte stimulator binding polypeptides obtained herein may easily be tailored to isolate B lymphocyte stimulator target protein from a particular feed stream, using or routinely modifying conditions and techniques known in the art. If an alternate production method for B lymphocyte stimulator is used, producing a different feed stream, a different set of B lymphocyte stimulator binding polypeptides and/or conditions may be necessary to achieve the same level of purification. The new set of B lymphocyte stimulator binding polypeptides and/or conditions can be readily obtained following or modifying procedures outlined herein, or otherwise known in the art.

Use of B lymphocyte stimulator Binding Polypeptides for Epitope Mapping

The present invention provides B lymphocyte stimulator binding polypeptides (including molecules comprising, or alternatively consisting of, B lymphocyte stimulator binding polypeptide fragments or variants thereof), that can be used to identify epitopes of B lymphocyte stimulator. In particular, the B lymphocyte stimulator binding polypeptides of the present invention can be used to identify epitopes of human B lymphocyte stimulator (SEQ ID NOs:173 and/or 174) or B lymphocyte stimulator expressed on human monocytes; murine B lymphocyte stimulator (SEQ ID NOs:175 and/or 176) or B lymphocyte stimulator expressed on murine monocytes; rat B lymphocyte stimulator (either the soluble forms as given in SEQ ID NOs:177, 178, 179 and/or 180 or in a membrane associated form, e.g., on the surface of rat monocytes); or monkey B lymphocyte stimulator (e.g., the monkey B lymphocyte stimulator polypeptides of SEQ ID NOS:181 and/or 182, the soluble form of monkey B lymphocyte stimulator, or B lymphocyte stimulator expressed on monkey monocytes) using techniques described herein or otherwise known in the art. Fragments which function as epitopes may be produced by any conventional means. (See, e.g., Houghten, *Proc. Natl. Acad. Sci. USA,* 82:5131-5135 (1985), further described in U.S. Pat. No. 4,631,211.)

Diagnostic Uses of B lymphocyte stimulator Binding Polypeptides

Labeled and non-labelled B lymphocyte stimulator binding polypeptides (including molecules comprising, or alternatively consisting of, B lymphocyte stimulator binding polypeptide fragments or variants thereof) which specifically bind to B lymphocyte stimulator can be used for diagnostic purposes to detect, diagnose, prognose, or monitor diseases and/or disorders associated with the aberrant expression and/or activity of B lymphocyte stimulator or B lymphocyte stimulator receptor. The invention provides for the detection of aberrant expression of B lymphocyte stimulator comprising: (a) assaying the expression of B lymphocyte stimulator in a biological sample from an individual using one or more B lymphocyte stimulator binding polypeptides that specifically binds to B lymphocyte stimulator; and (b) comparing the level of B lymphocyte stimulator with a standard level of B lymphocyte stimulator, e.g., in normal biological samples, whereby an increase or decrease in the assayed level of B lymphocyte stimulator compared to the standard level of B lymphocyte stimulator is indicative of aberrant expression.

By "biological sample" is intended any fluids and/or cells obtained from an individual, body fluid, body tissue, body cell, cell line, tissue culture, or other source which may contain B lymphocyte stimulator protein or mRNA. Body fluids include, but are not limited to, sera, plasma, urine, synovial fluid, spinal fluid, saliva, and mucous. Tissues samples may be taken from virtually any tissue in the body. Tissue samples may also be obtained from autopsy material. Methods for obtaining tissue biopsies and body fluids from mammals are well known in the art. Where the biological sample is to include mRNA, a tissue biopsy is the preferred source.

The invention also provides for the detection of aberrant expression of B lymphocyte stimulator receptor comprising (a) assaying the expression of B lymphocyte stimulator receptor in a biological sample from an individual using one or more B lymphocyte stimulator binding polypeptides or fragments or variants thereof that specifically binds only to soluble B lymphocyte stimulator, but does not inhibit B lymphocyte stimulator/B lymphocyte stimulator receptor binding. Such a B lymphocyte stimulator binding polypeptide, by way of an example that is not to be construed as limiting, would be one that is able to capture a biotinylated B lymphocyte stimulator from solution, but that would not prevent B lymphocyte stimulator from binding to it receptor expressed, for example on IM-9 cells, and (b) comparing the level of B lymphocyte stimulator receptor with a standard level of B lymphocyte stimulator receptor, e.g., in normal tissue or cell samples, whereby an increase or decrease in the assayed level of B lymphocyte stimulator receptor compared to the standard level of B lymphocyte stimulator receptor is indicative of aberrant expression.

B lymphocyte stimulator binding polypeptides (including molecules comprising, or alternatively consisting of, B lymphocyte stimulator binding polypeptide fragments or variants thereof) which specifically bind to B lymphocyte stimulator can be used for diagnostic purposes to detect, diagnose, prognose, or monitor immune system diseases and disorders, including but not limited to autoimmune diseases and disorders and/or immunodeficiencies, and/or diseases, disorders, or conditions associated therewith. The invention provides for the detection of aberrant expression of B lymphocyte stimulator comprising: (a) assaying the expression of B lymphocyte stimulator in a biological sample from an individual using one or more B lymphocyte stimulator binding polypeptides that specifically binds to B lymphocyte stimulator; and (b) comparing the level of B lymphocyte stimulator with a standard level of B lymphocyte stimulator, e.g., in normal biological samples, whereby an increase or decrease in the assayed level of B lymphocyte stimulator compared to the standard level of B lymphocyte stimulator is indicative of an autoimmune disorder or disease and/or an immunodeficiency. In specific embodiments, an increase in the assayed level of B lymphocyte stimulator is indicative of an autoimmune disorder or disease. In other specific embodiments, a decrease in the assayed level of B lymphocyte stimulator is indicative of an immunodeficiency.

B lymphocyte stimulator binding polypeptides (including molecules comprising, or alternatively consisting of, B lymphocyte stimulator binding polypeptide fragments or variants thereof) which specifically bind to B lymphocyte stimulator but do not inhibit B lymphocyte stimulator/B lymphocyte stimulator receptor binding can be used for diagnostic purposes to detect, diagnose, prognose, or monitor immune system diseases and disorders, including but not limited to autoimmune diseases and disorders and/or immunodeficiencies, and/or diseases, disorders, or conditions associated therewith. The invention provides for the detection of aberrant expression of B lymphocyte stimulator receptor comprising: (a) assaying the expression of B lymphocyte stimulator receptor in a biological sample from an individual using one or more B lymphocyte stimulator binding polypeptides that specifically binds to B lymphocyte stimulator; and (b) comparing the level of B lymphocyte stimulator receptor with a standard level of B lymphocyte stimulator receptor, e.g., in normal biological samples, whereby an increase or decrease in the assayed level of B lymphocyte stimulator receptor compared to the standard level of B lymphocyte stimulator receptor is indicative of an autoimmune disorder or disease and/or an immunodeficiency. In specific embodiments, an increase in the assayed level of B lymphocyte stimulator receptor is indicative of an autoimmune disorder or disease. In other specific embodiments, a decrease in the assayed level of B lymphocyte stimulator receptor is indicative of an immunodeficiency.

Autoimmune disorders, diseases, or conditions that may be detected, diagnosed, prognosed, or monitored using the B lymphocyte stimulator binding polypeptides include, but are not limited to, autoimmune hemolytic anemia, autoimmune neonatal thrombocytopenia, idiopathic thrombocytopenia purpura, autoimmune neutropenia, autoimmunocytopenia, hemolytic anemia, antiphospholipid syndrome, dermatitis, gluten-sensitive enteropathy, allergic encephalomyelitis, myocarditis, relapsing polychondritis, rheumatic heart disease, glomerulonephritis (e.g., IgA nephropathy), multiple sclerosis, neuritis, uveitis ophthalmia, polyendocrinopathies, purpura (e.g., Henloch-Scoenlein purpura), Reiter's Disease, Stiff-Man Syndrome, autoimmune pulmonary inflammation, myocarditis, IgA glomerulonephritis, dense deposit disease, rheumatic heart disease, Guillain-Barre Syndrome, insulin dependent diabetes mellitis, and autoimmune inflammatory eye, autoimmune thyroiditis, hypothyroidism (i.e., Hashimoto's thyroiditis), systemic lupus erhythematosus, discoid lupus, Goodpasture's syndrome, Pemphigus, receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen B lymphocyte stimulator binding polypeptides, mixed connective tissue disease, polymyositis/dermatomyositis, pernicious anemia, idiopathic Addison's disease, infertility, glomerular nephritis such as primary glomerular nephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders.

In specific embodiments, the present invention encompasses methods and compositions for detecting, diagnosing, prognosing, and/or monitoring diseases or disorders associated with hypergammaglobulinemia (e.g., AIDS, autoimmune diseases, and some immunodeficiencies). In other specific embodiments, the present invention encompasses methods and compositions for detecting, diagnosing, prognosing, and/or monitoring diseases or disorders associated with hypogammaglobulinemia (e.g., an immunodeficiency).

Immunodeficiencies that may be detected, diagnosed, prognosed, or monitored using the B lymphocyte stimulator binding polypeptides include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

Elevated levels of soluble B lymphocyte stimulator have been observed in the serum of patients with Systemic Lupus Erythematosus (SLE). In comparing the sera of 150 SLE patients with that of 38 control individuals, it was found that most of the SLE patients had more than 5 ng/ml of serum B lymphocyte stimulator, more than 30% of SLE patients had levels greater than 10 ng/ml, and approximately 10% of SLE patients had serum B lymphocyte stimulator levels greater than 20 ng/ml. In contrast, the majority of normal controls had B lymphocyte stimulator levels less than 5 ng/ml, and less than 10% had levels higher than 10 ng/ml. The elevated levels of B lymphocyte stimulator protein in sera is present in the soluble form and has biologic activity as assayed by the ability to stimulate anti-IgM treated B cells in vitro. SLE patients with more than 15 ng/ml serum B lymphocyte stimulator were also found to have elevated levels of anti-dsDNA antibodies compared to both normal controls and SLE patients with less than 5 ng/ml of serum B lymphocyte stimulator (unpublished data).

In addition the serum of two subgroups of patients which were positive for anti-nuclear antibodies (ANA+) but did not meet the formal requirements of the American College of Rheumatology (ACR) for classification of SLE were anaylzed for B lymphocyte stimulator levels. The first subgroup of sera was ANA+ sera that came from patients who did not present with the clinical impression of SLE. This group had only slightly elevated levels of B lymphocyte stimulator (~9 ng/ml B lymphocyte stimulator). The second subgroup, however, which was ANA+ sera from patients who presented with the clinical impression of SLE, had significantly increased B lymphocyte stimulator levels (~15 ng/ml). These results suggest that an elevated level of B lymphocyte stimulator precedes the formal fulfillment of the ACR criteria. The ACR criteria are described in Tan et al., *Arthritis and Rheumatism*, 25:1271-1277 (1982).

Thus, in specific embodiments, B lymphocyte stimulator binding polypeptides which specifically bind to B lymphocyte stimulator can be used for diagnostic purposes to detect, diagnose, prognose, or monitor Systemic Lupus Erythematosus or conditions associated therewith. The invention provides for the detection of aberrant expression of B lymphocyte stimulator comprising: (a) assaying the expression of B lymphocyte stimulator in a biological sample (e.g., serum, synovial fluid) of an individual using one or more B lymphocyte stimulator binding polypeptides that specifically binds to B lymphocyte stimulator; and (b) comparing the level of B lymphocyte stimulator with a standard level of B lymphocyte stimulator, e.g., in normal biological samples, whereby an increase in the assayed level of B lymphocyte stimulator compared to the standard level of B lymphocyte stimulator is indicative of SLE.

In additional embodiments, B lymphocyte stimulator binding polypeptides which specifically bind to B lymphocyte stimulator can be used for diagnostic purposes to detect, diagnose, prognose, or monitor Rheumatoid Arthritis. The invention provides for the detection of aberrant expression of B lymphocyte stimulator comprising: (a) assaying the expression of B lymphocyte stimulator in a biological sample (e.g., serum, synovial fluid) of an individual using one or more B lymphocyte stimulator binding polypeptides that specifically binds to B lymphocyte stimulator; and (b) comparing the level of B lymphocyte stimulator with a standard level of B lymphocyte stimulator, e.g., in normal biological samples, whereby an increase in the assayed level of B lymphocyte stimulator compared to the standard level of B lymphocyte stimulator is indicative of Rheumatoid Arthritis.

In specific embodiments, the present invention encompasses methods and compositions for detecting, diagnosing and/or prognosing diseases or disorders of cells of hematopoietic origin. Cells of hematopoietic origin include, but are not limited to, lymphocytes (e.g., B cells and T cells), monocytes, macrophages, dendritic cells, polymorphonuclear leukocytes (e.g., basophils, eosinophils, neutrophils), mast cells, platelets, erythrocytes and progenitor cells of these lineages. Cells of hematopoietic origin include, but are not limited to, healthy and diseased cell as found present in an animal, preferably a mammal and most preferably a human, or as isolated from an animal, transformed cells, cell lines derived from the above listed cell types, and cell cultures derived from the above listed cell types. Cells of hematopoietic origin may be found or isolated in, for example, resting, activated or anergic states.

In specific embodiments, the present invention encompasses methods and compositions for detecting, diagnosing, prognosing and or monitoring growth, progression, and/or metastases of malignancies and proliferative diseases or disorders associated with increased cell survival, or the inhibition of apoptosis. For a review of such disorders, see Fishman et al., *Medicine,* 2d Ed. (J. B. Lippincott Co., Philadelphia 1985). An extensive list of examples of proliferative diseases and disorders is presented below in the section of this application entitled "Therapeutic Uses of B lymphocyte stimulator Binding Polypeptides." Proliferative diseases and disorders is also extended to include premalignant conditions (e.g., benign tumors, hyperproliferative disorders, and benign proliferative disorders—see below) as well as proliferative disorders of B cells, monocytes, macrophages, and T cells. Other abnormal growth conditions that may be treated, diagnosed, prognosed or monitored include, but are not limited to, hyperplasia, metaplasia, or most particularly, dysplasia has occurred (for review of such abnormal growth conditions, see Robbins and Angell, *Basic Pathology, 2d Ed*. (W.B. Saunders Co., Philadelphia 1976), pp. 68-79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

In preferred embodiments, the present invention encompasses methods and compositions for detecting, diagnosing, prognosing and or monitoring growth, progression, and/or metastases of malignancies and proliferative diseases or disorders of monocytic cells.

In specific embodiments, the present invention encompasses methods and compositions for detecting, diagnosing, prognosing and or monitoring growth, progression, and/or metastases of malignancies and proliferative diseases or disorders of B cells.

The invention provides a diagnostic assay for diagnosing or prognosing a disease or disorder, comprising: (a) assaying for the level of B lymphocyte stimulator in a biological sample of an individual using one or more B lymphocyte stimulator binding polypeptides that specifically bind to B lymphocyte stimulator; and (b) comparing the level of B lymphocyte stimulator with a standard B lymphocyte stimulator level, e.g., in a biological sample from a patient without the disease or disorder, whereby an increase or decrease in the assayed B lymphocyte stimulator level compared to the standard level of B lymphocyte stimulator is indicative of a particular disease or disorder. With respect to cancer, the presence of a relatively high amount of B lymphocyte stimulator in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

In specific embodiments, the presence of a relatively high amount of membrane-bound B lymphocyte stimulator in a biological sample is indicative of monocytic cell related leukemias or lymphomas, such as, for example acute myelogenous leukemia, and/or the severity thereof.

In other specific embodiments, the presence of a relatively high amount of B lymphocyte stimulator receptor in a biological sample (as determined using B lymphocyte stimulator binding polypeptides that bind to soluble B lymphocyte stimulator, but do not inhibit B lymphocyte stimulator/B lymphocyte stimulator receptor binding) is indicative of B cell related leukemias or lymphomas (e.g., chronic lymphocytic leukemia, multiple myeloma, non-Hodgkin's lymphoma, and Hodgkin's disease), and/or the severity thereof.

B lymphocyte stimulator binding polypeptides (including molecules comprising, or alternatively consisting of, B lymphocyte stimulator binding polypeptide fragments or variants thereof) can be used to assay protein levels in a biological sample using classical immunohistological methods as described herein or as known to those of skill in the art (e.g., see Jalkanen et al., *J. Cell. Biol.,* 101:976-985 (1985); Jalkanen et al., *J. Cell. Biol.,* 105:3087-3096 (1987)). Other methods that can be used for detecting protein gene expression that might utilize B lymphocyte stimulator binding polypeptides or fragments or variants thereof include, but are not limited to, the enzyme linked immunosorbent assay (ELISA) and the radioimmunoassay (RIA). Suitable antibody assay labels are known in the art and include enzyme labels, such as, glucose oxidase, alkaline phophatase, and horseradish peroxidase; radioisotopes, such as iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In) technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rb, and $^{97}$Ru; luminescent labels, such as luminol; and fluorescent labels, such as fluorescein and rhodamine, and biotin.

Certain embodiments of the invention are directed to the detection and diagnosis of a disease or disorder associated with aberrant expression of B lymphocyte stimulator or B lymphocyte stimulator receptor in an animal, preferably a mammal and most preferably a human. In one embodiment, diagnosis comprises: (a) administering (for example, parenterally, subcutaneously, or intraperitoneally) to a subject an effective amount of a labeled B lymphocyte stimulator binding polypeptide (including molecules comprising, or alternatively consisting of, B lymphocyte stimulator binding polypeptide fragments or variants thereof) that specifically binds to B lymphocyte stimulator; (b) waiting for a time interval following the administering for permitting the labeled B lymphocyte stimulator binding polypeptide to preferentially concentrate at sites in the subject where B lymphocyte stimulator is expressed (and for unbound labeled molecule to be cleared to background level); (c) determining background level; and (d) detecting the labeled B lymphocyte stimulator binding polypeptide in the subject, such that detection of labeled B lymphocyte stimulator binding polypeptide or fragment thereof above the background level and above or below the level observed in a person without the disease or disorder indicates that the subject has a particular disease or disorder associated with aberrant expression of B lymphocyte stimulator or B lymphocyte stimulator receptor. Background level can be determined by various methods, including comparing the amount of labeled molecule detected to a standard value previously determined for a particular system.

It will be understood by those skilled in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled B lymphocyte stimulator binding polypeptide will then preferentially accumulate at the location of cells which contain the specific protein. In vivo tumor imaging is described in Burchiel et al., "Immunopharmacokinetics of Radiolabeled Antibodies and Their Fragments," Chapter 13 in *Tumor Imaging: The Radiochemical Detection of Cancer*, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment for monitoring of the disease or disorder, the method is carried out by repeating the method for diagnosing the disease or disorder, for example, one month after initial diagnosis, six months after initial diagnosis, one year after initial diagnosis, etc. and comparing the results of the successive tests.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (see, e.g., Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Immunophenotyping Using B lymphocyte stimulator Binding Polypeptides

The B lymphocyte stimulator binding polypeptides (including molecules comprising, or alternatively consisting of, B lymphocyte stimulator binding polypeptide fragments or variants thereof) may be utilized for immunophenotyping of cell lines and biological samples by their B lymphocyte stimulator expression or B lymphocyte stimulator receptor expression. Various techniques can be employed utilizing B lymphocyte stimulator binding polypeptides, fragments, or variants to screen for cellular populations (i.e., immune cells, particularly monocytic cells or B-cells) expressing B lymphocyte stimulator or B lymphocyte stimulator receptor. Such techniques include magnetic separation using B lymphocyte stimulator binding polypeptide-coated magnetic beads, "panning" with B lymphocyte stimulator binding polypeptide attached to a solid matrix (i.e., plate), and flow cytometry (see, e.g., U.S. Pat. No. 5,985,660; and Morrison et al., *Cell*, 96:737-49 (1999)).

These techniques allow for the screening of particular populations of cells, such as might be found with hematological malignancies (i.e., minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

In one embodiment, B lymphocyte stimulator binding polypeptides (including molecules comprising, or alternatively consisting of, B lymphocyte stimulator binding polypeptide fragments or variants thereof) are used to identify cells of monocytic or B cell origin.

Therapeutic Uses of B lymphocyte stimulator Binding Polypeptides

The present invention is further directed to B lymphocyte stimulator binding polypeptide-based therapies which involve administering B lymphocyte stimulator binding polypeptides (including molecules comprising, or alternatively consisting of, B lymphocyte stimulator binding polypeptide fragments or variants thereof) to an animal, preferably a mammal, and most preferably a human, patient for treating one or more of the disclosed diseases, disorders, or conditions. Therapeutic compounds of the invention include, but are not limited to, B lymphocyte stimulator binding polypeptides and nucleic acids encoding B lymphocyte stimulator binding polypeptides and antibodies that bind B lymphocyte stimulator binding polypeptides as described herein. The B lymphocyte stimulator binding polypeptides can be used to treat, ameliorate or prevent diseases, disorders or conditions associated with aberrant expression and/or activity of B lymphocyte stimulator or B lymphocyte stimulator receptor, including, but not limited to, any one or more of the diseases, disorders, or conditions described herein. The treatment and/or prevention of diseases, disorders, or conditions associated with aberrant B lymphocyte stimulator expression and/or activity or aberrant B lymphocyte stimulator receptor expression and/or activity includes, but is not limited to, alleviating symptoms associated with those diseases, disorders or conditions. B lymphocyte stimulator binding polypeptides may be provided in pharmaceutically acceptable compositions as known in the art or as described herein.

B lymphocyte stimulator binding polypeptides of the present invention (including molecules comprising, or alternatively consisting of, B lymphocyte stimulator binding polypeptide fragments or variants thereof) that function as agonists or antagonists of B lymphocyte stimulator, preferably of B lymphocyte stimulator-induced signal transduction, can be administered to an animal to treat, prevent or ameliorate a disease or disorder associated with aberrant B lymphocyte stimulator expression, lack of B lymphocyte stimulator function, aberrant B lymphocyte stimulator receptor expression, or lack of B lymphocyte stimulator receptor function. For example, B lymphocyte stimulator binding polypeptides which disrupt the interaction between B lymphocyte stimulator and one or more of its receptors may be administered to an animal to treat, prevent or ameliorate a disease or disorder associated with aberrant B lymphocyte stimulator expression, excessive B lymphocyte stimulator function, aberrant B lymphocyte stimulator receptor expression, or excessive B lymphocyte stimulator receptor function. B lymphocyte stimulator binding polypeptides which do not prevent B lymphocyte stimulator from binding its receptor but inhibit or downregulate B lymphocyte stimulator-induced signal transduction can be administered to an animal to treat, prevent or ameliorate a disease or disorder associated with aberrant B lymphocyte stimulator expression, excessive B lymphocyte stimulator function, aberrant B lymphocyte stimulator receptor expression, or excessive B lymphocyte stimulator receptor function. In particular, B lymphocyte stimulator binding polypeptides of the present invention which prevent B lymphocyte stimulator-induced signal transduction by specifically recognizing the unbound B lymphocyte stimulator, receptor-bound B lymphocyte stimulator, or both unbound and receptor-bound B lymphocyte stimulator can be administered to an animal to treat, prevent or ameliorate a disease or disorder associated with aberrant B lymphocyte stimulator expression, excessive B lymphocyte stimulator function, aberrant B lymphocyte stimulator receptor expression, or excessive B lymphocyte stimulator receptor function.

The ability of a B lymphocyte stimulator binding polypeptide to inhibit or downregulate B lymphocyte stimulator-induced signal transduction may be determined by techniques described herein or otherwise known in the art. For example, B lymphocyte stimulator-induced receptor activation and the activation of signaling molecules can be determined by detecting the phosphorylation (e.g., tyrosine or serine/threonine) of the receptor or a signaling molecule by immunoprecipitation followed by western blot analysis (for example, as described herein).

In a specific embodiment, a B lymphocyte stimulator binding polypeptide of the present invention (including molecules comprising, or alternatively consisting of, B lymphocyte stimulator binding polypeptide fragments or variants thereof) that inhibits or reduces B lymphocyte stimulator activity by at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to B lymphocyte stimulator activity in the absence of the B lymphocyte stimulator binding polypeptide, is administered to an animal to treat, prevent or ameliorate a disease or disorder associated with aberrant B lymphocyte stimulator expression, excessive B lymphocyte stimulator function, aberrant B lymphocyte stimulator receptor expression, or excessive B lymphocyte stimulator receptor function. In another embodiment, a combination of B lymphocyte stimulator binding polypeptides, a combination of B lymphocyte stimulator binding polypeptide fragments, a combination of B lymphocyte stimulator binding polypeptide variants, or a combination of B lymphocyte stimulator binding polypeptides, B lymphocyte stimulator binding polypeptide fragments, and/or variants that inhibit or reduce B lymphocyte stimulator activity by at least 95%, at least 90%, at least 85%, at least 80%, at least 75%, at least 70%, at least 65%, at least 60%, at least 55%, at least 50%, at least 45%, at least 40%, at least 45%, at least 35%, at least 30%, at least 25%, at least 20%, or at least 10% relative to B lymphocyte stimulator activity in absence of said B lymphocyte stimulator binding polypeptides, B lymphocyte stimulator binding polypeptide fragments, and/or B lymphocyte stimulator binding polypeptide variants are administered to an animal to treat, prevent or ameliorate a disease or disorder associated with aberrant B lymphocyte stimulator expression, excessive B lymphocyte stimulator function, aberrant B lymphocyte stimulator receptor expression, or excessive B lymphocyte stimulator receptor function.

Further, B lymphocyte stimulator binding polypeptides of the present invention (including molecules comprising, or alternatively consisting of, B lymphocyte stimulator binding polypeptide fragments or variants thereof) which activate B lymphocyte stimulator-induced signal transduction can be administered to an animal to treat, prevent or ameliorate a disease or disorder associated with aberrant B lymphocyte stimulator expression, lack of B lymphocyte stimulator function, aberrant B lymphocyte stimulator receptor expression, or lack of B lymphocyte stimulator receptor function. These B lymphocyte stimulator binding polypeptides may potentiate or activate either all or a subset of the biological activities of B lymphocyte stimulator-mediated receptor activation, for example, by inducing multimerization of B lymphocyte stimulator and/or multimerization of the receptor. The B lymphocyte stimulator binding polypeptides may be administered with or without being pre-complexed with B lymphocyte stimulator. In a specific embodiment, a B lymphocyte stimulator binding polypeptide of the present invention that increases B lymphocyte stimulator activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% or more relative to B lymphocyte stimulator activity in absence of the B lymphocyte stimulator binding polypeptide is administered to an animal to treat, prevent or ameliorate a disease or disorder associated with aberrant B lymphocyte stimulator expression, lack of B lymphocyte stimulator function, aberrant B lymphocyte stimulator receptor expression, or lack of B lymphocyte stimulator receptor function. In another embodiment, a combination of B lymphocyte stimulator binding polypeptides, a combination of B lymphocyte stimulator binding polypeptide fragments, a combination of B lymphocyte stimulator binding polypeptide variants, or a combination of B lymphocyte stimulator binding polypeptides, B lymphocyte stimulator binding polypeptide fragments and/or B lymphocyte stimulator binding polypeptide variants that increase B lymphocyte stimulator activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% or more relative to B lymphocyte stimulator activity in absence of the said B lymphocyte stimulator binding polypeptides or B lymphocyte stimulator binding polypeptide fragments and/or B lymphocyte stimulator binding polypeptide variants is administered to an animal to treat, prevent or ameliorate a disease or disorder associated with aberrant B lymphocyte stimulator expression, lack of B lymphocyte stimulator function, aberrant B lymphocyte stimulator receptor expression, or lack of B lymphocyte stimulator receptor function.

In a specific embodiment, the present invention provides a method of treating, preventing or ameliorating a disease or disorder associated with aberrant B lymphocyte stimulator or B lymphocyte stimulator receptor expression or activity, comprising administering to an animal in which such treatment, prevention or amelioration is desired, a B lymphocyte stimulator binding polypeptide in an amount effective to treat, prevent or ameliorate the disease or disorder. Diseases and disorders which may be treated, prevented or ameliorated by this method include, but are not limited to, immune system diseases and disorders (e.g., autoimmune diseases and disorders, immunodeficiencies, lupus, rheumatoid arthritis, multiple sclerosis, hypogammaglobulinemia and hypergammaglobulinemia), graft vs. host disease, proliferative diseases and disorders (e.g., cancer) and infectious diseases and disorders.

In a specific embodiment, the present invention provides a method of treating, preventing or ameliorating a disease or disorder of cells of hematopoietic origin, comprising administering to an animal in which such treatment, prevention, or amelioration is desired, a B lymphocyte stimulator binding polypeptide in an amount effective to treat, prevent or ameliorate the disease or disorder. Cells of hematopoietic origin include, but are not limited to, lymphocytes (e.g., B cells and T cells), monocytes, macrophages, dendritic cells, polymorphonuclear leukocytes (e.g., basophils, eosinophils, neutrophils), mast cells, platelets, erythrocytes and progenitor cells of these lineages.

One or more B lymphocyte stimulator binding polypeptides of the present invention (including molecules comprising, or alternatively consisting of, B lymphocyte stimulator binding polypeptide fragments or variants thereof) that specifically bind to B lymphocyte stimulator may be used locally or systemically in the body as a therapeutic. The B lymphocyte stimulator binding polypeptides (including molecules comprising, or alternatively consisting of, B lymphocyte stimulator binding polypeptide fragments or variants thereof) may also be advantageously utilized in combination with monoclonal or chimeric antibodies, lymphokines and/or hematopoietic growth factors (such as, e.g., IL-2, IL-3 and IL-7), for example, which serve to increase the number or activity of effector cells which interact with the B lymphocyte stimulator binding polypeptides.

The B lymphocyte stimulator binding polypeptides (including molecules comprising, or alternatively consisting of, B lymphocyte stimulator binding polypeptide fragments or variants thereof) may be administered alone or in combination with other types of treatments (e.g., radiation therapy, chemotherapy, hormonal therapy, immunotherapy, anti-tumor agents, anti-angiogenesis and anti-inflammatory agents).

It is preferred to use high affinity and/or potent in vivo inhibiting and/or neutralizing B lymphocyte stimulator binding polypeptides (including molecules comprising, or alternatively consisting of, B lymphocyte stimulator binding polypeptide fragments or variants thereof) that specifically bind to B lymphocyte stimulator, or polynucleotides encoding B lymphocyte stimulator binding polypeptides that specifically bind to B lymphocyte stimulator, for both immunoassays directed to and therapy of disorders related to B lymphocyte stimulator polynucleotides or polypeptides, including fragments thereof. Such B lymphocyte stimulator binding polypeptides will preferably have an affinity for B lymphocyte stimulator and/or B lymphocyte stimulator fragments. Preferred binding affinities include those with a dissociation constant or $K_D$ of less than or equal to $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, or $10^{-5}$ M. More preferably, B lymphocyte stimulator binding polypeptides bind B lymphocyte stimulator target proteins with a dissociation constant or $K_D$ less than or equal to $5 \times 10^{-6}$ M, $10^{-6}$ M, $5 \times 10^{-7}$ M, $10^{-7}$ M, $5 \times 10^{-8}$ M, or $10^{-8}$ M. Even more preferably, B lymphocyte stimulator binding polypeptides bind B lymphocyte stimulator target proteins with a dissociation constant or $K_D$ less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, $10^{-15}$ M.

In a preferred embodiment, B lymphocyte stimulator binding polypeptides neutralize B lymphocyte stimulator activity. In another preferred embodiment, B lymphocyte stimulator binding polypeptides inhibit B cell proliferation.

In a preferred embodiment, B lymphocyte stimulator binding polypeptides (including molecules comprising, or alternatively consisting of, B lymphocyte stimulator binding polypeptide fragments or variants thereof) inhibit or reduce binding of the soluble form of B lymphocyte stimulator to a B lymphocyte stimulator receptor. In another preferred embodiment B lymphocyte stimulator binding polypeptides inhibit or reduce B cell proliferation induced by the soluble form of B lymphocyte stimulator. In another preferred embodiment B lymphocyte stimulator binding polypeptides inhibit or reduce immunoglobulin production induced by the soluble form of B lymphocyte stimulator.

In a preferred embodiment, B lymphocyte stimulator binding polypeptides (including molecules comprising, or alternatively consisting of, B lymphocyte stimulator binding polypeptide fragments or variants thereof) inhibit or reduce binding of membrane-bound B lymphocyte stimulator to a B lymphocyte stimulator receptor. In another preferred embodiment, B lymphocyte stimulator binding polypeptides inhibit or reduce B cell proliferation induced by the membrane-bound form of B lymphocyte stimulator. In another preferred embodiment, B lymphocyte stimulator binding polypeptides inhibit or reduce immunoglobulin production induced by the membrane bound form of B lymphocyte stimulator.

In a preferred embodiment, B lymphocyte stimulator binding polypeptides (including molecules comprising, or alternatively consisting of, B lymphocyte stimulator binding polypeptide fragments or variants thereof) inhibit or reduce binding of both the soluble and membrane-bound forms of B lymphocyte stimulator to a B lymphocyte stimulator receptor. In another preferred embodiment, B lymphocyte stimulator binding polypeptides inhibit or reduce B cell proliferation induced by either or both forms of B lymphocyte stimulator. In another preferred embodiment, B lymphocyte stimulator binding polypeptides inhibit or reduce immunoglobulin production induced by either or both forms of B lymphocyte stimulator.

In one embodiment, the invention provides a method of delivering radiolabelled B lymphocyte stimulator binding polypeptide and/or B lymphocyte stimulator binding polypeptide conjugates to targeted cells, such as, for example, monocytic cells expressing the membrane-bound form of B lymphocyte stimulator, or B cells expressing a B lymphocyte stimulator receptor.

In one embodiment, the invention provides methods and compositions for inhibiting or reducing immunoglobulin production (e.g., IgM, IgG, and/or IgA production), comprising, or alternatively consisting of, contacting an effective amount of B lymphocyte stimulator binding polypeptide with B lymphocyte stimulator, wherein the effective amount of B lymphocyte stimulator binding polypeptide inhibits or reduces B lymphocyte stimulator mediated immunoglobulin production. In another embodiment, the invention provides methods and compositions for inhibiting or reducing immunoglobulin production (e.g., IgM, IgG, and/or IgA production), comprising, or alternatively consisting of, administering to an animal in which such inhibition or reduction is desired, a B lymphocyte stimulator binding polypeptide in an amount effective to inhibit or reduce immunoglobulin production.

In another embodiment, the invention provides methods and compositions for stimulating immunoglobulin production (e.g., IgM, IgG, and/or IgA production), comprising, or alternatively consisting of, contacting an effective amount of B lymphocyte stimulator binding polypeptide with B lymphocyte stimulator, wherein the effective amount of the B lymphocyte stimulator binding polypeptide stimulates B lymphocyte stimulator mediated immunoglobulin production. In another embodiment, the invention provides methods and compositions for stimulating immunoglobulin production (e.g., IgM, IgG, and/or IgA production) comprising, or alternatively consisting of, administering to an animal in which such stimulation is desired, a B lymphocyte stimulator binding polypeptide in an amount effective to stimulate immunoglobulin production. Determination of immunoglobulin levels are most often performed by comparing the level of immunoglobulin in a sample to a standard containing a known amount of immunoglobulin using ELISA assays. Determination of immunoglobulin levels in a given sample, can readily be determined using ELISA or other method known in the art.

Receptors belonging to the TNF receptor (TNFR) super family (e.g., TACI and BCMA) can be classified into two types based on the presence or absence of a conserved cytoplasmic domain responsible for apoptosis called a "death domain." TNF receptors without death domains, such as TNF-R2 HVEM/ATAR, RANK, CD27, CD30, CD40, and OX40 interact with TNF receptor associated factors (TRAF 1-6) and mediate anti-apoptotic survival and or proliferative responses via activation of the transcription factor NF-kappaB (reviewed in Wajant et al., *Cytokine and Growth Factor Reviews*, 10(1):15-26, 1999). TACI and BCMA do not contain death domains.

Investigation of B lymphocyte stimulator induced signaling in human tonsillar B cells co-stimulated with *Staph. aureus* Cowan consistently revealed that mRNA for ERK-1 and PLK were upregulated by B lymphocyte stimulator+SAC treatment (see Example 12). Polo like kinases (PLK) belong to a sub family of serine/threonine kinases related to *Saccharomyces cerevisiae* cell cycle protein CDC5 (29). The expression of PLK is induced during G2 and S phase of the cell cycle. PLK is reported to play a role in cell proliferation (Lee et al., *Proc. Natl. Acad. Sci.*, 95:9301-9306, 1998). The role or extracellular-signal related kinases (ERK1/2) in cell survival and proliferative effects of growth factors and other agonists has been extensively studied. The induced expression of PLK and ERK-1 is consistent with the survival and proliferative effects of B lymphocyte stimulator on B cells.

Additionally, in some samples of human tonsillar B cells stimulated with B lymphocyte stimulator and SAC, mRNA for CD25 (IL-2Ralpha) was upregulated. Nuclear extracts from Human tonsillar B cells treated with B lymphocyte stimulator and from IM-9 cells treated with B lymphocyte stimulator were able to shift probes from the CD25 promoter region containing sites for NF-kappaB, SRF, ELF-1 and HMGI/Y in an electromobility shift assay. ELF-1 for example, is a transcription factor that is part of the ETS family of proteins and whose expression appears to be restricted to T and B cells. Binding sites for ELF-1 have been described in the promoters of a number of proteins that are important in the regulation of the immune response.

Thus B lymphocyte stimulator induced signaling has been shown to be consistent with the activation of cellular activation and cellular proliferation pathways as well as with cellular signaling pathways that regulate B cell lifespan. Further, B lymphocyte stimulator treatment of B cells induces cellular proliferation immunoglobulin secretion, a characteristic of activated B cells (Moore et al., *Science*, 285:260-263, 1999). B lymphocyte stimulator binding polypeptides complexed with B lymphocyte stimulator may inhibit, stimulate, or not significantly alter these B lymphocyte stimulator mediated activities.

In one embodiment, the invention provides methods and compositions for inhibiting or reducing B cell proliferation, comprising, or alternatively consisting of, contacting an effective amount of B lymphocyte stimulator binding polypeptide with B lymphocyte stimulator, wherein the effective amount of B lymphocyte stimulator binding polypeptide inhibits or reduces B lymphocyte stimulator mediated B cell proliferation. In another embodiment, the invention provides methods and compositions for inhibiting or reducing B cell proliferation comprising, or alternatively consisting of, administering to an animal in which such inhibition or reduction is desired, a B lymphocyte stimulator binding polypeptide in an amount effective to inhibit or reduce B cell proliferation.

In one embodiment, the invention provides methods and compositions for stimulating B cell proliferation, comprising, or alternatively consisting of, contacting an effective amount of B lymphocyte stimulator binding polypeptide with B lymphocyte stimulator, wherein the effective amount of B lymphocyte stimulator binding polypeptide stimulates B lymphocyte stimulator mediated B cell proliferation.

In one embodiment, the invention provides methods and compositions for stimulating B cell proliferation, comprising, or alternatively consisting of, administering to an animal in which such stimulation is desired, a B lymphocyte stimulator binding polypeptide in an amount effective to stimulate B cell proliferation.

B cell proliferation is most commonly assayed in the art by measuring tritiated thymidine incorporation (see Examples 7 and 8). This and other assays are commonly known in the art and may be routinely adapted for the use of determining the effect of B lymphocyte stimulator binding polypeptides on B cell proliferation.

In one embodiment, the invention provides methods and compositions for inhibiting or reducing activation of B cells, comprising, or alternatively consisting of, contacting an effective amount of B lymphocyte stimulator binding polypeptide with B lymphocyte stimulator, wherein the effective amount of B lymphocyte stimulator binding polypeptide inhibits or reduces B lymphocyte stimulator mediated B cell activation.

In one embodiment, the invention provides methods and compositions for inhibiting or reducing activation of B cells, comprising, or alternatively consisting of, administering to an animal in which such inhibition or reduction is desired, a B lymphocyte stimulator binding polypeptide in an amount effective to inhibit or reduce B cell activation.

In one embodiment, the invention provides methods and compositions for increasing activation of B cells, comprising, or alternatively consisting of, contacting an effective amount of B lymphocyte stimulator binding polypeptide with B lymphocyte stimulator, wherein the effective amount of B lymphocyte stimulator binding polypeptide increases B lymphocyte stimulator mediated activation of B cells.

In one embodiment, the invention provides methods and compositions for increasing activation of B cells, comprising, or alternatively consisting of, administering to an animal in which such increase is desired, a B lymphocyte stimulator binding polypeptide in an amount effective to increase B cell activation.

B cell activation can measured in a variety of ways, such as FACS analysis of activation markers expressed on B cells. B cells activation markers include, but are not limited to, CD26, CD 28, CD 30, CD 38, CD 39, CD 69, CD70 CD71, CD 77, CD 83, CD126, CDw130, and B220. Additionally, B cell activation may be measured by analysis of the activation of signaling molecules involved in B cell activation. By way of non-limiting example, such analysis may take the form of analyzing mRNA levels of signaling molecules by Northern analysis or real time PCR (Example 12). One can also measure, for example, the phosphorylation of signaling molecules using anti-phosphotyrosine antibodies in a Western blot. B cell activation may also be measured by measuring the calcium levels in B cells. These and other methods of determining B cell activation are commonly known in the art and may be routinely adapted for the use of determining the effect of B lymphocyte stimulator binding polypeptides on B cell activation.

In one embodiment, the invention provides methods and compositions for decreasing lifespan of B cells, comprising, or alternatively consisting of, contacting an effective amount of B lymphocyte stimulator binding polypeptide with B lymphocyte stimulator, wherein the effective amount of B lymphocyte stimulator binding polypeptide inhibits or reduces B lymphocyte stimulator regulated lifespan of B cells.

In one embodiment, the invention provides methods and compositions for decreasing lifespan of B cells, comprising, or alternatively consisting of, administering to an animal in which such decrease is desired, a B lymphocyte stimulator binding polypeptide in an amount effective to decrease B cell lifespan.

In one embodiment, the invention provides methods and compositions for increasing lifespan of B cells, comprising, or alternatively consisting of, contacting an effective amount of B lymphocyte stimulator binding polypeptide with B lymphocyte stimulator, wherein the effective amount of B lymphocyte stimulator binding polypeptide increases B lymphocyte stimulator regulated lifespan of B cells.

In one embodiment, the invention provides methods and compositions for increasing lifespan of B cells, comprising, or alternatively consisting of, administering to an animal in which such increase is desired, a B lymphocyte stimulator binding polypeptide in an amount effective to increase lifespan of B cells.

B cell life span in vivo may be measured by 5-bromo-2'-deoxyuridine (BrdU) labeling experiments which are well known to one skilled in the art. BrdU is a thymidine analogue that gets incorporated into the DNA of dividing cells. Cells containing BrdU in their DNA can be detected using, for example fluorescently labeled anti-BrdU antibody and flow cytometry. Briefly, an animal is injected with BrdU in an amount sufficient to label developing B cells. Then, a sample of B cells is withdrawn from the animal, for example, from peripheral blood, and analyzed for the percentage of cells that contain BrdU. Such an analysis performed at several time points can be used to calculate the half life of B cells. Alternatively, B cell survival may be measured in vitro. For example B cells may be cultured under conditions where proliferation does not occur, (for example the media should contain no reagents that crosslink the immunoglobulin receptor, such as anti-IgM antibodies) for a period of time (usually 2-4 days). At the end of this time, the percent of surviving cells is determined, using for instance, the vital dye Trypan Blue, or by staining cells with propidium iodide or any other agent designed to specifically stain apoptotic cells and analyzing the percentage of cells stained using flow cytometry. One could perform this experiment under several conditions, such as B cells treated with B lymphocyte stimulator, B cells treated with B lymphocyte stimulator/B lymphocyte stimulator binding polypeptide complexes, and untreated B cells in order to determine the effects of B lymphocyte stimulator and B lymphocyte stimulator binding polypeptides on B cells survival. These and other methods for determining B cell lifespan are commonly known in the art and could routinely be adapted to determining the effect of B lymphocyte stimulator binding polypeptides on B lymphocyte stimulator regulated B cell lifespan.

In one embodiment, the invention provides a method for the specific delivery of B lymphocyte stimulator binding polypeptides and B lymphocyte stimulator binding polypeptide conjugates to cells by administering molecules that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) in the targeted cell.

In another embodiment, the invention provides for a method of killing cells of hematopoietic origin, comprising, or alternatively consisting of, contacting B lymphocyte stimulator binding polypeptides with B lymphocyte stimulator to form a complex; and contacting the complex with cells of hematopoietic origin. In specific embodiments, the method of killing cells of hematopoietic origin, comprises, or alternatively consists of, administering to an animal in which such killing is desired, a B lymphocyte stimulator binding polypeptide in an amount effective to kill cells of hematopoietic origin. Cells of hematopoietic origin include, but are not limited to, lymphocytes (e.g., B cells and T cells), monocytes, macrophages, dendritic cells, polymorphonuclear leukocytes (e.g., basophils, eosinophils, neutrophils), mast cells, platelets, erythrocytes and progenitor cells of these lineages. Cells of hematopoietic origin include, but are not limited to, healthy and diseased cell as found present in an animal, preferably a mammal and most preferably a human, or as isolated from an animal, transformed cells, cell lines derived from the above listed cell types, and cell cultures derived from the above listed cell types. Cells of hematopoietic origin may be found or isolated in, for example, resting, activated or anergic states.

In another embodiment, the invention provides a method for the specific destruction (i.e., killing) of cells (e.g., the destruction of tumor cells) by administering B lymphocyte stimulator binding polypeptides or B lymphocyte stimulator binding polypeptide conjugates (e.g., radiolabeled B lymphocyte stimulator binding polypetides and/or B lymphocyte stimulator binding polypeptides conjugated with radioisotopes, toxins, or cytotoxic prodrugs). In a specific embodiment, the invention provides a method for the specific destruction of cells of monocytic lineage (e.g., monocytic cell related leukemias or lymphomas, such as, for example acute myelogenous leukemia) by administering B lymphocyte stimulator binding polypeptides or B lymphocyte stimulator binding polypeptide conjugates (e.g., B lymphocyte stimulator binding polypeptides conjugated with radioisotopes, toxins, or cytotoxic prodrugs) that specifically bind the membrane-bound form of B lymphocyte stimulator. In another specific embodiment, the invention provides a method for the specific destruction of cells of B cell lineage (e.g., B cell related leukemias or lymphomas (e.g., chronic lymphocytic leukemia, multiple myeloma, non-Hodgkin's lymphoma, and Hodgkin's disease) by administering B lymphocyte stimulator binding polypeptides or B lymphocyte stimulator binding polypeptide conjugates (e.g., B lymphocyte stimulator binding polypeptides conjugated with radioisotopes, toxins, or cytotoxic prodrugs) that bind soluble B lymphocyte stimulator, but do not inhibit B lymphocyte stimulator binding to a B lymphocyte stimulator receptor on B cells.

In another embodiment of the invention, therapeutic or pharmaceutical compositions are administered to an animal to treat, prevent or ameliorate diseases and disorders of the immune system. In a specific embodiment, the invention provides a method of treating, preventing, or ameliorating an immune system disease or disorder, comprising, or alternatively consisting of, administering to an animal in which such treatment, prevention, or amelioration is desired, a B lymphocyte stimulator binding polypeptide in an amount effective to treat, prevent, or ameliorate the immune system disease or disorder. Diseases and disorders of the immune system include, but are not limited to, autoimmune diseases and disorders (e.g., arthritis, graft rejection, Hashimoto's thyroiditis, insulin-dependent diabetes, lupus, rheumatoid arthritisidiopathic thrombocytopenic purpura, systemic lupus erythramatosus and multiple sclerosis, and other autoimmune diseases or disorders named or described herein), hypogammaglobulinemia, hypergammaglobulinemia, elective IgA deficiency, ataxia-telangiectasia, immunodeficiencies (e.g., common variable immunodeficiency (CVID), X-linked agammaglobulinemia, severe combined immunodeficiency (SCID), and Wiskott-Aldrich syndrome), graft vs. host disease, idiopathic hyper-eosinophilic syndrome, monocytic leukemoid reaction, monocytic leukocytosis, monocytic leukopenia, monocytopenia, monocytosis, graft or transplant rejection, as well as infectious diseases (e.g., AIDS and hepatitis).

As discussed herein, B lymphocyte stimulator binding polypeptides and B lymphocyte stimulator binding polypeptide compositions, may be used to treat, prevent, ameliorate, diagnose or prognose various immune system-related disorders and/or conditions associated with these disorders, in mammals, preferably humans. Many autoimmune disorders result from inappropriate recognition of self as foreign material by immune cells. This inappropriate recognition results in an immune response leading to the destruction of the host tissue. Therefore, the administration of B lymphocyte stimulator binding polypeptides and B lymphocyte stimulator binding polypeptide compositions that can inhibit an immune response, particularly the proliferation of B cells and/or the production of immunoglobulins, may be an effective therapy in treating and/or preventing autoimmune disorders. Thus, in preferred embodiments, B lymphocyte stimulator binding polypeptides and B lymphocyte stimulator binding polypeptide compositions are used to treat, prevent, ameliorate, diagnose or prognose an autoimmune disorder, or condition(s) associated with such disorder.

Autoimmune disorders and conditions associated with these disorders that may be treated, prevented, ameliorated, diagnosed and/or prognosed according to the invention with the therapeutic and pharmaceutical compositions described herein include, but are not limited to, autoimmune hemolytic anemia, autoimmune neonatal thrombocytopenia, idiopathic thrombocytopenia purpura, autoimmune neutropenia, autoimmunocytopenia, hemolytic anemia, antiphospholipid syndrome, dermatitis, gluten-sensitive enteropathy, allergic encephalomyelitis, myocarditis, relapsing polychondritis, rheumatic heart disease, glomerulonephritis (e.g., IgA nephropathy), multiple sclerosis, neuritis, uveitis ophthalmia, polyendocrinopathies, purpura (e.g., Henloch-Scoenlein purpura), Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, insulin dependent diabetes mellitus, and autoimmune inflammatory eye disease.

Additional autoimmune disorders and conditions associated with these disorders that may be treated, prevented, ameliorated, diagnosed and/or prognosed according to the present invention with the therapeutic and pharmaceutical compositions described herein include, but are not limited to, autoimmune thyroiditis, hypothyroidism (i.e., Hashimoto's thyroiditis) (often characterized, e.g., by cell-mediated and humoral thyroid cytotoxicity), systemic lupus erhythematosus (often characterized, e.g., by circulating and locally generated immune complexes), discoid lupus, Goodpasture's syndrome (often characterized, e.g., by anti-basement membrane antibodies), Pemphigus (often characterized, e.g., by epidermal acantholytic antibodies), Receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized RBCs), autoimmune thrombocytopenic purpura (often characterized, e.g., by phagocytosis of antibody-sensitized platelets.H Additional autoimmune disorders and conditions associated with these disorders that may be treated, prevented, ameliorated, diagnosed and/or prognosed according to the present invention with the therapeutic and pharmaceutical compositions described herein include, but are not limited to, rheumatoid arthritis (often characterized, e.g., by immune complexes in joints), schleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis/dermatomyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes) such as primary glomerulonephritis and IgA nephropathy, bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies), chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), inflammatory myopathies, and many other inflammatory, granulamatous, degenerative, and atrophic disorders.

In a preferred embodiment, therapeutic and pharmaceutical compositions are used to treat, prevent, ameliorate, diagnose or prognose, a member of the group: autoimmune hemolytic anemia, as primary glomerulonephritis, IgA glomerulonephritis, Goodpasture's syndrome, idiopathic thrombocytopenia, Multiple Sclerosis, Myasthenia Gravis, Pemphigus, polymyositis/dermatomyositis, relapsing polychondritis, rheumatoid arthritis, Sjogren's syndrome, systemic lupus erhythematosus, Uveitis, vasculitis, and primary biliary cirrhosis.

In another specific preferred embodiment, therapeutic and pharmaceutical compositions are used to treat, prevent, amelioate, diagnose or prognose, rheumatoid arthritis and/or medical conditions associated therewith.

In a specific preferred embodiment, therapeutic and pharmaceutical compositions are used to treat, prevent, amelioate, diagnose or prognose, lupus and/or medical conditions associated therewith. Lupus-associated conditions that may be treated, prevented, ameliorated, prognosed and/or diagnosed with the B lymphocyte stimulator binding polypeptides and B lymphocyte stimulator binding polypeptide compositions include, but are not limited to, hematologic disorders (e.g., hemolytic anemia, leukopenia, lymphopenia, and thrombocytopenia), immunologic disorders (e.g., anti-DNA antibodies, and anti-Sm antibodies), rashes, photosensitivity, oral ulcers, arthritis, fever, fatigue, weight loss, serositis (e.g., pleuritus (pleurisy)), renal disorders (e.g., nephritis), neurological disorders (e.g., seizures, peripheral neuropathy, CNS related disorders), gastroinstestinal disorders, Raynaud phenomenon, and pericarditis. In a preferred embodiment, therapeutic and pharmaceutical compositions are used to treat, prevent, ameliorate, diagnose, or prognose, renal disorders associated with systemic lupus erythematosus. In a most preferred embodiment, therapeutic and pharmaceutical compositions are used to treat, prevent, ameliorate, diagnose, or prognose, nephritis associated with systemic lupus erythematosus. In another most preferred embodiment, therapeutic or pharmaceutical compositions are administered to an animal to treat, prevent or ameliorate lupus or glomerular nephritis.

In another embodiment, therapeutic or pharmaceutical compositions are administered to an animal to treat, prevent or ameliorate an IgE-mediated allergic reaction or histamine-mediated allergic reaction. Examples of allergic reactions include, but are not limited to, asthma, rhinitis, eczema, chronic urticaria, and atopic dermatitis. In another embodiment, therapeutic or pharmaceutical compositions are administered to an animal to treat, prevent, or ameliorate anaphylaxis, hypersensitivity to an antigenic molecule, or blood group incompatibility. In another embodiment, therapeutic or pharmaceutical compositions are administered to an animal to treat, prevent or ameliorate or modulate inflammation or an inflammatory disorder. Examples of chronic and acute inflammatory disorders that may be treated prevented or ameliorated with the therapeutic and pharmaceutical compositions include, but are not limited to, chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, Crohn's disease, inflammatory bowel disease, chronic and acute inflammatory pulmonary diseases, bacterial infection, psoriasis, septicemia, cerebral malaria, arthritis, gastroenteritis, and glomerular nephritis.

In another embodiment, therapeutic or pharmaceutical compositions are administered to an animal to treat, prevent or ameliorate ischemia and arteriosclerosis. Examples of such disorders include, but are not limited to, reperfusion damage (e.g., in the heart and/or brain) and cardiac hypertrophy.

Therapeutic or pharmaceutical compositions may also be administered to modulate blood clotting and to treat or prevent blood clotting disorders, such as, for example, antibody-mediated thrombosis (i.e., antiphospholipid antibody syndrome (APS)). For example, therapeutic or pharmaceutical compositions as described herein may be used to inhibit the proliferation and differentiation of cells involved in producing anticardiolipin antibodies. These compositions can be used to treat, prevent, ameliorate, diagnose, and/or prognose thrombotic related events including, but not limited to, stroke (and recurrent stroke), heart attack, deep vein thrombosis, pulmonary embolism, myocardial infarction, coronary artery disease (e.g., antibody-mediated coronary artery disease), thrombosis, graft reocclusion following cardiovascular surgery (e.g., coronary arterial bypass grafts, recurrent fetal loss, and recurrent cardiovascular thromboembolic events.

Therapeutic or pharmaceutical compositions containing B lymphocyte stimulator binding polypeptides may also be administered to treat, prevent, or ameliorate organ rejection or graft-versus-host disease (GVHD) and/or conditions associated therewith. Organ rejection occurs by host immune cell destruction of the transplanted tissue through an immune response. Similarly, an immune response is also involved in GVHD, but, in this case, the foreign transplanted immune cells destroy the host tissues. Administration of B lymphocyte stimulator binding polypeptides that inhibit an immune response may be an effective therapy in preventing organ rejection or GVHD. In specific embodiments the present invention provides a method of inhibiting or reducing graft rejection, comprising administering to an animal in which such inhibition or reduction is desired, a B lymphocyte stimulator binding polypeptide in an amount effective to inhibit or reduce graft rejection.

In another embodiment, therapeutic or pharmaceutical compositions are administered to an animal to treat, prevent or ameliorate a disease or disorder diseases associated with increased apoptosis including, but not limited to, AIDS, neurodegenerative disorders (such as Alzheimer's disease, Parkinson's disease, Amyotrophic lateral sclerosis, Retinitis pigmentosa, Cerebellar degeneration), myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia. In another embodiment, therapeutic or pharmaceutical compositions are administered to an animal to treat, prevent or ameliorate bone marrow failure, for example, aplastic anemia and myelodysplastic syndrome.

In other embodiment, therapeutic or pharmaceutical compositions as described herein are used to treat or prevent a proliferative disorder (e.g., cancer). In preferred embodiments, therapeutic or pharmaceutical compositions as described herein are used to treat or prevent proliferative disorders of monocytic cells. In other preferred embodiments, therapeutic or pharmaceutical compositions as described herein are used to treat or prevent a proliferative disorders of B cells (e.g., leukemia).

In another embodiment, therapeutic or pharmaceutical compositions as described herein are administered to an animal to treat, prevent or ameliorate growth, progression, and/or metastases of malignancies and proliferative diseases and disorders associated with increased cell survival, or the inhibition of apoptosis. In a specific embodiment, the present invention provides a method of treating a proliferative disease or disorder, comprising administering to an animal in which such treatment is desired, a B lymphocyte stimulator binding polypeptide in an amount effective to treat the proliferative disease or disorder. For a review of such disorders, see Fishman et al., Medicine, 2d Ed. (J. B. Lippincott Co., Philadelphia 1985). Examples of such disorders, include, but are not limited to, leukemia (e.g., acute leukemia such as acute lymphocytic leukemia and acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia), Polycythemia vera, lymphomas (e.g. Hodgkin's lymphoma, non-Hodgkin's lymphoma) Hodgkin's disease, non-Hodgkin's disease, multiple myeloma, Waldenstrom's macroglobulinemia, neoplasms, tumors (e.g., fibrosarcoma, myxosarcoma, liposarcoma, chondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, nasopharyngeal carcinoma, bronchogenic carcinoma, esophageal carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma) heavy chain disease, metastases, or any disease or disorder characterized by uncontrolled cell growth. This method of treating a proliferative diseases or disorders can also be used to treat premalignant conditions (e.g., benign tumors, hyperproliferative disorders, and benign proliferative disorders—see below) as well as proliferative disorders of B cells, monocytes, macrophages, and T cells.

In another embodiment of the present invention, therapeutic or pharmaceutical compositions as described herein can also be administered to treat a subset of proliferative disorders, namely, premalignant conditions (e.g., benign tumors, hyperproliferative disorders, benign proliferative disorders) and to prevent progression to a neoplastic or malignant state, including but not limited to those disorders listed above. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed. (W.B. Saunders Co., Philadelphia 1976), pp. 68-79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a therapeutic or pharmaceutical composition as described herein. Characteristics of a transformed phenotype include, but are nor limited to, morphology changes, looser substratum attachment, loss of contact inhibition, loss of anchorage dependence, protease release, increased sugar transport, decreased serum requirement, expression of fetal antigens, and disappearance of the 250,000 dalton cell surface protein.

In other embodiments, a patient which exhibits one or more of the following predisposing factors for malignancy is treated by administration of an effective amount of a therapeutic or pharmaceutical composition as described herein: a chromosomal translocation associated with a malignancy (e.g., the Philadelphia chromosome for chronic myelogenous leukemia, t(14; 18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, supra, pp. 112-113), etc.)

In a specific embodiment, therapeutic or pharmaceutical compositions as described herein are used to treat or prevent a disorder characterized by hypergammagloulinemia (e.g., AIDS, autoimmune diseases, and some immunodeficiencies).

In a specific embodiment, therapeutic or pharmaceutical compositions as described herein are used to treat or prevent a disorder characterized by deficient serum immunoglobulin production, recurrent infections, and/or immune system dysfunction. Moreover, therapeutic or pharmaceutical compositions as described herein may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pheumocystis carnii.

Therapeutic or pharmaceutical compositions as described herein thereof, may be used to diagnose, prognose, treat or prevent one or more of the following diseases or disorders, or conditions associated therewith: primary immuodeficiencies, immune-mediated thrombocytopenia, Kawasaki syndrome, bone marrow transplant (e.g., recent bone marrow transplant in adults or children), chronic B-cell lymphocytic leukemia, HIV infection (e.g., adult or pediatric HIV infection), chronic inflammatory demyelinating polyneuropathy, and post-transfusion purpura.

Additionally, therapeutic or pharmaceutical compositions as described herein may be used to diagnose, prognose, treat or prevent one or more of the following diseases, disorders, or conditions associated therewith, Guillain-Barre syndrome, anemia (e.g., anemia associated with parvovirus B19, patients with stable multiple myeloma who are at high risk for infection (e.g., recurrent infection), autoimmune hemolytic anemia (e.g., warm-type autoimmune hemolytic anemia), thrombocytopenia (e.g., neonatal thrombocytopenia), and immune-mediated neutropenia), transplantation (e.g., cytamegalovirus (CMV)-negative recipients of CMV-positive organs), hypogammaglobulinemia (e.g., hypogammaglobulinemic neonates with risk factor for infection or morbidity), epilepsy (e.g., intractable epilepsy), systemic vasculitic syndromes, myasthenia gravis (e.g., decompensation in myasthenia gravis), dermatomyositis, and polymyositis.

Additional preferred embodiments of the invention include, but are not limited to, the use of therapeutic or pharmaceutical compositions as described herein in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response. In a specific nonexclusive embodiment, therapeutic or pharmaceutical compositions as described herein are administered to boost the immune system to produce increased quantities of IgG. In another specific nonexclusive embodiment, B lymphocyte stimulator binding polypeptides of the are administered to boost the immune system to produce increased quantities of IgA. In another specific non-limiting embodiment, B lymphocyte stimulator binding polypeptides are administered to boost the immune system to produce increased quantities of IgM.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT applications WO 98/24893, WO 96/34096, WO 96/33735, and WO 91/10741).

Additional preferred embodiments of the invention include, but are not limited to, the use of therapeutic or pharmaceutical compositions as described herein in the following applications:

A vaccine adjuvant that enhances immune responsiveness to specific antigen. In a specific embodiment, the vaccine is a B lymphocyte stimulator binding polypeptide described herein. In another specific embodiment, the vaccine adjuvant is a polynucleotide described herein (e.g., a B lymphocyte stimulator binding polypeptide polynucleotide genetic vaccine adjuvant). As discussed herein, therapeutic or pharmaceutical compositions as described herein may be administered using techniques known in the art, including but not limited to, liposomal delivery, recombinant vector delivery, injection of naked DNA, and gene gun delivery.

An adjuvant to enhance tumor-specific immune responses.

An adjuvant to enhance anti-viral immune responses. Antiviral immune responses that may be enhanced using the compositions as described herein as an adjuvant, include, but are not limited to, virus and virus associated diseases or symptoms described herein or otherwise known in the art. In specific embodiments, the compositions are used as an adjuvant to enhance an immune response to a virus, disease, or symptom selected from the group consisting of: AIDS, meningitis, Dengue, EBV, and hepatitis (e.g., hepatitis B). In another specific embodiment, the compositions are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever. In another specific embodiment, the compositions as described herein are used as an adjuvant to enhance an immune response to the HIV gp120 antigen.

An adjuvant to enhance anti-bacterial or anti-fungal immune responses. Anti-bacterial or anti-fungal immune responses that may be enhanced using the compositions as described herein as an adjuvant, include bacteria or fungus and bacteria or fungus associated diseases or symptoms described herein or otherwise known in the art. In specific embodiments, the compositions as described herein are used as an adjuvant to enhance an immune response to a bacteria or fungus, disease, or symptom selected from the group consisting of: tetanus, diphtheria, botulism, and meningitis type B. In another specific embodiment, the compositions are used as an adjuvant to enhance an immune response to a bacteria or fungus, disease, or symptom selected from the group consisting of: *Vibrio cholerae, Mycobacterium leprae, Salmonella typhi, Salmonella paratyphi, Neisseria meningitidis, Streptococcus pneumoniae*, Group B *Streptococcus, Shigella* spp., Enterotoxigenic *Escherichia coli*, Enterohemorrhagic *E. coli, Borrelia burgdorferi*, and *Plasmodium* (malaria).

An adjuvant to enhance anti-parasitic immune responses. Anti-parasitic immune responses that may be enhanced using the compositions as described herein as an adjuvant, include parasite and parasite associated diseases or symptoms described herein or otherwise known in the art. In specific embodiments, the compositions are used as an adjuvant to enhance an immune response to a parasite. In another specific embodiment, the compositions are used as an adjuvant to enhance an immune response to *Plasmodium* (malaria).

As a stimulator of B cell responsiveness to pathogens.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions as described herein may be administered prior to, concomitant with, and/or after transplantation. In a specific embodiment, compositions are administered after transplantation, prior to the beginning of recovery of T cell populations. In another specific embodiment, compositions are first administered after transplantation, after the beginning of recovery of T cell populations, but prior to full recovery of B cell populations.

As an agent to boost immunoresponsiveness among B cell immunodeficient individuals, such as, for example, an individual who has undergone a partial or complete splenectomy. B cell immunodeficiencies that may be ameliorated or treated by administering the B lymphocyte stimulator binding polypeptides and/or compositions as described herein include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non-X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

In a specific embodiment, B lymphocyte stimulator binding polypeptides and/or compositions are administered to treat or ameliorate selective IgA deficiency.

In another specific embodiment, B lymphocyte stimulator binding polypeptides and/or compositions are administered to treat or ameliorate ataxia-telangiectasia.

In another specific embodiment B lymphocyte stimulator binding polypeptides and/or compositions are administered to treat or ameliorate common variable immunodeficiency.

In another specific embodiment, B lymphocyte stimulator binding polypeptides and/or compositions are administered to treat or ameliorate X-linked agammaglobulinemia.

In another specific embodiment, B lymphocyte stimulator binding polypeptides and/or compositions are administered to treat or ameliorate severe combined immunodeficiency (SCID).

In another specific embodiment, B lymphocyte stimulator binding polypeptides and/or compositions are administered to treat or ameliorate Wiskott-Aldrich syndrome.

In another specific embodiment, B lymphocyte stimulator binding polypeptides and/or compositions are administered to treat or ameliorate X-linked Ig deficiency with hyper IgM.

As an agent to boost immunoresponsiveness among individuals having an acquired loss of B cell function. Conditions resulting in an acquired loss of B cell function that may be ameliorated or treated by administering B lymphocyte stimulator binding polypeptides and/or compositions include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering B lymphocyte stimulator binding polypeptides and/or compositions include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, T cells and/or B cells. In one embodiment, B lymphocyte stimulator binding polypeptides or polynucleotides enhance antigen presentation or antagonize antigen presentation in vitro or in vivo. Moreover, in related embodiments, this enhancement or antagonization of antigen presentation may be useful in anti-tumor treatment or to modulate the immune system.

As a mediator of mucosal immune responses. The expression of B lymphocyte stimulator on monocytes, the expression of B lymphocyte stimulator receptor on B cells, and the responsiveness of B cells to B lymphocyte stimulator suggests that it may be involved in exchange of signals between B cells and monocytes or their differentiated progeny. This activity is in many ways analogous to the CD40-CD154 signaling between B cells and T cells. B lymphocyte stimulator binding polypeptides and compositions may therefore be good regulators of T cell independent immune responses to environmental pathogens. In particular, the unconventional B cell populations (CD5+) that are associated with mucosal sites and responsible for much of the innate immunity in humans may respond to B lymphocyte stimulator binding polypeptides or compositions as described herein thereby enhancing or inhibiting individual's immune status.

As an agent to direct an individual's immune system towards development of a humoral response (i.e., TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly, their susceptibility profile would likely change.

As a monocyte cell specific binding protein to which specific activators or inhibitors of cell growth may be attached.

The result would be to focus the activity of such activators or inhibitors onto normal, diseased, or neoplastic moncytic cell populations.

As a macrophage cell specific binding protein to which specific activators or inhibitors of cell growth may be attached. The result would be to focus the activity of such activators or inhibitors onto normal, diseased, or neoplastic macrophage cell populations.

As a B cell specific binding protein to which specific activators or inhibitors of cell growth may be attached. The result would be to focus the activity of such activators or inhibitors onto normal, diseased, or neoplastic B cell populations.

As a means of detecting monocytic cells by virtue of its specificity. This application may require labeling the protein with biotin or other agents (e.g., as described herein) to afford a means of detection.

As a means of detecting macrophage cells by virtue of its specificity. This application may require labeling the protein with biotin or other agents (e.g., as described herein) to afford a means of detection.

As a means of detecting B-lineage cells by virtue of its specificity. This application may require labeling the protein with biotin or other agents (e.g., as described herein) to afford a means of detection.

As a stimulator of B cell production in pathologies such as AIDS, chronic lymphocyte disorder and/or Common Variable Immunodificiency.

As part of a monocyte selection device the function of which is to isolate monocytes from a heterogenous mixture of cell types. B lymphocyte stimulator binding polypeptides could be coupled to a solid support to which monocytes would then specifically bind. Unbound cells would be washed out and the bound cells subsequently eluted. A non-limiting use of this selection would be to allow purging of tumor cells from, for example, bone marrow or peripheral blood prior to transplant.

As part of a B cell selection device the function of which is to isolate B cells from a heterogenous mixture of cell types. B lymphocyte stimulator binding polypeptides (that do not inhibit B lymphocyte stimulator/B lymphocyte stimulator Receptor intereaction) binding soluble B lymphocyte stimulator could be coupled to a solid support to which B cells would then specifically bind. Unbound cells would be washed out and the bound cells subsequently eluted. A non-limiting use of this selection would be to allow purging of tumor cells from, for example, bone marrow or peripheral blood prior to transplant.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance B lymphocyte stimulator mediated responses.

As a means of activating monocytes/macrophages to defend against parasitic diseases that effect monocytes such as Leshmania.

As pretreatment of bone marrow samples prior to transplant. Such treatment would increase B cell representation and thus accelerate recovery.

As a means of regulating secreted cytokines that are elicited by B lymphocyte stimulator and/or B lymphocyte stimulator receptor.

B lymphocyte stimulator binding polypeptides or polynucleotides may be used to modulate IgE concentrations in vitro or in vivo.

Additionally, B lymphocyte stimulator binding polypeptides or polynucleotides may be used to treat, prevent, and/or diagnose IgE-mediated allergic reactions. Such allergic reactions include, but are not limited to, asthma, rhinitis, and eczema.

In a specific embodiment, B lymphocyte stimulator binding polypeptides or polynucleotides are administered to treat, prevent, diagnose, and/or ameliorate selective IgA deficiency.

In another specific embodiment B lymphocyte stimulator binding polypeptides or polynucleotides are administered to treat, prevent, diagnose, and/or ameliorate ataxia-telangiectasia.

In another specific embodiment, B lymphocyte stimulator binding polypeptides or polynucleotides are administered to treat, prevent, diagnose, and/or ameliorate common variable immunodeficiency.

In another specific embodiment, B lymphocyte stimulator binding polypeptides or polynucleotides are administered to treat, prevent, diagnose, and/or ameliorate X-linked agammaglobulinemia.

In another specific embodiment, B lymphocyte stimulator binding polypeptides or polynucleotides are administered to treat, prevent, diagnose, and/or ameliorate severe combined immunodeficiency (SCID).

In another specific embodiment, B lymphocyte stimulator binding polypeptides or polynucleotides are administered to treat, prevent, diagnose, and/or ameliorate Wiskott-Aldrich syndrome.

In another specific embodiment, B lymphocyte stimulator binding polypeptides or polynucleotides are administered to treat, prevent, diagnose, and/or ameliorate X-linked Ig deficiency with hyper IgM. In a specific embodiment B lymphocyte stimulator binding polypeptides or polynucleotides are administered to treat, prevent, diagnose, and/or ameliorate X-linked Ig deficiency with hyper IgM.

In another specific embodiment, B lymphocyte stimulator binding polypeptides or polynucleotides are administered to treat, prevent, and/or diagnose chronic myelogenous leukemia, acute myelogenous leukemia, leukemia, hystiocytic leukemia, monocytic leukemia (e.g., acute monocytic leukemia), leukemic reticulosis, Shilling Type monocytic leukemia, and/or other leukemias derived from monocytes and/or monocytic cells and/or tissues.

In another specific embodiment, B lymphocyte stimulator binding polypeptides or polynucleotides are administered to treat, prevent, diagnose, and/or ameliorate monocytic leukemoid reaction, as seen, for example, with tuberculosis.

In another specific embodiment, B lymphocyte stimulator binding polypeptides or polynucleotides are administered to treat, prevent, diagnose, and/or ameliorate monocytic leukocytosis, monocytic leukopenia, monocytopenia, and/or monocytosis.

In a specific embodiment, B lymphocyte stimulator binding polypeptides or polynucleotides are used to treat, prevent, detect, and/or diagnose monocyte disorders and/or diseases, and/or conditions associated therewith.

In a specific embodiment, B lymphocyte stimulator binding polypeptides or polynucleotides are used to treat, prevent, detect, and/or diagnose primary B lymphocyte disorders and/or diseases, and/or conditions associated therewith. In one embodiment, such primary B lymphocyte disorders, diseases, and/or conditions are characterized by a complete or partial loss of humoral immunity. Primary B lymphocyte disorders, diseases, and/or conditions associated therewith that are characterized by a complete or partial loss of humoral immunity and that may be prevented, treated, detected and/or diagnosed with compositions as described herein include, but are not limited to, X-Linked Agammaglobulinemia (XLA), severe combined immunodeficiency disease (SCID), and selective IgA deficiency.

In a preferred embodiment B lymphocyte stimulator binding polypeptides or polynucleotides are used to treat, prevent, and/or diagnose diseases or disorders affecting or conditions associated with any one or more of the various mucous membranes of the body. Such diseases or disorders include, but are not limited to, for example, mucositis, mucoclasis, mucocolitis, mucocutaneous leishmaniasis (such as, for example, American leishmaniasis, leishmaniasis americana, nasopharyngeal leishmaniasis, and New World leishmaniasis), mucocutaneous lymph node syndrome (for example, Kawasaki disease), mucoenteritis, mucoepidermoid carcinoma, mucoepidermoid tumor, mucoepithelial dysplasia, mucoid adenocarcinoma, mucoid degeneration, myxoid degeneration; myxomatous degeneration; myxomatosis, mucoid medial degeneration (for example, cystic medial necrosis), mucolipidosis (including, for example, mucolipidosis I, mucolipidosis II, mucolipidosis III, and mucolipidosis IV), mucolysis disorders, mucomembranous enteritis, mucoenteritis, mucopolysaccharidosis (such as, for example, type I mucopolysaccharidosis (i.e., Hurler's syndrome), type IS mucopolysaccharidosis (i.e., Scheie's syndrome or type V mucopolysaccharidosis), type II mucopolysaccharidosis (i.e., Hunter's syndrome), type III mucopolysaccharidosis (i.e., Sanfilippo's syndrome), type IV mucopolysaccharidosis (i.e., Morquio's syndrome), type VI mucopolysaccharidosis (i.e., Maroteaux-Lamy syndrome), type VII mucopolysaccharidosis (i.e, mucopolysaccharidosis due to beta-glucuronidase deficiency), and mucosulfatidosis), mucopolysacchariduria, mucopurulent conjunctivitis, mucopus, mucormycosis (i.e., zygomycosis), mucosal disease (i.e., bovine virus diarrhea), mucous colitis (such as, for example, mucocolitis and myxomembranous colitis), and mucoviscidosis (such as, for example, cystic fibrosis, cystic fibrosis of the pancreas, Clarke-Hadfield syndrome, fibrocystic disease of the pancreas, mucoviscidosis, and viscidosis). In a highly preferred embodiment, B lymphocyte stimulator binding polypeptides or polynucleotides are used to treat, prevent, and/or diagnose mucositis, especially as associated with chemotherapy.

In a preferred embodiment, B lymphocyte stimulator binding polypeptides or polynucleotides are used to treat, prevent, and/or diagnose diseases or disorders affecting or conditions associated with sinusitis.

An additional condition, disease or symptom that can be treated, prevented, and/or diagnosed by B lymphocyte stimulator binding polypeptides or polynucleotides is osteomyelitis.

An additional condition, disease or symptom that can be treated, prevented, and/or diagnosed by B lymphocyte stimulator binding polypeptides or polynucleotides is endocarditis.

All of the above described applications as they may apply to veterinary medicine.

B lymphocyte stimulator binding polypeptides or polynucleotides may be used to treat, prevent, and/or diagnose diseases and disorders of the pulmonary system (e.g., sinopulmonary and bronchial infections) and conditions associated with such diseases and disorders and other respiratory diseases and disorders. In specific embodiments, such diseases and disorders include, but are not limited to, bronchial adenoma, bronchial asthma, pneumonia (such as, e.g., bronchial pneumonia, bronchopneumonia, and tuberculous bronchopneumonia), chronic obstructive pulmonary disease (COPD), bronchial polyps, bronchiectasia (such as, e.g., bronchiectasia sicca, cylindrical bronchiectasis, and saccular bronchiectasis), bronchiolar adenocarcinoma, bronchiolar carcinoma, bronchiolitis (such as, e.g., exudative bronchiolitis, bronchiolitis fibrosa obliterans, and proliferative bronchiolitis), bronchiolo-alveolar carcinoma, bronchitic asthma, bronchitis (such as, e.g., asthmatic bronchitis, Castellani's bronchitis, chronic bronchitis, croupous bronchitis, fibrinous bronchitis, hemorrhagic bronchitis, infectious avian bronchitis, obliterative bronchitis, plastic bronchitis, pseudomembranous bronchitis, putrid bronchitis, and verminous bronchitis), bronchocentric granulomatosis, bronchoedema, bronchoesophageal fistula, bronchogenic carcinoma, bronchogenic cyst, broncholithiasis, bronchomalacia, bronchomycosis (such as, e.g., bronchopulmonary aspergillosis), bronchopulmonary spirochetosis, hemorrhagic bronchitis, bronchorrhea, bronchospasm, bronchostaxis, bronchostenosis, Biot's respiration, bronchial respiration, Kussmaul respiration, Kussmaul-Kien respiration, respiratory acidosis, respiratory alkalosis, respiratory distress syndrome of the newborn, respiratory insufficiency, respiratory scleroma, respiratory syncytial virus, and the like.

In a specific embodiment, B lymphocyte stimulator binding polypeptides or polynucleotides are used to treat, prevent, and/or diagnose chronic obstructive pulmonary disease (COPD).

In another embodiment, B lymphocyte stimulator binding polypeptides or polynucleotides are used to treat, prevent, and/or diagnose fibroses and conditions associated with fibroses, including, but not limited to, cystic fibrosis (including such fibroses as cystic fibrosis of the pancreas, Clarke-Hadfield syndrome, fibrocystic disease of the pancreas, mucoviscidosis, and viscidosis), endomyocardial fibrosis, idiopathic retroperitoneal fibrosis, leptomeningeal fibrosis, mediastinal fibrosis, nodular subepidermal fibrosis, pericentral fibrosis, perimuscular fibrosis, pipestem fibrosis, replacement fibrosis, subadventitial fibrosis, and Symmers' clay pipestem fibrosis.

In another embodiment, therapeutic or pharmaceutical compositions are administered to an animal to treat, prevent or ameliorate infectious diseases. Infectious diseases include diseases associated with yeast, fungal, viral and bacterial infections. Viruses causing viral infections which can be treated or prevented in accordance with this invention include, but are not limited to, retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus, HHV6-HHV8, and cytomegalovirus), arenavirues (e.g., lassa fever virus), paramyxoviruses (e.g., morbillivirus virus, human respiratory syncytial virus, mumps, and pneumovirus), adenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., influenza viruses A, B and C), papovaviruses (e.g., papillomavirues), picornaviruses (e.g., rhinoviruses, enteroviruses and hepatitis A viruses), poxviruses, reoviruses (e.g., rotavirues), togaviruses (e.g., rubella virus), rhabdoviruses (e.g., rabies virus). Microbial pathogens causing bacterial infections include, but are not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter* (Vibrio) *fetus, Campylobacter jejuni, Aeromonas hydrophila, Bacillus* cereus, *Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia tsutsugumush, Chlamydia* spp., and *Helicobacter pylori*.

Gene Therapy

In a specific embodiment, nucleic acids comprising sequences encoding B lymphocyte stimulator binding polypeptides or functional derivatives thereof, are administered to treat, inhibit or prevent a disease or disorder associated with aberrant expression and/or activity of B lymphocyte stimulator and/or its receptor, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., *Clinical Pharmacy*, 12:488-505 (1993); Wu and Wu, *Biotherapy*, 3:87-95 (1991); Tolstoshev, *Ann. Rev. Pharmacol. Toxicol.*, 32:573-596 (1993); Mulligan, *Science*, 260:926-932 (1993); and Morgan and Anderson, *Ann. Rev. Biochem.*, 62:191-217 (1993); May, TIBTECH, 11(5):155-215 (1993). Methods commonly known in the art of recombinant DNA technology which can be used are described in *Current Protocols in Molecular Biology*, Ausubel et al., eds. (John Wiley & Sons, NY 1993); and Kriegler, *Gene Transfer and Expression, A Laboratory Manual* (Stockton Press, NY 1990).

In a preferred aspect, a composition useful in the methods of the invention comprises, or alternatively consists of, nucleic acids encoding a B lymphocyte stimulator binding polypeptide, said nucleic acids being part of an expression vector that expresses the B lymphocyte stimulator binding polypeptide or fragment thereof or chimeric protein including it in a suitable host. In particular, such nucleic acids have promoters, preferably heterologous promoters, operably linked to the B lymphocyte stimulator binding polypeptide coding region, said promoter being inducible or constitutive, and, optionally, tissue-specific. In another particular embodiment, nucleic acid molecules are used in which the B lymphocyte stimulator binding polypeptide coding sequences and any other desired sequences are flanked by regions that promote homologous recombination at a desired site in the genome, thus providing for intrachromosomal expression of the B lymphocyte stimulator binding polypeptide encoding nucleic acids (Koller and Smithies, *Proc. Natl. Acad. Sci. USA,* 86:8932-8935 (1989); Zijlstra et al., *Nature,* 342:435-438 (1989).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J. Biol. Chem.,* 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT publications WO 92/06180; WO 92/22635; WO 92/20316; WO 93/14188, WO 93/20221). Alternatively, the nucleic acid can be introduced intracellularly and incorporated within host cell DNA for expression, by homologous recombination (Koller and Smithies, *Proc. Natl. Acad. Sci. USA,* 86:8932-8935 (1989); Zijlstra et al., *Nature,* 342:435-438 (1989)).

In a specific embodiment, viral vectors that contains nucleic acid sequences encoding a B lymphocyte stimulator binding polypeptide or fragments or variants thereof are used. For example, a retroviral vector can be used (see Miller et al., *Meth. Enzymol.,* 217:581-599 (1993)). These retroviral vectors contain the components necessary for the correct packaging of the viral genome and integration into the host cell DNA. The nucleic acid sequences encoding the B lymphocyte stimulator binding polypeptide to be used in gene therapy are cloned into one or more vectors, which facilitates delivery of the gene into a patient. Additional details concerning retroviral vectors can be found in Boesen et al., *Biotherapy,* 6:29 1-302 (1994), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., *J. Clin. Invest.,* 93:644-651 (1994); Klein et al., *Blood,* 83:1467-1473 (1994); Salmons and Gunzberg, *Human Gene Therapy,* 4:129-141 (1993); and Grossman and Wilson, *Curr. Opin. in Genetics and Devel.,* 3:110-114 (1993).

Other viral vectors that can be used in gene therapy are adenoviruses. Adenoviruses are especially attractive vehicles for delivering genes to respiratory epithelia. Adenoviruses naturally infect respiratory epithelia, where they cause a mild disease. Other targets for adenovirus-based delivery systems are liver, the central nervous system, endothelial cells, and muscle. Adenoviruses have the advantage of being capable of infecting non-dividing cells. See, Kozarsky and Wilson, *Current Opinion in Genetics and Development,* 3:499-503 (1993), presenting a review of adenovirus-based gene therapy. Bout et al., *Human Gene Therapy,* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science,* 252:431-434 (1991); Rosenfeld et al., *Cell,* 68:143-155 (1992); Mastrangeli et al., *J. Clin. Invest.,* 91:225-234 (1993); PCT publication WO 94/12649; and Wang et al., *Gene Therapy,* 2:775-783 (1995).

In a preferred embodiment, adenovirus vectors are used.

Adeno-associated virus (AAV) has also been proposed for use in gene therapy (Walsh et al., *Proc. Soc. Exp. Biol. Med.,* 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, *Meth. Enzymol.,* 217:599-618 (1993); Cohen et al., *Meth. Enzymol.,* 217:618-644 (1993); *Clin. Pharma. Ther.,* 29:69-92m (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding a B lymphocyte stimulator binding polypeptide or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells that can be isolated and maintained in vitro can potentially be used in accordance with this embodiment of the present invention (see, e.g., PCT publication WO 94/08598; Stemple and Anderson, *Cell,* 7 1:973-985 (1992); Rheinwald, *Meth. Cell Bio.,* 21A:229 (1980); and Pittelkow and Scott, *Mayo Clinic Proc.,* 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Utility of a Composition

The compounds are preferably tested in vitro, and then in vivo for the desired therapeutic or prophylactic activity, prior to use in humans. For example, in vitro assays which can be used to determine whether administration of a specific B lymphocyte stimulator binding polypeptide or composition of the present invention is indicated, include in vitro cell culture assays in which a patient tissue sample is grown in culture, and exposed to, or otherwise administered, a B lymphocyte stimulator binding polypeptide or composition of the present invention, and the effect of such a B lymphocyte stimulator binding polypeptide or composition of the present invention upon the tissue sample is observed. In various specific embodiments, in vitro assays can be carried out with representative cells of cell types involved in a patient's disorder, to determine if a B lymphocyte stimulator binding polypeptide or composition of the present invention has a desired effect upon such cell types. Preferably, the B lymphocyte stimulator binding polypeptides or compositions are also tested in in vitro assays and animal model systems prior to administration to humans.

B lymphocyte stimulator binding polypeptides or compositions of the present invention for use in therapy can be tested for their toxicity in suitable animal model systems, including but not limited to rats, mice, chicken, cows, monkeys, and rabbits. For in vivo testing of a B lymphocyte stimulator binding polypeptide or composition's toxicity any animal model system known in the art may be used.

Efficacy in treating or preventing viral infection may be demonstrated by detecting the ability of a B lymphocyte stimulator binding polypeptide or composition to inhibit the replication of the virus, to inhibit transmission or prevent the virus from establishing itself in its host, or to prevent, ameliorate or alleviate the symptoms of disease a progression. The treatment is considered therapeutic if there is, for example, a reduction in viral load, amelioration of one or more symptoms, or a decrease in mortality and/or morbidity following administration of a B lymphocyte stimulator binding polypeptide or composition.

B lymphocyte stimulator binding polypeptides or compositions can be tested for the ability to induce the expression of cytokines such as IFN-γ, by contacting cells, preferably human cells, with a B lymphocyte stimulator binding polypeptide or composition or a control B lymphocyte stimulator binding polypeptide or control composition and determining the ability of the B lymphocyte stimulator binding polypeptide or composition to induce one or more cytokines. Techniques known to those skilled in the art can be used to measure the level of expression of cytokines. For example, the level of expression of cytokines can be measured by analyzing the level of RNA of cytokines by, for example, RT-PCR and Northern blot analysis, and by analyzing the level of cytokines by, for example, immunoprecipitation followed by western blot analysis and ELISA. In a preferred embodiment, a compound is tested for its ability to induce the expression of IFN-γ.

B lymphocyte stimulator binding polypeptides or compositions can be tested for their ability to modulate the biological activity of immune cells by contacting immune cells, preferably human immune cells (e.g., T cells, B cells, and Natural Killer cells), with a B lymphocyte stimulator binding polypeptide or composition or a control compound and determining the ability of the B lymphocyte stimulator binding polypeptide or compostion to modulate (i.e, increase or decrease) the biological activity of immune cells. The ability of a B lymphocyte stimulator binding polypeptide or composition to modulate the biological activity of immune cells can be assessed by detecting the expression of antigens, detecting the proliferation of immune cells (i.e., B cell proliferation), detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Antigen expression can be assayed, for example, by immunoassays including, but not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs). In a preferred embodiment, the ability of a B lymphocyte stimulator binding polypeptide or composition to induce B cell proliferation is measured. In another preferred embodiment, the ability of a B lymphocyte stimulator binding polypeptide or composition to modulate immunoglobulin expression is measured.

B lymphocyte stimulator binding polypeptides or compositions can be tested for their ability to reduce tumor formation in in vitro, ex vivo and in vivo assays. B lymphocyte stimulator binding polypeptides or compositions can also be tested for their ability to inhibit viral replication or reduce viral load in in vitro and in vivo assays. B lymphocyte stimulator binding polypeptides or compositions can also be tested for their ability to reduce bacterial numbers in in vitro and in vivo assays known to those of skill in the art. B lymphocyte stimulator binding polypeptides or compositions can also be tested for their ability to alleviate of one or more symptoms associated with cancer, an immune disorder (e.g., an inflammatory disease), a neurological disorder or an infectious disease. B lymphocyte stimulator binding polypeptides or compositions can also be tested for their ability to decrease the time course of the infectious disease. Further, B lymphocyte stimulator binding polypeptides or compositions can be tested for their ability to increase the survival period of animals suffering from disease or disorder, including cancer, an immune disorder or an infectious disease. Techniques known to those of skill in the art can be used to analyze the function of the B lymphocyte stimulator binding polypeptides or compositions in vivo.

Therapeutic/Prophylactic Compositions and Administration

The invention provides methods of treatment, inhibition and prophylaxis by administration to a subject of an effective amount of B lymphocyte stimulator binding polypeptide (or fragment or variant thereof) or pharmaceutical composition, preferably a B lymphocyte stimulator binding polypeptide. In a preferred aspect, a B lymphocyte stimulator binding polypeptide or fragment or variant thereof is substantially purified (i.e., substantially free from substances that limit its effect or produce undesired side-effects). The subject is preferably an animal, including but not limited to, animals such as cows, pigs, horses, chickens, cats, dogs, etc., and is preferably a mammal, and most preferably a human.

Formulations and methods of administration that can be employed when the compound comprises a nucleic acid or an immunoglobulin are described above; additional appropriate formulations and routes of administration can be selected from among those described herein below.

Various delivery systems are known and can be used to administer B lymphocyte stimulator binding polypeptide or fragment or variant thereof, e.g., encapsulation in liposomes, microparticles, microcapsules, recombinant cells capable of expressing the B lymphocyte stimulator binding polypeptide or B lymphocyte stimulator binding polypeptide fragment, receptor-mediated endocytosis (see, e.g., Wu and Wu, *J. Biol. Chem.*, 262:4429-4432 (1987)), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including a B lymphocyte stimulator binding polypeptide, care must be taken to use materials to which the protein does not absorb.

In another embodiment, the composition can be delivered in a vesicle, in particular a liposome (see, Langer, Science, 249:1527-1533 (1990); Treat et al., in *Liposomes in the Therapy of Infectious Disease and Cancer*, Lopez-Berestein and Fidler, eds. (Liss, New York 1989), pp. 353-365; Lopez-Berestein, ibid., pp. 317-327; see, generally, ibid.).

In yet another embodiment, the composition can be delivered in a controlled release system. In one embodiment, a pump may be used (see Langer, supra; Sefton, *CRC Crit. Ref. Biomed. Eng.*, 14:201 (1987); Buchwald et al., *Surgery*, 88:507 (1980); Saudek et al., *N. Engl. J. Med.*, 321:574 (1989)). In another embodiment, polymeric materials can be used (see, *Medical Applications of Controlled Release*, Langer and Wise, eds. (CRC Press, Boca Raton, Fla. 1974); *Controlled Drug Bioavailability, Drug Product Design and Performance*, Smolen and Ball, eds. (Wiley, New York 1984); Ranger and Peppas, *Macromol. Sci. Rev. Macromol. Chem.*, 23:61 (1983); see also Levy et al., *Science*, 228:190 (1985); During et al., *Ann. Neurol.*, 25:35 1 (1989); Howard et al., *J. Neurosurg.*, 7 1:105 (1989)). In yet another embodiment, a controlled release system can be placed in proximity of the therapeutic target, e.g., the brain, thus requiring only a fraction of the systemic dose (see, e.g., Goodson, in *Medical Applications of Controlled Release*, supra, vol. 2, pp. 115-138 (1984)). Other controlled release systems are discussed in the review by Langer (*Science*, 249:1527-1533 (1990)).

In a specific embodiment where the composition to be used in the method of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., *Proc. Natl. Acad. Sci. USA*, 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a B lymphocyte stimulator binding polypeptide or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences*, 18th Ed., Gennaro, ed. (Mack Publishing Co., 1990). Such compositions will contain a therapeutically effective amount of the B lymphocyte stimulator binding polypeptide or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions for use in the methods of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylaminoethanol, histidine, procaine, etc.

The amount of the composition which will be effective in the treatment, inhibition and prevention of a disease or disorder associated with aberrant expression and/or activity of a polypeptide can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For B lymphocyte stimulator binding polypeptides, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Further, the dosage and frequency of administration of therapeutic or pharmaceutical compositions may be reduced by enhancing uptake and tissue penetration (e.g., into the brain) of the B lymphocyte stimulator binding polypeptides by modifications such as, for example, lipidation.

The B lymphocyte stimulator binding polypeptides and B lymphocyte stimulator binding polypeptide compositions may be administered alone or in combination with other molecules including B lymphocyte stimulator. In further embodiments of the invention, the B lymphocyte stimulator binding polypeptides are administered in complex with B lymphocyte stimulator. Preferably the B lymphocyte stimulator binding polypeptide is radiolabelled or in complex with a radioisotope, toxin, or prodrug. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The B lymphocyte stimulator binding polypeptides and B lymphocyte stimulator binding polypeptide compositions may be administered alone or in combination with other adjuvants. Adjuvants that may be administered with the B lymphocyte stimulator binding polypeptides and B lymphocyte stimulator binding polypeptide compositions include, but are not limited to, alum, alum plus deoxycholate (ImmunoAg), MTP-PE (Biocine Corp.), QS21 (Genentech, Inc.), BCG, and MPL. In a specific embodiment, B lymphocyte stimulator binding polypeptides and B lymphocyte stimulator binding polypeptide compositions are administered in combination with alum. In another specific embodiment, B lymphocyte stimulator binding polypeptides and B lymphocyte stimulator binding polypeptide compositions are administered in combination with QS-21. Further adjuvants that may be administered with the B lymphocyte stimulator binding polypeptides and B lymphocyte stimulator binding polypeptide compositions include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the B lymphocyte stimulator binding polypeptides and B lymphocyte stimulator binding polypeptide compositions include, but are not limited to, vaccines directed toward protection against MMR (measles, mumps, rubella), polio, varicella, tetanus/diptheria, hepatitis A, hepatitis B, *haemophilus influenzae* B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™.

In another specific embodiment, B lymphocyte stimulator binding polypeptides and B lymphocyte stimulator binding polypeptide compositions are used in combination with PNEUMOVAX-23™ (Pneumonococcal vaccine polyvalent) to treat, prevent, and/or diagnose infection and/or any disease, disorder, and/or condition associated therewith. In one embodiment, B lymphocyte stimulator binding polypeptides and B lymphocyte stimulator binding polypeptide compositions are used in combination with PNEUMOVAX-23™ to treat, prevent, and/or diagnose any Gram positive bacterial infection and/or any disease, disorder, and/or condition associated therewith. In another embodiment, B lymphocyte stimulator binding polypeptides and B lymphocyte stimulator binding polypeptide compositions are used in combination with PNEUMOVAX-23™ to treat, prevent, and/or diagnose infection and/or any disease, disorder, and/or condition associated with one or more members of the genus *Enterococcus* and/or the genus *Streptococcus*. In another embodiment, B lymphocyte stimulator binding polypeptides and B lymphocyte stimulator binding polypeptide compositions are used in any combination with PNEUMOVAX-23™ to treat, prevent, and/or diagnose infection and/or any disease, disorder, and/or condition associated with one or more members of the Group B streptococci. In another embodiment, B lymphocyte stimulator binding polypeptides and B lymphocyte stimulator binding polypeptide compositions are used in combination with PNEUMOVAX-23™ to treat, prevent, and/or diagnose infection and/or any disease, disorder, and/or condition associated with *Streptococcus pneumoniae*.

The B lymphocyte stimulator binding polypeptides and B lymphocyte stimulator binding polypeptide compositions may be administered alone or in combination with other therapeutic agents, including but not limited to, chemotherapeutic agents, antibiotics, antivirals, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the B lymphocyte stimulator binding polypeptides and B lymphocyte stimulator binding polypeptide compositions are administered in combination with other members of the TNF family. TNF, TNF-related or TNF-like molecules that may be administered with the B lymphocyte stimulator binding polypeptides and B lymphocyte stimulator binding polypeptide compositions include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (PCT publication WO 96/14328), TRAIL, AIM-II (PCT publication WO 97/34911), APRIL (*J. Exp. Med.*, 188(6):1185-1190 (1998)), endokine-alpha (PCT publication WO 98/07880), Neutrokine-alpha (PCT publication WO 98/18921), OPG, OX40, and nerve growth factor (NGF), and soluble forms of fas, CD30, CD27, CD40 and 4-IBB, TR2 (PCT publication WO 96/34095), DR3 (PCT publication WO 97/33904), DR4 (PCT publication WO 98/32856), TR5 (PCT publication WO 98/30693), TR6 (PCT publication WO 98/30694), TR7 (PCT publication WO 98/41629), TRANK, TR9 (PCT publication WO 98/56892), 312C2 (PCT publication WO 98/06842), and TR12, and soluble forms CD154, CD70, and CD153.

In a preferred embodiment, the B lymphocyte stimulator binding polypeptides and B lymphocyte stimulator binding polypeptide compositions are administered in combination with CD40 ligand (CD40L), a soluble form of CD40L (e.g., AVREND™), bioloigically active fragments, variants, or derivatives of CD40L, anti-CD40L antibodies (e.g., agonistic or antagonistic antibodies), and/or anti-CD40 antibodies (e.g., agonistic or antagonistic antibodies).

In an additional embodiment, the B lymphocyte stimulator binding polypeptides and B lymphocyte stimulator binding polypeptide compositions are administered alone or in combination with an anti-angiogenic agent(s). Anti-angiogenic agents that may be administered with the B lymphocyte stimulator binding polypeptides and B lymphocyte stimulator binding polypeptide compositions include, but are not limited to, Angiostatin (Entremed, Rockville, Md.), Troponin-1 (Boston Life Sciences, Boston, Mass.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., *Cancer Res.*, 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., *J. Bio. Chem.*, 267:17321-17326, 1992); Chymostatin (Tomkinson et al., *Biochem J.*, 286:475-480, 1992); Cyclodextrin Tetradecasulfate; Eponemycin; Camptothecin; Fumagillin (Ingber et al., *Nature*, 348:555-557, 1990); Gold Sodium Thiomalate ("GST"; Matsubara and Ziff, *J. Clin. Invest.*, 79:1440-1446, 1987); anticollagenase-serum; alpha2-antiplasmin (Holmes et al., *J. Biol. Chem.*, 262(4): 1659-1664, 1987); Bisantrene (National Cancer Institute); Lobenzarit disodium (N-(2)-carboxyphenyl-4-chloroanthronilic acid disodium or "CCA"; (Takeuchi et al., *Agents Actions*, 36:312-316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (Brem and Folkman, *J. Pediatr. Surg.*, 28:445-51 (1993)); an integrin alpha v beta 3 antagonist (Storgard et al., *J. Clin. Invest.*, 103:47-54 (1999)); carboxynaminolimidazole; Carboxyamidotriazole (CAI) (National Cancer Institute, Bethesda, Md.); Conbretastatin A-4 (CA4P) (OXiGENE, Boston, Mass.); Squalamine (Magainin Pharmaceuticals, Plymouth Meeting, Pa.); TNP-470, (Tap Pharmaceuticals, Deerfield, Ill.); ZD-0101 AstraZeneca (London, UK); APRA (CT2584); Benefin, Byrostatin-1 (SC339555); CGP-41251 (PKC 412); CM101; Dexrazoxane (ICRF187); DMXAA; Endostatin; Flavopridiol; Genestein; GTE; ImmTher; Iressa (ZD1839); Octreotide (Somatostatin); Panretin; Penacillamine; Photopoint; PI-88; Prinomastat (AG-3340) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with the compounds may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the B lymphocyte stimulator binding polypeptides and B lymphocyte stimulator binding polypeptide compositions include, but are not limited to, AG-3340 (Agouron, La Jolla, Calif.), BAY-12-9566 (Bayer, West Haven, Conn.), BMS-275291 (Bristol Myers Squibb, Princeton, N.J.), CGS-27032A (Novartis, East Hanover, N.J.), Marimastat (British Biotech, Oxford, UK), and Metastat (Aeterna, St-Foy, Quebec).

Examples of anti-angiogenic inhibitors that act by blocking the function of endothelial cell-extracellular matrix adhesion molecules and which may be administered in combination with the B lymphocyte stimulator binding polypeptides and B lymphocyte stimulator binding polypeptide compositions include, but are not limited to, EMD-121974 (Merck KcgaA Darmstadt, Germany) and Vitaxin (Ixsys, La Jolla, Calif./Medimmune, Gaithersburg, Md.). Examples of anti-angiogenic agents that act by directly antagonizing or inhibiting angiogenesis inducers and which may be administered in combination with the B lymphocyte stimulator binding polypeptides and B lymphocyte stimulator binding polypeptide compositions include, but are not limited to, Angiozyme (Ribozyme, Boulder, Colo.), Anti-VEGF B lymphocyte stimulator binding polypeptide (Genentech, S. San Francisco, Calif.), PTK-787/ZK-225846 (Novartis, Basel, Switzerland), SU-101 (Sugen, S. San Francisco, Calif.), SU-5416 (Sugen/Pharmacia Upjohn, Bridgewater, N.J.), and SU-6668 (Sugen). Other anti-angiogenic agents act to indirectly inhibit angiogenesis. Examples of indirect inhibitors of angiogenesis which may be administered in combination with the B lymphocyte stimulator binding polypeptides and B lymphocyte stimulator binding polypeptide compositions include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In particular embodiments, the use of B lymphocyte stimulator binding polypeptides and B lymphocyte stimulator binding polypeptide compositions in combination with anti-angiogenic agents is contemplated for the treatment, prevention, and/or amelioration of an autoimmune disease, such as for example, an autoimmune disease described herein.

In a particular embodiment, the use of B lymphocyte stimulator binding polypeptides and B lymphocyte stimulator binding polypeptide compositions in combination with anti-angiogenic agents is contemplated for the treatment, prevention, and/or amelioration of arthritis. In a more particular embodiment, the use of B lymphocyte stimulator binding polypeptides and B lymphocyte stimulator binding polypeptide compositions in combination with anti-angiogenic agents is contemplated for the treatment, prevention, and/or amelioration of rheumatoid arthritis.

In another embodiment, B lymphocyte stimulator binding polypeptides and B lymphocyte stimulator binding polypeptide compositions are administered in combination with an anticoagulant. Anticoagulants that may be administered with the B lymphocyte stimulator binding polypeptides and B lymphocyte stimulator binding polypeptide compositions include, but are not limited to, heparin, warfarin, and aspirin. In a specific embodiment, B lymphocyte stimulator binding polypeptides and B lymphocyte stimulator binding polypeptide compositions are administered in combination with heparin and/or warfarin. In another specific embodiment, B lymphocyte stimulator binding polypeptides and B lymphocyte stimulator binding polypeptide compositions are administered in combination with warfarin. In another specific embodiment, B lymphocyte stimulator binding polypeptides and B lymphocyte stimulator binding polypeptide compositions are administered in combination with warfarin and aspirin. In another specific embodiment, B lymphocyte stimulator binding polypeptides and B lymphocyte stimulator binding polypeptide compositions are administered in combination with heparin. In another specific embodiment, B lymphocyte stimulator binding polypeptides and B lymphocyte stimulator binding polypeptide compositions are administered in combination with heparin and aspirin.

In another embodiment, B lymphocyte stimulator binding polypeptides and B lymphocyte stimulator binding polypeptide compositions are administered in combination with an agent that suppresses the production of anticardiolipin antibodies. In specific embodiments, the polypeptides are administered in combination with an agent that blocks and/or reduces the ability of anticardiolipin antibodies to bind phospholipid-binding plasma protein beta 2-glycoprotein I (b2GPI).

In certain embodiments, B lymphocyte stimulator binding polypeptides and B lymphocyte stimulator binding polypeptide compositions are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the B lymphocyte stimulator binding polypeptides and B lymphocyte stimulator binding polypeptide compositions, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the B lymphocyte stimulator binding polypeptides and B lymphocyte stimulator binding polypeptide compositions, include, but are not limited to, VIRAMUNE™ (nevirapine), RESCRIPTOR™ (delavirdine), and SUSTIVA™ (efavirenz). Protease inhibitors that may be administered in combination with the B lymphocyte stimulator binding polypeptides and B lymphocyte stimulator binding polypeptide compositions, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with B lymphocyte stimulator binding polypeptides and B lymphocyte stimulator binding polypeptide compositions to treat, prevent, and/or diagnose AIDS and/or to treat, prevent, and/or diagnose HIV infection.

In other embodiments, B lymphocyte stimulator binding polypeptides and B lymphocyte stimulator binding polypeptide compositions may be administered in combination with anti-opportunistic infection agents. Anti-opportunistic agents that may be administered in combination with the B lymphocyte stimulator binding polypeptides and B lymphocyte stimulator binding polypeptide compositions, include, but are not limited to, trimethoprim-sulfamethoxazole, DAPSONE™ (diamino diphenyl sulfone), pentamidine, atovaquone, isoniazid, rifampin, PYRAZINAMIDE™ (pyrazinamide), ethambutol, rifabutin, clarithromycin, azithromycin, ganciclovir, foscarnet, cidofovir, fluconazole, itraconazole, ketoconazole, acyclovir, famciclovir, pyrimethamine, leucovorin, NEUPOGEN™ (filgrastim/G-CSF), and LEUKINE™ (sargramostim/GM-CSF). In a specific embodiment, B lymphocyte stimulator binding polypeptides and B lymphocyte stimulator binding polypeptide compositions are used in any combination with trimethoprim-sulfamethoxazole, DAPSONE™ (diamino diphenyl sulfone), pentamidine, and/or atovaquone to prophylactically treat, prevent, and/or diagnose an opportunistic *Pneumocystis carinii* pneumonia infection. In another specific embodiment, B lymphocyte stimulator binding polypeptides and B lymphocyte stimulator binding polypeptide compositions are used in any combination with isoniazid, rifampin, PYRAZINAMIDE™ (pyrazinamide), and/or ethambutol to prophylactically treat, prevent, and/or diagnose an opportunistic *Mycobacterium avium* complex infection. In another specific embodiment, B lymphocyte stimulator binding polypeptides and B lymphocyte stimulator binding polypeptide compositions are used in any combination with rifabutin, clarithromycin, and/or azithromycin to prophylactically treat, prevent, and/or diagnose an opportunistic *Mycobacterium tuberculosis* infection. In another specific embodiment, B lymphocyte stimulator binding polypeptides and B lymphocyte stimulator binding polypeptide compositions are used in any combination with ganciclovir, foscarnet, and/or cidofovir to prophylactically treat, prevent, and/or diagnose an opportunistic cytomegalovirus infection. In another specific embodiment, B lymphocyte stimulator binding polypeptides and B lymphocyte stimulator binding polypeptide compositions are used in any combination with fluconazole, itraconazole, and/or ketoconazole to prophylactically treat, prevent, and/or diagnose an opportunistic fungal infection. In another specific embodiment, B lymphocyte stimulator binding polypeptides and B lymphocyte stimulator binding polypeptide compositions are used in any combination with acyclovir and/or famciclovir to prophylactically treat, prevent, and/or diagnose an opportunistic herpes simplex virus type I and/or type II infection. In another specific embodiment, B lymphocyte stimulator binding polypeptides and B lymphocyte stimulator binding polypeptide compositions are used in any combination with pyrimethamine and/or leucovorin to prophylactically treat, prevent, and/or diagnose an opportunistic *Toxoplasma gondii* infection. In another specific embodiment, B lymphocyte stimulator binding polypeptides and B lymphocyte stimulator binding polypeptide compositions are used in any combination with leucovorin and/or NEUPOGEN™ to prophylactically treat, prevent, and/or diagnose an opportunistic bacterial infection.

In a further embodiment, the B lymphocyte stimulator binding polypeptides and B lymphocyte stimulator binding polypeptide compositions are administered in combination with an antiviral agent. Antiviral agents that may be administered with the B lymphocyte stimulator binding polypeptides and B lymphocyte stimulator binding polypeptide compositions include, but are not limited to, acyclovir, ribavirin, amantadine, and remantidine.

In a further embodiment, the B lymphocyte stimulator binding polypeptides and B lymphocyte stimulator binding polypeptide compositions are administered in combination with an antibiotic agent. Antibiotic agents that may be administered with the B lymphocyte stimulator binding polypeptides and B lymphocyte stimulator binding polypeptide compositions include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the B lymphocyte stimulator binding polypeptides and B lymphocyte stimulator binding polypeptide compositions include, but are not limited to, steroids, cyclosporine, cyclosporine analogs cyclophosphamide, cyclophosphamide IV, methylprednisolone, prednisolone, azathioprine, FK-506, 15-deoxyspergualin, and other immunosuppressive agents that act by suppressing the function of responding T cells.

In specific embodiments, B lymphocyte stimulator binding polypeptides and B lymphocyte stimulator binding polypeptide compositions are administered in combination with immunosuppressants. Immunosuppressant preparations that may be administered with the B lymphocyte stimulator binding polypeptides and B lymphocyte stimulator binding polypeptide compositions include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In a preferred embodiment, the B lymphocyte stimulator binding polypeptides and B lymphocyte stimulator binding polypeptide compositions are administered in combination with steroid therapy. Steroids that may be administered in combination with the B lymphocyte stimulator binding polypeptides and B lymphocyte stimulator binding polypeptide compositions, include, but are not limited to, oral corticosteroids, prednisone, and methylprednisolone (e.g., IV methylprednisolone). In a specific embodiment, B lymphocyte stimulator binding polypeptides and B lymphocyte stimulator binding polypeptide compositions are administered in combination with prednisone. In a further specific embodiment, the B lymphocyte stimulator binding polypeptides and B lymphocyte stimulator binding polypeptide compositions are administered in combination with prednisone and an immunosuppressive agent. Immunosuppressive agents that may be administered with the B lymphocyte stimulator binding polypeptides and B lymphocyte stimulator binding polypeptide compositions and prednisone are those described herein, and include, but are not limited to, azathioprine, cylophosphamide, and cyclophosphamide IV. In a another specific embodiment, B lymphocyte stimulator binding polypeptides and B lymphocyte stimulator binding polypeptide compositions are administered in combination with methylprednisolone. In a further specific embodiment, the B lymphocyte stimulator binding polypeptides and B lymphocyte stimulator binding polypeptide compositions are administered in combination with methylprednisolone and an immunosuppressive agent. Immunosuppressive agents that may be administered with the B lymphocyte stimulator binding polypeptides and B lymphocyte stimulator binding polypeptide compositions and methylprednisolone are those described herein, and include, but are not limited to, azathioprine, cylophosphamide, and cyclophosphamide IV.

In a preferred embodiment, the B lymphocyte stimulator binding polypeptides and B lymphocyte stimulator binding polypeptide compositions are administered in combination with an antimalarial. Antimalarials that may be administered with the B lymphocyte stimulator binding polypeptides and B lymphocyte stimulator binding polypeptide compositions include, but are not limited to, hydroxychloroquine, chloroquine, and/or quinacrine.

In a preferred embodiment, the B lymphocyte stimulator binding polypeptides and B lymphocyte stimulator binding polypeptide compositions are administered in combination with an NSAID.

In a nonexclusive embodiment, the B lymphocyte stimulator binding polypeptides and B lymphocyte stimulator binding polypeptide compositions are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In a preferred embodiment, the B lymphocyte stimulator binding polypeptides and B lymphocyte stimulator binding polypeptide compositions are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™

(Etanercept), anti-TNF antibody, LJP 394 (La Jolla Pharmaceutical Company, San Diego, Calif.) and prednisolone.

In a more preferred embodiment, the B lymphocyte stimulator binding polypeptides and B lymphocyte stimulator binding polypeptide compositions are administered in combination with an antimalarial, methotrexate, anti-TNF antibody, REMICADET™, ENBREL™ and/or suflasalazine. In one embodiment, the B lymphocyte stimulator binding polypeptides and B lymphocyte stimulator binding polypeptide compositions are administered in combination with methotrexate. In another embodiment, the B lymphocyte stimulator binding polypeptides and B lymphocyte stimulator binding polypeptide compositions are administered in combination with anti-TNF antibody. In another embodiment, the B lymphocyte stimulator binding polypeptides and B lymphocyte stimulator binding polypeptide compositions are administered in combination with methotrexate and anti-TNF antibody. In another embodiment, the B lymphocyte stimulator binding polypeptides and B lymphocyte stimulator binding polypeptide compositions are administered in combination with suflasalazine. In another specific embodiment, the B lymphocyte stimulator binding polypeptides and B lymphocyte stimulator binding polypeptide compositions are administered in combination with methotrexate, anti-TNF antibody, and suflasalazine. In another embodiment, the B lymphocyte stimulator binding polypeptides and B lymphocyte stimulator binding polypeptide compositions are administered in combination ENBREL™. In another embodiment, the B lymphocyte stimulator binding polypeptides and B lymphocyte stimulator binding polypeptide compositions are administered in combination with ENBREL™ and methotrexate. In another embodiment, the B lymphocyte stimulator binding polypeptides and B lymphocyte stimulator binding polypeptide compositions are administered in combination with ENBREL™, methotrexate and suflasalazine. In another embodiment, the B lymphocyte stimulator binding polypeptides and B lymphocyte stimulator binding polypeptide compositions are administered in combination with ENBREL™, methotrexate and suflasalazine. In other embodiments, one or more antimalarials is combined with one of the above-recited combinations. In a specfic embodiment, the B lymphocyte stimulator binding polypeptides and B lymphocyte stimulator binding polypeptide compositions are administered in combination with an antimalarial (e.g., hydroxychloroquine), ENBREL™, methotrexate and suflasalazine. In another specfic embodiment, the B lymphocyte stimulator binding polypeptides and B lymphocyte stimulator binding polypeptide compositions are administered in combination with an antimalarial (e.g., hydroxychloroquine), sulfasalazine, anti-TNF antibody, and methotrexate.

In an additional embodiment, B lymphocyte stimulator binding polypeptides and B lymphocyte stimulator binding polypeptide compositions are administered alone or in combination with one or more intravenous immune globulin preparations. Intravenous immune globulin preparations that may be administered with the B lymphocyte stimulator binding polypeptides and B lymphocyte stimulator binding polypeptide compositions include, but not limited to, GAMMAR™ (immune globulin (intravenous)), IVEEGAM™ (immune globulin (intravenous)), SANDOGLOBULIN™ (immune globulin (intravenous)), GAMMAGARD S/D™ (immune globulin (intravenous)), and GAMIMUNE™ (immune globulin (intravenous)). In a specific embodiment, B lymphocyte stimulator binding polypeptides and B lymphocyte stimulator binding polypeptide compositions are administered in combination with intravenous immune globulin preparations in transplantation therapy (e.g., bone marrow transplant).

CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In an additional embodiment, the B lymphocyte stimulator binding polypeptides and B lymphocyte stimulator binding polypeptide compositions are administered alone or in combination with an anti-inflammatory agent. Anti-inflammatory agents that may be administered with the B lymphocyte stimulator binding polypeptides and B lymphocyte stimulator binding polypeptide compositions include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions are administered in combination with a chemotherapeutic agent. Chemotherapeutic agents that may be administered with the B lymphocyte stimulator binding polypeptides and B lymphocyte stimulator binding polypeptide compositions include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, B lymphocyte stimulator binding polypeptides and B lymphocyte stimulator binding polypeptide compositions are administered in combination with CHOP (cyclophosphamide, doxorubicin, vincristine, and prednisone) or any combination of the components of CHOP. In another embodiment, B lymphocyte stimulator binding polypeptides and B lymphocyte stimulator binding polypeptide compositions are administered in combination with Rituximab. In a further embodiment, B lymphocyte stimulator binding polypeptides and B lymphocyte stimulator binding polypeptide compositions are administered with Rituxmab and CHOP, or Rituxmab and any combination of the components of CHOP.

In an additional embodiment, the B lymphocyte stimulator binding polypeptides and B lymphocyte stimulator binding polypeptide compositions are administered in combination with cytokines. Cytokines that may be administered with the B lymphocyte stimulator binding polypeptides and B lymphocyte stimulator binding polypeptide compositions include, but are not limited to, GM-CSF, G-CSF, IL-2, IL-3, IL-4, IL-5, IL-6, IL-7, IL-10, IL-12, IL13, IL-15, anti-CD40, CD40L, IFN-alpha (IFN-α), IFN-beta (IFN-β), IFN-gamma (IFN-γ), TNF-alpha (TNF-α), and TNF-beta (TNF-β). In preferred embodiments, B lymphocyte stimulator binding polypeptides and B lymphocyte stimulator binding polypeptide compositions are administered with B lymphocyte stimulator (e.g., amino acids 134-285 of SEQ ID NO:173). In another embodiment, B lymphocyte stimulator binding polypeptides and B lymphocyte stimulator binding polypeptide compositions may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22. In preferred embodiments, the B lymphocyte stimulator binding polypeptides and B lymphocyte stimulator binding polypeptide compositions are administered in combination with IL-4 and IL-10.

In one embodiment, the B lymphocyte stimulator binding polypeptides and B lymphocyte stimulator binding polypeptide compositions are administered in combination with one or more chemokines. In specific embodiments, the B lymphocyte stimulator binding polypeptides and B lymphocyte stimulator binding polypeptide compositions are administered in combination with an α(C×C) chemokine selected from the group consisting of gamma-interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B cell stimulatory factor (PBSF)); and/or a β(CC) chemokine selected from the group consisting of: RANTES (regulated on activation, normal T expressed and secreted), macrophage inflammatory protein-1 alpha (MIP-1α), macrophage inflammatory protein-1 beta (MIP-1β), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1γ), macrophage inflammatory protein-3 alpha (MIP-30α), macrophage inflammatory protein-3 beta (MIP-3β), macrophage inflammatory protein-4 (MIP-4/DC-CK-1/PARC), eotaxin, Exodus, and I-309; and/or the γ(C) chemokine, lymphotactin.

In another embodiment, the B lymphocyte stimulator binding polypeptides and B lymphocyte stimulator binding polypeptide compositions are administered with chemokine beta-8, chemokine beta-1, and/or macrophage inflammatory protein-4. In a preferred embodiment, the B lymphocyte stimulator binding polypeptides and B lymphocyte stimulator binding polypeptide compositions are administered with chemokine beta-8.

In an additional embodiment, the B lymphocyte stimulator binding polypeptides and B lymphocyte stimulator binding polypeptide compositions are administered in combination with an IL-4 antagonist. IL-4 antagonists that may be administered with the B lymphocyte stimulator binding polypeptides and B lymphocyte stimulator binding polypeptide compositions include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including B lymphocyte stimulator binding polypeptide fragments, such as, for example, those described herein).

The invention also encompasses combining the polynucleotides and/or polypeptides (and/or agonists or antagonists thereof) with other proposed or conventional hematopoietic therapies. Thus, for example, the polynucleotides and/or polypeptides (and/or agonists or antagonists thereof) can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations of the B lymphocyte stimulator binding polypeptides and B lymphocyte stimulator binding polypeptide compositions with compounds generally used to treat aplastic anemia, such as, for example, methenolene, stanozolol, and nandrolone; to treat iron-deficiency anemia, such as, for example, iron preparations; to treat malignant anemia, such as, for example, vitamin $B_{12}$ and/or folic acid; and to treat hemolytic anemia, such as, for example, adrenocortical steroids, e.g., corticoids. See, e.g., Resegotti et al., *Panminerva Medica,* 23:243-248 (1981); Kurtz, *FEBS Letters,* 14a:105-108 (1982); McGonigle et al., *Kidney Int.,* 25:437-444 (1984); and Pavlovic-Kantera, Expt. Hematol., 8(supp. 8):283-291 (1980), the contents of each of which are hereby incorporated by reference in their entireties.

Compounds that enhance the effects of or synergize with erythropoietin are also useful as adjuvants herein, and include but are not limited to, adrenergic agonists, thyroid hormones, androgens, hepatic erythropoietic factors, erythrotropins, and erythrogenins. See, for example, Dunn, *Current Concepts in Erythropoiesis* (John Wiley and Sons, Chichester, England 1983); Kalmani, *Kidney Int.,* 22:383-391 (1982); Shahidi, *New Eng. J. Med.,* 289:72-80 (1973); Urabe et al., *J. Exp. Med.,* 149:1314-1325 (1979); Billat et al., *Expt. Hematol.,* 10:133-140 (1982); Naughton et al., *Acta Haemat.,* 69:171-179 (1983); Cognote et al., in abstract 364, *Proceedings 7th Intl. Cong. of Endocrinology* (Quebec City, Quebec, Jul. 1-7, 1984); and Rothman et al., *J. Surg. Oncol.,* 20:105-108 (1982). Methods for stimulating hematopoiesis comprise administering a hematopoietically effective amount (i.e., an amount which effects the formation of blood cells) of a pharmaceutical composition containing polynucleotides and/or polypeptides (and/or agonists or antagonists thereof) to a patient. The polynucleotides and/or polypeptides and/or agonists or antagonists thereof are administered to the patient by any suitable technique, including but not limited to parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin $B_{12}$, folic acid and/or adrenocortical steroids.

In an additional embodiment, the B lymphocyte stimulator binding polypeptides and B lymphocyte stimulator binding polypeptide compositions are administered in combination with hematopoietic growth factors. Hematopoietic growth factors that may be administered with the B lymphocyte stimulator binding polypeptides and B lymphocyte stimulator binding polypeptide compositions include, but are not limited to, LEUKINE™ (sargramostim) and NEUPOGEN™ (filgrastim).

In an additional embodiment, the B lymphocyte stimulator binding polypeptides and B lymphocyte stimulator binding polypeptide compositions are administered in combination with fibroblast growth factors. Fibroblast growth factors that may be administered with the B lymphocyte stimulator binding polypeptides and B lymphocyte stimulator binding polypeptide compositions include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

Additionally, the B lymphocyte stimulator binding polypeptides and B lymphocyte stimulator binding polypeptide compositions may be administered alone or in combination with other therapeutic regimens, including but not limited to, radiation therapy. Such combinatorial therapy may be administered sequentially and/or concomitantly.

Kits for Detecting and/or Quantitating B Lymphocyte Stimulator or B Lymphocyte Stimulator-like Polypeptides The present invention is also directed to an assay kit which can be useful in screening for the presence of B lymphocyte stimulator and/or quantitating B lymphocyte stimulator concentrations in a fluid, such as, for example, a biological fluid (e.g., blood, serum, synovial fluid).

In a particular embodiment of the present invention, an assay kit is contemplated which comprises in one or more containers one or more B lymphocyte stimulator binding polypeptides and optionally, a detection means for determining the presence of a B lymphocyte stimulator-B lymphocyte stimulator binding polypeptide interaction or the absence thereof. The kit further optionally contains B lymphocyte stimulator protein that may be used, for example as a control. The B lymphocyte stimulator binding polypeptide may be free or expressed on the surface of a phage.

In a specific embodiment, either the B lymphocyte stimulator binding polypeptide or the B lymphocyte stimulator protein is labeled. As further discussed herein, a wide range of labels can be used accordance with the present invention, including but not limited to conjugating the recognition unit to biotin by conventional means. Alternatively, the label may comprise, e.g., a fluorogen, an enzyme, an epitope, a chromogen, or a radionuclide. Preferably, the biotin is conjugated by covalent attachment to either the B lymphocyte stimulator binding polypeptide or the B lymphocyte stimulator protein. Preferably, the B lymphocyte stimulator binding polypeptide is immobilized on a solid support. The detection means employed to detect the label will depend on the nature of the label and can be any known in the art, e.g., film to detect a radionuclide, an enzyme substrate that gives rise to a detectable signal to detect the presence of an enzyme, antibody to detect the presence of an epitope, etc.

The invention also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. In one preferred embodiment the kit comprises a vial containing B lymphocyte stimulator binding polypeptides conjugated to a toxin or a label (as described herein). Such conjugated binding polypeptide may be used to kill a particular population of cells or to quantitate a particular population of cells. In a preferred embodiment, such conjugated B lymphocyte stimulator binding polypeptides are used to kill monocyte cells expressing the membrane-bound form of B lymphocyte stimulator. In another preferred embodiment, such conjugated B lymphocyte stimulator binding polypeptides are used to quantitate monocyte cells expressing the membrane-bound form of B lymphocyte stimulator. In another preferred embodiment, such conjugated B lymphocyte stimulator binding polypeptides are used to kill B cells expressing B lymphocyte stimulator receptor on their surface. In another preferred embodiment, such conjugated B lymphocyte stimulator binding polypeptides are used to quantitate B cells expressing B lymphocyte stimulator receptor on their surface.

The present invention provides kits that can be used in the above methods. In one embodiment, a kit comprises a B lymphocyte stimulator binding polypeptide, preferably a purified B lymphocyte stimulator binding polypeptide, in one or more containers. In an alternative embodiment, a kit comprises a B lymphocyte stimulator binding polypeptide fragment that specifically binds to B lymphocyte stimulator. In a specific embodiment, the kits of the present invention contain a substantially isolated B lymphocyte stimulator polypeptide as a control. Preferably, the kits of the present invention further comprise a control binding polypeptide which does not react with B lymphocyte stimulator. In another specific embodiment, the kits of the present invention contain a means for detecting the binding of a B lymphocyte stimulator binding polypeptide to B lymphocyte stimulator (e.g., the B lymphocyte stimulator binding polypeptide may be conjugated to a detectable substrate such as a fluorescent compound, an enzymatic substrate, a radioactive compound or a luminescent compound, or a second antibody which recognizes the B lymphocyte stimulator binding polypeptide may be conjugated to a detectable substrate). In specific embodiments, the kit may include a recombinantly produced or chemically synthesized B lymphocyte stimulator. The B lymphocyte stimulator provided in the kit may also be attached to a solid support. In a more specific embodiment the detecting means of the above-described kit includes a solid support to which B lymphocyte stimulator is attached. Such a kit may also include a non-attached reporter-labeled anti-B lymphocyte stimulator binding polypeptide antibody. In this embodiment, binding of the B lymphocyte stimulator binding polypeptide to B lymphocyte stimulator can be detected by binding of the said reporter-labeled antibody. Alternatively, or in addition, the detecting means may include a labeled, competing antigen.

In an additional embodiment, the invention includes a diagnostic kit for use in screening serum containing B lymphocyte stimulator or B lymphocyte stimulator-like polypeptides. The diagnostic kit includes a substantially isolated B lymphocyte stimulator binding polypeptide specifically reactive with B lymphocyte stimulator target, and means for detecting the binding of B lymphocyte stimulator target to the B lymphocyte stimulator binding polypeptide. In one embodiment, the B lymphocyte stimulator binding polypeptide is attached to a solid support.

In one diagnostic configuration, test serum is reacted with a solid phase reagent having a surface-bound B lymphocyte stimulator binding polypeptide according to the present invention. After B lymphocyte stimulator binds to a specific B lymphocyte stimulator binding polypeptide, the unbound serum components are removed by washing, reporter-labeled anti-B lymphocyte stimulator binding polypeptide antibody is added, unbound anti-B lymphocyte stimulator binding polypeptide antibody is removed by washing, and a reagent is reacted with reporter-labeled anti-B lymphocyte stimulator binding polypeptide antibody to bind reporter to the reagent in proportion to the amount of bound B lymphocyte stimulator binding polypeptide on the solid support. Typically, the reporter is an enzyme which is detected by incubating the solid phase in the presence of a suitable fluorometric, luminescent or colorimetric substrate.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated B lymphocyte stimulator binding polypeptides.

Thus, the invention provides an assay system or kit for carrying out this diagnostic method. The kit generally includes a support with surface-bound recombinant B lymphocyte stimulator, and a reporter-labeled anti-B lymphocyte stimulator binding polypeptide antibody for detecting surface-bound anti-B lymphocyte stimulator binding polypeptide.

Methods of Screening for B Lymphocyte Stimulator Binding Molecules

The invention also encompasses screening methods for identifying polypeptides and nonpolypeptides that bind B lymphocyte stimulator, and the B lymphocyte stimulator binding molecules identified thereby. This method comprises the steps of:
(a) contacting B lymphocyte stimulator or B lymphocyte stimulator-like polypeptide with a plurality of molecules; and
(b) identifying molecule(s) that binds the B lymphocyte stimulator or B lymphocyte stimulator-like polypeptide.

The step of contacting the B lymphocyte stimulator protein or B lymphocyte stimulator-like protein with the plurality of molecules may be effected in a number of ways. For example, one may contemplate immobilizing B lymphocyte stimulator target on a solid support and bringing a solution of the plurality of molecules in contact with the immobilized B lymphocyte stimulator target. Such a procedure would be akin to an affinity chromatographic process, with the affinity matrix being comprised of the immobilized B lymphocyte stimulator protein or B lymphocyte stimulator-like polypeptide. The molecules having a selective affinity for the B lymphocyte stimulator or B lymphocyte stimulator-like polypeptide can then be purified by affinity selection. The nature of the solid support, process for attachment of the B lymphocyte stimulator or B lymphocyte stimulator-like polypeptide to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" using a B lymphocyte stimulator target protein, optionally in the presence of an inducer should one be required for expression, to determine if any selective affinity interaction takes place between the B lymphocyte stimulator target protein and the individual clone. Prior to contacting the B lymphocyte stimulator target protein with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for B lymphocyte stimulator or B lymphocyte stimulator-like polypeptide. Furthermore, the amino acid sequence of the polypeptide having a selective affinity for the B lymphocyte stimulator protein or B lymphocyte stimulator-like protein can be determined directly by conventional means, or the coding sequence of the DNA encoding the polypeptide can frequently be determined more conveniently. The primary amino acid sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any B lymphocyte stimulator or B lymphocyte stimulator-like polypeptide, or alternatively, unbound polypeptides, from a mixture of B lymphocyte stimulator or B lymphocyte stimulator-like polypeptide and the plurality of polypeptides prior to attempting to determine or to detect the presence of a selective affinity interaction. One or more such a wash steps may be particularly desirable when the B lymphocyte stimulator or B lymphocyte stimulator-like polypeptide or the plurality of polypeptides is bound to a solid support.

The plurality of molecules provided according to this method may be provided by way of diversity libraries, such as random or combinatorial peptide or non-peptide libraries which can be screened for molecules that specifically bind to B lymphocyte stimulator. Peptide libraries may be designed such that the polypeptides encoded by the libraries are automatically fused to a polypeptide linker moiety, for example. Many libraries are known in the art that can be used, e.g., chemically synthesized libraries, recombinant (e.g., phage display libraries), and in vitro translation-based libraries. Examples of chemically synthesized libraries are described in Fodor et al., *Science,* 251:767-773 (1991); Houghten et al., *Nature,* 354:84-86 (1991); Lam et al., *Nature,* 354:82-84 (1991); Medynski, *Bio/Technology,* 12:709-710 (1994); Gallop et al., *J. Medicinal Chemistry,* 37(9):1233-1251 (1994); Ohlmeyer et al., *Proc. Natl. Acad. Sci. USA,* 90:10922-10926 (1993); Erb et al., *Proc. Natl. Acad. Sci. USA,* 91:11422-11426 (1994); Houghten et al., *Biotechniques,* 13:412 (1992); Jayawickreme et al., *Proc. Natl. Acad. Sci. USA,* 91:1614-1618 (1994); Salmon et al., *Proc. Natl. Acad. Sci. USA,* 90:11708-11712 (1993); PCT publication WO 93/20242; and Brenner and Lerner, *Proc. Natl. Acad. Sci. USA,* 89:5381-5383 (1992).

Examples of phage display libraries are described in Scott and Smith, *Science,* 249:386-390 (1990); Devlin et al., *Science,* 249:404-406 (1990); Christian et al., *J. Mol. Biol.,* 227:711-718 (1992); Lenstra, *J. Immunol. Meth.,* 152:149-157 (1992); Kay et al., *Gene,* 128:59-65 (1993); and PCT publication WO 94/18318.

In vitro translation-based libraries include but are not limited to those described in PCT publication WO 91/05058 and Mattheakis et al., *Proc. Natl. Acad. Sci. USA,* 91:9022-9026 (1994).

By way of examples of non-peptide libraries, a benzodiazepine library (see, e.g., Bunin et al., *Proc. Natl. Acad. Sci. USA,* 91:4708-4712 (1994) can be adapted for use. Peptoid libraries (Simon et al., *Proc. Natl. Acad. Sci. USA,* 89:9367-9371 (1992)) can also be used. Another example of a library that can be used, in which the amide functionalities in peptides have been permethylated to generate a chemically transformed combinatorial library, is described by Ostresh et al. (*Proc. Natl. Acad. Sci. USA,* 91:11138-11142 (1994)).

The variety of non-peptide libraries that are useful in the present invention is great. For example, Ecker and Crooke, *Bio/Technology,* 13:351-360 (1995) list benzodiazepines, hydantoins, piperazinediones, biphenyls, sugar analogs, betamercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, *Adv. Exp. Med. Biol.,* 251:215-218 (1989); Scott and Smith, Science, 249:386-390 (1990); Fowlkes et al., *BioTechniques,* 13:422-427 (1992); Oldenburg et al., *Proc. Natl. Acad. Sci. USA,* 89:5393-5397 (1992); Yu et al., *Cell,* 76:933-945 (1994); Staudt et al., *Science,* 241:577-580 (1988); Bock et al., *Nature,* 355:564-566 (1992); Tuerk et al., *Proc. Natl. Acad. Sci. USA,* 89:6988-6992 (1992); Ellington et al., *Nature,* 355:850-852 (1992); U.S. Pat. No. 5,096,815; U.S. Pat. No. 5,223,409; and U.S. Pat. No. 5,198,346, all to Ladner et al.; Rebar and Pabo, *Science,* 263:671-673 (1993); and PCT publication WO 94/18318.

In a specific embodiment, screening to identify a molecule that binds B lymphocyte stimulator can be carried out by contacting the library members with B lymphocyte stimulator or B lymphocyte stimulator-like polypeptide immobilized on a solid phase and harvesting those library members that bind to the B lymphocyte stimulator or B lymphocyte stimulator-like polypeptide. Examples of such screening methods, termed "panning" techniques are described by way of example in Parmley and Smith, *Gene,* 73:305-318 (1998); Fowlkes et al., *BioTechniques,* 13:422-427 (1992); PCT publication WO 94/18318; and in references cited therein.

In another embodiment, the two-hybrid system for selecting interacting proteins in yeast (Fields and Song, *Nature*, 340:245-246 (1989); Chien et al., *Proc. Natl. Acad. Sci. USA*, 88:9578-9582 (1991)) can be used to identify molecules that specifically bind to B lymphocyte stimulator or B lymphocyte stimulator-like polypeptides.

Where the B lymphocyte stimulator binding molecule is a polypeptide, the polypeptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid, that certain amino acid positions in a peptide remain fixed (e.g., as cysteine), or that positions 4, 8, and 9, for example, of a decapeptide library be limited to permit several but less than all of the twenty naturally-occurring amino acids. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a B lymphocyte stimulator binding molecule that is a polypeptide, the polypeptide may have about 6 to less than about 60 amino acid residues, preferably about 6 to about 10 amino acid residues, and most preferably, about 6 to about 22 amino acids. In another embodiment, a B lymphocyte stimulator binding polypeptide has in the range of 15-100 amino acids, or 20-50 amino acids.

The selected B lymphocyte stimulator binding polypeptide can be obtained by chemical synthesis or recombinant expression.

The specific B lymphocyte stimulator binding polypeptides disclosed herein were isolated using phage display technology, to identify B lymphocyte stimulator binding polypeptides exhibiting particular preselected binding properties. These B lymphocyte stimulator binding polypeptides were isolated initially by screening nine phage display libraries, that is, populations of recombinant bacteriophage transformed to express an exogenous recombinant polypeptide on their surface. In order to isolate new polypeptide binding moieties for a particular target, such as B lymphocyte stimulator, screening of peptide libraries, for example using phage display techniques, is especially advantageous, in that very large numbers (e.g., $5 \times 10^9$) of potential binders can be tested and successful binders isolated in a short period of time.

In order to prepare a phage library of potential binding polypeptides to screen for members of the library that are B lymphocyte stimulator binding polypeptides, a candidate binding domain is selected to serve as a structural template for the polypeptides to be displayed in the library. The phage library is made up of polypeptide analogues of this template or "parental binding domain." The parental binding domain is a polypeptide molecule that may be a naturally occurring or synthetic protein or polypeptide, or polypeptide region or domain of a protein. The parental binding domain may be selected based on knowledge of a known interaction between the parental binding domain and a target protein, but this is not critical. In fact, it is not essential that the parental binding domain have any affinity for a target at all because its purpose is to provide a structure from which a multiplicity of polypeptide analogues (a "library") can be generated, which multiplicity of polypeptide analogues will include one or more binding polypeptides that exhibit the desired binding and release properties with respect to B lymphocyte stimulator target proteins (and any other properties selected).

Knowledge of the exact polypeptide that will serve as the parental binding domain, or knowledge of a class of proteins or domains to which the parental binding domain belongs can be useful in determining the conditions under which B lymphocyte stimulator binding polypeptides optimally bind B lymphocyte stimulator target proteins as well as the conditions under which B lymphocyte stimulator binding polypeptides optimally release B lymphocyte stimulator target proteins. Similarly, the binding and/or release conditions may be selected with regard to known interactions between a binding domain and the B lymphocyte stimulator target protein, for example, to favor the interaction under the binding and/or release conditions, or they may be selected without regard to such known interactions. Likewise, the parental binding domain can be selected taking into account a desired binding and/or release condition or not. It is understood that if the binding domain analogues of a library are unstable under a proposed or desired binding or release condition, no useful binding polypeptides may be obtained.

In selecting the parental binding domain, the most important consideration is how the analogue domains will be presented to the B lymphocyte stimulator target protein, that is, in what conformations the B lymphocyte stimulator target and the polypeptide analogues will contact one another. In preferred embodiments, for example, the polypeptide analogues will be generated by insertion of synthetic DNA encoding the polypeptide analogue into a replicable genetic package, resulting in display of the domain on the surface of a microorganism, such as M13 phage, using techniques as described in Kay et al., *Phage Display of Peptides and Proteins: A Laboratory Manual* (Academic Press, Inc.; San Diego 1996) and U.S. Pat. No. 5,223,409 (Ladner et al.), incorporated herein by reference. For formation of phage display libraries, it is preferred to use structured polypeptides as the parental binding domain or template, as opposed to unstructured, linear peptides. Mutation of surface residues in a protein domain or polypeptide molecule will usually have little effect on the overall structure or general properties (such as size, stability, and temperature of denaturation) of the protein; while at the same time mutation of surface residues may profoundly affect the binding properties of the molecule. The more tightly a polypeptide segment is constrained, the less likely it is to bind to any particular target. If it does bind, however, the binding is likely to be tighter and more specific. Thus, it is preferred to select a parental binding domain wherein the parental polypetide has structure and, thereby in turn, select a structure for the polypeptide analogues of the library, which is constrained within a framework having some degree of rigidity.

Preferably the protein domain that is used as the template or parental domain for generating the library of domain analogues will be a peptide molecule that is a relatively small protein or polypeptide. Small polypeptides offer several advantages over large proteins: First, the mass per binding site is reduced. Highly stable protein domains having low molecular weights, for example, Kunitz domains (~7 kilodaltons, kDa), Kazal domains (~7 kDa), *Cucurbida maxima* trypsin inhibitor (CMTI) domains (~3.5 kDa), and endothelin (~2 kDa), can show much higher binding per gram than do antibodies (150 kDa) or single chain scFv antibodies (30 kDa). Second, the possibility of non-specific binding is reduced because there is less molecular surface available for nonspecific binding. Third, small polypeptides can be engineered to have unique tethering sites in a way that is impracticable for larger proteins or antibodies. For example, small proteins and polypeptides can be engineered to have lysines only at sites suitable for tethering to a chromatography matrix. This is not feasible for antibodies. Fourth, a constrained polypeptide structure is more likely to retain its functionality when transferred (with the structural domain intact) from one framework to another. For instance, the binding domain structure is likely to be transferable from the framework used for presentation in a library, such as displayed on a phage, to an isolated protein removed from the presentation framework or immobilized on a chromatographic substrate.

In specific embodiments, the B lymphocyte stimulator binding polypeptides are immobilized. B lymphocyte stimulator binding polypeptide molecules according to the invention may be immobilized, for example, on chromatographic support materials to form efficient B lymphocyte stimulator separation or affinity chromatographic media. Immobilized B lymphocyte stimulator binding polypeptides have uses that include, but are not limited to, detecting, isolating or removing B lymphocyte stimulator target proteins from solutions. One strategy for generating B lymphocyte stimulator binding polypeptide molecules that can be immobilized, for example, on matrices, resins, or supports, involves selecting appropriate binding domain templates such that B lymphocyte stimulator binding polypeptide molecules are generated that have one or more amino acids that may be used to covalently link the B lymphocyte stimulator binding polypeptide to a chromatographic resin or substrate to form an affinity resin. Similarly, the N-terminal amino group or the C-terminal carboxyl group of a peptide molecule may be modified by adding a capping group to render it inert or a functional group, which permits linkage to a support medium. For example, the C-terminal carboxyl group of a protein domain may be converted to an amide or a hydrazide ($-NH-NH_2$) group for reaction with an aldehyde-functional substrate or other amine-reactive substrate. This technique is preferred. Another preferred modification of B lymphocyte stimulator binding polypeptides useful for linking a B lymphocyte stimulator binding polypeptide molecule to a chromatography material is a polypeptide linker comprising, or alternatively consisting of, the amino acid sequence Pro-Gly-Pro-Glu-Gly-Gly-Gly-Lys (SEQ ID NO:13).

In one non-limiting example of a screening procedure to obtain B lymphocyte stimulator binding polypeptides encompassed by the invention, the phage in a phage display library are contacted with and allowed to bind a B lymphocyte stimulator target protein that is immobilized on a solid support. Those phage that display non-binding polypeptides are separated from those that bind the B lymphocyte stimulator target protein. Any of various techniques known in the art may be applied to dissociate the bound phage from the immobilized B lymphocyte stimulator protein, and to collect and/or amplify the phage and/or their nucleic acid contents. Using these techniques it is possible to identify a B lymphocyte stimulator binding phage that is about 1 in 20 million in the population. Libraries, displaying 10-20 million or more potential binding peptide molecules each, are rapidly screened to find high-affinity B lymphocyte stimulator binding polypeptides.

In each round of screening, the diversity of a population falls until only efficient binding polypeptides remain, that is, the process converges. Typically, a phage display library will contain several closely related binding polypeptides (10 to 50 different binding polypeptides out of 10 million). Indications of convergence include increased binding (measured by phage titers) and recovery of closely related sequences. After a first set of binding polypeptide molecules is identified, the sequence information can be used to design other libraries biased for members having additional desired properties, for example, discrimination between different forms of B lymphocyte stimulator (e.g., the membrane form and the soluble form of B lymphocyte stimulator) and fragments thereof, or discrimination between B lymphocyte stimulator and closely related impurities in a feed stream.

Such techniques make it possible not only to screen a large number of potential binding polypeptides, but make it practical to repeat the binding and elution cycles and to build secondary, biased libraries for screening polypeptide analogue-displaying phage that meet specific criteria. Using these techniques, a polypeptide analogue biased library may be screened to reveal members that bind tightly, that is, have high affinity for B lymphocyte stimulator target protein, under the screening conditions.

In the present invention target B lymphocyte stimulator protein molecules were biotinylated and then bound to streptavidin-coated magnetic particles. Nine phage display libraries of different design were screened for the ability to bind the immobilized B lymphocyte stimulator. Each library was characterized by M13 phage displaying variegated peptides of different lengths and overall structure: A library designated TN6/6 ($2\times10^8$ variants) displayed a variegated 12-mer with two internal invariant cysteines to form a hexamer loop structure. A library designated TN7/4 ($2.3\times10^9$ variants) presented a variegated 13-mer having two internal invariant cysteines to form a heptamer loop structure. A library designated TN8/9 ($5\times10^9$ variants) displayed a variegated 14-mer with two internal invariant cysteines to form an octamer loop structure. A library designated TN9/4 ($3.2\times10^9$ variants) presented a variegated 16-mer having two internal invariant cysteines to form a nonamer loop structure. A library designated TN10/9 ($2.5\times10^9$ variants) displayed a variegated 16-mer with two internal invariant cysteines to form a decamer loop structure. A library designated TN12/1 ($1.4\times10^9$ variants) presented a variegated 18-mer having two internal invariant cysteines to form a dodecamer loop structure. A library designated as Substrate Phage Library #2, having a diversity of about $2\times10^8$ amino acid sequences, was designed to include a linear peptide-variegated region in the display polypeptide consisting of 13 consecutive amino acids, and the display polypeptide design allowed any amino acid residue except cysteine to occur at each position. Finally, two commercially available linear phage display libraries were also screened, designated PhD 7 and PhD 12, respectively (New England Biolabs). The PhD 7 library displayed a linear random-sequence 7-mer; the PhD 12 library displayed a random-sequence 12-mer.

B lymphocyte stimulator binding phage were isolated and collected from all of the libraries except PhD 7.

After analysis of the sequences isolated from the library screenings, several families of B lymphocyte stimulator binding peptides were defined (see, consensus sequences A-G and H-L, above). The amino acid sequences of the B lymphocyte stimulator-binding "hits" from the first rounds of screening are set forth in Tables 1-8 (infra).

In order to obtain B lymphocyte stimulator binding polypeptides having an even higher affinity for B lymphocyte stimulator targets, a specialized library was prepared, i.e., a B lymphocyte stimulator affinity maturation library, based on variegation of high affinity examplars of the PhD 12 library (see Example 6). This library was designed to provide a population enriched with polypeptides likely to show high affinity for B lymphocyte stimulator. The selections from this library were performed to eliminate, by prolonged competition with soluble eluants of soluble B lymphocyte stimulator or other B lymphocyte stimulator binding polypeptides, all but the polypeptides having the highest affinity for B lymphocyte stimulator. A large family of high affinity B lymphocyte stimulator binding polypeptides was isolated from four rounds of screening the affinity maturation library, and their amino acid sequences appear in Table 13 (infra).

As it within the scope of the present invention to screen phage libraries that bind one or more of the various forms of B lymphocyte stimulator, the following outlines some assays that may be used in screening for B lymphocyte stimulator binding polypeptides that bind the soluble form of B lymphocyte stimulator, the membrane-bound form of B lymphocyte stimulator, or both the soluble and the membrane-bound forms of B lymphocyte stimulator. Assays to determine the specificity of binding polypeptides for different forms of a protein are commonly known in the art and may be readily adapted for determining the specificity of B lymphocyte stimulator binding polypeptides for different forms of B lymphocyte stimulator.

B lymphocyte stimulator binding polypeptides (including molecules comprising, or alternatively consisting of, B lymphocyte stimulator binding polypeptide fragments or variants thereof) may be screened in a variety of assays to identify those B lymphocyte stimulator binding polypeptides that specifically bind to the soluble form of B lymphocyte stimulator. B lymphocyte stimulator binding polypeptides may be assayed in neutralization assays described herein (see Examples 7 and 8) or otherwise known in the art. For example, B lymphocyte stimulator binding polypeptides may be tested for their ability to inhibit soluble B lymphocyte stimulator from binding a B lymphocyte stimulator receptor. The B lymphocyte stimulator receptor used in these assays may be an isolated B lymphocyte stimulator receptor (e.g., B lymphocyte stimulator receptor conjugated to agaorose beads) or may be present on the cell surface of cell lines that express B lymphocyte stimulator receptors which include, but are not limited to, peripheral CD20+ B cells, IM-9, REH, ARH-77, Namalwa, and RPMI-8226 B cell tumor lines.

B lymphocyte stimulator binding polypeptides (including molecules comprising, or alternatively consisting of, B lymphocyte stimulator binding polypeptide fragments or variants thereof) may be screened in a variety of assays commonly known in the art to identify those B lymphocyte stimulator binding polypeptides that specifically bind to the membrane-bound form of B lymphocyte stimulator. For example, B lymphocyte stimulator binding polypeptides may be assayed for binding B lymphocyte stimulator protein present on cell membranes of cells that express B lymphocyte stimulator. Cell lines that express B lymphocyte stimulator that might be useful for testing B lymphocyte stimulator binding polypeptide binding to membrane-bound form of B lymphocyte stimulator include, K-562, HL-60, THP-1, and U937 cells.

Additionally, B lymphocyte stimulator binding polypeptides may be screened against cells engineered to express an "uncleavable" form of B lymphocyte stimulator in order to determine their specificity for the membrane-bound form of B lymphocyte stimulator. Mutations in B lymphocyte stimulator which may achieve this result include, but are not limited to, the mutation or deletion of amino acid residues Lys-132 and/or Arg-133 of the B lymphocyte stimulator sequence shown in SEQ ID NO:173. A typical mutagenesis might include mutation of one or both of residues Lys-132 or Arg-133 to alanine residues. Cells expressing such an "uncleavable" form of B lymphocyte stimulator provide a profound reagent to use in assaying the ability of B lymphocyte stimulator binding polypeptides to bind the membrane-bound form of B lymphocyte stimulator.

B lymphocyte stimulator binding polypeptides (including molecules comprising, or alternatively consisting of, B lymphocyte stimulator binding polypeptide fragments or variants) may be screened in a variety of assays to identify those B lymphocyte stimulator binding polypeptides or B lymphocyte stimulator binding polypeptide fragments or variants that specifically bind to the soluble form and membrane-bound form of B lymphocyte stimulator. This can readily be determined by performing assays to distinguish binding to the soluble form and assays to distinguish binding to the membrane-bound form (such as the assays described herein or otherwise known in the art), and identifying the B lymphocyte stimulator binding polypeptides that bind both forms.

Additionally, B lymphocyte stimulator binding polypeptides may be screened for the ability to inhibit, stimulate or not significantly alter B lymphocyte stimulator activity, e.g., the ability of B lymphocyte stimulator: to bind to its receptor (e.g., TACI and BCMA), to stimulate B cell proliferation, to stimulate immunoglobulin secretion by B cells, to activate B cells, to increase B cell lifespan and/or to stimulate a B lymphocyte stimulator receptor signaling cascade (e.g., to activate calcium-modulator and cyclophilin ligand ("CAML"), calcineurin, nuclear factor of activated T cells transcription factor ("NF-AT"), nuclear factor-kappa B ("NF-kappa B"; NF-κB), activator protein-1 (AP-1), SRF, extracellular-signal regulated kinase 1 (ERK-1), polo like kinases (PLK), ELF-1, high mobility group I (HMG-I), and/or high mobility group Y (HMG-Y)). Assays that may be used to screen for the effects on B lymphocyte stimulator activity are described herein (see, for example, Examples 7, 8, and 12) and are commonly known in the art.

Anti-B lymphocyte stimulator Binding Polypeptide Antibodies

Further polypeptides useful herein relate to antibodies and T-cell antigen receptors (TCR) which immunospecifically bind a B lymphocyte stimulator binding polypeptide (as determined by immunoassays well known in the art for assaying specific antibody-antigen binding). Antibodies include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-id) antibodies (including, e.g., anti-id antibodies to antibodies), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins may have both a heavy and light chain. In specific embodiments, the immunoglobulin molecules are IgG1. In other specific embodiments, the immunoglobulin molecules are IgG4. An array of IgG, IgE, IgM, IgD, IgA, and IgY heavy chains may be paired with a light chain of the kappa or lambda forms.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 to Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715, WO 92/08802, WO 91/00360, WO 92/05793; Tutt et al., *J. Immunol.*, 147:60-69 (1991); U.S. Pat. Nos. 4,474, 893; 4,714,681; 4,925,648; 5,573,920; 5,601,819; Kostelny et al., *J. Immunol.*, 148:1547-1553 (1992).

Antibodies of the present invention may be described or specified in terms of the epitope(s) or portion(s) of a B lymphocyte stimulator binding polypeptide of the present invention which they recognize or specifically bind. Antibodies which specifically bind any epitope or polypeptide of the present invention may also be excluded. Therefore, the present invention includes antibodies that specifically bind B lymphocyte stimulator binding polypeptides of the present invention, and allows for the exclusion of the same.

In further preferred, nonexclusive embodiments, the antibodies (e.g., anti-idiotypic antibodies) inhibit one or more biological activities of B lymphocyte stimulator through specific binding to B lymphocyte stimulator. In more preferred embodiments, the antibody inhibits B lymphocyte stimulator-mediated B cell proliferation.

Antibodies of the present invention may also be described or specified in terms of their cross-reactivity. Antibodies that do not bind any other B lymphocyte stimulator binding polypeptide are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a B lymphocyte stimulator binding polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a B lymphocyte stimulator binding polypeptide of the present invention are also included in the present invention. Further included in the present invention are antibodies which bind polypeptides encoded by polynucleotides, the complement of which hybridize to a polynucleotides of the present invention under stringent hybridization conditions (as described herein). Antibodies of the present invention may also be described or specified in terms of their binding affinity to a B lymphocyte stimulator binding polypeptide. Preferred binding affinities include those with a dissociation constant or Kd less than $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to a B lymphocyte stimulator binding polypeptide as determined by any method known in the art for determining competitive binding. In preferred embodiments, the antibody competitively inhibits binding to the B lymphocyte stimulator binding polypeptide by at least 95%, at least 90%, at least 85%, at least 80%, at least 75%, at least 70%, at least 60%, or at least 50%.

Antibodies of the present invention (e.g., anti-idiotypic antibodies) may act as agonists or antagonists of B lymphocyte stimulator or alternatively may not significantly alter B lymphocyte stimulator mediated activity. For example, the present invention includes antibodies (e.g., anti-idiotypic antibodies) which disrupt B lymphocyte stimulator/B lymphocyte stimulator receptor (e.g., TACI and BCMA) interactions either partially or fully. In another example, antibodies of the invention enhance B lymphocyte stimulator/B lymphocyte stimulator receptor interactions either partially or fully. Such activity may be the result of, for example, the antibody binding to a B lymphocyte stimulator binding polypeptide, or alternatively as a result of direct binding of the antibody (e.g., an anti-idiotypic antibody to B lymphocyte stimulator).

Preferably, antibodies of the present invention bind a B lymphocyte stimulator binding polypeptide disclosed herein, a portion thereof, or an antibody that binds a B lymphocyte stimulator binding polypeptide disclosed herein, or a portion thereof. The invention features both B lymphocyte stimulator binding polypeptide-specific antibodies and antibodies that are specific to B lymphocyte stimulator binding polypeptide/B lymphocyte stimulator complexes. The invention features antibodies that enhance B lymphocyte stimulator/B lymphocyte stimulator binding polypeptide binding and/or B lymphocyte stimulator/B lymphocyte stimulator receptor binding. The invention also features antibodies that do not inhibit or reduce B lymphocyte stimulator/B lymphocyte stimulator binding polypeptide binding and/or B lymphocyte stimulator/B lymphocyte stimulator receptor binding. The invention also features B lymphocyte stimulator binding polypeptide specific antibodies that inhibit binding of the B lymphocyte stimulator binding polypeptide to B lymphocyte stimulator or B lymphocyte stimulator binding to B lymphocyte stimulator receptor. In specific embodiments, antibodies are provided that inhibit B lymphocyte stimulator activity or B lymphocyte stimulator receptor activity by at least 95%, at least 90%, at least 85%, at least 80%, at least 75%, at least 70%, at least 60%, or at least 50% of the activity in absence of the antibody. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra).

The antibodies of the present invention may be used, for purposes including, but not limited to, purify, detect, and target the B lymphocyte stimulator binding polypeptides of the present invention, including both in vitro and in vivo diagnostic and therapeutic methods. For example, the antibodies have use in immunoassays for qualitatively and quantitatively measuring levels of B lymphocyte stimulator in biological samples. See, e.g., Harlow et al., *Antibodies: A Laboratory Manual* (Cold Spring Harbor Laboratory Press, Cold Spring Harbor 1988).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugated) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396 387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/ blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

According to certain embodiments of the invention, multivalent B lymphocyte stimulator binding polypeptides are administered to the host animal. Multivalent B lymphocyte stimulator binding polypeptide complexes may be prepared using techniques and materials known in the art such as, for example, by cross-linking the polypeptide to a carrier protein (e.g., bovine serum albumin (BSA), human albumin, keyhole limpet hemocyanin (KLH), or succinylated KLH) by use of conventional cross-linking reagents.

In specific embodiments multivalent B lymphocyte stimulator binding polypeptides are administered in the form of multiple antigen peptides (MAP) (Tam, *J. Imm. Meth.*, 124: 53-61 (1989); Tam, *Proc. Natl. Acad. Sci. USA*, 85:5409-5413 (1988)). In this form, the multivalent B lymphocyte stimulator binding polypeptide is synthesized on a branching lysyl matrix using solid-phase peptide synthesis methods. Recognition units in the form of MAP may be prepared by methods known in the art (Tam, 1989, supra; Tam, 1988, supra), or, for example, by a stepwise solid-phase procedure on MAP resins (Applied Biosystems), utilizing methodology established by the manufacturer. MAP peptides may be synthesized comprising (B lymphocyte stimulator binding polypeptide)$_2$ Lys$_1$, (B lymphocyte stimulator binding polypeptide)$_4$ Lys$_3$, (B lymphocyte stimulator binding polypeptide)$_8$ Lys$_6$ or more levels of branching.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual* (Cold Spring Harbor Laboratory Press, Cold Spring Harbor 1988); Hammerling et al., in *Monoclonal Antibodies and T-Cell Hybridomas* (Elsevier, N.Y. 1981), pp. 563-681 (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

A "monoclonal antibody" may comprise, or alternatively consist of, two proteins, i.e., a heavy and a light chain.

Methods for producing and screening for specific antibodies using hybridoma technology are routine and well known in the art and are discussed in detail in the Examples (e.g., Example 9). In a non-limiting example, mice can be immunized with a polypeptide or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC), to form hybridoma cells. Hybridomas are selected and cloned by limited dilution. The hybridoma clones are then assayed by methods known in the art for cells that secrete antibodies capable of binding a polypeptide. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen according to the invention with myeloma cells and then screening the hybridomas resulting from the fusion for hybridoma clones that secrete an antibody able to bind a B lymphocyte stimulator binding polypeptide.

Antibody fragments that recognize specific epitopes may be generated by known techniques. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles that carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods,* 182:41-50 (1995); Ames et al., *J. Immunol. Methods,* 184:177-186 (1995); Kettleborough et al., *Eur. J. Immunol.,* 24:952-958 (1994); Persic et al., *Gene,* 187 9-18 (1997); Burton et al., *Advances in Immunology,* 57:191-280 (1994); PCT international application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., *BioTechniques,* 12(6):864-869 (1992); and Sawai et al., *AJRI,* 34:26-34 (1995); and Better et al., *Science,* 240:1041-1043 (1988) (said references incorporated herein by reference in their entireties).

Examples of techniques which can be used to produce single-chain Fvs and antibodies include those described in U.S. Pat. Nos. 4,946,778 and 5,258,498; Huston et al., *Methods in Enzymology,* 203:46-88 (1991); Shu et al., *Proc. Natl. Acad. Sci. USA,* 90:7995-7999 (1993); and Skerra et al., *Science,* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science,* 229:1202 (1985); Oi et al., *BioTechniques,* 4:214 (1986); Gillies et al., *J. Immunol. Methods,* 125:191-202 (1989); U.S. Pat. Nos. 5,807,715; 4,816,567; and 4,816397, which are incorporated herein by reference in their entirety. A humanized antibody is an antibody molecule made using one or more complementarity determining regions (CDRs) from a non-human species antibody that binds the desired antigen and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature,* 332:323 (1988), which are incorporated herein by reference in their entireties.) Antibodies can be humanized using a variety of techniques known in the art including, for example, CDR-grafting (EP 239 400; PCT publication WO 91/09967; U.S. Pat. Nos. 5,225,539; 5,530,101; and 5,585,089), veneering or resurfacing (EP 592 106; EP 519 596; Padlan, *Molecular Immunology,* 28(4/5):489-498 (1991); Studnicka et al., *Protein Engineering,* 7(6):805-814 (1994); Roguska. et al., *Proc. Natl. Acad. Sci. USA,* 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a binding polypeptide. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, *Int. Rev. Immunol.,* 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent 598 877; U.S. Pat. Nos. 5,413,923; 5,625,126; 5,633,425; 5,569,825; 5,661,016; 5,545,806; 5,814,318; 5,885,793; 5,916,771; and 5,939,598, each of which is incorporated by reference herein in its entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope. (See, Jespers et al., *Bio/technology,* 12:899-903 (1988).)

Further, antibodies to the B lymphocyte stimulator binding polypeptides can, in turn, be utilized to generate anti-idiotype antibodies that "mimic" B lymphocyte stimulator binding polypeptides, using techniques well known to those skilled in the art. (See, e.g., Greenspan & Bona, *FASEB J.,* 7(5):437-444 (1989) and Nissinoff, *J. Immunol.,* 147(8):2429-2438 (1991).) For example, antibodies which bind to and competitively inhibit the binding of B lymphocyte stimulator binding polypeptide to B lymphocyte stimulator can be used to generate anti-idiotypes that "mimic" the B lymphocyte stimulator/B lymphocyte stimulator binding polypeptide binding domain and, as a consequence, bind to and neutralize or enhance B lymphocyte stimulator binding to B lymphocyte stimulator receptor (e.g., TACI and BCMA). Such neutralizing anti-idiotypes or Fab fragments of such anti-idiotypes can be used in therapeutic regimens to bind B lymphocyte stimulator and/or neutralize or enhance B lymphocyte stimulator mediated activity. In a specific embodiment, anti-idiotypic antibodies can be used to bind B lymphocyte stimulator, and thereby block its biological activity. In another specific embodiment, anti-idiotypic antibodies can be used to bind B lymphocyte stimulator, and thereby enhance its biological activity (e.g., via multimerization of B lymphocyte stimulator).

Polynucleotides Encoding Antibodies

The invention further provides polynucleotides comprising a nucleotide sequence encoding an antibody of the invention and fragments thereof. The invention also encompasses polynucleotides that hybridize under stringent hybridization conditions, e.g., as defined supra, to polynucleotides that encode an antibody, preferably, that specifically binds to B lymphocyte stimulator or a B lymphocyte stimulator binding polypeptide.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques,* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning: A Laboratory Manual,* 2d Ed. (Cold Spring Harbor Laboratory, Cold Spring Harbor, N.Y. 1990) and *Current Protocols in Molecular Biology,* Ausubel et al., eds. (John Wiley & Sons, NY 1993), which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., *J. Mol. Biol.,* 278: 457-479 (1998) for a listing of human framework regions). Preferably, the polynucleotide generated by the combination of the framework regions and CDRs encodes an antibody that specifically binds B lymphocyte stimulator or a B lymphocyte stimulator binding polypeptide. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci. USA,* 81:851-855 (1984); Neuberger et al., *Nature,* 312:604-608 (1984); Takeda et al., *Nature,* 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine antibody and a human immunoglobulin constant region, e.g., humanized antibodies.

Alternatively, techniques described for the production of single chain antibodies (U.S. Pat. No. 4,946,778; Bird, *Science,* 242:423-42 (1988); Huston et al., *Proc. Natl. Acad. Sci. USA,* 85:5879-5883 (1988); and Ward et al., *Nature,* 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., *Science,* 242:1038-1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody, or fragment, derivative or analog thereof, (e.g., a heavy or light chain of an antibody or a single chain antibody), requires construction of an expression vector containing a polynucleotide that encodes the antibody. Once a polynucleotide encoding an antibody molecule or a heavy or light chain of an antibody or portion thereof (preferably containing the heavy or light chain variable domain) has been obtained, the vector for the production of the antibody molecule may be produced by recombinant DNA technology using techniques well known in the art. Thus, methods for preparing a protein by expressing a polynucleotide containing an antibody-encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule, or a heavy or light chain thereof, or a heavy or light chain variable domain, operably linked to a promoter. Such vectors may include the nucleotide sequence encoding the constant region of the antibody molecule (see, e.g., PCT publication WO 86/05807; PCT publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody. Thus, the invention includes host cells containing a polynucleotide encoding an antibody, or a heavy or light chain thereof, or a single chain antibody, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules. Such host-expression systems represent vehicles by which the coding sequences of interest may be produced and subsequently purified, but also represent cells which may, when transformed or transfected with the appropriate nucleotide coding sequences, express an antibody molecule in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene*, 45:101 (1986); Cockett et al., *Bio/Technology*, 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO J.*, 2:1791 (1983)), in which the antibody coding sequence may be ligated individually into the vector in frame with the lacZ coding region so that a fusion protein is produced; pIN vectors (Inouye & Inouye, *Nucleic Acids Res.*, 13:3101-3109 (1985); Van Heeke & Schuster, *J. Biol. Chem.*, 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. See, e.g., Logan & Shenk, *Proc. Natl. Acad. Sci. USA*, 81:355-359 (1984). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, Bittner et al., *Methods in Enzymol.*, 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed.

To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, NSO, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell*, 11:223 (1977)), hypoxanthine-guanine phosphoribosyltransferase (Szybalska & Szybalski, *Proc. Natl. Acad. Sci. USA*, 48:202 (1992)), and adenine phosphoribosyltransferase (Lowy et al., *Cell*, 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Proc. Natl. Acad. Sci. USA*, 77:357 (1980); O'Hare et al., *Proc. Natl. Acad. Sci. USA*, 78:1527 (1981)); gpt, which confers resistance to mycophenolic acid (Mulligan & Berg, *Proc. Natl. Acad. Sci. USA*, 78:2072 (1981)); neo, which confers resistance to the aminoglycoside G-418; Wu and Wu, *Biotherapy*, 3:87-95 (1991); Tolstoshev, *Ann. Rev. Pharmacol. Toxicol.*, 32:573-596 (1993); Mulligan, *Science*, 260:926-932 (1993); and Morgan and Anderson, *Ann. Rev. Biochem.*, 62:191-217 (1993); May, 1993, TIB TECH 11(5):155-215); and hygro, which confers resistance to hygromycin (Santerre et al., *Gene*, 30:147 (1984)). Methods commonly known in the art of recombinant DNA technology may be routinely applied to select the desired recombinant clone, and such methods are described, for example, in *Current Protocols in Molecular Biology*, Ausubel et al., eds. (John Wiley & Sons, NY 1993); Kriegler, *Gene Transfer and Expression, A Laboratory Manual* (Stockton Press, NY 1990); and *Current Protocols in Human Genetics*, Dracopoli et al., eds. (John Wiley & Sons, NY 1994), Chapters 12 and 13; Colberre-Garapin et al., *J. Mol. Biol.*, 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.*, 3:257 (1983)).

The host cell may be co-transfected with two expression vectors, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature*, 322:52 (1986); Kohler, *Proc. Natl. Acad. Sci. USA*, 77:2197 (1980)). The coding sequences for the heavy and light chains may comprise cDNA or genomic DNA.

Once an antibody molecule has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalent and non-covalent conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than B lymphocyte stimulator binding polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., *Immunol. Lett.*, 39:91-99 (1994); U.S. Pat. No. 5,474,981; Gillies et al., *Proc. Natl. Acad. Sci. USA*, 89:1428-1432 (1992); Fell et al., *J. Immunol.*, 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307 434; EP 367 166; PCT publications WO 96/04388; WO 91/06570; Ashkenazi et al., *Proc. Natl. Acad. Sci. USA,* 88:10535-10539 (1991); Zheng et al., J. Immunol. 154:5590-5600 (1995); and Vil et al., *Proc. Natl. Acad. Sci. USA,* 89:11337-11341 (1992) (said references incorporated by reference in their entireties).

As discussed, supra, the polypeptides corresponding to a B lymphocyte stimulator binding polypeptide may be fused or conjugated to the above antibody portions to increase the in vivo half life of the polypeptides or for use in immunoassays using methods known in the art. Further, the B lymphocyte stimulator binding polypeptides may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394 827; Traunecker et al., *Nature,* 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., *J. Biochem.,* 270:3958-3964 (1995)). In many cases, the Fc part in a fusion protein is beneficial in therapy and diagnosis, and thus can result in, for example, improved pharmacokinetic properties (see, EP-A-232 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., *J. Molecular Recognition,* 8:52-58 (1995); Johanson et al., *J. Biol. Chem.,* 270:9459-9471 (1995). Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA,* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell,* 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (See, PCT publication WO 97/33899), AIM II (See, PCT publication WO 97/34911), Fas Ligand (Takahashi et al., *Int. Immunol.,* 6:1567-1574 (1994)), VEGI (See, PCT publication WO 99/23105), CD40 Ligand, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in *Monoclonal Antibodies And Cancer Therapy,* Reisfeld et al., eds. (Alan R. Liss, Inc. 1985), pp. 243-56; Hellstrom et al., "Antibodies For Drug Delivery", in *Controlled Drug Delivery (2nd Ed.),* Robinson et al., eds. (Marcel Dekker, Inc. 1987), pp. 623-53; Thorpe, "Antibody Carriers Of Cytotoxic Agents In Cancer Therapy: A Review", in *Monoclonal Antibodies '84: Biological And Clinical Appli-* cations, Pinchera et al., eds., pp. 475-506 (1985); "Analysis, Results, And Future Prospective Of The Therapeutic Use Of Radiolabeled Antibody in Cancer Therapy", in *Monoclonal Antibodies For Cancer Detection And Therapy*, Baldwin et al., eds. (Academic Press 1985), pp. 303-16; and Thorpe et al., "The Preparation And Cytotoxic Properties Of Antibody-Toxin Conjugates", *Immunol. Rev.*, 62:119-58 (1982).

Antibodies may also be attached to solid supports, which are particularly useful for immunoassays or purification of the B lymphocyte stimulator binding polypeptide. Such solid supports include, but are not limited to, glass, cellulose, polyacrylamide, nylon, polystyrene, polyvinyl chloride or polypropylene.

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., *Current Protocols in Molecular Biology*, Ausubel et al., eds. (John Wiley & Sons, NY 1993), which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., *Current Protocols in Molecular Biology*, Ausubel et al., eds. (John Wiley & Sons, NY 1993) at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., *Current Protocols in Molecular Biology*, Ausubel et al., eds. (John Wiley & Sons, NY 1993) at 10.8.1.

ELISAs comprise preparing antigen, coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., *Current Protocols in Molecular Biology*, Ausubel et al., eds. (John Wiley & Sons, NY 1993) at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., $^{3}H$ or $^{125}I$) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the diseases, disorders, or conditions disclosed herein. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant B lymphocyte stimulator expression and/or activity, including, but not limited to, any one or more of the diseases, disorders, or conditions described herein.

The treatment and/or prevention of diseases, disorders, or conditions associated with aberrant expression and/or activity of B lymphocyte stimulator or B lymphocyte stimulator receptor includes, but is not limited to, alleviating symptoms associated with those diseases, disorders or conditions. The antibodies of the invention may also be used to target and kill cells expressing B lymphocyte stimulator on their surface and/or cells having B lymphocyte stimulator bound to their surface. This targeting may be the result of binding of the antibody to B lymphocyte stimulator binding polypeptides that have been coadministered, or alternatively, the result of direct binding of the antibody to B lymphocyte stimulator. Antibodies of the invention may be provided in pharmaceutically acceptable compositions as known in the art or as described herein.

Non-limiting examples of the ways in which the antibodies of the present invention may be used therapeutically includes binding B lymphocyte stimulator binding polypeptides of the present invention that have been coadministered in order to bind or neutralize B lymphocyte stimulator, or by direct cytotoxicity of the antibody, e.g., as mediated by complement (CDC) or by effector cells (ADCC). B lymphocyte stimulator binding polypeptides and anti-B lymphocyte stimulator binding polypeptide antibodies may be administered either locally or systemically. Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy, anti-tumor agents, antibiotics, and immunoglobulin). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides of the present invention, fragments or regions thereof, for both immunoassays directed to and therapy of disorders related to polypeptides, including fragments thereof, of the present invention. Such antibodies, fragments, or regions, will preferably have an affinity for polypeptides, including fragments thereof. Preferred binding affinities include those with a dissociation constant or $K_D$ less than $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Demonstration of Therapeutic or Prophylactic Activity of Antibodies

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic and/or Prophylactic Administration and Composition

The invention provides methods of treatment, inhibition and prophylaxis by administration to a subject of an effective amount of a B lymphocyte stimulator binding compound or pharmaceutical composition, preferably an antibody. In a preferred embodiment, the compound is substantially purified (e.g., substantially free from substances that limit its effect or produce undesired side effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound, e.g., encapsulation in liposomes, microparticles, microcapsules, recombinant cells capable of expressing the compound, receptor-mediated endocytosis (see, e.g., Wu and Wu, *J. Biol. Chem.*, 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, care must be taken to use materials to which the protein does not absorb.

In another embodiment, the compound or composition can be delivered in a vesicle, in particular a liposome (see Langer, *Science*, 249:1527-1533 (1990); Treat et al., in *Liposomes in the Therapy of Infectious Disease and Cancer*, Lopez-Berestein and Fidler, eds. (Liss, New York 1989), pp. 353-365; Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng., 14:201 (1987); Buchwald et al., Surgery, 88:507 (1980); Saudek et al., N. Engl. J. Med., 321: 574 (1989)). In another embodiment, polymeric materials can be used (see Medical Applications of Controlled Release, Langer and Wise, eds. (CRC Press, Boca Raton, Fla. 1974); Controlled Drug Bioavailability, Drug Product Design and Performance, Smolen and Ball, eds. (Wiley, New York 1984); Ranger and Peppas, J. Macromol. Sci. Rev. Macromol. Chem., 23:61 (1983); see also Levy et al., Science, 228:190 (1985); During et al., Ann. Neurol., 25:351 (1989); Howard et al., J. Neurosurg., 71:105 (1989)). In yet another embodiment, a controlled release system can be placed in proximity of the therapeutic target, thus requiring only a fraction of the systemic dose (see, e.g., Goodson, in Medical Applications of Controlled Release, Langer and Wise, eds. (CRC Press, Boca Raton, Fla. 1974), vol. 2, pp. 115-138 (1984)).

Other controlled release systems are discussed in the review by Langer (Science 249:1527-1533 (1990)).

In a specific embodiment where the compound is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA, 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds for use in the methods of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound used which will be effective in the treatment, inhibition and prevention of a disease or disorder associated with aberrant expression and/or activity of a polypeptide can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions. Optionally associated with such container(s) can be a notice in the

Diagnosis and Imaging

Labeled antibodies, and derivatives and analogs thereof, which specifically bind to a B lymphocyte stimulator binding polypeptide of interest can be used for diagnostic purposes to detect, diagnose, or monitor diseases and/or disorders associated with the aberrant expression and/or activity of B lymphocyte stimulator. The invention provides for the detection of aberrant expression of B lymphocyte stimulator, comprising (a) contacting cells or body fluid with a B lymphocyte stimulator binding polypeptide; (b) assaying the expression of B lymphocyte stimulator in cells or body fluid of an individual using one or more antibodies specific to the B lymphocyte stimulator binding polypeptide and (c) comparing the level of B lymphocyte stimulator expression with a standard B lymphocyte stimulator expression level, whereby an increase or decrease in the assayed B lymphocyte stimulator expression level compared to the standard expression level is indicative of aberrant expression.

The invention provides a diagnostic assay for diagnosing a disorder, comprising (a) contacting cells or body fluid with a B lymphocyte stimulator binding polypeptide; (b) assaying the expression of B lymphocyte stimulator in cells or body fluid of an individual using one or more antibodies specific to the B lymphocyte stimulator binding polypeptide of interest and (c) comparing the level of B lymphocyte stimulator expression with a standard B lymphocyte stimulator expression level, whereby an increase or decrease in the assayed B lymphocyte stimulator expression level compared to the standard expression level is indicative of a particular disorder. With respect to cancer, the presence of a relatively high amount of B lymphocyte stimulator in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies can be used to assay B lymphocyte stimulator protein levels in a biological sample using or routinely modifying classical immunohistological methods known to those of skill in the art (e.g., see Jalkanen et al., *J. Cell. Biol.*, 101:976-985 (1985); Jalkanen et al., *J. Cell. Biol.*, 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I) carbon, ($^{14}$C) sulfur ($^{35}$S), tritium ($^{3}$H), indium ($^{115}$In, $^{113m}$In, $^{112}$In, $^{111}$In) and technetium ($^{99}$Tc, $^{99m}$Tc), thallium (201Ti), gallium (68Ga, $^{67}$Ga), palladium ($^{103}$Pd), molybdenum ($^{99}$Mo), xenon ($^{133}$Xe), fluorine ($^{18}$F), $^{53}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

Techniques known in the art may be applied to label antibodies. Such techniques include, but are not limited to, the use of bifunctional conjugating agents (see, e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

One embodiment of the invention is the detection and diagnosis of a disease or disorder associated with aberrant expression of B lymphocyte stimulator in an animal, preferably a mammal and most preferably a human. In one embodiment, diagnosis comprises: (a) administering (for example, parenterally, subcutaneously, or intraperitoneally) to a subject an effective amount of a labeled molecule which specifically binds to B lymphocyte stimulator (e.g., a B lymphocyte stimulator binding polypeptide) or which specifically binds to a molecule that specifically binds to B lymphocyte stimulator (e.g., an anti-B lymphocyte stimulator binding polypeptide antibody); (b) waiting for a time interval following the administering for permitting the labeled molecule to preferentially concentrate at sites in the subject where the polypeptide is expressed (and for unbound labeled molecule to be cleared to background level); (c) determining background level; and (d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system. As described herein, specific embodiments of the invention are directed to the use of the antibodies to quantitate or qualitate concentrations of cells of B cell lineage or cells of monocytic lineage.

It will be understood by those skilled in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled antibody or antibody fragment will then preferentially accumulate at the location of cells which contain the specific polypeptide. In vivo tumor imaging is described in S. W. Burchiel et al., "Immunopharmacokinetics of Radiolabeled Antibodies and Their Fragments." (Chapter 13 in *Tumor Imaging: The Radiochemical Detection of Cancer*, S. W. Burchiel and B. A. Rhodes, eds. (Masson Publishing Inc. 1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In a further embodiment, monitoring of the disease or disorder is carried out by repeating the method for diagnosing the disease or disorder, for example, one month after initial diagnosis, six months after initial diagnosis, one year after initial diagnosis, etc. and comparing the results.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include but are not limited to computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Antibody Kits

The present invention provides kits that can be used in the above methods. In one embodiment, a kit comprises an antibody, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention comprise two or more antibodies (monoclonal and/or polyclonal) that recognize the same and/or different sequences or regions of a polypeptide according to the invention. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated protein(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

In another specific embodiment, any of the antibodies listed above are conjugated to a toxin or a label (as described supra). Such conjugated antibodies are used to kill a particular population of cells or to quantitate a particular population of cells. In a preferred embodiment, such conjugated antibodies are used to kill B cells expressing B lymphocyte stimulator receptor on their surface. In another preferred embodiment, such conjugated antibodies are used to quantitate B cells expressing B lymphocyte stimulator receptor on their surface.

In another specific embodiment, any of the antibodies listed above are conjugated to a toxin or a label (as described supra). Such conjugated antibodies are used to kill a particular population of cells or to quantitate a particular population of cells. In a preferred embodiment, such conjugated antibodies are used to kill monocyte cells expressing the membrane-bound form of B lymphocyte stimulator. In another preferred embodiment, such conjugated antibodies are used to quantitate monocyte cells expressing the membrane-bound form of B lymphocyte stimulator.

The antibodies of the invention also have uses as therapeutics and/or prophylactics which include, but are not limited to, in activating monocytes or blocking monocyte activation and/or killing monocyte lineages that express the membrane bound form of B lymphocyte stimulator on their cell surfaces (e.g., to treat, prevent, and/or diagnose myeloid leukemias, monocyte based leukemias and lymphomas, monocytosis, monocytopenia, rheumatoid arthritis, and other diseases or conditions associated with activated monocytes). In a specific embodiment, the antibodies fix complement. In other specific embodiments, as further described herein, the antibodies (or fragments thereof) are associated with heterologous polypeptides or nucleic acids (e.g. toxins, such as, compounds that bind and activate endogenous cytotoxic effecter systems, and radioisotopes; and cytotoxic prodrugs).

As discussed above, antibodies to the B lymphocyte stimulator binding polypeptides can, in turn, be utilized to generate anti-idiotype antibodies that "mimic" the B lymphocyte stimulator binding polypeptide, using techniques well known to those skilled in the art. (See, e.g., Greenspan & Bona, *FASEB J.*, 7(5):437-444 (1989), and Nissinoff, J. Immunol., 147(8):2429-2438 (1991)). For example, antibodies which bind to B lymphocyte stimulator binding polypeptides and competitively inhibit B lymphocyte stimulator/B lymphocyte stimulator binding polypeptide binding can be used to generate anti-idiotypes that "mimic" the B lymphocyte stimulator binding polypeptide/B lymphocyte stimulator binding domain and, as a consequence, bind to and, for example, neutralize B lymphocyte stimulator. Such neutralizing anti-idiotypes or Fab fragments of such anti-idiotypes can be used in therapeutic regimens to neutralize B lymphocyte stimulator. For example, such anti-idiotypic antibodies can be used to bind B lymphocyte stimulator and thereby block B lymphocyte stimulator mediated B cell activation, proliferation, survival and/or differentiation.

EXAMPLES

Isolation of B lymphocyte stimulator binding polypeptides and their use in accordance with this invention will be further illustrated below. The specific parameters included in the following examples are intended to illustrate the practice of the invention, and they are not presented to in any way limit the scope of the invention.

Example 1

Screening of Phage Display Libraries

Streptavidin-coated magnetic beads (Dynal M-280) were chosen for presentation of the target during screening because of their superior binding capacity compared to that of a 96 well plate. The binding capacity of the beads for biotinylated antibodies was 5-10 µg/mg of beads as stated by the manufacturer. For this study and the screening to follow, 5 µg of biotinylated recombinant B lymphocyte stimulator (obtained from Human Genome Sciences, Inc.) was allowed for each mg of beads. This amount of biotinylated B lymphocyte stimulator represents a 10-fold excess of target, for saturation of the beads. Unbound B lymphocyte stimulator was washed away. Bound biotinylated B lymphocyte stimulator was confirmed with detection using Mab 16C9 (murine anti-B lymphocyte stimulator, Human Genome Sciences) primary antibody and a goat anti-mouse HRP conjugate as the secondary antibody. An irrelevant monoclonal antibody (anti-TNFα) was used to probe a second set of beads to control for non-specific binding. The color reagent TMB was used and the assay read at OD 630 nm.

Nine phage display libraries, TN6/6, TN7/4, TN8/9, TN9/4, TN10/9, TN12/1, and Substrate Phage #2 (Dyax Corp., Cambridge, Mass. (US)), and PhD7 and PhD12 (New England Biolabs), were screened for B lymphocyte stimulator binders. The makeup of these libraries was as follows:

The TN6/6 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Cys-Xaa-Xaa-Xaa (SEQ ID NO:14) and providing 2.0×$10^8$ peptide diversity.

The TN7/4 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Cys-Xaa-Xaa-Xaa-Xaa (SEQ ID NO:15) and providing 2.3×$10^9$ peptide diversity.

The TN8/9 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Xaa-Xaa-Cys-Xaa-Xaa-Xaa (SEQ ID NO:16) and providing about 5×$10^9$ peptide diversity. The TN9/4 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Xaa-Xaa-Xaa-Cys-Xaa-Xaa-Xaa (SEQ ID NO:17) and providing about 3.2×$10^9$ peptide diversity.

The TN10/9 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Xaa-Xaa-Xaa-Xaa-Cys-Xaa-Xaa-Xaa (SEQ ID NO:18) and providing 2.5×$10^9$ peptide diversity.

The TN12/1 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Xaa-Xaa-Xaa-Xaa-Xaa-Xaa-Cys-Xaa-Xaa-Xaa (SEQ ID NO:19) and providing 1.4×$10^9$ peptide diversity.

Substrate Phage Library #2 was composed of recombinant M13 phage displaying a polypeptide insert of approximately 80 amino acids, having two streptavidin binding domains, a linear variegated segment of thirteen amino acids where all amino acids except Cys were permitted at each position, and a Factor Xa cleavage site, linked together with peptide linkers. This library provided a diversity of 2×$10^8$ display polypeptides.

Libraries PhD7 and PhD12 were composed of recombinant M13 phage displaying randomized linear seven- and twelve-amino acid peptides, respectively.

Screening was performed as described in PCT/US01/[ ], entitled "Binding Polypeptides for B Lymphocyte Stimulator Protein (BLyS™)", filed concurrently herewith.

At the conclusion of screening individual phage isolates were randomly selected and tested by ELISA for binding to B lymphocyte stimulator. The same isolates were submitted for DNA sequence analysis to identify the nucleotide and deduced amino acid sequence of the displayed peptide. Isolates were also tested for their ability to bind to recombinant B lymphocyte stimulator in feed streams of CHO supernatant and Sf9 supernatant (supplied by Human Genome Sciences, Inc.).

Each isolate was tested for binding to B lymphocyte stimulator by standard ELISA techniques where bound phage were detected with a monoclonal anti-phage antibody/HRP conjugate.

Amino acid sequences of the displayed peptides were derived from sequencing the phage isolate DNA inserts. Sequence data from the phage isolates were grouped by library and sorted according to the degree of similarity. The B lymphocyte stimulator binding phage isolate peptides are shown in Tables 1-8 below. These peptides represent the translation of the DNA sequences across the varied regions of the genes encoding the phage display fusion/peptide.

TABLE 1

TN6/6 Library B lymphocyte stimulator-binding Sequences

| Phage Isolate | Amino Acid Sequence | SEQ ID NO: |
|---|---|---|
| 453-01-B06 | HLRCWSTNCRYD | 20 |
| 453-01-A04 | VMDCLINRCDTV | 21 |

TABLE 2

TN7/4 Library B lymphocyte stimulator-binding Sequences

| Phage Isolate | Amino Acid Sequence | SEQ ID NO: |
|---|---|---|
| 453-01-B04 | KSKCFFPWECQQA | 22 |
| 453-01-D11 | AMKCYFPWECANG | 23 |
| 453-01-A05 | NVACYFPWECHHP | 24 |
| 453-01-D01 | NAPCYFPWECFSI | 25 |
| 453-01-D03 | SVNCWFPWECVGN | 26 |
| 453-01-A08 | KEPCYFYWECAVS | 27 |

TABLE 3

TN8/9 Library B lymphocyte stimulator-binding Sequences

| Phage Isolate | Amino Acid Sequence | SEQ ID NO: |
|---|---|---|
| 453-01-D04 | DTNCDLLTKMCGPQ | 28 |
| 453-01-C06 | GTPCDLLTKLCLLW | 29 |
| 453-01-D10 | MSECDLLTKICLMG | 30 |
| 453-01-B07 | VPFCDLLTKHCFEA | 31 |
| 453-01-B09 | VPFCDLLTKHCFEA | 32 |
| 453-01-C02 | WSACDLLTKQCVQV | 33 |
| 453-01-A06 | -DGCDELTKICGMK | 34 |
| 453-01-B03 | KSWCDELTKVCFDP | 35 |
| 453-01-B11 | KWMCDELTKQCQYV | 36 |
| 453-01-A02 | MKYCDELTKICVGW | 37 |
| 453-01-B05 | YFQCDELTKMCWQK | 38 |
| 453-01-A11 | AMHCDKLTKHCKFH | 39 |
| 453-01-A03 | VPYCDKLTKICQW- | 40 |
| 453-01-A07 | EVFCDVLTKVCFHD | 41 |
| 453-01-C09 | KPKCDVLTKMCDWL | 42 |
| 453-01-B02 | TQHCDVLTKQCFTI | 43 |
| 453-01-C01 | GHFCDRLTKYCFEP | 44 |
| 453-01-A09 | HIQCDRLTKSCLSV | 45 |
| 453-01-D05 | IKACDILTKVCWPP | 46 |
| 453-01-A01 | QFDCDPLTKYCGEF | 47 |
| 453-01-C07 | KMYCDHLTGYCWPE | 48 |
| 453-01-C11 | MQSCDILTGYCFKR | 49 |
| 453-01-D12 | GPWCDILTGFCLAQ | 50 |
| 453-01-C04 | SVRCDLLTGWCPVW | 51 |
| 453-01-B10 | PADCDPLTNICFWK | 52 |
| 453-01-D02 | TNVCDPLTNVCFMN | 53 |
| 453-01-C05 | EHWCDDLTHLCFRL | 54 |

TABLE 3-continued

TN8/9 Library B lymphocyte stimulator-binding Sequences

| Phage Isolate | Amino Acid Sequence | SEQ ID NO: |
|---|---|---|
| 453-01-D08 | GYWCDVLTNNCWKI | 55 |
| 453-01-C10 | LYNCDYLTRLCFEP | 56 |
| 453-01-C08 | HVDCLLHPKACYKY | 57 |
| 453-01-D07 | VQDCLLHPKACQMQ | 58 |
| 453-01-D09 | KFDCLLKPMFCSNH | 59 |
| 453-01-C12 | FADCLIHPKSCKPL | 60 |
| 453-01-D06 | HGNCYPFPWECESK | 61 |
| 453-01-B01 | MIIVLLLLRFAISR | 62 |
| 453-01-A12 | SLLVIFLLIGAGSL | 63 |

TABLE 4

TN9/4 Library B lymphocyte stimulator-binding Sequences

| Phage Isolate | Amino Acid Sequence | SEQ ID NO: |
|---|---|---|
| 453-01-G06 | FHPCDMLTGIWCQPN | 64 |
| 453-01-H01 | SKRCDLLTKMWCETE | 65 |
| 453-01-F02 | TKFCDRLTMPKCVWK | 66 |
| 453-01-E03 | NTFCPDPLTGRCVNP | 67 |
| 453-01-E11 | DWTCDPLFHRECIFE | 68 |
| 453-01-H09 | PQPCDLLFEKKCSIK | 69 |
| 453-01-H02 | RWHCDMLINPSCLPD | 70 |
| 453-01-E04 | KIQCDIVNLSSCVYP | 71 |
| 453-01-G11 | LNACDIVHPNYCSGM | 72 |
| 453-01-F01 | AKACSIVNLESCEYL | 73 |
| 453-01-H06 | RQACSIITPWGCPIP | 74 |
| 453-01-F10 | ADNCTVATLDFCYWT | 75 |
| 453-01-E05 | KPECNITKPQFCFGE | 76 |

TABLE 5

TN10 Library B lymphocyte stimulator-binding Sequences

| Phage Isolate | Amino Acid Sequence | SEQ ID NO: |
|---|---|---|
| 453-01-H07 | -NNCQWDELTSMCDPF | 77 |
| 453-01-F05 | SRLCHMDELTHVCVHF | 78 |
| 453-01-F09 | SRPCQIDELTKACFYN | 79 |
| 453-01-G09 | DRVCKLDFLTYNCLNH | 80 |
| 453-01-F04 | HSNCIMDLLTNRCFYD | 81 |
| 453-01-H03 | PFNCFHDPLTGLCLHS | 82 |

TABLE 5-continued

TN10 Library B lymphocyte stimulator-binding Sequences

| Phage Isolate | Amino Acid Sequence | SEQ ID NO: |
|---|---|---|
| 453-01-F03 | YDSCTYDRLTKQCYPS | 83 |
| 453-01-F07 | FHDCMYDALLGYCLPY | 84 |
| 453-01-G08 | NRSCDPLTRPKSCGL | 85 |
| 453-01-G04 | LSNCDWDDLIRQCLHD | 86 |
| 453-01-E01 | FWDCLFHPNSRYCVLS | 87 |
| 453-01-E10 | SRDCLLSPAMAWCGLD | 88 |

TABLE 6

TN12/1 Library B lymphocyte stimulator-binding Sequences

| Phage Isolate | Amino Acid Sequence | SEQ ID NO: |
|---|---|---|
| 453-01-H05 | GGNCYTDSLTKLHFCMGD | 89 |
| 453-01-H04 | --MCPRDPLTKAKLCNWH | 90 |
| 453-01-G03 | PNQCQDDLTKQWYSCHYH | 91 |
| 453-01-F11 | FDMCFDALTKQNFYCRFH | 92 |
| 453-01-F06 | RNMCVDRLTKLQHGCEGA | 93 |
| 453-01-G07 | DPECLTSFDRLTKMCWPW | 94 |
| 453-01-H11 | DDECHYDYLTHYMRCDYR | 95 |
| 453-01-G05 | FGGCNIDLLTNTMMCHRN | 96 |
| 453-01-G10 | HGPCYWDELTMQWHCNHH | 97 |
| 453-01-H12 | GAMCVDLLTYTFRPCMYA | 98 |
| 453-01-E07 | SNKCWDELTHAWAECGRF | 99 |
| 453-01-E09 | RPVCYKGYDILTTQCMPW | 100 |
| 453-01-G01 | PSRCWFDLLFNKFVCKRN | 101 |
| 453-01-H08 | RSGCVYDMLLMTMYCPSN | 102 |
| 453-01-H10 | SNRCEGDQLMRPPSCRHL | 103 |
| 453-01-F08 | YRMCWWDDLLRGFVCDFH | 104 |
| 453-01-E06 | HDGCYDELLYRWTRCEHR | 105 |
| 453-01-E08 | WAWCFDELVQRYFTCFDH | 106 |
| 453-01-E02 | LPECRQYFPWEKQVCSYW | 107 |

TABLE 7

PhD 12 Library B lymphocyte stimulator-binding Sequences

| Phage Isolate | Amino Acid Sequence | SEQ ID NO: |
|---|---|---|
| 453-02-B05 | VHYDSLTKMWTR | 108 |
| 453-02-D09 | FTDPLTKMSLHS | 109 |
| 453-02-C12 | GYDVLTKLYFVP | 110 |

TABLE 7-continued

PhD 12 Library B lymphocyte stimulator-binding Sequences

| Phage Isolate | Amino Acid Sequence | SEQ ID NO: |
|---|---|---|
| 453-02-A05 | YYDRLTKLYSSM | 111 |
| 453-02-B06 | LXKDPLTKLYIS | 112 |
| 453-02-A04 | GYDVLTKLXFVP | 113 |
| 453-02-B03 | RLYDPLTKLVLS | 114 |
| 453-02-B01 | MFDPLTKIAFPA | 115 |
| 453-02-D04 | FYDSLTKTNLRD | 116 |
| 453-02-B02 | GIYDKLTRAWLP | 117 |
| 453-02-B08 | KYDPLTRARXPL | 118 |
| 453-02-D06 | YIDQLTRLSLPS | 119 |
| 453-02-A09 | HqTFDILTRLHF | 120 |
| 453-02-B04 | WQFDVLTRSWTP | 121 |
| 453-02-A02 | GAAYDHLTRTWL | 122 |
| 453-02-D05 | YFDQLTHLSIKK | 123 |
| 453-02-A06 | AWDPLTMLVLPW | 124 |
| 453-02-D03 | ALWMDPLTGLAF | 125 |
| 453-02-B12 | WQFDVLTXSWTP | 126 |
| 453-02-A01 | WTDPLTHMEIYH | 127 |
| 453-02-C04 | WTDSLTGLWFPD | 128 |
| 453-02-C05 | YTDPLTGIVXPF | 129 |
| 453-02-D08 | YWDKLTMLHLGV | 130 |
| 453-02-D02 | YYDFLTRTVLPS | 131 |
| 453-02-A03 | RLDPLSKNDFPR | 132 |
| 453-02-A11 | LRYDPLLKSXIY | 133 |
| 453-02-D07 | LRYDPLLKSYIY | 134 |
| 453-02-A07 | YFDQFTHLSIKK | 135 |
| 453-02-C08 | YFDQXTHLSIKK | 136 |

TABLE 8

Substrate Phage Library B lymphocyte stimulator-binding Sequences

| Phage Isolate | Amino Acid Sequence | SEQ ID NO: |
|---|---|---|
| 453-02-E04 | EHYYTDPLTGARI | 137 |
| 453-02-F01 | EHYXTDPLTGARI | 138 |
| 453-02-E09 | EHYSTDPLTGARI | 139 |
| 453-02-E07 | EHYYTDPLXGXRI | 140 |
| 453-02-G05 | EHYYTDPLXGXRX | 141 |
| 453-02-G09 | EHYYTDPLXGARX | 142 |

TABLE 8-continued

Substrate Phage Library B lymphocyte stimulator-binding Sequences

| Phage Isolate | Amino Acid Sequence | SEQ ID NO: |
|---|---|---|
| 453-02-E06 | EHXYTDPLNGARX | 143 |
| 453-02-E05 | EHYYNDPLNGARX | 144 |
| 453-02-F04 | XHXYNDPLNGARX | 145 |
| 453-02-G07 | KPYYDPITKMTHH | 146 |
| 453-02-F06 | KPYYDPITKMSHH | 147 |
| 453-02-E08 | KPYYDPISKMTHH | 148 |
| 453-02-G08 | KPXXDPISKMTHH | 149 |
| 453-02-E01 | QIGYDELTKAWVT | 150 |
| 453-02-G02 | QLGYDELTKAWVT | 151 |
| 453-02-H06 | KIDELXMQNIIIW | 152 |
| 453-02-F08 | DHTDPLIQGLTKR | 153 |
| 453-02-H01 | WHDPLKHMHFHHE | 154 |
| 453-02-F03 | KHIDMETGLILQN | 155 |
| 453-02-G03 | MQVDPETGLKYEH | 156 |
| 453-02-E03 | XLDQHVNXXXYQS | 157 |
| 453-02-F10 | EXXXTXXLTGARX | 158 |
| 453-02-F02 | GPYNIXRLXGErX | 159 |
| 453-02-E02 | HIKMLHQGSFVGV | 160 |
| 453-02-H08 | HPTNTXXHQXVYS | 161 |
| 453-02-H05 | HRGQVXXLNGMvX | 162 |

X = amino acid unknown (all tables)
lower case = amino acid identity probable but not completely characterized Example 2

Immobilization of B lymphocyte stimulator Binding Polypeptides on Sepharose-4FF Beads On the basis of the above results, six display phage sequences were chosen for further study: TN7-01-A08 (SEQ ID NO:27), TN8-01-B07 (SEQ ID NO:31), TN10-01-F05 (SEQ ID NO:78), TN12-01-H05 (SEQ ID NO:89), PhD-02-C04 (SEQ ID NO:128), and PhD-02-C12 (SEQ ID NO:110).

In order to develop a suitable B lymphocyte stimulator affinity ligand, the identified display peptides were synthesized to order by a commercial vendor, with slight modifications:

Two amino acids of leader were added to each binding peptide at the N-terminus, in order to avoid leaving a free amine at the first amino acid of the sequence corresponding to the variegated region of the phage display template; the N-terminus was acetylated to prevent immobilization of the peptide to the chromatographic matrix through that position; a C-terminal linker was added (i.e., -PGPEGGGK; SEQ ID NO:13); and any internal lysines in the peptide were blocked with the group: ivDde (i.e., 1-(4,4-dimethyl-2,6-dioxocyclohex-1-ylidene)-3-methyl butyl-L-lysine). This group was intact on the finished synthesized peptides and was removed after immobilization or fluorescein labeling. As an alternative modification, peptides with internal lysines were also synthesized with C-terminal hydrazide functional groups, which could be immobilized onto activated aldehyde chromatographic media.

The peptides were immobilized onto NHS-activated SEPHAROSE-4 Fast Flow agarose media (Pharmaceia) at ligand densities targeted to 2 μmmol/ml. Actual ligand densities of peptides on the media ranged from 0.76 μmol/ml to 1.98 mmol/ml, as determined by amino acid analysis of immobilized peptide. All but one peptide was immobilized in aqueous conditions of 100 mM $KH_2PO_4$/150 mM NaCl/ 0.05% Tween 20, pH 7.5. For solubility reasons, the peptide DX217 (see, Table 9, below) was immobilized in 30% dimethyl formamide(DMF)/100 mM $KH_2PO_4$/150 mM NaCl/ 0.05% Tween 20, pH 7.5. Immobilization reactions were allowed to proceed for 2 hours at ambient temperature, followed by brief washing with pH 7.5 buffer. The Fast Flow SEPHAROSE media was then allowed to tumble at ambient temperature overnight to hydrolyze remaining NHS esters after which the media was washed to remove any unbound peptide. A solution of 2% hydrazine/DMF was used to deblock ligands containing ivDde-lysine. Media was then further washed with aqueous buffers and stored at 4° C. until packed into columns. Table 9 shows the sequences of the synthesized peptides and their measured densities on the agarose media.

TABLE 9

B lymphocyte stimulator Binding Peptides Synthesizes as Affinity Ligands

| Peptide Name | Isolate source | Sequence (potential disulfide loop underlined) | SEQ ID NO: |
|---|---|---|---|
| DX212 | 01-A08 | Ac-AGKEP<u>CYFYWEC</u>AVSGPGPEGGGK | 163 |
| DX214 | 01-B07 | Ac-AGVPF<u>CDLLTKHC</u>FEAGPGPEGGGK | 164 |
| DX216 | 01-F-5 | Ac-GSSRL<u>CHMDELTHVC</u>VHFAPPGPEGGGK | 165 |
| DX217 | 01-H05 | Ac-GDGGN<u>CYTDSLTKLHFC</u>MGDEPGPEGGGK | 166 |
| DX219 | 02-C12 | Ac-GYDVLTKLYFVPGGPGPEGGGK | 167 |
| DX221 | 02-C04 | Ac-WTDSLTGLWFPDGGPGPEGGGK | 168 |

Ac denotes N-terminal acetylation

B lymphocyte stimulator-Ligand Affinity Determination (Overview of Procedure)

Dissociation constants between the synthetic peptides and B lymphocyte stimulator (free in solution) were measured by fluorescence anisotropy (FA). In these experiments, the concentration of the fluorescein-labeled peptide is held constant and the B lymphocyte stimulator protein concentration was varied. The observed change in anisotropy is fit to the following equation via nonlinear regression to obtain the apparent $K_D$.

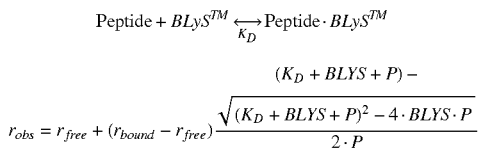

$$\text{Peptide} + BLyS^{TM} \underset{K_D}{\longleftrightarrow} \text{Peptide} \cdot BLyS^{TM}$$

$$r_{obs} = r_{free} + (r_{bound} - r_{free}) \frac{(K_D + BLYS + P) - \sqrt{(K_D + BLYS + P)^2 - 4 \cdot BLYS \cdot P}}{2 \cdot P}$$

where:
$r_{obs}$=observed anisotrpy, $r_{free}$=anisotropy of free peptide, $r_{bound}$=anisotropy of bound peptide, $K_D$=dissociation constant, BLyS™=total BLyS™ concentration, and P=total fluorescein labeled peptide concentration.

Binding reactions containing 50 nM fluorescein-labeled peptide and a varied concentration of B lymphocyte stimulator in a volume between 10 and 20 μL per well were performed in 384 well microplates. Reactions were assayed using a Tecan Polarion fluorescence polarization plate reader. Cross-competition studies between peptides were performed using 50 nM fluorescein-labeled peptide and 1-2 μM B lymphocyte stimulator in the presence and absence of 100 μM unlabeled peptide. The influence of pH on the observed $K_D$ was investigated at pH 6.0 using the primary binding buffer [15 mM sodium citrate, 120 mM NaCl, 0.01% Tween 20] and at pH 9.0 using 200 mM sodium bicarbonate, 125 mM sodium chloride. Other buffers in which dissociation constants of B lymphocyte stimulator Binding polypeptides were determined include: [pH 6.0, 0.01% Tween], [pH 6.0, 0.1% gelatin], [pH5.0, 0.01% Tween], [pH9.0, 0.1% Tween], [pH6.0, 15% ethylene glycol, 0.01% Tween], ], [pH5.0, 15% ethylene glycol, 0.01% Tween], and [pH9.0, 15% ethylene glycol, 0.01% Tween]. All six of the peptides (DX212, DX214, DX216, DX217, DX219, and DX221) bound B lymphocyte stimulator in solution with approximately the same affinity ($K_D$=0.5-2 μM). Cross-competition studies demonstrated that all peptides compete with each other for B lymphocyte stimulator binding, which suggests that they all bind to the same site on B lymphocyte stimulator.

Example 3

Design of Modified B Lymphocyte Stimulator Binding Peptides

Once a promising B lymphocyte stimulator binding polypeptide has been isolated, improvements to that polypeptide can be made by changing, adding or removing individual or multiple amino acid residues from the polypeptide. Amino acid substitutions can be conservative or non conservative. Conservative amino acids exchanges include, for example, the exchange of aromatic residues (e.g., phenylalanine, tryptophan, and tyrosine) for one another, the exchange of hydrophobic residues (e.g, leucine, isoleucine, and valine) for one another, the exchange of polar residues (e.g., glutamine and asparagine) for one another, the exchange of acidic residues (e.g., arginine, lysine, and histidine) for one another, and the exchange of small residues (e.g., alanine, serine, threonine, methionine, and glycine) for one another, the exchange of aromatic residues for one another. Additionally, nonclassical amino acids, chemical amino acid analogs, or chemically modified classical amino acids can be introduced as a substitution or addition to a B lymphocyte stimulator binding polypeptide of the invention. Non-classical amino acids include, but are not limited to, the D-isomers of the common amino acids, 2,4-diaminobutyric acid (Dbu), 4-aminobutyric acid (bAbu), 2-aminobutyric acid (Abu), 6-amino hexanoic acid (epsilon-Ahx), 2-aminoisobutyric acid (Aib), 3-aminoisobutyric acid (bAib), 3-aminopropanoic acid (bAla), ornithine (Orn), norleucine (Nle), norvaline (Nva), 3-hydroxyproline (3Hyp), 4-hydroxyproline (4Hyp), sarcosine (MeGly), citrulline, homocitrulline, cysteic acid, t-butylglycine, t-butylalanine, phenylglycine, cyclohexylalanine, fluoro-amino acids, designer amino acids such as β-methyl amino acids, Cα-methyl amino acids, Nα-methyl amino acids, and amino acid analogs in general. By way of example, four modified peptides based on the DX212 sequence have been designed:

1. Ac-AGK(Ac)EPCYFYWECAVSGPGPEGGGK (SEQ ID NO:169)—internal lysine side chain acetylated;
2. Ac-AGREPCYFYWECAVSGPGPEGGGK (SEQ ID NO:170)—arginine substitution;
3. Ac-AGQEPCYFYWECAVSGPGPEGGGK (SEQ ID NO:171)—glutamine substitution;
4. Ac-AGNleEPCYFYWECAVSGPGPEGGGK (SEQ ID NO:172)—norleucine substitution.

Ac denotes N-terminal acetylation.

Example 4

Biacore Analysis of the Affinity of B Lymphocyte Stimulator Binding Polypeptides Binding of B lymphocyte stimulator binding polypeptides to B lymphocyte stimulator, for example, can be analyzed by BIAcore analysis. Either B lymphocyte stimulator (or another antigen for which one wants to know the affinity of a B lymphocyte stimulator binding polypeptide) or B lymphocyte stimulator binding polpeptide can be covalently immobilized to a BIAcore sensor chip (CM5 chip) via amine groups using N-ethyl-N'-(dimethylaminopropyl)carbodiimide/N-hydroxysuccinimide chemistry. Various dilutions of B lymphocyte stimulator binding polypeptides or B lymphocyte stimulator (or other antigen for which one wants to know the affinity of a B lymphocyte stimulator binding polypeptide), respectively are flowed over the derivatized CM5 chip in flow cells at 15 microliters/min. for a total volume of 50 microliters. The amount of bound protein is determined during washing of the flow cell with HBS buffer (10 mM HEPES, pH7.4, 150 mM NaCl, 3.4 mM EDTA, 0.005% surfactant P20). Binding specificity for the protein of interest is determined by competition with soluble competitor in the presence the protein of interest.

The flow cell surface can be regenerated by displacing bound protein by washing with 20 microliters of 10 mM glycine-HCl, pH2.3. For kinetic analysis, the flow cells are tested at different flow rates and different polypeptide densities on the CM5 chip. The on-rates and off-rates can be determined using the kinetic evaluation program in BIAevaluation 3 software.

Example 5

B Lymphocyte Stimulator Binding Polypeptide Neutralization of Murine Splenocyte Proliferation To determine if an B lymphocyte stimulator binding polypeptide inhibits B lymphocyte stimulator mediated B cell proliferation, a splenocyte proliferation assay can be performed Briefly, murine splenocytes are isolated by flushing spleen with complete medium using a 25 g needle and 10 ml of complete medium (RPMI 1640 with 10% FBS containing 100 U/ml penicillin, 100 μl/ml streptomycin, 4 mM glutamine, $5\times10^{-5}$M (3-mercaptoethanol). The cells are passed through a 100 micron nylon filter to remove cell clumps. The cell suspension is then separated by gradient centrifugation at 400×g for 25 minutes at room temperature (one 15 ml conical tube/spleen; 3 ml Ficol, 10 ml cell suspension/spleen; Ficol 1083 from Sigma). The recovered cells are washed 3 times in complete medium and counted. Recovered cells are then diluted to a concentration of 3×10$^6$/ml in complete medium containing a 3× concentration of SAC (3×32 1:33,333 dilution of stock *Staph. aureus* Cowan strain; Calbiochem).

For each B lymphocyte stimulator binding polypeptide, 50 microliters of dilutions at 30 µg/ml, 3.0 µg/ml, and 0.3 µg/ml concentrations are aliquotted into individual wells of a 96 well plate in triplicate. Suitable positive controls, such as, for example monoclonal antibody 15C10, can also be used. Medium containing no B lymphocyte stimulator binding polypeptide is used as negative control. B lymphocyte stimulator protein is diluted in complete medium to concentrations of 300 ng/ml, 90 ng/ml and 30 ng/ml. 50 microliters of each of the B lymphocyte stimulator dilutions were then added to the B lymphocyte stimulator binding polypeptide dilution series in the plates. The plate containing the B lymphocyte stimulator binding polypeptide and B lymphocyte stimulator dilutions are then incubated for 30 minutes at 37° C., 5% $CO_2$, after which 50 microliters of the splenocyte cell suspension containing SAC is added to all wells. The plates are then incubated for 72 hours (37° C., 5% $CO_2$).

After 72 hours, each well is supplemented with 50 µlof complete medium containing 0.5 µCi of $^3$H-thymidine (6.7 Ci/mM; Amersham) and cells are incubated for an additional 20-24 hours at (37° C., 5% $CO_2$). Following incubation cells are harvested using a Tomtec Cell Harvester and filters counted in a TopCount Scintillation counter (Packard).

Example 6

In Vitro Screening of B lymphocyte stimulator Antagonists

The bioassay for assessing the effects of putative B lymphocyte stimulator antagonists is performed in triplicate in 96 well format by mixing equal volumes of B lymphocyte stimulator, responder cells, and putative antagonist each of which is prepared as a 3× stock reagent.

B-lymphocytes are purified from human tonsil by MACS (anti-CD3 depletion), washed, and resuspended in complete medium (CM) (RPMI 1640 with 10% FBS containing 100 U/ml penicillin, 100 µg/ml streptomycin, 4 mM glutamine, 5×10E-5 M beta-mercaptoethanol) at a concentration of 3×10e6 cells/mL. *Staphylococcus aureus*, Cowan I (SAC, CalBiochem) is added to cells at 3× concentration (3×=1:33, 333 dilution of stock).

Meanwhile, eight serial dilutions (3-fold) of potential antagonists are prepared in CM such that the diluted antagonists are at 3× the final concentrations to be tested in the assay. B lymphocyte stimulator binding polypeptides are routinely tested starting at a final concentration of 10 µg/mL and going down to about 1.5 ng/mL.

Human rBLyS was prepared in CM to 3× concentration (3×=300 ng/mL, 30 ng/mL, and 3 ng/mL) in CM. Potential inhibitors are routinely tested at several concentrations of B lymphocyte stimulator to avoid false negatives due to unexpectedly low affinity or antagonist concentration.

Fifty microliters of diluted antagonist and 50 µL of diluted B lymphocyte stimulator are added to the putative antagonist dilution series. Cells are then incubated for 72 hours (37° C., 5% $CO_2$) in a fully humidified chamber. After 72 hrs., the cells are supplemented with 0.5 µCi/well 3H-thymidine (e.g., 6.7 Ci/mmol) and incubated for an additional 24 hours. Plates are harvested using a Tomtec Cell Harvester and filters counted in a TopCount Scintillation counter (Packard).

Example 7

Protein Fusions of B lymphocyte stimulator Binding Polypeptides

B lymphocyte stimulator binding polypeptides of the invention are optionally fused to other proteins. These fusion proteins can be used for a variety of applications. For example, fusion of B lymphocyte stimulator binding polypeptides to His-tag, HA-tag, protein A, IgG domains, and maltose binding protein facilitates purification. (See, EP A 394 827; Traunecker et al., *Nature,* 331:84-86 (1988)). Similarly, fusion to IgG-1, IgG-3, and albumin increases the half-life time in vivo. Nuclear localization signals fused to B lymphocyte stimulator binding polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule.

Briefly, the human Fc portion of the IgG molecule can be PCR amplified, using primers that span the 5' and 3' ends of the sequence described below (SEQ ID NO:447). These primers also preferably contain convenient restriction enzyme sites that will facilitate cloning into an expression vector, preferably a mammalian expression vector.

For example, if the pC4 (Accession No. 209646) expression vector is used, the human Fc portion can be ligated into the BamHI cloning site. Note that the 3' BamHI site should be destroyed. Next, the vector containing the human Fc portion is re-restricted with BamHI, linearizing the vector, and B lymphocyte stimulator binding polynucleotide is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc Region:

```
                                         (SEQ ID NO: 449)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC
```

-continued

```
ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT
```

Example 8

Isolation of scFV Molecules Recognizing B Lymphocyte Stimulator Binding Polypeptides Naturally occurring V-genes isolated from human PBLs are constructed into a large library of antibody fragments which contain reactivities against polypeptides of the present invention to which the donor may or may not have been exposed (see, e.g., U.S. Pat. No. 5,885,793, incorporated herein by reference in its entirety).
Rescue of the Library A library of scFvs is constructed from the RNA of human PBLs as described in WO 92/01047. To rescue phage displaying antibody fragments, approximately $10^9$ E. coli harbouring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, 2×108 TU of Δ gene 3 helper phage (M13 Δ gene III, see WO 92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 ug/ml ampicillin and 50 ug/ml kanamycin and grown overnight. Phage are prepared as described in WO92/01047.

M13 Δ gene III is prepared as follows: M13 Δ gene III helper phage does not encode gene III protein, hence the phage(mid) displaying antibody fragments have a greater avidity of binding to antigen. Infectious M13 Δ gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min. for 10 min.), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).
Panning of the Library Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately 1013 TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 μg/ml ampicillin. The resulting bacterial library is then rescued with A gene III helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.
Characterization of Binders Eluted phage from the 3rd and 4th rounds of selection are used to infect E. coli HB 2151 and soluble scFv is produced (Marks et al., 1991) from single colonies for assay. ELISAs are performed with microtitre plates coated with either 10 pg/ml of the polypeptide of the present invention in 50 mM bicarbonate, pH 9.6. Clones positive in ELISA are further characterized by PCR fingerprinting (see, e.g., WO 92/01047) and then by sequencing.

Additionally, scFvs may be converted to complete Ig molecules using techniques which are commonly known in the art.

Example 9

Production of an Anti-B Lymphocyte Stimulator Binding Polypeptide Antibody

The antibodies of the present invention can be prepared by a variety of methods. (See, Current Protocols, Chapter 2.) As one example of such methods, cells expressing B lymphocyte stimulator binding polypeptides are administered to an animal to induce the production of sera containing polyclonal antibodies. In a preferred method, a preparation of B lymphocyte stimulator binding polypeptide is prepared and purified to render it substantially free of natural contaminants which is then conjugated to a carrier molecule such as keyhole limpet hemocyanin (KLH), suucinylated KLH, or chicken gamma globulin (CGG). Such a preparation is then introduced into an animal in order to produce polyclonal antisera of greater specific activity.

In the most preferred method, the antibodies of the present invention are monoclonal antibodies (or B lymphocyte stimulator protein binding fragments thereof). Such monoclonal antibodies can be prepared using hybridoma technology. (Kohler et al., Nature, 256:495 (1975); Kohler et al., Eur. J. Immunol., 6:511 (1976); Kohler et al., Eur. J. Immunol., 6:292 (1976); Hammerling et al., in Monoclonal Antibodies and T-Cell Hybridomas (Elsevier, N.Y. 1981), pp. 563-681.) In general, such procedures involve immunizing an animal (preferably a mouse) with B lymphocyte stimulator binding polypeptide or, more preferably, with a secreted B lymphocyte stimulator binding polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2/0), available from the ATCC. After fusion, the resulting hybridoma cells are selectively maintained in HAT medium, and then cloned by limiting dilution as described by Wands et al. (*Gastroenterology,* 80:225-232 (1981).) The hybridoma cells obtained through such a selection are then assayed to identify clones which secrete antibodies capable of binding the B lymphocyte stimulator binding polypeptide.

Alternatively, additional antibodies capable of binding to B lymphocyte stimulator binding polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the B lymphocyte stimulator binding polypeptide-specific antibody can be blocked by B lymphocyte stimulator binding polypeptide. Such antibodies comprise anti-idiotypic antibodies to the B lymphocyte stimulator binding protein-specific antibody and can be used to immunize an animal to induce formation of further B lymphocyte stimulator binding polypeptide-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, secreted B lymphocyte stimulator binding protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, *Science,* 229:1202 (1985); Oi et al., *BioTechniques,* 4:214 (1986); Cabilly et al., U.S. Pat. No. 4,816,567; Taniguchi et al., EP 171 496; Morrison et al., EP 173 494; Neuberger et al., WO 86/01533; Robinson et al., WO 87/02671; Bouliannne et al., *Nature,* 312:643 (1984); Neuberger et al., *Nature,* 314:268 (1985).)

Example 10

B Lymphocyte Stimulator-Induced Signalling in B Cells

Total RNA was prepared from tonsillar B cells unstimulated or stimulated with SAC or SAC plus B lymphocyte stimulator (100 ng/mL) for 12 hours. Messenger RNA levels of ERK-1 and PLK was determined by real time quantitaive PCR using ABI 7700 Taqman sequence detector. Amplification primers and probes were designed to span the region from nucleotides 252-332 of the human PLK sequence and nucleotides 373 to 446 of the human ERK-1 mRNA (GenBank accession numbers X75932 and X60188, respectively). For quantitation of RNA, the comparative delta CT method was used (Perkin-Elmer user Bulletin #2 and #4, 1997) using an 18S ribosomal RNA probe as endogenous reference. Expression levels were characterized relative to observed levels in unstimulated B-cells.

Example 11

Affinity Maturation of B Lymphocyte Stimulator Binding Polypeptides

In order to identify high affinity B lymphocyte stimulator-binding polypeptides, a B lymphocyte stimulator Affinity Maturation Library (BAML) was designed around a 14-mer linear peptide template sequence having fixed amino acid residues at 5 of the 14 positions. 3 of the 5 fixed residues corresponded to a highly conserved DxLT tetrapeptide amino acid motif (SEQ ID NO:446) isolated from both the constrained and linear peptide libraries. The design of the 14-mer allowed for some amino acid variation at each of the remaining 9 positions, however, preference was given for a particular amino acid at each of these positions. Analysis of binding affinity of the newly isolated peptides for B lymphocyte stimulator was evaluated by direct and indirect phage ELISA and fluorescence anisotropy.

BAML was designed on a 14-mer linear (non-constrained) template peptide sequence having fixed residues at positions 1 (Ala), 5 (Asp), 7 (Leu), 8 (Thr), and 10 (Leu). The amino acid sequence of positions 3-14 in the BAML template most closely resembles a binding polypeptide isolated from the PhD 12 linear polypeptide library (see Table 7, supra). Residues at position 1 (fixed Ala) and position 2 (variable) were included to extend the length and presentation of the B lymphocyte stimulator-binding sequence. Positions 5-8 correspond to the D×LT motif found in peptide isolates from both the constrained and linear peptide libraries (see Tables 1-8, supra). Since hydrophobic amino acids (L, M, I, A, and G) were found at position 10 in 85% of the original isolates, a Leu residue, occurring in 42% of the isolates, was fixed at that position in the BAML template peptide.

Table 10 shows the design of the 14-mer BAML template sequence.

TABLE 10

| BAML template sequence (14-mer) | | | | | | | | | | | | | | |
|---|---|---|---|---|---|---|---|---|---|---|---|---|---|---|
| amino acid position | | | | | | | | | | | | | | SEQ ID |
| 1 | 2 | 3 | 4 | 5 | 6 | 7 | 8 | 9 | 10 | 11 | 12 | 13 | 14 | NO: |
| A | n | w | y | D | s | L | T | k | L | w | l | p | d | 184 |

Referring to Table 10, the upper case letters indicate the fixed residues at positions 1, 5, 7, 8, and 10 of the template. Lower case letters designate preferred amino acids at those positions, however the design of the variegated DNA template encoding the 14-mer allows for some sequence variation at these positions.

Table 11 shows the design of the variegated DNA template used to generate the BAML peptides.

TABLE 11

BAML DNA template sequence (14-mer)

codon position

| 1 | 2 | 3 | 4 | 5 | 6 | 7 | 8 | 9 | 10 | 11 | 12 | 13 | 14 |
|---|---|---|---|---|---|---|---|---|----|----|----|----|----| codons*

GCT eez zjj zez GAT zqz CTT ACT eej CTC zjj qzz qqz jez

*The sequence of codons is SEQ ID NO: 185.

Referring to Table 11, the nucleotide coding sequences for the fixed amino acids in the BAML 14-mer template are shown in upper case letters. The letters "e", "j", "q", and "z" in the variegated DNA template each represent a particular mixture of nucleoside bases present in the input dNTPs for each position:

j=79% guanine, 7% cytosine, 7% adenine, 7% thymine
q=7% guanine, 79% cytosine, 7% adenine, 7% thymine
e=7% guanine, 7% cytosine, 79% adenine, 7% thymine
z=7% guanine, 7% cytosine, 7% adenine, 79% thymine.

The codons of the DNA template were designed to skew the encoded variable amino acid toward the preferred amino acid at each position shown in SEQ ID NO:184 (Table 10, lower case). Later sequencing of phage isolates showed that, at any particular position, preferred residues occurred at a frequency of from 44% to 70%.

Synthetic DNA sequences fitting the DNA template were amplified by large scale PCR. The amplified DNAs were restriction digested for insertion into a M13 phage expression vector (MANP vector, Dyax Corp., Cambridge, Mass.), and vectors bearing the inserts were used to transform M13 phage by electroporation, to produce the BAML. Recombinant phage were collected and purified by PEG precipitation and titered. A total of $3.2 \times 10^{13}$ PFU were amplified in BAML from $1.6 \times 10^9$ transformants.

Screening BAML

As outlined in Table 12 below, a two-step competition method, starting with the original BAML library, was used over 4 rounds of screening to isolate the highest affinity B lymphocyte stimulator-binding polypeptides from the BAML. Prior to screening, the amplified BAML was contacted with Seradyn streptavidin-coated magnetic beads (MG-SA, Seradyn, Indianapolis, Ind.), to remove bead- and streptavidin-binding phage.

For screening BAML, phage were incubated in solution with biotinylated B lymphocyte stimulator (b-B lymphocyte stimulator) in 200 µl PBS, pH 7.4, Tween-20 (0.1%), to form phage/b-B lymphocyte stimulator binding complexes. For the first competition step, unlabeled B lymphocyte stimulator (1-2 µM) was added to the phage/b-B lymphocyte stimulator binding complex mixture in solution and incubated for 1-20 hrs. (See Table 12.) The phage/b-B lymphocyte stimulator complexes remaining in solution after incubation with unlabeled B lymphocyte stimulator were captured by brief (10 min. on rotator) incubation with MG-SA streptavidin beads (50 µl). After capture of the phage/b-B lymphocyte stimulator complexes on streptavidin beads, the unbound fraction was removed and beads were washed 15-20 times with 1 ml PBS-Tween 20 prior to the second competition step. The phage/unlabeled B lymphocyte stimulator complexes from the round 1 competition step only, were collected and used as a fraction of the input phage for the second round of screening along with the bead-captured phage/b-B lymphocyte stimulator complexes, however, in each subsequent round of screening only the bead-associated phage were collected after the first competition step for further screening, and the phage/unlabeled B lymphocyte stimulator complexes were discarded.

For the second competition step, the competitor peptide was a polypeptide (DX221; SEQ ID NO:168) based on a B lymphocyte stimulator-binding polypeptide isolated from the PhD 12 library in the initial screenings described above. The phage/b-B lymphocyte stimulator complexes bound to streptavidin, collected after the first competition incubation step, were serially diluted with 50 µM DX221 B lymphocyte stimulator-binding peptide ($K_D=3$ µM) in 300 µl PBS-Tween-20 (0.1%). A series of short incubations (3-4 per round, for 1 hour) of the phage/b-B lymphocyte stimulator complexes with DX221 followed by a final incubation of from overnight (O/N, for rounds 1, 2, and 4) to 3 days (for round 3). (See Table 12.) The second competition step in round 4 included an incubation with 67 nM B lymphocyte stimulator for 1 hour prior to incubation with DX221. The streptavidin bead-associated phage/b-B lymphocyte stimulator binding complexes remaining after the DX221 competition step in round 4 were collected for further analysis.

TABLE 12

B lymphocyte stimulator affinity maturation library (BAML) screening conditions

| Screening Round | Input phage[1] | b-BLyS ™[2] | First Competition Incubation Time (hrs) | Competitor (BLyS ™) | Second Competition Incubation Time (hrs) | Peptide Elutions |
|---|---|---|---|---|---|---|
| 1 | $1.5 \times 10^{11}$ | 100 nM | 2 | 2 µM | 1 | 50 µM DX221, 4 × 1 hr, then O/N |
| 2 | $2 \times 10^{10}$ | 100 nM | 1 | 1 µM | 20 | 50 µM DX221, 3 × 1 hr, then O/N |
| 3 | $6.5 \times 10^{10}$ | 100 pM | 16 | 1 µM | 3 | 50 µM DX221, 4 × 1 hr, then 3 days |
| 4 | $6.0 \times 10^{10}$ | 10 pM | 16 | 1 µM | 2 | 67 nM BLyS ™, 1 hr; 50 µM DX221 + |

TABLE 12-continued

B lymphocyte stimulator affinity maturation library (BAML) screening conditions

| Screening Round | Input phage[1] | b-BLyS ™[2] | First Competition Incubation Time (hrs) | Competitor (BLyS ™) | Second Competition Incubation Time (hrs) | Peptide Elutions |
|---|---|---|---|---|---|---|
| | | | | | | 67 nM BLyS ™ 3 × 1 hr, O/N, then add'l 4 hrs |

[1]Input phage for round 1 was original BAML; for round 2 was amplified output phage from overnight (final) peptide elution and bead-associated phage from round 1; for round 3 was amplified bead-associated output phage from round 2; and for round 4 was amplified bead-associated output phage from round 3.
All amplified phage samples were pre-cleared on streptavidin beads before incubation with biotin-B lymphocyte stimulator in solution.
[2]b-BLyS ™ = biotinylated B lymphocyte stimulator ELISA Analysis Approximately four hundred BAML isolates from rounds 2, 3 and 4 of the above screening were analyzed by direct and indirect phage ELISA assays.

For indirect phage ELISA, Immulon-2HB plates (Dynex Technologies, Inc., Chantilly, Va.) were coated with 100 μl of 1 μg/ml Immunopure streptavidin (Pierce, Rockford, Ill.) diluted in PBS. 100 μl of a series of 10-fold dilutions of b-B lymphocyte stimulator (0-0.1 μg/ml in PBS) were immobilized in the streptavidin-coated wells (1 hr, 37° C.). After washing, 1-25 μl of overnight culture of *E. coli* infected with the individual phage plaques were added to the appropriate wells and incubated for 1 hour, followed by 10 washes with PBS-Tween-20. Anti-M13 antibody conjugated to horseradish peroxidase (1:10,000 in PBS-Tween-20) was added to the wells (30 min., room temperature), the color reagent TMB was used and the plates read at OD 630 nm.

Individual phage isolates binding to immobilized B lymphocyte stimulator were sequenced and the sequences analyzed. The unique sequences of the BAML B lymphocyte stimulator-binding 14-mer display peptides are shown in Table 13.

Analysis of the peptides reveals a significant sequence "collapse" around one motif: $W_3YDPLTKLWL_{12}$ (SEQ ID NO:436) (subscripts indicate amino acid position in the 14-mer display peptide sequence). This most numerous core motif includes the four fixed residues from the original BAML template, i.e., Asp (D) at position 5, Leu (L) at position 7, Thr (T) at position 8, and Leu (L) at position 10. In addition, 5 of the 6 preferred residues from the original BAML template sequence were included in this motif (see Table 10).

73% (143 of 197) of the round 4 isolates included this core motif (SEQ ID NO:436). Single residue substitutions within the 10-mer core motif centered on positions 4 (Y→F) and 12 (L→F, I, or V), with the substitutions at position 12 being alternative hydrophobic residues for Leu.

For the three remaining variable positions (i.e., 2, 13, and 14), selection was not as stringent, although some preferences were apparent, being either built into the library or persisting through rounds of selection. For example, in round 4 isolates, 51% included Asn at position 2; 77% included Pro at position 13; and 32% included Asp at position 14. The presence of Val (27%) or Glu (19%) at position 14 was among the most highly selected in the round 4 isolates, in comparison to their theoretical proportion (4% each) at position 14 in BAML.

The sequences in Table 13 are grouped according to their degree of difference from the core sequence (SEQ ID NO:436).

TABLE 13

Sequences of BAML Phage Isolates (from Rounds 2, 3, 4)

14-mer amino acid position

| 1 | 2 | 3 | 4 | 5 | 6 | 7 | 8 | 9 | 10 | 11 | 12 | 13 | 14 | SEQ ID NO: |
|---|---|---|---|---|---|---|---|---|---|---|---|---|---|---|
| A | n | w | y | D | s | L | T | k | L | w | l | p | d | consensus; 184 |
| A | N | W | Y | D | P | L | T | K | L | W | L | P | D | 186 |
| A | N | W | Y | D | P | L | T | K | L | W | L | P | E | 187 |
| A | N | W | Y | D | P | L | T | K | L | W | L | P | G | 188 |
| A | N | W | Y | D | P | L | T | K | L | W | L | P | V | 189 |
| A | N | W | Y | D | P | L | T | K | L | W | L | S | D | 190 |
| A | N | W | Y | D | P | L | T | K | L | W | L | N | D | 191 |
| A | N | W | Y | D | P | L | T | K | L | W | L | P | T | 192 |
| A | N | W | Y | D | P | L | T | K | L | W | L | P | A | 193 |
| A | N | W | Y | D | P | L | T | K | L | W | L | P | N | 194 |
| A | N | W | Y | D | P | L | T | K | L | W | L | V | D | 195 |
| A | N | W | Y | D | P | L | T | K | L | W | L | H | D | 196 |
| A | N | W | Y | D | P | L | T | K | L | W | L | T | D | 197 |
| A | N | W | Y | D | P | L | T | K | L | W | L | P | H | 198 |
| A | N | W | Y | D | P | L | T | K | L | W | L | T | V | 199 |
| A | N | W | Y | D | P | L | T | K | L | W | L | L | D | 200 |
| A | N | W | Y | D | P | L | T | K | L | W | L | L | E | 201 |
| A | N | W | Y | D | P | L | T | K | L | W | L | H | E | 202 |
| A | N | W | Y | D | P | L | T | K | L | W | L | P | R | 203 |
| A | N | W | Y | D | P | L | T | K | L | W | L | A | D | 204 |
| A | N | W | Y | D | P | L | T | K | L | W | L | P | Y | 205 |
| A | N | W | Y | D | P | L | T | K | L | W | L | P | I | 206 |
| A | N | W | Y | D | P | L | T | K | L | W | L | I | D | 207 |
| A | N | W | Y | D | P | L | T | K | L | W | L | R | D | 208 |
| A | Y | W | Y | D | P | L | T | K | L | W | L | P | D | 209 |
| A | Y | W | Y | D | P | L | T | K | L | W | L | L | E | 210 |
| A | Y | W | Y | D | P | L | T | K | L | W | L | R | V | 211 |

TABLE 13-continued

Sequences of BAML Phage Isolates (from Rounds 2, 3, 4)

| 14-mer amino acid position | | | | | | | | |
|---|---|---|---|---|---|---|---|---|
| 1 2 3 | 4 5 6 | 7 8 9 | 10 | 11 | 12 | 13 | 14 | SEQ ID NO: |
| A Y W | Y D P | L T K | L | W | L | P | E | 212 |
| A Y W | Y D P | L T K | L | W | L | P | V | 213 |
| A Y W | Y D P | L T K | L | W | L | H | Q | 214 |
| A Y W | Y D P | L T K | L | W | L | P | A | 215 |
| A Y W | Y D P | L T K | L | W | L | R | V | 216 |
| A Y W | Y D P | L T K | L | W | L | P | G | 217 |
| A Y W | Y D P | L T K | L | W | L | R | Y | 218 |
| A Y W | Y D P | L T K | L | W | L | P | Y | 219 |
| A Y W | Y D P | L T K | L | W | L | L | Y | 220 |
| A Y W | Y D P | L T K | L | W | L | R | D | 221 |
| A Y W | Y D P | L T K | L | W | L | P | V | 222 |
| A Y W | Y D P | L T K | L | W | L | L | G | 223 |
| A Y W | Y D P | L T K | L | W | L | T | H | 224 |
| A Y W | Y D P | L T K | L | W | L | P | T | 225 |
| A Y W | Y D P | L T K | L | W | L | L | V | 226 |
| A Y W | Y D P | L T K | L | W | L | Y | Y | 227 |
| A Y W | Y D P | L T K | L | W | L | S | D | 228 |
| A S W | Y D P | L T K | L | W | L | P | A | 229 |
| A S W | Y D P | L T K | L | W | L | H | D | 230 |
| A S W | Y D P | L T K | L | W | L | P | G | 231 |
| A S W | Y D P | L T K | L | W | L | P | Q | 232 |
| A S W | Y D P | L T K | L | W | L | P | Y | 233 |
| A S W | Y D P | L T K | L | W | L | P | H | 234 |
| A S W | Y D P | L T K | L | W | L | P | V | 235 |
| A S W | Y D P | L T K | L | W | L | P | I | 236 |
| A S W | Y D P | L T K | L | W | L | P | E | 237 |
| A F W | Y D P | L T K | L | W | L | R | V | 238 |
| A F W | Y D P | L T K | L | W | L | P | E | 239 |
| A F W | Y D P | L T K | L | W | L | L | E | 240 |
| A F W | Y D P | L T K | L | W | L | P | V | 241 |
| A I W | Y D P | L T K | L | W | L | P | E | 242 |
| A I W | Y D P | L T K | L | W | L | P | D | 243 |
| A I W | Y D P | L T K | L | W | L | H | D | 244 |
| A I W | Y D P | L T K | L | W | L | T | D | 245 |
| A I W | Y D P | L T K | L | W | L | P | F | 246 |
| A I W | Y D P | L T K | L | W | L | L | D | 247 |
| A I W | Y D P | L T K | L | W | L | P | R | 248 |
| A I W | Y D P | L T K | L | W | L | P | A | 249 |
| A I W | Y D P | L T K | L | W | L | T | A | 250 |
| A I W | Y D P | L T K | L | W | L | A | V | 251 |
| A I W | Y D P | L T K | L | W | L | P | G | 252 |
| A I W | Y D P | L T K | L | W | L | R | V | 253 |
| A I W | Y D P | L T K | L | W | L | P | H | 254 |
| A I W | Y D P | L T K | L | W | L | R | E | 255 |
| A I W | Y D P | L T K | L | W | L | S | D | 256 |
| A T W | Y D P | L T K | L | W | L | P | A | 257 |
| A T W | Y D P | L T K | L | W | L | A | D | 258 |
| A T W | Y D P | L T K | L | W | L | T | S | 259 |
| A T W | Y D P | L T K | L | W | L | P | G | 260 |
| A T W | Y D P | L T K | L | W | L | P | Y | 261 |
| A T W | Y D P | L T K | L | W | L | S | G | 262 |
| A T W | Y D P | L T K | L | W | L | P | V | 263 |
| A T W | Y D P | L T K | L | W | L | P | D | 264 |
| A D W | Y D P | L T K | L | W | L | P | V | 265 |
| A D W | Y D P | L T K | L | W | L | P | K | 266 |
| A D W | Y D P | L T K | L | W | L | P | D | 267 |
| A D W | Y D P | L T K | L | W | L | P | E | 268 |
| A D W | Y D P | L T K | L | W | L | H | Q | 269 |
| A E W | Y D P | L T K | L | W | L | R | D | 270 |
| A E W | Y D P | L T K | L | W | L | P | D | 271 |
| A E W | Y D P | L T K | L | W | L | P | Y | 272 |
| A L W | Y D P | L T K | L | W | L | P | A | 273 |
| A L W | Y D P | L T K | L | W | L | P | D | 274 |
| A L W | Y D P | L T K | L | W | L | R | G | 275 |
| A L W | Y D P | L T K | L | W | L | L | G | 276 |
| A M W | Y D P | L T K | L | W | L | P | A | 277 |
| A M W | Y D P | L T K | L | W | L | Q | V | 278 |
| A M W | Y D P | L T K | L | W | L | L | G | 279 |
| A A W | Y D P | L T K | L | W | L | P | D | 280 |
| A A W | Y D P | L T K | L | W | L | A | D | 281 |
| A A W | Y D P | L T K | L | W | L | L | D | 282 |
| A H W | Y D P | L T K | L | W | L | T | D | 283 |

TABLE 13-continued

Sequences of BAML Phage Isolates (from Rounds 2, 3, 4)

| 1 | 2 | 3 | 4 | 5 | 6 | 7 | 8 | 9 | 10 | 11 | 12 | 13 | 14 | SEQ ID NO: |
|---|---|---|---|---|---|---|---|---|----|----|----|----|----|------------|
| A | H | W | Y | D | P | L | T | K | L | W | L | P | V | 284 |
| A | H | W | Y | D | P | L | T | K | L | W | L | H | D | 285 |
| A | H | W | Y | D | P | L | T | K | L | W | L | P | D | 286 |
| A | P | W | Y | D | P | L | T | K | L | W | L | H | D | 287 |
| A | P | W | Y | D | P | L | T | K | L | W | L | P | V | 288 |
| A | Q | W | Y | D | P | L | T | K | L | W | L | P | E | 289 |
| A | Q | W | Y | D | P | L | T | K | L | W | L | P | Y | 290 |
| A | Q | W | Y | D | P | L | T | K | L | W | L | P | R | 291 |
| A | K | W | Y | D | P | L | T | K | L | W | L | P | D | 292 |
| A | K | W | Y | D | P | L | T | K | L | W | L | P | V | 293 |
| A | K | W | Y | D | P | L | T | K | L | W | L | P | V | 294 |
| A | K | W | Y | D | P | L | T | K | L | W | L | N | G | 295 |
| A | W | W | Y | D | P | L | T | K | L | W | L | P | A | 296 |
| A | V | W | Y | D | P | L | T | K | L | W | L | T | D | 297 |
| A | N | W | Y | D | P | L | T | K | L | W | L | P | D | 186 |
| A | Y | E | Y | D | P | L | T | K | L | W | L | L | Y | 298 |
| A | T | K | Y | D | P | L | T | K | L | W | L | P | D | 299 |
| A | T | L | Y | D | P | L | T | K | L | W | L | P | G | 300 |
| A | I | R | Y | D | P | L | T | K | L | W | L | P | Y | 301 |
| A | E | R | Y | D | P | L | T | K | L | W | L | P | H | 302 |
| A | D | R | Y | D | P | L | T | K | L | W | L | P | Q | 303 |
| A | N | S | Y | D | P | L | T | K | L | W | L | P | E | 304 |
| A | I | L | Y | D | P | L | T | K | L | W | L | P | D | 305 |
| A | N | W | Y | D | P | L | T | K | L | W | L | P | D | 186 |
| A | N | W | F | D | P | L | T | K | L | W | L | P | Q | 306 |
| A | N | W | F | D | P | L | T | K | L | W | L | P | V | 307 |
| A | N | W | F | D | P | L | T | K | L | W | L | T | D | 308 |
| A | N | W | F | D | P | L | T | K | L | W | L | P | D | 309 |
| A | N | W | F | D | P | L | T | K | L | W | L | P | G | 310 |
| A | N | W | F | D | P | L | T | K | L | W | L | P | E | 311 |
| A | N | W | F | D | P | L | T | K | L | W | L | P | A | 312 |
| A | N | W | F | D | P | L | T | K | L | W | L | P | N | 313 |
| A | N | W | F | D | P | L | T | K | L | W | L | S | E | 314 |
| A | N | W | F | D | P | L | T | K | L | W | L | H | D | 315 |
| A | N | W | F | D | P | L | T | K | L | W | L | V | D | 316 |
| A | Y | W | F | D | P | L | T | K | L | W | L | P | D | 317 |
| A | Y | W | F | D | P | L | T | K | L | W | L | P | V | 318 |
| A | Y | W | F | D | P | L | T | K | L | W | L | P | A | 319 |
| A | Q | W | F | D | P | L | T | K | L | W | L | P | D | 320 |
| A | H | W | F | D | P | L | T | K | L | W | L | P | D | 321 |
| A | T | W | F | D | P | L | T | K | L | W | L | P | V | 322 |
| A | N | W | Y | D | P | L | T | K | L | W | L | P | D | 186 |
| A | Y | W | Y | D | S | L | T | K | L | W | L | P | V | 323 |
| A | Y | W | Y | D | S | L | T | K | L | W | L | H | D | 324 |
| A | N | W | Y | D | S | L | T | K | L | W | L | P | D | 325 |
| A | N | W | Y | D | S | L | T | K | L | W | L | P | V | 326 |
| A | N | W | Y | D | S | L | T | K | L | W | L | P | D | 327 |
| A | N | W | Y | D | S | L | T | K | L | W | L | A | D | 328 |
| A | N | W | Y | D | S | L | T | K | L | W | L | P | A | 329 |
| A | N | W | Y | D | S | L | T | K | L | W | L | Y | E | 330 |
| A | N | W | Y | D | P | L | T | K | L | W | L | P | D | 186 |
| A | G | W | Y | D | S | L | T | K | L | W | L | P | D | 331 |
| A | V | W | Y | D | S | L | T | K | L | W | L | T | D | 332 |
| A | N | W | Y | D | A | L | T | K | L | W | L | P | V | 333 |
| A | Y | W | Y | D | T | L | T | K | L | W | L | P | N | 334 |
| A | N | W | Y | D | P | L | T | K | L | W | L | P | D | 186 |
| A | F | W | Y | D | P | L | T | N | L | W | L | L | E | 335 |
| A | Y | W | Y | D | P | L | T | G | L | W | L | L | V | 336 |
| A | Y | W | Y | D | P | L | T | G | L | W | L | L | Y | 337 |
| A | Y | W | Y | D | P | L | T | G | L | W | L | R | V | 338 |
| A | Y | W | Y | D | P | L | T | E | L | W | L | R | L | 339 |
| A | N | W | Y | D | P | L | T | K | L | W | L | P | D | 186 |
| A | M | W | Y | D | P | L | T | K | L | S | L | P | D | 340 |
| A | Y | W | Y | D | P | L | T | K | L | S | L | L | V | 341 |
| A | I | W | Y | D | P | L | T | K | L | S | L | T | V | 342 |
| A | I | W | Y | D | P | L | T | K | L | S | L | L | V | 343 |
| A | D | W | Y | D | P | L | T | K | L | S | L | L | L | 344 |
| A | Y | W | Y | D | P | L | T | K | L | R | L | L | E | 345 |
| A | D | W | Y | D | P | L | T | K | L | R | L | L | V | 346 |
| A | D | W | Y | D | P | L | T | K | L | R | L | I | V | 347 |
| A | I | W | Y | D | P | L | T | K | L | Y | L | P | D | 348 |
| A | I | W | Y | D | P | L | T | K | L | G | L | L | V | 349 |

TABLE 13-continued

Sequences of BAML Phage Isolates (from Rounds 2, 3, 4)

| 14-mer amino acid position 1 2 3 | 4 5 6 | 7 8 9 | 10 | 11 | 12 | 13 | 14 | SEQ ID NO: |
|---|---|---|---|---|---|---|---|---|
| A N W | Y D P | L T K | L | T | L | L | V | 350 |
| A N W | Y D P | L T K | L | L | L | P | N | 351 |
| A N W | Y D P | L T K | L | W | L | P | D | 186 |
| A S W | Y D P | L T K | L | W | F | P | D | 352 |
| A N W | Y D P | L T K | L | W | F | P | D | 353 |
| A N W | Y D P | L T K | L | W | F | S | D | 354 |
| A S W | Y D P | L T K | L | W | F | P | V | 355 |
| A D W | Y D P | L T K | L | W | F | P | V | 356 |
| A S W | Y D P | L T K | L | W | F | P | K | 357 |
| A K W | Y D P | L T K | L | W | F | P | D | 358 |
| A S W | Y D P | L T K | L | W | F | L | E | 359 |
| A N W | Y D P | L T K | L | W | F | P | A | 360 |
| A T W | Y D P | L T K | L | W | F | P | D | 361 |
| A I W | Y D P | L T K | L | W | F | P | E | 362 |
| A I W | Y D P | L T K | L | W | F | P | D | 363 |
| A I W | Y D P | L T K | L | W | F | P | G | 364 |
| A Y W | Y D P | L T K | L | W | F | P | H | 365 |
| A N W | Y D P | L T K | L | W | F | P | V | 366 |
| A Y W | Y D P | L T K | L | W | F | P | D | 367 |
| A G W | Y D P | L T K | L | W | F | P | D | 368 |
| A I W | Y D P | L T K | L | W | F | P | T | 369 |
| A K W | Y D P | L T K | L | W | F | P | A | 370 |
| A Y W | Y D P | L T K | L | W | F | F | D | 371 |
| A N W | Y D P | L T K | L | W | F | A | D | 372 |
| A N W | Y D P | L T K | L | W | L | P | D | 186 |
| A N W | Y D P | L T K | L | W | F | P | Y | 373 |
| A D W | Y D P | L T K | L | W | F | R | D | 374 |
| A N W | Y D P | L T K | L | W | V | P | D | 375 |
| A D W | Y D P | L T K | L | W | V | P | A | 376 |
| A N W | Y D P | L T K | L | W | V | P | N | 377 |
| A N W | Y D P | L T K | L | W | V | P | E | 378 |
| A N W | Y D P | L T K | L | W | V | P | Q | 379 |
| A E W | Y D P | L T K | L | W | V | P | K | 380 |
| A Q W | Y D P | L T K | L | W | V | P | V | 381 |
| A N W | Y D P | L T K | L | W | V | P | Y | 382 |
| A L W | Y D P | L T K | L | W | V | P | Y | 383 |

TABLE 13-continued

Sequences of BAML Phage Isolates (from Rounds 2, 3, 4)

| 14-mer amino acid position 1 2 3 | 4 5 6 | 7 8 9 | 10 | 11 | 12 | 13 | 14 | SEQ ID NO: |
|---|---|---|---|---|---|---|---|---|
| A N W | Y D P | L T K | L | W | V | P | G | 384 |
| A S W | Y D P | L T K | L | W | I | P | Y | 385 |
| A D W | Y D P | L T K | L | W | I | P | G | 386 |
| A N W | Y D P | L T K | L | W | I | P | Y | 387 |
| A K W | Y D P | L T K | L | W | I | P | Y | 388 |
| A I W | Y D P | L T K | L | W | I | P | N | 389 |
| A T W | Y D P | L T K | L | W | I | P | Q | 390 |
| A N W | Y D P | L T K | L | W | L | P | D | 186 |
| A S W | Y D P | L T N | L | W | V | P | D | 391 |
| A Y E | Y D P | L T N | L | W | L | L | Y | 392 |
| A Y W | Y D P | L T N | L | S | L | L | V | 393 |
| A Y W | Y D P | L T K | L | S | I | L | E | 394 |
| A N W | Y D S | L T K | L | W | I | P | Y | 395 |
| A H W | F D P | L T Q | L | K | I | R | V | 396 |
| A Y W | C D P | L T K | L | C | I | L | E | 397 |
| A N S | Y D P | L T K | L | W | F | P | Y | 398 |
| A N L | Y D P | L T K | L | W | V | P | Y | 399 |
| A N W | Y D A | L T K | L | W | L | H | D | 400 |
| A N W | Y D S | L T K | L | W | F | P | D | 401 |
| A T S | Y D S | L T K | L | W | L | P | A | 402 |
| A C W | Y D S | L T K | L | C | H | R | E | 403 |
| A I G | N D P | L T K | L | W | I | P | Y | 404 |
| A N W | Q D C | L T K | L | C | L | A | G | 405 |
| A Y W | F D P | L T N | L | W | L | L | E | 406 |
| A Y W | Y D P | L T N | L | S | L | L | V | 407 |
| A N C | F D S | L T R | L | W | L | C | D | 408 |
| A C A | Y D A | L T K | L | C | L | P | A | 409 |
| A N W | Y D P | L T N | L | S | L | L | L | 410 |
| A Y W | Y D P | L T Q | L | S | L | L | V | 411 |
| A Y R | Y D A | L T G | L | W | L | L | Y | 412 |
| A Y W | N D P | L T K | L | K | L | R | L | 413 |
| A Y W | Y D P | L T Q | L | S | L | L | V | 414 |
| A Y R | Y D A | L T G | L | W | L | L | Y | 415 |
| A Y R | Y D S | L T N | L | W | L | L | Y | 416 |
| A Y W | Y D P | L T K | L | S | I | L | E | 417 |
| A S C | Y D P | L T K | L | C | F | P | V | 418 |

TABLE 13-continued

Sequences of BAML Phage Isolates (from Rounds 2, 3, 4)

| 1 | 2 | 3 | 4 | 5 | 6 | 7 | 8 | 9 | 10 | 11 | 12 | 13 | 14 | SEQ ID NO: |
|---|---|---|---|---|---|---|---|---|----|----|----|----|----|------------|
| A | F | W | F | D | P | L | T | G | L  | W  | L  | L  | E  | 419 |
| A | N | W | Y | D | P | L | T | K | L  | W  | L  | P  | D  | 186 |
| A | H | W | Y | D | P | L | T | K | L  | S  | I  | R  | V  | 420 |
| A | P | W | Y | D | S | L | T | K | L  | W  | F  | P  | S  | 421 |
| A | N | C | Y | D | T | L | T | K | L  | W  | L  | T  | C  | 422 |
| A | N | W | Y | D | S | L | T | K | L  | S  | L  | P  | D  | 423 |
| A | Y | A | Y | D | F | L | T | Q | L  | S  | L  | P  | D  | 424 |
| A | F | R | Y | D | S | L | T | G | L  | W  | L  | R  | Y  | 425 |
| A | N | C | Y | D | S | L | T | K | L  | W  | L  | P  | C  | 426 |
| A | N | G | Y | D | L | L | T | N | L  | S  | V  | S  | D  | 427 |
| A | N | W | Y | D | P | L | T | R | L  | W  | I  | P  | V  | 428 |
| A | L | K | F | D | Y | L | T | K | L  | W  | L  | P  | D  | 429 |
| A | Y | R | Y | D | S | L | T | K | L  | W  | L  | P  | G  | 430 |
| A | Y | C | Y | D | S | L | T | K | L  | W  | I  | P  | D  | 431 |
| A | S | W | E | D | S | L | T | K | L  | W  | L  | S  | K  | 432 |
| A | Y | W | Y | D | S | L | T | G | L  | S  | L  | L  | V  | 433 |
| A | Y | W | Y | D | P | L | T | Y | L  | R  | L  | R  | V  | 434 |
| A | K | C | Y | D | S | L | T | N | L  | W  | L  | C  | D  | 435 |

Nearly all of the ELISA signals of the BAML isolates were higher than those isolated in the initial screen (see Example 1). For comparison, peptide 453-01-B07 (SEQ ID NO:31) ($K_D$=700 nM) was used as a reference (positive control). Negative control MAEX (M13 phage with no insert) did not bind b-B lymphocyte stimulator at any concentration tested.

For direct phage ELISA, the signal measured is a reflection of the ability of a set number of phage to bind to various concentrations of b-B lymphocyte stimulator. Peptides tested by the direct phage ELISA assay were chosen based on high affinity for B lymphocyte stimulator as determined in the indirect phage ELISA assay. For this assay, Immulon-2HB plates were coated with 0 or 1000 ng anti-Fd antibody (Sigma, St. Louis, Mo.). After washing (PBS-Tween-20), phage dilutions were added to saturate the available antibody and incubated for 1 hour, washed, then incubated with 100 µl of 10-fold dilutions of b-B lymphocyte stimulator (0-1 µg/ml) for 1 hour at room temperature. Streptavidin-HRP (1:1000 in PBS-tween-20; Endogen, Woburn, Mass.) was added to the wells and incubated for 1 hour, developed using TMB and reading at OD 630 nm.

Determination of BAML Peptide KD by Fluoresence Anisotropy

Several peptides containing the 10-mer core structural motif or single-position variants of that motif identified by sequence analysis were synthesized with a short Gly-Gly-Lys linker sequence and the C-terminal lysine was labeled with fluorescein. These peptides, shown in Table 14, below, were synthesized by solid phase synthesis for determination of dissociation constant with respect to B lymphocyte stimulator. The DX815 and DX876 polypeptides were derived from DX814 (SEQ ID NO:186) by deletion of two N-terminal amino acids or the two amino acids N-terminal and C-terminal to the core peptide at (positions 3-12). DX816, DX817, DX819, and DX822 correspond to other BAML isolates (SEQ ID NOs:189, 309, 353, 327, respectively). DX818 corresponds to isolate SEQ ID NO:340, except that Asn has been substituted for Met at position 2. The $K_D$ of several B lymphocyte stimulator binding BAML peptides was determined by fluorescence anisotropy, performed as previously described. The sequence of DX822 without the -GGK linker (see SEQ ID NO:327) matches the BAML template sequence (see Table 10). The BAML consensus sequence found in DX822 resulted in a more than 10-fold improvement in binding affinity for B lymphocyte stimulator, as compared to one of the highest affinity binders isolated in the initial screen (453-01-B07, SEQ ID NO:31).

TABLE 14

Dissociation Constants of Synthetic BLyS™-binding Polypeptides

| Peptide | Sequence | SEQ ID NO: | $K_D$ (nM) |
|---------|----------|------------|------------|
| DX814 | Ac-ANWYDPLTKLWLPDGGK-fitc | 437 | 26 ± 7 |
| DX815 | Ac-WYDPLTKLWLPDGGK-fitc | 438 | 31 ± 13 |
| DX876 | Ac-WYDPLTKLWLGGK-fitc | 439 | 171 ± 90 |
| DX816 | Ac-ANWYDPLTKLWLPVGGK-fitc | 440 | 44 ± 15 |
| DX817 | Ac-ANWFDPLTKLWLPDGGK-fitc | 441 | 32 ± 26 |
| DX818 | Ac-ANWYDPLTKLSLPDGGK-fitc | 442 | 342 ± 108 |
| DX819 | Ac-ANWYDPLTKLWFPDGGK-fitc | 443 | 69 ± 38 |
| DX822 | Ac-ANWYDSLTKLWLPDGGK-fitc | 444 | 79 ± 54 |

Analysis of the BAML isolates revealed a lack of sequence conservation at position 2 (varied in the BAML template, see Table 10). To examine whether the N-terminal residues at positions 1 and 2 in the BAML sequence were necessary for binding to B lymphocyte stimulator, a truncated version of DX814 comprising only residues 3-14 (DX815; see Table 14) was synthesized and analyzed by fluorescence anisotropy. The $K_D$ for DX815 was indistinguishable from that of DX814, suggesting that residues 1-2 are not required for high affinity binding to B lymphocyte stimulator. Further truncation of DX814 to the minimal core (residues 1-10, DX876) increased the $K_D$ to 171 nM, indicating a contribution from Pro at position 13 and/or Asp at position 14 of the 14-mer to high affinity B lymphocyte stimulator binding. Substitution of Val in DX816 at that position had little effect on the $K_D$ (see Table 14). In comparing the B lymphocyte stimulator-binding polypeptide DX221 (Ac-WTDSLTGLWFPDGGPG-PEGGGK; $K_D$=3 □M; SEQ ID NO:168) with the BAML peptide closest in sequence (DX819, Ac-ANWYDPLTKLW-FPDGGK; $K_D$=69 nM; SEQ ID NO:443), differences are seen at three positions 4 (T→Y), 6 (S→P), and 9 (G→K), indicating the contribution of these residues in binding affinity. The synthesized BAML peptides exhibited $K_D$ values in the low nanomolar range, two orders of magnitude lower than primary isolate-derived peptides (see Example 1). Phenylalanine substitutions ($F_4 \rightarrow Y_4$; $F_{12} \rightarrow L_{12}$; Table 14) were the most common minor variations to the core sequence and these changes failed to significantly affect the dissociation constants of the synthesized peptides. A change at position 11 ($W_{11} \rightarrow S_{11}$; DX818), however, resulted in an approximately 10-fold decrease in affinity compared to DX814.

Following the foregoing description, the characteristics important for using various affinity binding polypeptides for targeting of B lymphocyte stimulator or B lymphocyte stimulator-like polypeptides (B lymphocyte stimulator target protein) in vitro or in vivo can be appreciated. Additional binding polypeptide uses of the invention and alternative methods adapted to a particular use will be evident from studying the foregoing description. For instance, any spacer or linker sequences associated with B lymphocyte stimulator binding polypeptides discussed above may be removed or substituted to yield additional B lymphocyte stimulator binding polypeptides for use in the methods of this invention. All such embodiments and obvious alternatives are intended to be within the scope of this invention, as defined by the claims that follow.

Publications referred to above are hereby incorporated by reference.

The invention claimed is:

1. An isolated B lymphocyte stimulator binding polypeptide comprising an amino acid sequence at least 90% identical to $X_1$-$X_2$-$X_3$-Cys-$X_5$-$X_6$-$X_7$-$X_8$-$X_9$-$X_{10}$-$X_{11}$-$X_{12}$-$X_{13}$-$X_{14}$-Cys-$X_{16}$-$X_{17}$-$X_{18}$ (SEQ ID NO:5), wherein
   $X_1$ is Arg, Asp, Gly, His, Leu, Phe, Pro, Ser, Trp, Tyr, or is absent;
   $X_2$ is Ala, Arg, Asn, Asp, Gly, Pro, Ser, or is absent;
   $X_3$ is Arg, Asn, Gln, Glu, Gly, Lys, Met, Pro, Trp or Val;
   $X_5$ is Arg, Asn, Gln, Glu, His, Leu, Phe, Pro, Trp, Tyr, or Val;
   $X_6$ is Arg, Asp, Gln, Gly, Ile, Lys, Phe, Thr, Trp or Tyr;
   $X_7$ is Ala, Arg, Asp, Glu, Gly, Leu, Ser, or Tyr;
   $X_8$ is Asp, Gln, Glu, Leu, Met, Phe, Pro, Ser, or Tyr;
   $X_9$ is Asp, Leu, Pro, Thr, or Val;
   $X_{10}$ is Arg, Gln, His, Ile, Leu, Lys, Met, Phe, Thr, Trp or Tyr;
   $X_{11}$ is Ala, Arg, Asn, Gln, Glu, His, Leu, Lys, Met, or Thr;
   $X_{12}$ is Ala, Asn, Gln, Gly, Leu, Lys, Phe, Pro, Thr, Trp, or Tyr;
   $X_{13}$ is Ala, Arg, Gln, His, Lys, Met, Phe, Pro, Thr, Trp, or Tyr;
   $X_{14}$ is Arg, Gln, Glu, Gly, His, Leu, Met, Phe, Pro, Ser, Thr, Tyr, or Val;
   $X_{16}$ is Arg, Asp, Gly, His, Lys, Met, Phe, Pro, Ser, or Trp;
   $X_{17}$ is Arg, Asn, Asp, Gly, His, Phe, Pro, Ser, Trp or Tyr; and
   $X_{18}$ is Ala, Arg, Asn, Asp, His, Leu, Phe, or Trp, and
   wherein the B lymphocyte stimulator binding polypeptide binds a B lymphocyte stimulator protein selected from the group consisting of:
      (a) a protein whose amino acid sequence consists of amino acid residues 1-285 of SEQ ID NO: 173;
      (b) a protein whose amino acid sequence consists of amino acid residues 134-285 of SEQ ID NO:173; and
      (c) a trimer of the protein of (b).

2. The B lymphocyte stimulator binding polypeptide of claim 1, wherein $X_8$ and $X_9$ are Leu (SEQ ID NO: 460).

3. The B lymphocyte stimulator binding polypeptide of claim 1, wherein $X_2$ and $X_{17}$ are Pro (SEQ ID NO: 461).

4. The B lymphocyte stimulator binding polypeptide of claim 1, wherein $X_3$ is Gly.

5. The B lymphocyte stimulator binding polypeptide of claim 1, wherein $X_6$ and $X_{13}$ are Trp (SEQ ID NO: 462).

6. The B lymphocyte stimulator binding polypeptide of claim 1, wherein $X_7$ and $X_{16}$ are Asp (SEQ ID NO: 463).

7. The B lymphocyte stimulator binding polypeptide of claim 1, wherein $X_{10}$ is Ile.

8. The B lymphocyte stimulator binding polypeptide of claim 1, wherein $X_{11}$ is Lys.

9. The B lymphocyte stimulator binding polypeptide of claim 1, wherein $X_{12}$ is Gln.

10. The B lymphocyte stimulator binding polypeptide of claim 1, wherein $X_{14}$ is Val.

11. A fusion protein comprising the B lymphocyte stimulator binding polypeptide of claim 1 fused to a heterologous polypeptide.

12. The fusion protein of claim 11, wherein the heterologous polypeptide comprises an Fc region of an immunoglobulin.

13. A method of isolating a B lymphocyte stimulator or B lymphocyte stimulator-like polypeptide comprising
   (a) contacting a solid support that comprises the B lymphocyte stimulator binding polypeptide of claim 1 immobilized thereon with a solution containing a B lymphocyte stimulator or B lymphocyte stimulator-like polypeptide, and
   (b) separating the solution from the support.

14. A method for detecting a B lymphocyte stimulator or B lymphocyte stimulator-like polypeptide in a solution comprising
   (a) contacting the solution with the B lymphocyte stimulator binding polypeptide of claim 1, and
   (b) detecting binding of B lymphocyte stimulator or B lymphocyte stimulator-like polypeptide to the B lymphocyte stimulator binding polypeptide, thereby detecting the presence of a B lymphocyte stimulator or B lymphocyte stimulator-like polypeptide in the solution.

15. The B lymphocyte stimulator binding polypeptide of claim 1, wherein $X_1$ is Leu.

16. The B lymphocyte stimulator binding polypeptide of claim 1, wherein $X_5$ is Arg.

17. The B lymphocyte stimulator binding polypeptide of claim 1, wherein $X_{18}$ is Leu.

18. The B lymphocyte stimulator binding polypeptide of claim 1, wherein $X_6$ is Trp, $X_7$ is Asp, $X_9$ is Leu, $X_{12}$ is Gln, and $X_{13}$ is Trp (SEQ ID NO: 464).

19. A fusion protein comprising the B lymphocyte stimulator binding polypeptide of claim 18 fused to a heterologous polypeptide.

20. The fusion protein of claim 19, wherein the heterologous polypeptide comprises an Fc region of an immunoglobulin.

21. A method of isolating a B lymphocyte stimulator or B lymphocyte stimulator-like polypeptide comprising
   (a) contacting a solid support that comprises the B lymphocyte stimulator binding polypeptide of claim 8 immobilized thereon with a solution containing a B lymphocyte stimulator or B lymphocyte stimulator-like polypeptide, and
   (b) separating the solution from the support.

22. A method for detecting a B lymphocyte stimulator or B lymphocyte stimulator-like polypeptide in a solution comprising
   (a) contacting the solution with the B lymphocyte stimulator binding polypeptide of claim 8, and
   (b) detecting binding of B lymphocyte stimulator or B lymphocyte stimulator-like polypeptide to the B lymphocyte stimulator binding polypeptide, thereby detecting the presence of a B lymphocyte stimulator or B lymphocyte stimulator-like polypeptide in the solution.

23. The B lymphocyte stimulator binding polypeptide of claim 1, wherein $X_6$ is Trp, $X_7$ is Asp, $X_9$ is Leu, $X_{14}$ is Val, and $X_{16}$ is Asp (SEQ ID NO: 465).

24. A fusion protein comprising the B lymphocyte stimulator binding polypeptide of claim 23 fused to a heterologous polypeptide.

25. The fusion protein of claim 24, wherein the heterologous polypeptide comprises an Fc region of an immunoglobulin.

26. A method of isolating a B lymphocyte stimulator or B lymphocyte stimulator-like polypeptide comprising
   (a) contacting a solid support that comprises the B lymphocyte stimulator binding polypeptide of claim 23 immobilized thereon with a solution containing a B lymphocyte stimulator or B lymphocyte stimulator-like polypeptide, and
   (b) separating the solution from the support.

27. A method for detecting a B lymphocyte stimulator or B lymphocyte stimulator-like polypeptide in a solution comprising
   (a) contacting the solution with the B lymphocyte stimulator binding polypeptide of claim 23, and
   (b) detecting binding of B lymphocyte stimulator or B lymphocyte stimulator-like polypeptide to the B lymphocyte stimulator binding polypeptide, thereby detecting the presence of a B lymphocyte stimulator or B lymphocyte stimulator-like polypeptide in the solution.

* * * * *

UNITED STATES PATENT AND TRADEMARK OFFICE
CERTIFICATE OF CORRECTION

| | |
|---|---|
| PATENT NO. | : 8,062,906 B2 |
| APPLICATION NO. | : 12/701301 |
| DATED | : November 22, 2011 |
| INVENTOR(S) | : Beltzer et al. |

It is certified that error appears in the above-identified patent and that said Letters Patent is hereby corrected as shown below:

On the title page, item [56]:

PAGE 7 (CONTINUATION OF OTHER PUBLICATIONS)

Right column, line 47, "Cat" should read -- CAT --

PAGE 9 (CONTINUATION OF OTHER PUBLICATIONS)

Right column, line 25, "Ep" should read -- EP --

Right column, line 50, "against against" should read -- against --

PAGE 10 (CONTINUATION OF OTHER PUBLICATIONS)

Right column, line 59, "dated Nov. 29, 2007 dated Nov. 29, 2007" should read -- dated Nov. 29, 2007 --

Right column, line 69, "feb." should read -- Feb. --

PAGE 11 (CONTINUATION OF OTHER PUBLICATIONS)

Right column, line 6, "Dec. 2007)" should read -- (Dec. 2007) --

Right column, line 39, "Uk" should read -- UK --

IN THE CLAIMS

Claim 21, column 366, line 29, "claim 8" should read -- claim 18 --

Signed and Sealed this
Thirteenth Day of March, 2012

David J. Kappos
*Director of the United States Patent and Trademark Office*

CERTIFICATE OF CORRECTION (continued)
U.S. Pat. No. 8,062,906 B2

Claim 22, column 366, line 38, "claim 8" should read -- claim 18 --